United States Patent
Malley et al.

(10) Patent No.: US 11,305,001 B2
(45) Date of Patent: Apr. 19, 2022

(54) **MULTIPLE ANTIGEN PRESENTING SYSTEM (MAPS)-BASED *STAPHYLOCOCCUS AUREUS* VACCINE, IMMUNOGENIC COMPOSITION, AND USES THEREOF**

(71) Applicant: THE CHILDREN'S MEDICAL CENTER CORPORATION, Boston, MA (US)

(72) Inventors: Richard Malley, Beverly, MA (US); Fan Zhang, Chestnut Hill, MA (US); Yingjie Lu, Chestnut Hill, MA (US)

(73) Assignee: The Children's Medical Center Corporation, Boston, MA (US)

( * ) Notice: Subject to any disclaimer, the term of this patent is extended or adjusted under 35 U.S.C. 154(b) by 0 days.

(21) Appl. No.: 16/498,856

(22) PCT Filed: Mar. 28, 2018

(86) PCT No.: PCT/US2018/024810
§ 371 (c)(1),
(2) Date: Sep. 27, 2019

(87) PCT Pub. No.: WO2018/183475
PCT Pub. Date: Oct. 4, 2018

(65) Prior Publication Data
US 2021/0008192 A1    Jan. 14, 2021

Related U.S. Application Data

(60) Provisional application No. 62/477,618, filed on Mar. 28, 2017.

(51) Int. Cl.
*A61K 39/085* (2006.01)
*A61K 39/00* (2006.01)
*A61K 39/39* (2006.01)

(52) U.S. Cl.
CPC ............ *A61K 39/085* (2013.01); *A61K 39/39* (2013.01); *A61K 2039/57* (2013.01)

(58) Field of Classification Search
None
See application file for complete search history.

(56) References Cited

U.S. PATENT DOCUMENTS

| | | |
|---|---|---|
| 6,287,568 B1 | 9/2001 | Wang et al. |
| 7,588,920 B2 | 9/2009 | Doucette-Stamm et al. |
| 9,499,593 B2 | 11/2016 | Malley et al. |
| 10,017,548 B2 | 7/2018 | Malley et al. |
| 2002/0032323 A1 | 3/2002 | Kunsch et al. |
| 2005/0002948 A1 | 1/2005 | Ryall |
| 2006/0251675 A1 | 11/2006 | Hagen |
| 2007/0128183 A1 | 6/2007 | Meinke et al. |
| 2008/0032340 A1 | 2/2008 | Ghosh et al. |
| 2008/0112964 A1 | 5/2008 | Kirkham et al. |
| 2009/0054251 A1 | 2/2009 | O'Connor et al. |
| 2009/0148894 A1 | 6/2009 | Broedel et al. |
| 2009/0148897 A1 | 6/2009 | Dai |
| 2009/0285846 A1 | 11/2009 | Tweten |
| 2010/0003266 A1 | 1/2010 | Simon |
| 2010/0020945 A1 | 1/2010 | Li et al. |
| 2010/0022401 A1 | 1/2010 | Nordlund et al. |
| 2010/0166802 A1 | 7/2010 | Caplan et al. |
| 2010/0209450 A1 | 8/2010 | Biemans et al. |
| 2011/0065660 A1 | 3/2011 | Baron et al. |
| 2013/0115230 A1 | 5/2013 | Simon |
| 2014/0154286 A1 | 6/2014 | Malley et al. |
| 2014/0154287 A1 | 6/2014 | Malley et al. |
| 2014/0178425 A1 | 6/2014 | Bagnoli et al. |
| 2015/0374811 A1 | 12/2015 | Malley et al. |
| 2016/0090404 A1 | 3/2016 | Malley et al. |
| 2019/0119335 A1 | 4/2019 | Malley et al. |
| 2020/0407404 A1 | 12/2020 | Malley et al. |

FOREIGN PATENT DOCUMENTS

| | | |
|---|---|---|
| WO | 1995021195 A1 | 8/1995 |
| WO | 1996029094 A1 | 9/1996 |
| WO | 1998018930 A2 | 5/1998 |
| WO | 1998047530 A2 | 10/1998 |

(Continued)

OTHER PUBLICATIONS

Zhang et al. "Multiple antigen-presenting system (MAPS) to induce comprehensive B-and T-cell immunity." Proceedings of the National Academy of Sciences 110(33): 13564-13569 (2013).

Zhang et al. "Protection against *Staphylococcus aureus* colonization and infection by B-and T-Cell-mediated mechnisms." MBio 9(5): 1-13 (2018).

Menzies et al., "Site-directed mutagenesis of the alpha-toxin gene of *Staphylococcus aureus*: Role of histidines in toxin activity in vitro and in a murine model", Infection and Immunity, American Society for Microbiology, 62(5) 1843-1847 (May 1, 1994).

(Continued)

*Primary Examiner* — Gary B Nickol
*Assistant Examiner* — Jegatheesan Seharaseyon
(74) *Attorney, Agent, or Firm* — David S. Resnick; Susanna Benn; Jeanne Jodoin

(57) ABSTRACT

The present embodiments provide for an *S. aureus* (SA) Multiple Antigen Presenting System (MAPS) immunogenic composition comprising an immunogenic polysaccharide which induces an immune response, where at least one *S. aureus* (SA) peptide or polypeptide antigen is associated to the immunogenic polysaccharide by complementary affinity molecules. In some embodiments, the immunogenic polysaccharide can be an antigenic capsular polysaccharide of a Type 5 or Type 8 from *S. aureus*, or alternatively, a different immunogenic capsular or noncapsular polysaccharide, and where the protein or peptide SA antigens are indirectly linked via an affinity binding pair. The present SA-MAPS immunogenic compositions can elicit both humoral and cellular immune responses to the immunogenic polysaccharide and one or multiple SA antigens at the same time.

7 Claims, 13 Drawing Sheets
Specification includes a Sequence Listing.

(56) References Cited

FOREIGN PATENT DOCUMENTS

| | | | |
|---|---|---|---|
| WO | 2002077021 | A2 | 10/2002 |
| WO | 2003094960 | A2 | 11/2003 |
| WO | 2004092209 | A2 | 10/2004 |
| WO | 2005037190 | A2 | 4/2005 |
| WO | 2005039501 | A2 | 5/2005 |
| WO | 2006017929 | A1 | 2/2006 |
| WO | 2006067632 | A2 | 6/2006 |
| WO | 2006084467 | A1 | 8/2006 |
| WO | 2007026249 | A2 | 3/2007 |
| WO | 2007067681 | A2 | 6/2007 |
| WO | 2007081583 | A2 | 7/2007 |
| WO | 2007150020 | A1 | 12/2007 |
| WO | 2008094986 | A2 | 8/2008 |
| WO | 2008152448 | A2 | 12/2008 |
| WO | 2009016515 | A2 | 2/2009 |
| WO | 2009021548 | A1 | 2/2009 |
| WO | 2009029831 | A1 | 3/2009 |
| WO | 2010053559 | A1 | 5/2010 |
| WO | 2010071986 | A1 | 7/2010 |
| WO | 2010081875 | A1 | 7/2010 |
| WO | 2011008548 | A1 | 1/2011 |
| WO | 2011137354 | A2 | 11/2011 |
| WO | 2012155007 | A1 | 11/2012 |
| WO | 2012155053 | A1 | 11/2012 |
| WO | 2014018904 | A1 | 1/2014 |
| WO | 2014124228 | A1 | 8/2014 |
| WO | 2018183475 | A1 | 10/2018 |

OTHER PUBLICATIONS

Walker et al., "Key residues for membrane binding, oligomerization, and pore forming activity of staphylococcal alpha-hemolysin identified by cysteine scanning mutagenesis and targeted chemical modification", Journal of Biological Chemistry, American Society for Biochemistry and Molecular Biology, 270(39): 23065-23071 (Sep. 29, 1995).

"Centers for Disease Control and Prevention. ""Preventing pneumococcal disease among infants and young children.""Morbidity and Mortality Weekly Report, 49: 1-55 (2000)".

Anttila, M. et al., Avidity of IgG for Streptococcus pneumoniae type 6B and 23F polysaccharides in infants primed with pneumococcal conjugates and boosted with polysaccharide or conjugate vaccines, J. Infect. Dis., 177 (6):1614-1621 (1998).

Avci, F.Y. et al., A mechanism for glycoconjugate vaccine activation of the adaptive immune system and its implications or vaccine design, Nat. Med., 17(12): 1602-1609 (2011).

Berry, M. A. et al.,, Effect of Defined Point Mutations in Pneumolysin Gene on the Virulence of Streptococcus pneumonia, Infection and Immunity, 63(5):1969-1974 (1995).

Centers for Disease Control and Prevention. "Prevention of pneumococcal disease among infants and children—use of 13-valent pneumococcal conjugate vaccine and 23-valent pneumococcal polysaccharide vaccine." Morbidity and Mortality Weekly Report. 59: 1-24 (2010).

Colino, J. et al., Non-covalent association of protein and capsular polysaccharide on bacteria-sized latex beads as a model for polysaccharide-specific humoral immunity to intact Gram-positive extracellular bacteria, J. Immunol., 191 (6) 3254-3263 (2013).

Colino, J. et al., Parameters Underlying Distinct T Ceii-Dependent Polysaccharide-Specific IgG Responses to an Intact Gram-Positive Bacterium versus a Soluble Conjugate Vaccine, The Journal of Immunology, 1552-1559 (2009).

Cortajarena, A.L., et al., A receptor-binding region in Escherichia coli alpha-haemolysin, J. Biol. Chem., 278 (21): 19159-63 (2003).

Dagan, R. et al., Glycoconjugate vaccines and immune interference: A review, Vaccine, 28(34): 5513-5523 (2010).

Daniels, C. C. et al., The Proline-Rich Region of Pneumococcal Surface Proteins A and C Contains Surface-Accessible Epitopesn Common to All Pneumococci and Elicits Antibody-Mediated Protection against Sepsis, Infection and Immunity, 78(5):2163-2172 (2010).

Database, UniProt KB/TrEMBL, B3Q265_RHIE6, retrieved Jan. 3, 2021.

Database, UniProt KB/TrEMBL, F2AA21_RHIET, retrieved Jan. 4, 2021.

Database, UniProf KB/TrEMBL, Q8KKW2_RHIEC, retrieved Jan. 4, 2021.

Douce, G. et al., Genetically detoxified mutants of heat-labile toxin from Escherichia coli are able to act as oral adjuvants, Infect Immun., 67(9):4400-4406 (1999).

Douce, G. et al., Mutants of Escherichia coli heat-labile toxin lacking ADP-ribosyitransferase activity act as non-toxic, mucosal adjuvants, PNAS 92:1644-1648 (1995).

Elgert, K. D., Immunology Understanding the Immune System, John Wiley & Sons, Inc. Hoboken, New Jersey, p. 111 (2009).

EP Communication dated Apr. 9, 2015 in corresponding EP Application No. 12781636.1.

Evans, J. T. et al., Enhancement of antigen-specific immunity via the TLR4 ligands MPL adjuvant and Ribi.529, Expert Rev Vaccines, 2(2):219-229 (2003).

Fauvart, M. et al., Genome Sequence of Rhizobium etli CNPAF512, a Nitrogen-Fixing Symbiont isolated from Bean Root Nodules in Brazil, Journal of Bacteriology, 193(12): 3158-3159 (2011).

Ferreira, D. M. et al., DNA vaccines based on genetically detoxified derivatives of oneumolysin fail to protect mice against challenge with Streptococcus pneumonia, FEMS Immunology Med. Microbial 46: 291-297 (2006).

Gaj, T. et al., The AviD-tag, a NeutrAvidin/avidin specific peptide affinity tag for the immobilization and purification of recombinant proteins, Protein Expr. Purif., 56(1):54-61 (2007).

Giuliani, M. M. et al., Mucosal adjuvanticity and immunogenicity of LTR72, a novel mutant of Escherichia coli heat-labile enterotoxin with partial knockout of ADP-ribosyltransferase activity, J. Exp. Med., 187(7):1123-1132 (1998).

González, V et al., The mosaic structure of the symbiotic plasmid of Rhizobium etli CFN42 and its relation to other symbiotic genome compartments, Genome Biol., 4(6): R36 (2003).

Gruber, M.F. et al., Pratt D, Haase M. Licensing of pneumococcal conjugate vaccines for children and adults Regulatory perspective from the European Medicines Agency and the U.S. Food and Drug Administration, Pneumococcal Vaccines: The Impact of Conjugate Vaccine, 183-96 (2008).

Grun, C. H. et al, One-step biotinylation procedure for carbohydrates to study carbohydrate-protein interactions, Anal. Biochem., 354(1):54-63 (2006).

Helppolainen, S. H. et al., Bradavidin II from Bradyrhizobiumjaponicum: a new avidin-like biotin-binding protein, Biochim. Biophys. Acta., 1784(7-8):1002-10 (2008).

Helppolainen, S.H. et al., Rhizavidin from Rhizobium etli: the first natural dimer in the avidin protein family, Biochem J., 405(3): 397-405 (2007).

Hermanson, G. T., Bioconjugate Techniques, Elsevier Science, ProQuest Ebook Central, http://ebookcentral.proquest.com/lib.uspto-ebooks/detail.action?docID=307203, created from USPTO-ebooks on Sep. 6, 2017, 570-592 (1996).

Holliger, P. et al., "Diabodies": small bivalent and bi specific antibody fragments, Proc. Natl. Acad, Sci, USA, 90:6444-6448 (1993).

Hsu, T-L. et al., Profiling Carbohydrate-Receptor Interaction with Recombinant innate Immunity Receptor-Fc Fusion Proteins, J. Biol. Chem., 284(50): 34479-34489 (2009).

Huang, H. et al, Robust stimulation of humoral and cellular immune responses following vaccination with antigen-loaded beta-glucan particles, MBio, 1(3):e00164-10 (2010).

Hytonen, V.P. et al., Efficient production of active chicken avidin using a bacterial signal peptide in Escherichia coli, Biochem J., 384(Pt 2): 385-90 (2004).

Insel, R. et al., Response to oligosaccharide-protein conjugate vaccine against Hemophilus influenzae b in two patients with IgG2 deficiency unresponsive to capsular polysaccharide vaccine, N. Engl J. Med., 315:8, p. 499-503 (1986).

(56) References Cited

OTHER PUBLICATIONS

International Search Report for PCT/US2012/037412 (Multiple Antigen Presenting Immunogenic Composition, and Methods and Uses Thereof, filed May 11, 2012), issued by ISA/FIPS, 3 pages (dated Aug. 23, 2012).
International Search Report for PCT/US2012/037541 (Modified Biotin-Binding Protein, Fusion Proteins Thereof and Applications, filed May 11, 2012), issued by ISA/FIPS, 4 pages (dated Aug. 30, 2012).
International Search Report for PCT/US2018/24810, 6 pages (dated Aug. 31, 2018).
Ishizaka, S.T. and Hawkins, L.D., E6020: a synthetic Torı-like receptor 4 agonist as a vaccine adjuvant, Expert Rev. Vaccines, 6(5):773-784 (2007).
Izard, J. W. and Kendall, D. A., Signal peptides: exquisitely designed transport promoters, Mol. Microbiol. 13 (5):765-73 (1994).
Jin, Z. et al., Conjugates of group A and W135 capsular polysaccharides of neisseria meningitidis bound to recombinant *Staphylococcus aureus* enterotoxin C1: preparation, physicochemical characterization, and immunological properties in mice, Infect Immun, 73(12):7887-7893 (2005).
Kehoe, M. et al., Cloning, Expression, and Mapping of the *Staphylococcus aureus* a-Hemolysin Determinant in *Escherichia coli* K-12,41(3):1105-1111 (1985).
Kim, K. H. et al., Efficiency of a Pneumococcal Opsonophagocytic Killing Assay Improved by Multiplexing and by Coloring Colonies, Clin. Diagn, Lab. Immunol., 10(4):616-621 (2003).
Kojima, K. et al., Quantitation of IgG subclass antibodies to pneumococcal capsular polysaccharides by ELISA, using Pneumovax-specific antibodies as a reference, Tohoku J. Exp. Med., 161 (3):209-215 (1990).
Koskela, M. and Leinonen, M., Comparison of ELISA and RIA for measurement of pneumococcal antibodies before and after vaccination with 14-valent pneumococcal capsular polysaccharide vaccine, J. Clin. Pathol., 34 (1)193-98 (1981).
Lees, A. et al., Enhanced immunogenicity of protein-dextran conjugates: I. Rapid stimulation of enhanced antibody-responses to poorly immunogenic molecules, Vaccine, 12(13): 1160-1166 (1994).
Martinez, J. E. et al., A flow cytometric opsonophagocytic assay for measurement of functional antibodies elicited after vaccination with the 23-valent pneumococcal polysaccharide vaccine, Clin. Diagn. Lab Immunol., 6(4):581-586 (1999).
Moffitt et al., "Identification of protective pneumococcal T(H)17 antigens from the soluble fraction of a killed whole ceil vaccine" PLoS One 7(8) e43445 (2012).
Munro, C. S. et al., Assessment of biological activity of immunoglobulin preparations by using opsonized micro-organisms to stimulate neutrophil chemiluminescence, Clin. Exp. Immunol., 61 (1):183-188 (1985).
Ojo-Amaize, E. A. et al., A rapid and sensitive chemiluminescence assay for evaluation of functional opsonic activity of Haemophilus influenzae type b—specific antibodies, Clin. Diagn. Lab. Immunol., 2(3):286-290 (1995).
O'Reilly, M. et al., Inactivation of the alpha-haemolysin gene of *Staphylococcus aureus* 8325—4 by site-directed mutagenesis and studies on the expression of its haemolysins, Microbial Pathogenesis, 1:125-138 (1986),
Paton, P C. et al.,, Purification and immunogenicity of genetically obtained pneumolysin toxoids and their conjugation to *Streptococcus pneumoniae* type 19F polysaccharide, Infect. Lmmun., 59(7):2297-2304 (1991).
PNEUMOVAX® 23 (prescribing information). Whitehouse Station, NJ: Merck & Co.; May 2015.
Poljak, R. J., Production and structure of diabodies, Structure. 2(12):1121-1123 (1994).

Pollabauer, E. M. et al., The influence of carrier protein on the immunogenicity of simultaneously administered conjugate vaccines in infants, Vaccine, 27(11): 1674-1679 (2009).
PREVNAR 13® (prescribing information). New York, NY: Pfizer; Aug. 2017.
Richter, S. S. et al., Changes in pneumococcal serotypes and antimicrobial resistance after introduction of the 13 valent conjugate vaccine in the United States, Antimicrob Agents Chemother., 58:6484-6489 (2014).
Romero-Steiner, S. et al., Avidity determinations for Haemophilus influenzae Type b anti-polyribosyiribitol phosphate antibodies, Clin. Diagn. Lab. Immunol., 12(9):1029-1035 (2005).
Romero-Steiner, S. et al., Standardization of an opsonophagocytic assay for the measurement of functional antibody activity against *Streptococcus pneumoniae* using differentiated HL-60 cells, Clin. Diagn. Lab. Immunol., 4 (4)415-422 (1997).
Rosenberg, I.M., Protein Analysis and Purification, Springer Science + Business Media New York, 153-182 (1996).
Saeland, E et al., Pneumococcal pneumonia and bacteremia model in mice for the analysis of protective antibodies, Microb. Pathog., 29(2):81-91 (2000).
Sanabria-Valentin, Dissertation, Department of Basic Medical Sciences, NYU, p. 8-9 describing the general structure of LPS (2008).
Sano, T. et al., Methods in Enzymology, Elsevier, 326: 305-307 (2000).
Saunders, F. K. et al., Pneurolysin, the thiol-activated toxin of *Streptococcus pneumoniae*, does not require a thiol group for in vitro activity, Infect. Immun. 57(8):2547-2552 (1989).
Scott, D. et al., Immunogenicity of biotinylated hapten-avidin complexes, Mol. Immunol., 21 (11):1055-1060 (1984).
Sen, G. et al., In vivo humoral immune responses to isolated Pneumococcal polysaccharides are dependent on the presence of associated TLR ligands, The Journal of Immunology, 175(5):3084-3091 (2005).
Singh, M. and Indresh S., Advances in vaccine adjuvants for infectious diseases, Current HIV research 1 (3): 309-320 (2003).
Stack, A. M. et al., Minimum protective serum concentrations of pneumococcal anti-capsular antibodies in infant rats, J. Infect. Dis., 177(4):986-990 (1998).
Takakura, Y. et al., Tamavidin, a versatile affinity tag for protein purification and immobilization, J. Biotechnol., 145 (4): 317-322 (2010).
Thermo Scientific Avidin-Biotin Technical Handbook, 2009, p. 16-17. Found on the Internet on May 5, 2016 at: https://www.thermofisher.com/content/dam/LifeTech/Images/integration/1601675__AvBi_HB_INTL.pdf.
Wardenburg, J. and Schneewind, O., Vaccine protection against *Staphylococcus aureus pneumonia*, J. Exp. Med., 205(2): 287-94 (2008).
Williams et al., Innate Imprinting by the Modified Heat-Labile Toxin of *Escherichia coli* (LTK63) Provides Generic Protection against Lung Infectious Disease, The Journal of Immunology, 173: 7435-7443 (2004).
Written Opinion for PCT/US2012/037412 (Multiple Antigen Presenting Immunogenic Composition, and Methods and Uses Thereof, filed May 11, 2012), issued by ISA/FIPS, 4 pages (dated Aug. 23, 2012).
Written Opinion for PCT/US2012/037541 (Modified Biotin-Binding Protein, Fusion Proteins Thereof and Applications, filed May 11, 2012), issued by ISA/FIPS, 3 pages (dated Aug. 30, 2012).
Written Opinion for PCT/US2018/24810, 9 pages (dated Aug. 31, 2018).
Wu, W. et al., Thi 7-stimulating protein vaccines confer protection against Pseudomonas aeruginosa pneumonia, Am. J. Respir. Grit. Care Med., 186(5):420-427 (2012).
Zhang, F. et al., Design and evaluation of multiple antigen presenting system (MAPS)-based pneumococcal vaccine to prevent invasive disease and carriage, poster presented at the 10th international Symposium on Pneumococci and Pneumococcal Diseases (ISPPD-10), Glasgow, Scotland, Jun. 26-30, 2016.

| Groups | | No Ag | Mix | MAPS |
|---|---|---|---|---|
| Lesion | Yes | 10 | 3 | 3 |
| | No | 0 | 7 | 7 |
| Total | | 10 | 10 | 10 |
| P | | - | 0.0031 | 0.0031 |

| Groups | | No Ag | Mix | MAPS |
|---|---|---|---|---|
| Abscess | Yes | 10 | 10 | 3 |
| | No | 0 | 0 | 7 |
| Total | | 10 | 10 | 10 |
| P | | - | 1 | 0.0031 |

FIG. 3B, cont

SEQUENCE LISTING

```
<160> NUMBER OF SEQ ID NOS: 58

<210> SEQ ID NO 1
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Phe Asp Ala Ser Asn Phe Lys Asp Phe Ser Ser Ile Ala Ser Ala Ser
1               5                   10                  15

Ser Ser Trp Gln Asn Gln Ser Gly Ser Thr Met Ile Ile Gln Val Asp
            20                  25                  30

Ser Phe Gly Asn Val Ser Gly Gln Tyr Val Asn Arg Ala Gln Gly Thr
        35                  40                  45

Gly Cys Gln Asn Ser Pro Tyr Pro Leu Thr Gly Arg Val Asn Gly Thr
    50                  55                  60

Phe Ile Ala Phe Ser Val Gly Trp Asn Asn Ser Thr Glu Asn Cys Asn
65                  70                  75                  80

Ser Ala Thr Gly Trp Thr Gly Tyr Ala Gln Val Asn Gly Asn Asn Thr
                85                  90                  95

Glu Ile Val Thr Ser Trp Asn Leu Ala Tyr Glu Gly Gly Ser Gly Pro
            100                 105                 110

Ala Ile Glu Gln Gly Gln Asp Thr Phe Gln Tyr Val Pro Thr Thr Glu
        115                 120                 125

Asn Lys Ser Leu Leu Lys Asp
    130                 135
```

```
      130                 135

<210> SEQ ID NO 2
<211> LENGTH: 894
<212> TYPE: PRT
<213> ORGANISM: Staphylococcus aureus

<400> SEQUENCE: 2

Ser Glu Asn Ser Val Thr Gln Ser Asp Ser Ala Ser Asn Glu Ser Lys
1               5                   10                  15

Ser Asn Asp Ser Ser Val Ser Ala Ala Pro Lys Thr Asp Asp Thr
            20                  25                  30

Asn Val Ser Asp Thr Lys Thr Ser Asn Thr Asn Gly Glu Thr
            35                  40                  45

Ser Val Ala Gln Asn Pro Ala Gln Gln Glu Thr Thr Gln Ser Ser Ser
    50                  55                  60

Thr Asn Ala Thr Thr Glu Glu Thr Pro Val Thr Gly Glu Ala Thr Thr
65                  70                  75                  80

Thr Thr Thr Asn Gln Ala Asn Thr Pro Ala Thr Thr Gln Ser Ser Asn
                85                  90                  95

Thr Asn Ala Glu Glu Leu Val Asn Gln Thr Ser Asn Glu Thr Thr Phe
            100                 105                 110

Asn Asp Thr Asn Thr Val Ser Ser Val Asn Ser Pro Gln Asn Ser Thr
            115                 120                 125

Asn Ala Glu Asn Val Ser Thr Thr Gln Asp Thr Ser Thr Glu Ala Thr
130                 135                 140

Pro Ser Asn Asn Glu Ser Ala Pro Gln Ser Thr Asp Ala Ser Asn Lys
145                 150                 155                 160

Asp Val Val Asn Gln Ala Val Asn Thr Ser Ala Pro Arg Met Arg Ala
                165                 170                 175

Phe Ser Leu Ala Ala Val Ala Ala Asp Ala Pro Ala Ala Gly Thr Asp
            180                 185                 190

Ile Thr Asn Gln Leu Thr Asn Val Thr Val Gly Ile Asp Ser Gly Thr
            195                 200                 205

Thr Val Tyr Pro His Gln Ala Gly Tyr Val Lys Leu Asn Tyr Gly Phe
    210                 215                 220

Ser Val Pro Asn Ser Ala Val Lys Gly Asp Thr Phe Lys Ile Thr Val
225                 230                 235                 240

Pro Lys Glu Leu Asn Leu Asn Gly Val Thr Ser Thr Ala Lys Val Pro
                245                 250                 255

Pro Ile Met Ala Gly Asp Gln Val Leu Ala Asn Gly Val Ile Asp Ser
            260                 265                 270

Asp Gly Asn Val Ile Tyr Thr Phe Thr Asp Tyr Val Asn Thr Lys Asp
            275                 280                 285

Asp Val Lys Ala Thr Leu Thr Met Pro Ala Tyr Ile Asp Pro Glu Asn
    290                 295                 300

Val Lys Lys Thr Gly Asn Val Thr Leu Ala Thr Gly Ile Gly Ser Thr
305                 310                 315                 320

Thr Ala Asn Lys Thr Val Leu Val Asp Tyr Glu Lys Tyr Gly Lys Phe
                325                 330                 335

Tyr Asn Leu Ser Ile Lys Gly Thr Ile Asp Gln Ile Asp Lys Thr Asn
            340                 345                 350

Asn Thr Tyr Arg Gln Thr Ile Tyr Val Asn Pro Ser Gly Asp Asn Val
            355                 360                 365
```

```
Ile Ala Pro Val Leu Thr Gly Asn Leu Lys Pro Asn Thr Asp Ser Asn
370                 375                 380

Ala Leu Ile Asp Gln Gln Asn Thr Ser Ile Lys Val Tyr Lys Val Asp
385                 390                 395                 400

Asn Ala Ala Asp Leu Ser Glu Ser Tyr Phe Val Asn Pro Glu Asn Phe
                405                 410                 415

Glu Asp Val Thr Asn Ser Val Asn Ile Thr Phe Pro Asn Pro Asn Gln
                420                 425                 430

Tyr Lys Val Glu Phe Asn Thr Pro Asp Asp Gln Ile Thr Thr Pro Tyr
                435                 440                 445

Ile Val Val Val Asn Gly His Ile Asp Pro Asn Ser Lys Gly Asp Leu
450                 455                 460

Ala Leu Arg Ser Thr Leu Tyr Gly Tyr Asn Ser Asn Ile Ile Trp Arg
465                 470                 475                 480

Ser Met Ser Trp Asp Asn Glu Val Ala Phe Asn Asn Gly Ser Gly Ser
                485                 490                 495

Gly Asp Gly Ile Asp Lys Pro Val Val Pro Glu Gln Pro Asp Glu Pro
                500                 505                 510

Gly Glu Ile Glu Pro Ile Pro Glu Asp Ser Asp Ser Asp Pro Gly Ser
                515                 520                 525

Asp Ser Gly Ser Asp Ser Asn Ser Asp Ser Gly Ser Asp Ser Gly Ser
                530                 535                 540

Asp Ser Thr Ser Asp Ser Gly Ser Asp Ser Ala Ser Asp Ser Asp Ser
545                 550                 555                 560

Ala Ser Asp Ser Asp Ser Ala Ser Asp Ser Asp Ser Ala Ser Asp Ser
                565                 570                 575

Asp Ser Ala Ser Asp Ser Asp Ser Asp Asn Asp Ser Asp Ser Asp Ser
                580                 585                 590

Asp Ser Asp Ser Asp Ser Asp Ser Asp Ser Asp Ser Asp Ser Asp Ser
                595                 600                 605

Asp Ser Asp Ser Asp Ser Asp Ser Asp Ser Asp Ser Asp Ser Asp Ser
610                 615                 620

Asp Ser Asp Ser Asp Ser Asp Ser Asp Ser Asp Ser Asp Ser Asp Ser
625                 630                 635                 640

Asp Ser Asp Ser Asp Ser Asp Ser Asp Ser Asp Ser Asp Ser Asp Ser
                645                 650                 655

Asp Ser Asp Ser Asp Ser Asp Ser Asp Ser Asp Ser Asp Ser Asp Ser
                660                 665                 670

Asp Ser Asp Ser Asp Ser Asp Ser Asp Ser Asp Ser Asp Ser Asp Ser
                675                 680                 685

Asp Ser Asp Ser Asp Ser Asp Ser Asp Ser Asp Ser Asp Ser Asp Ser
                690                 695                 700

Asp Ser Asp Ser Asp Ser Asp Ser Asp Ser Asp Ser Asp Ser Asp Ser
705                 710                 715                 720

Asp Ser Asp Ser Asp Ser Asp Ser Ala Ser Asp Ser Asp Ser Asp Ser
                725                 730                 735

Asp Ser Asp Ser Asp Ser Asp Ser Asp Ser Asp Ser Asp Ser Asp Ser
                740                 745                 750

Asp Ser Asp Ser Asp Ser Asp Ser Asp Ser Asp Ser Asp Ser Asp Ser
                755                 760                 765

Glu Ser Asp Ser Asp Ser Glu Ser Asp Ser Asp Ser Asp Ser Asp Ser
                770                 775                 780

Asp Ser Asp Ser Asp Ser Asp Ser Asp Ser Asp Ser Asp Ser Ala Ser
```

```
                785                 790                 795                 800
Asp Ser Asp Ser Gly Ser Asp Ser Ser Asp Ser Asp Ser
                    805                 810                 815
Glu Ser Asp Ser Asn Ser Asp Ser Glu Ser Gly Ser Asn Asn Asn Val
                820                 825                 830
Val Pro Pro Asn Ser Pro Lys Asn Gly Thr Asn Ala Ser Asn Lys Asn
                835                 840                 845
Glu Ala Lys Asp Ser Lys Glu Pro Leu Pro Asp Thr Gly Ser Glu Asp
850                 855                 860
Glu Ala Asn Thr Ser Leu Ile Trp Gly Leu Leu Ala Ser Ile Gly Ser
865                 870                 875                 880
Leu Leu Leu Phe Arg Arg Lys Lys Glu Asn Lys Asp Lys Lys
                    885                 890

<210> SEQ ID NO 3
<211> LENGTH: 289
<212> TYPE: PRT
<213> ORGANISM: Staphylococcus aureus

<400> SEQUENCE: 3

Val Ala Ala Asp Ala Pro Ala Ala Gly Thr Asp Ile Thr Asn Gln Leu
1               5                   10                  15
Thr Asn Val Thr Val Gly Ile Asp Ser Gly Thr Thr Val Tyr Pro His
                20                  25                  30
Gln Ala Gly Tyr Val Lys Leu Asn Tyr Gly Phe Ser Val Pro Asn Ser
            35                  40                  45
Ala Val Lys Gly Asp Thr Phe Lys Ile Thr Val Pro Lys Glu Leu Asn
        50                  55                  60
Leu Asn Gly Val Thr Ser Thr Ala Lys Val Pro Pro Ile Met Ala Gly
65                  70                  75                  80
Asp Gln Val Leu Ala Asn Gly Val Ile Asp Ser Asp Gly Asn Val Ile
                85                  90                  95
Tyr Thr Phe Thr Asp Tyr Val Asn Thr Lys Asp Asp Val Lys Ala Thr
                100                 105                 110
Leu Thr Met Pro Ala Tyr Ile Asp Pro Glu Asn Val Lys Lys Thr Gly
            115                 120                 125
Asn Val Thr Leu Ala Thr Gly Ile Gly Ser Thr Thr Ala Asn Lys Thr
        130                 135                 140
Val Leu Val Asp Tyr Glu Lys Tyr Gly Lys Phe Tyr Asn Leu Ser Ile
145                 150                 155                 160
Lys Gly Thr Ile Asp Gln Ile Asp Lys Thr Asn Asn Thr Tyr Arg Gln
                165                 170                 175
Thr Ile Tyr Val Asn Pro Glu Asn Phe Glu Asp Val Thr Asn Ser Val
                180                 185                 190
Asn Ile Thr Phe Pro Asn Pro Asn Gln Tyr Lys Val Glu Phe Asn Thr
            195                 200                 205
Pro Asp Asp Gln Ile Thr Thr Pro Tyr Ile Val Val Asn Gly His
        210                 215                 220
Ile Asp Pro Asn Ser Lys Gly Asp Leu Ala Leu Arg Ser Thr Leu Tyr
225                 230                 235                 240
Gly Tyr Asn Ser Asn Ile Ile Trp Arg Ser Met Ser Trp Asp Asn Glu
                245                 250                 255
Val Ala Phe Asn Asn Gly Ser Gly Ser Gly Asp Gly Ile Asp Lys Pro
                260                 265                 270
```

Val Val Pro Glu Gln Pro Asp Glu Pro Gly Glu Ile Glu Pro Ile Pro
            275                 280                 285

Glu

<210> SEQ ID NO 4
<211> LENGTH: 855
<212> TYPE: PRT
<213> ORGANISM: Staphylococcus aureus

<400> SEQUENCE: 4

Ser Glu Gln Ser Asn Asp Thr Thr Gln Ser Ser Lys Asn Asn Ala Ser
1               5                   10                  15

Ala Asp Ser Glu Lys Asn Asn Met Ile Glu Thr Pro Gln Leu Asn Thr
            20                  25                  30

Thr Ala Asn Asp Thr Ser Asp Ile Ser Ala Asn Thr Asn Ser Ala Asn
        35                  40                  45

Val Asp Ser Thr Thr Lys Pro Met Ser Thr Gln Thr Ser Asn Thr Thr
50                  55                  60

Thr Thr Glu Pro Ala Ser Thr Asn Glu Thr Pro Gln Pro Thr Ala Ile
65                  70                  75                  80

Lys Asn Gln Ala Thr Ala Ala Lys Met Gln Asp Gln Thr Val Pro Gln
                85                  90                  95

Glu Ala Asn Ser Gln Val Asp Asn Lys Thr Thr Asn Asp Ala Asn Ser
            100                 105                 110

Ile Ala Thr Asn Ser Glu Leu Lys Asn Ser Gln Thr Leu Asp Leu Pro
        115                 120                 125

Gln Ser Ser Pro Gln Thr Ile Ser Asn Ala Gln Gly Thr Ser Lys Pro
130                 135                 140

Ser Val Arg Thr Arg Ala Val Arg Ser Leu Ala Val Ala Glu Pro Val
145                 150                 155                 160

Val Asn Ala Ala Asp Ala Lys Gly Thr Asn Val Asn Asp Lys Val Thr
                165                 170                 175

Ala Ser Asn Phe Lys Leu Glu Lys Thr Thr Phe Asp Pro Asn Gln Ser
            180                 185                 190

Gly Asn Thr Phe Met Ala Ala Asn Phe Thr Val Thr Asp Lys Val Lys
        195                 200                 205

Ser Gly Asp Tyr Phe Thr Ala Lys Leu Pro Asp Ser Leu Thr Gly Asn
210                 215                 220

Gly Asp Val Asp Tyr Ser Asn Ser Asn Asn Thr Met Pro Ile Ala Asp
225                 230                 235                 240

Ile Lys Ser Thr Asn Gly Asp Val Val Ala Lys Ala Thr Tyr Asp Ile
                245                 250                 255

Leu Thr Lys Thr Tyr Thr Phe Val Phe Thr Asp Tyr Val Asn Asn Lys
            260                 265                 270

Glu Asn Ile Asn Gly Gln Phe Ser Leu Pro Leu Phe Thr Asp Arg Ala
        275                 280                 285

Lys Ala Pro Lys Ser Gly Thr Tyr Asp Ala Asn Ile Asn Ile Ala Asp
    290                 295                 300

Glu Met Phe Asn Asn Lys Ile Thr Tyr Asn Tyr Ser Ser Pro Ile Ala
305                 310                 315                 320

Gly Ile Asp Lys Pro Asn Gly Ala Asn Ile Ser Ser Gln Ile Ile Gly
                325                 330                 335

Val Asp Thr Ala Ser Gly Gln Asn Thr Tyr Lys Gln Thr Val Phe Val
            340                 345                 350

```
Asn Pro Lys Gln Arg Val Leu Gly Asn Thr Trp Val Tyr Ile Lys Gly
            355                 360                 365

Tyr Gln Asp Lys Ile Glu Glu Ser Ser Gly Lys Val Ser Ala Thr Asp
370                 375                 380

Thr Lys Leu Arg Ile Phe Glu Val Asn Asp Ile Ser Lys Leu Ser Asp
385                 390                 395                 400

Ser Tyr Tyr Ala Asp Pro Asn Asp Ser Asn Leu Lys Glu Val Thr Asp
            405                 410                 415

Gln Phe Lys Asn Arg Ile Tyr Tyr Glu His Pro Asn Val Ala Ser Ile
            420                 425                 430

Lys Phe Gly Asp Ile Thr Lys Thr Tyr Val Val Leu Val Glu Gly His
            435                 440                 445

Tyr Asp Asn Thr Gly Lys Asn Leu Lys Thr Gln Val Ile Gln Glu Asn
450                 455                 460

Val Asp Pro Val Thr Asn Arg Asp Tyr Ser Ile Phe Gly Trp Asn Asn
465                 470                 475                 480

Glu Asn Val Val Arg Tyr Gly Gly Ser Ala Asp Gly Asp Ser Ala
            485                 490                 495

Val Asn Pro Lys Asp Pro Thr Pro Gly Pro Val Asp Pro Glu Pro
            500                 505                 510

Ser Pro Asp Pro Glu Pro Glu Pro Ser Pro Asp Pro Asp Pro Asp Ser
            515                 520                 525

Asp Ser Asp Ser Asp Ser Gly Ser Asp Ser Asp Gly Ser Asp Ser
            530                 535                 540

Asp Ser Glu Ser Asp Ser Asp Ser Asp Ser Asp Ser Asp Ser Asp Ser
545                 550                 555                 560

Asp Ser Asp Ser Glu Ser Asp Ser Asp Ser Glu Ser Asp Ser Asp Ser
            565                 570                 575

Asp Ser Asp Ser Asp Ser Asp Ser Asp Ser Asp Ser Asp Ser Asp Ser
            580                 585                 590

Asp Ser Asp Ser Asp Ser Asp Ser Asp Ser Asp Ser Asp Ser Glu Ser
            595                 600                 605

Asp Ser Asp Ser Glu Ser Asp Ser Glu Ser Asp Ser Asp Ser Asp Ser
            610                 615                 620

Asp Ser Asp Ser Asp Ser Asp Ser Asp Ser Asp Ser Asp Ser Asp Ser
625                 630                 635                 640

Asp Ser Asp Ser Asp Ser Asp Ser Asp Ser Asp Ser Asp Ser Asp Ser
            645                 650                 655

Asp Ser Asp Ser Asp Ser Asp Ser Asp Ser Asp Ser Asp Ser Asp Ser
            660                 665                 670

Asp Ser Asp Ser Asp Ser Asp Ser Asp Ser Asp Ser Asp Ser Asp Ser
            675                 680                 685

Asp Ser Asp Ser Asp Ser Asp Ser Asp Ser Asp Ser Asp Ser Asp Ser
            690                 695                 700

Asp Ser Asp Ser Asp Ser Asp Ser Asp Ser Asp Ser Asp Ser Asp Ser
705                 710                 715                 720

Asp Ser Asp Ser Asp Ser Asp Ser Asp Ser Asp Ser Asp Ser Asp Ser
            725                 730                 735

Asp Ser Asp Ser Asp Ser Asp Ser Asp Ser Asp Ser Asp Ser Asp Ser
            740                 745                 750

Asp Ser Asp Ser Asp Ser Asp Ser Asp Ser Asp Ser Asp Ser Asp Ser
            755                 760                 765

Asp Ser Asp Ser Asp Ser Asp Ser Asp Ser Asp Ser Asp Ser Arg Val
```

```
                    770                 775                 780
Thr Pro Pro Asn Asn Glu Gln Lys Ala Pro Ser Asn Pro Lys Gly Glu
785                 790                 795                 800

Val Asn His Ser Asn Lys Val Ser Lys Gln His Lys Thr Asp Ala Leu
                805                 810                 815

Pro Glu Thr Gly Asp Lys Ser Glu Asn Thr Asn Ala Thr Leu Phe Gly
            820                 825                 830

Ala Met Met Ala Leu Leu Gly Ser Leu Leu Leu Phe Arg Lys Arg Lys
        835                 840                 845

Gln Asp His Lys Glu Lys Ala
    850                 855

<210> SEQ ID NO 5
<211> LENGTH: 340
<212> TYPE: PRT
<213> ORGANISM: Staphylococcus aureus

<400> SEQUENCE: 5

Pro Val Val Asn Ala Ala Asp Ala Lys Gly Thr Asn Val Asn Asp Lys
1               5                   10                  15

Val Thr Ala Ser Asn Phe Lys Leu Glu Lys Thr Thr Phe Asp Pro Asn
            20                  25                  30

Gln Ser Gly Asn Thr Phe Met Ala Ala Asn Phe Thr Val Thr Asp Lys
        35                  40                  45

Val Lys Ser Gly Asp Tyr Phe Thr Ala Lys Leu Pro Asp Ser Leu Thr
    50                  55                  60

Gly Asn Gly Asp Val Asp Tyr Ser Asn Ser Asn Thr Met Pro Ile
65                  70                  75                  80

Ala Asp Ile Lys Ser Thr Asn Gly Asp Val Val Ala Lys Ala Thr Tyr
                85                  90                  95

Asp Ile Leu Thr Lys Thr Tyr Thr Phe Val Phe Thr Asp Tyr Val Asn
            100                 105                 110

Asn Lys Glu Asn Ile Asn Gly Gln Phe Ser Leu Pro Leu Phe Thr Asp
        115                 120                 125

Arg Ala Lys Ala Pro Lys Ser Gly Thr Tyr Asp Ala Asn Ile Asn Ile
    130                 135                 140

Ala Asp Glu Met Phe Asn Asn Lys Ile Thr Tyr Asn Tyr Ser Ser Pro
145                 150                 155                 160

Ile Ala Gly Ile Asp Lys Pro Asn Gly Ala Asn Ile Ser Ser Gln Ile
                165                 170                 175

Ile Gly Val Asp Thr Ala Ser Gly Gln Asn Thr Tyr Lys Gln Thr Val
            180                 185                 190

Phe Val Asn Pro Lys Gln Arg Val Leu Gly Asn Thr Trp Val Tyr Ile
        195                 200                 205

Lys Gly Tyr Gln Asp Lys Ile Glu Glu Ser Ser Gly Lys Val Ser Ala
    210                 215                 220

Thr Asp Thr Lys Leu Arg Ile Phe Glu Val Asn Asp Ile Ser Lys Leu
225                 230                 235                 240

Ser Asp Ser Tyr Tyr Ala Asp Pro Asn Asp Ser Asn Leu Lys Glu Val
                245                 250                 255

Thr Asp Gln Phe Lys Asn Arg Ile Tyr Tyr Glu His Pro Asn Val Ala
            260                 265                 270

Ser Ile Lys Phe Gly Asp Ile Thr Lys Thr Tyr Val Val Leu Val Glu
        275                 280                 285
```

```
Gly His Tyr Asp Asn Thr Gly Lys Asn Leu Lys Thr Gln Val Ile Gln
        290                 295                 300

Glu Asn Val Asp Pro Val Thr Asn Arg Asp Tyr Ser Ile Phe Gly Trp
305                 310                 315                 320

Asn Asn Glu Asn Val Val Arg Tyr Gly Gly Gly Ser Ala Asp Gly Asp
                325                 330                 335

Ser Ala Val Asn
        340

<210> SEQ ID NO 6
<211> LENGTH: 1329
<212> TYPE: PRT
<213> ORGANISM: Staphylococcus aureus

<400> SEQUENCE: 6

Ala Glu Ser Thr Asn Lys Glu Leu Asn Glu Ala Thr Thr Ser Ala Ser
1               5                   10                  15

Asp Asn Gln Ser Ser Asp Lys Val Asp Met Gln Gln Leu Asn Gln Glu
            20                  25                  30

Asp Asn Thr Lys Asn Asp Asn Gln Lys Glu Met Val Ser Ser Gln Gly
        35                  40                  45

Asn Glu Thr Thr Ser Asn Gly Asn Lys Leu Ile Glu Lys Glu Ser Val
50                  55                  60

Gln Ser Thr Thr Gly Asn Lys Val Glu Val Ser Thr Ala Lys Ser Asp
65                  70                  75                  80

Glu Gln Ala Ser Pro Lys Ser Thr Asn Glu Asp Leu Asn Thr Lys Gln
                85                  90                  95

Thr Ile Ser Asn Gln Glu Ala Leu Gln Pro Asp Leu Gln Glu Asn Lys
            100                 105                 110

Ser Val Val Asn Val Gln Pro Thr Asn Glu Glu Asn Lys Lys Val Asp
        115                 120                 125

Ala Lys Thr Glu Ser Thr Thr Leu Asn Val Lys Ser Asp Ala Ile Lys
130                 135                 140

Ser Asn Asp Glu Thr Leu Val Asp Asn Ser Asn Ser Asn Asn Glu
145                 150                 155                 160

Asn Asn Ala Asp Ile Ile Leu Pro Lys Ser Thr Ala Pro Lys Arg Leu
                165                 170                 175

Asn Thr Arg Met Arg Ile Ala Ala Val Gln Pro Ser Ser Thr Glu Ala
            180                 185                 190

Lys Asn Val Asn Asp Leu Ile Thr Ser Asn Thr Thr Leu Thr Val Val
        195                 200                 205

Asp Ala Asp Lys Asn Asn Lys Ile Val Pro Ala Gln Asp Tyr Leu Ser
210                 215                 220

Leu Lys Ser Gln Ile Thr Val Asp Lys Val Lys Ser Gly Asp Tyr
225                 230                 235                 240

Phe Thr Ile Lys Tyr Ser Asp Thr Val Gln Val Tyr Gly Leu Asn Pro
                245                 250                 255

Glu Asp Ile Lys Asn Ile Gly Asp Ile Lys Asp Pro Asn Asn Gly Glu
            260                 265                 270

Thr Ile Ala Thr Ala Lys His Asp Thr Ala Asn Asn Leu Ile Thr Tyr
        275                 280                 285

Thr Phe Thr Asp Tyr Val Asp Arg Phe Asn Ser Val Gln Met Gly Ile
290                 295                 300

Asn Tyr Ser Ile Tyr Met Asp Ala Asp Thr Ile Pro Val Ser Lys Asn
305                 310                 315                 320
```

```
Asp Val Glu Phe Asn Val Thr Ile Gly Asn Thr Thr Lys Thr Thr
            325                 330                 335

Ala Asn Ile Gln Tyr Pro Asp Tyr Val Val Asn Glu Lys Asn Ser Ile
            340                 345                 350

Gly Ser Ala Phe Thr Glu Thr Val Ser His Val Gly Asn Lys Glu Asn
            355                 360                 365

Pro Gly Tyr Tyr Lys Gln Thr Ile Tyr Val Asn Pro Ser Glu Asn Ser
370                 375                 380

Leu Thr Asn Ala Lys Leu Lys Val Gln Ala Tyr His Ser Ser Tyr Pro
385                 390                 395                 400

Asn Asn Ile Gly Gln Ile Asn Lys Asp Val Thr Asp Ile Lys Ile Tyr
            405                 410                 415

Gln Val Pro Lys Gly Tyr Thr Leu Asn Lys Gly Tyr Asp Val Asn Thr
            420                 425                 430

Lys Glu Leu Thr Asp Val Thr Asn Gln Tyr Leu Gln Lys Ile Thr Tyr
            435                 440                 445

Gly Asp Asn Asn Ser Ala Val Ile Asp Phe Gly Asn Ala Asp Ser Ala
450                 455                 460

Tyr Val Val Met Val Asn Thr Lys Phe Gln Tyr Thr Asn Ser Glu Ser
465                 470                 475                 480

Pro Thr Leu Val Gln Met Ala Thr Leu Ser Ser Thr Gly Asn Lys Ser
            485                 490                 495

Val Ser Thr Gly Asn Ala Leu Gly Phe Thr Asn Asn Gln Ser Gly Gly
            500                 505                 510

Ala Gly Gln Glu Val Tyr Lys Ile Gly Asn Tyr Val Trp Glu Asp Thr
            515                 520                 525

Asn Lys Asn Gly Val Gln Glu Leu Gly Glu Lys Gly Val Gly Asn Val
            530                 535                 540

Thr Val Thr Val Phe Asp Asn Thr Asn Thr Lys Val Gly Glu Ala
545                 550                 555                 560

Val Thr Lys Glu Asp Gly Ser Tyr Leu Ile Pro Asn Leu Pro Asn Gly
            565                 570                 575

Asp Tyr Arg Val Glu Phe Ser Asn Leu Pro Lys Gly Tyr Glu Val Thr
            580                 585                 590

Pro Ser Lys Gln Gly Asn Asn Glu Glu Leu Asp Ser Asn Gly Leu Ser
            595                 600                 605

Ser Val Ile Thr Val Asn Gly Lys Asp Asn Leu Ser Ala Asp Leu Gly
            610                 615                 620

Ile Tyr Lys Pro Lys Tyr Asn Leu Gly Asp Tyr Val Trp Glu Asp Thr
625                 630                 635                 640

Asn Lys Asn Gly Ile Gln Asp Gln Asp Glu Lys Gly Ile Ser Gly Val
            645                 650                 655

Thr Val Thr Leu Lys Asp Glu Asn Gly Asn Val Leu Lys Thr Val Thr
            660                 665                 670

Thr Asp Ala Asp Gly Lys Tyr Lys Phe Thr Asp Leu Asp Asn Gly Asn
            675                 680                 685

Tyr Lys Val Glu Phe Thr Thr Pro Glu Gly Tyr Thr Pro Thr Val
            690                 695                 700

Thr Ser Gly Ser Asp Ile Glu Lys Asp Ser Asn Gly Leu Thr Thr Thr
705                 710                 715                 720

Gly Val Ile Asn Gly Ala Asp Asn Met Thr Leu Asp Ser Gly Phe Tyr
            725                 730                 735
```

```
Lys Thr Pro Lys Tyr Asn Leu Gly Asn Tyr Val Trp Glu Asp Thr Asn
            740                 745                 750

Lys Asp Gly Lys Gln Asp Ser Thr Glu Lys Gly Ile Ser Gly Val Thr
        755                 760                 765

Val Thr Leu Lys Asn Glu Asn Gly Glu Val Leu Gln Thr Thr Lys Thr
    770                 775                 780

Asp Lys Asp Gly Lys Tyr Gln Phe Thr Gly Leu Glu Asn Gly Thr Tyr
785                 790                 795                 800

Lys Val Glu Phe Glu Thr Pro Ser Gly Tyr Thr Pro Thr Gln Val Gly
                805                 810                 815

Ser Gly Thr Asp Glu Gly Ile Asp Ser Asn Gly Thr Ser Thr Thr Gly
            820                 825                 830

Val Ile Lys Asp Lys Asp Asn Asp Thr Ile Asp Ser Gly Phe Tyr Lys
            835                 840                 845

Pro Thr Tyr Asn Leu Gly Asp Tyr Val Trp Glu Asp Thr Asn Lys Asn
            850                 855                 860

Gly Val Gln Asp Lys Asp Glu Lys Gly Ile Ser Gly Val Thr Val Thr
865                 870                 875                 880

Leu Lys Asp Glu Asn Asp Lys Val Leu Lys Thr Val Thr Thr Asp Glu
            885                 890                 895

Asn Gly Lys Tyr Gln Phe Thr Asp Leu Asn Asn Gly Thr Tyr Lys Val
            900                 905                 910

Glu Phe Glu Thr Pro Ser Gly Tyr Thr Pro Thr Ser Val Thr Ser Gly
            915                 920                 925

Asn Asp Thr Glu Lys Asp Ser Asn Gly Leu Thr Thr Thr Gly Val Ile
            930                 935                 940

Lys Asp Ala Asp Asn Met Thr Leu Asp Ser Gly Phe Tyr Lys Thr Pro
945                 950                 955                 960

Lys Tyr Ser Leu Gly Asp Tyr Val Trp Tyr Asp Ser Asn Lys Asp Gly
                965                 970                 975

Lys Gln Asp Ser Thr Glu Lys Gly Ile Lys Asp Val Lys Val Thr Leu
            980                 985                 990

Leu Asn Glu Lys Gly Glu Val Ile Gly Thr Thr Lys Thr Asp Glu Asn
            995                 1000                1005

Gly Lys Tyr Cys Phe Asp Asn Leu Asp Ser Gly Lys Tyr Lys Val
    1010                1015                1020

Ile Phe Glu Lys Pro Ala Gly Leu Thr Gln Thr Gly Thr Asn Thr
    1025                1030                1035

Thr Glu Asp Asp Lys Asp Ala Asp Gly Gly Glu Val Asp Val Thr
    1040                1045                1050

Ile Thr Asp His Asp Asp Phe Thr Leu Asp Asn Gly Tyr Tyr Glu
    1055                1060                1065

Glu Glu Thr Ser Asp Ser Asp Ser Asp Ser Asp Ser Asp Ser Asp
    1070                1075                1080

Ser Asp Arg Asp Ser Asp Ser Asp Ser Asp Ser Asp Ser Asp Ser
    1085                1090                1095

Asp Ser Asp Ser Asp Ser Asp Ser Asp Ser Asp Ser Asp Ser Asp
    1100                1105                1110

Ser Asp Arg Asp Ser Asp Ser Asp Ser Asp Ser Asp Ser Asp Ser
    1115                1120                1125

Asp Ser Asp Ser Asp Ser Asp Ser Asp Ser Asp Ser Asp Ser Asp
    1130                1135                1140

Ser Asp Ser Asp Ser Asp Ser Asp Ser Asp Ser Asp Ser Asp Ser
```

```
                1145                1150                1155

Asp Ser Asp Ser Asp Ser  Asp Ser Asp Ser  Asp Ser Asp
        1160                1165                1170

Ser Asp Ser Asp Ser Asp  Ser Asp Ser Asp  Ser Asp Ser
    1175                1180                1185

Asp Ser Asp Ser Asp Ser  Asp Ser Asp Ser  Asp Ser Asp
        1190                1195                1200

Ser Asp Ser Asp Ser Asp  Ser Asp Ser Asp  Ser Asp Ser
    1205                1210                1215

Asp Ser Asp Ser Asp Ser  Asp Ser Asp Ser  Asp Ser Asp
        1220                1225                1230

Ser Asp Ser Asp Ser Asp  Ser Asp Ser Asp  Ser Asp Ser
    1235                1240                1245

Asp Ser Asp Ser Asp Ser  Asp Ser Asp Ser  Asp Ser Asp
        1250                1255                1260

Ser Asp Ser Asp Ser Asp Ala  Gly Lys His Thr  Pro Val Lys Pro
    1265                1270                1275

Met Ser Thr Thr Lys Asp His  His Asn Lys Ala  Lys Ala Leu Pro
        1280                1285                1290

Glu Thr Gly Asn Glu Asn Ser  Gly Ser Asn Asn  Ala Thr Leu Phe
        1295                1300                1305

Gly Gly Leu Phe Ala Ala Leu  Gly Ser Leu Leu  Leu Phe Gly Arg
        1310                1315                1320

Arg Lys Lys Gln Asn Lys
        1325

<210> SEQ ID NO 7
<211> LENGTH: 437
<212> TYPE: PRT
<213> ORGANISM: Staphylococcus aureus

<400> SEQUENCE: 7

Asn Val Asn Asp Leu Ile Thr  Ser Asn Thr Thr  Leu Thr Val Val Asp
1               5                   10                  15

Ala Asp Lys Asn Asn Lys Ile  Val Pro Ala Gln  Asp Tyr Leu Ser Leu
            20                  25                  30

Lys Ser Gln Ile Thr Val Asp  Asp Lys Val Lys  Ser Gly Asp Tyr Phe
        35                  40                  45

Thr Ile Lys Tyr Ser Asp Thr  Val Gln Val Tyr  Gly Leu Asn Pro Glu
    50                  55                  60

Asp Ile Lys Asn Ile Gly Asp  Ile Lys Asp Pro  Asn Asn Gly Glu Thr
65                  70                  75                  80

Ile Ala Thr Ala Lys His Asp  Thr Ala Asn Asn  Leu Ile Thr Tyr Thr
                85                  90                  95

Phe Thr Asp Tyr Val Asp Arg  Phe Asn Ser Val  Gln Met Gly Ile Asn
            100                 105                 110

Tyr Ser Ile Tyr Met Asp Ala  Asp Thr Ile Pro  Val Ser Lys Asn Asp
        115                 120                 125

Val Glu Phe Asn Val Thr Ile  Gly Asn Thr Thr  Thr Lys Thr Thr Ala
    130                 135                 140

Asn Ile Gln Tyr Pro Asp Tyr  Val Val Asn Glu  Lys Asn Ser Ile Gly
145                 150                 155                 160

Ser Ala Phe Thr Glu Thr Val  Ser His Val Gly  Asn Lys Glu Asn Pro
                165                 170                 175
```

Gly Tyr Tyr Lys Gln Thr Ile Tyr Val Asn Pro Ser Glu Asn Ser Leu
            180                 185                 190

Thr Asn Ala Lys Leu Lys Val Gln Ala Tyr His Ser Ser Tyr Pro Asn
        195                 200                 205

Asn Ile Gly Gln Ile Asn Lys Asp Val Thr Asp Ile Lys Ile Tyr Gln
    210                 215                 220

Val Pro Lys Gly Tyr Thr Leu Asn Lys Gly Tyr Asp Val Asn Thr Lys
225                 230                 235                 240

Glu Leu Thr Asp Val Thr Asn Gln Tyr Leu Gln Lys Ile Thr Tyr Gly
            245                 250                 255

Asp Asn Asn Ser Ala Val Ile Asp Phe Gly Asn Ala Asp Ser Ala Tyr
        260                 265                 270

Val Val Met Val Asn Thr Lys Phe Gln Tyr Thr Asn Ser Glu Ser Pro
    275                 280                 285

Thr Leu Val Gln Met Ala Thr Leu Ser Ser Thr Gly Asn Lys Ser Val
290                 295                 300

Ser Thr Gly Asn Ala Leu Gly Phe Thr Asn Asn Gln Ser Gly Gly Ala
305                 310                 315                 320

Gly Gln Glu Val Tyr Lys Ile Gly Asn Tyr Val Trp Glu Asp Thr Asn
            325                 330                 335

Lys Asn Gly Val Gln Glu Leu Gly Glu Lys Gly Val Gly Asn Val Thr
        340                 345                 350

Val Thr Val Phe Asp Asn Asn Thr Asn Thr Lys Val Gly Glu Ala Val
    355                 360                 365

Thr Lys Glu Asp Gly Ser Tyr Leu Ile Pro Asn Leu Pro Asn Gly Asp
370                 375                 380

Tyr Arg Val Glu Phe Ser Asn Leu Pro Lys Gly Tyr Glu Val Thr Pro
            385                 390                 395                 400

Ser Lys Gln Gly Asn Asn Glu Glu Leu Asp Ser Asn Gly Leu Ser Ser
        405                 410                 415

Val Ile Thr Val Asn Gly Lys Asp Asn Leu Ser Ala Asp Leu Gly Ile
    420                 425                 430

Tyr Lys Pro Lys Tyr
        435

<210> SEQ ID NO 8
<211> LENGTH: 1068
<212> TYPE: PRT
<213> ORGANISM: Staphylococcus aureus

<400> SEQUENCE: 8

Ala Glu Asn Thr Ser Thr Glu Asn Ala Lys Gln Asp Asp Ala Thr Thr
1               5                   10                  15

Ser Asp Asn Lys Glu Val Val Ser Glu Thr Glu Asn Asn Ser Thr Thr
            20                  25                  30

Glu Asn Asn Ser Thr Asn Pro Ile Lys Lys Glu Thr Asn Thr Asp Ser
        35                  40                  45

Gln Pro Glu Ala Lys Lys Glu Ser Thr Ser Ser Thr Gln Lys Gln
    50                  55                  60

Gln Asn Asn Val Thr Ala Thr Glu Thr Lys Pro Gln Asn Ile Glu
65                  70                  75                  80

Lys Glu Asn Val Lys Pro Ser Thr Asp Lys Thr Ala Thr Glu Asp Thr
            85                  90                  95

Ser Val Ile Leu Glu Glu Lys Lys Ala Pro Asn Asn Thr Asn Asn Asp
        100                 105                 110

```
Val Thr Thr Lys Pro Ser Thr Ser Glu Pro Ser Thr Ser Glu Ile Gln
            115                 120                 125

Thr Lys Pro Thr Thr Pro Gln Glu Ser Thr Asn Ile Glu Asn Ser Gln
    130                 135                 140

Pro Gln Pro Thr Pro Ser Lys Val Asp Asn Gln Val Thr Asp Ala Thr
145                 150                 155                 160

Asn Pro Lys Glu Pro Val Asn Val Ser Lys Glu Glu Leu Lys Asn Asn
                165                 170                 175

Pro Glu Lys Leu Lys Glu Leu Val Arg Asn Asp Ser Asn Thr Asp His
            180                 185                 190

Ser Thr Lys Pro Val Ala Thr Ala Pro Thr Ser Val Ala Pro Lys Arg
    195                 200                 205

Val Asn Ala Lys Met Arg Phe Ala Val Ala Gln Pro Ala Ala Val Ala
210                 215                 220

Ser Asn Asn Val Asn Asp Leu Ile Lys Val Thr Lys Gln Thr Ile Lys
225                 230                 235                 240

Val Gly Asp Gly Lys Asp Asn Val Ala Ala His Asp Gly Lys Asp
                245                 250                 255

Ile Glu Tyr Asp Thr Glu Phe Thr Ile Asp Asn Lys Val Lys Lys Gly
            260                 265                 270

Asp Thr Met Thr Ile Asn Tyr Asp Lys Asn Val Ile Pro Ser Asp Leu
    275                 280                 285

Thr Asp Lys Asn Asp Pro Ile Asp Ile Thr Asp Pro Ser Gly Glu Val
    290                 295                 300

Ile Ala Lys Gly Thr Phe Asp Lys Ala Thr Lys Gln Ile Thr Tyr Thr
305                 310                 315                 320

Phe Thr Asp Tyr Val Asp Lys Tyr Glu Asp Ile Lys Ser Arg Leu Thr
                325                 330                 335

Leu Tyr Ser Tyr Ile Asp Lys Lys Thr Val Pro Asn Glu Thr Ser Leu
            340                 345                 350

Asn Leu Thr Phe Ala Thr Ala Gly Lys Glu Thr Ser Gln Asn Val Thr
    355                 360                 365

Val Asp Tyr Gln Asp Pro Met Val His Gly Asp Ser Asn Ile Gln Ser
370                 375                 380

Ile Phe Thr Lys Leu Asp Glu Asp Lys Gln Thr Ile Glu Gln Gln Ile
385                 390                 395                 400

Tyr Val Asn Pro Leu Lys Lys Ser Ala Thr Asn Thr Lys Val Asp Ile
                405                 410                 415

Ala Gly Ser Gln Val Asp Asp Tyr Gly Asn Ile Lys Leu Gly Asn Gly
            420                 425                 430

Ser Thr Ile Ile Asp Gln Asn Thr Glu Ile Lys Val Tyr Lys Val Asn
    435                 440                 445

Ser Asp Gln Gln Leu Pro Gln Ser Asn Arg Ile Tyr Asp Phe Ser Gln
450                 455                 460

Tyr Glu Asp Val Thr Ser Gln Phe Asp Asn Lys Lys Ser Phe Ser Asn
465                 470                 475                 480

Asn Val Ala Thr Leu Asp Phe Gly Asp Ile Asn Ser Ala Tyr Ile Ile
                485                 490                 495

Lys Val Val Ser Lys Tyr Thr Pro Thr Ser Asp Gly Glu Leu Asp Ile
            500                 505                 510

Ala Gln Gly Thr Ser Met Arg Thr Thr Asp Lys Tyr Gly Tyr Tyr Asn
    515                 520                 525
```

-continued

```
Tyr Ala Gly Tyr Ser Asn Phe Ile Val Thr Ser Asn Asp Thr Gly Gly
    530                 535                 540

Gly Asp Gly Thr Val Lys Pro Glu Glu Lys Leu Tyr Lys Ile Gly Asp
545                 550                 555                 560

Tyr Val Trp Glu Asp Val Asp Lys Asp Gly Val Gln Gly Thr Asp Ser
                565                 570                 575

Lys Glu Lys Pro Met Ala Asn Val Leu Val Thr Leu Thr Tyr Pro Asp
            580                 585                 590

Gly Thr Thr Lys Ser Val Arg Thr Asp Ala Asn Gly His Tyr Glu Phe
        595                 600                 605

Gly Gly Leu Lys Asp Gly Glu Thr Tyr Thr Val Lys Phe Glu Thr Pro
    610                 615                 620

Thr Gly Tyr Leu Pro Thr Lys Val Asn Gly Thr Thr Asp Gly Glu Lys
625                 630                 635                 640

Asp Ser Asn Gly Ser Ser Val Thr Val Lys Ile Asn Gly Lys Asp Asp
                645                 650                 655

Met Ser Leu Asp Thr Gly Phe Tyr Lys Glu Pro Lys Tyr Asn Leu Gly
            660                 665                 670

Asp Tyr Val Trp Glu Asp Thr Asn Lys Asp Gly Ile Gln Asp Ala Asn
        675                 680                 685

Glu Pro Gly Ile Lys Asp Val Lys Val Thr Leu Lys Asp Ser Thr Gly
    690                 695                 700

Lys Val Ile Gly Thr Thr Thr Thr Asp Ala Ser Gly Lys Tyr Lys Phe
705                 710                 715                 720

Thr Asp Leu Asp Asn Gly Asn Tyr Thr Val Glu Phe Glu Thr Pro Ala
                725                 730                 735

Gly Tyr Thr Pro Thr Val Lys Asn Thr Thr Ala Asp Asp Lys Asp Ser
            740                 745                 750

Asn Gly Leu Thr Thr Thr Gly Val Ile Lys Asp Ala Asp Asn Met Thr
        755                 760                 765

Leu Asp Ser Gly Phe Tyr Lys Thr Pro Lys Tyr Ser Leu Gly Asp Tyr
    770                 775                 780

Val Trp Tyr Asp Ser Asn Lys Asp Gly Lys Gln Asp Ser Thr Glu Lys
785                 790                 795                 800

Gly Ile Lys Asp Val Thr Val Thr Leu Gln Asn Glu Lys Gly Glu Val
                805                 810                 815

Ile Gly Thr Thr Lys Thr Asp Glu Asn Gly Lys Tyr Arg Phe Asp Asn
            820                 825                 830

Leu Asp Ser Gly Lys Tyr Lys Val Ile Phe Glu Lys Pro Ala Gly Leu
        835                 840                 845

Thr Gln Thr Val Thr Asn Thr Thr Glu Asp Asp Lys Asp Ala Asp Gly
    850                 855                 860

Gly Glu Val Asp Val Thr Ile Thr Asp His Asp Asp Phe Thr Leu Asp
865                 870                 875                 880

Asn Gly Tyr Phe Glu Glu Asp Thr Ser Asp Ser Asp Ser Asp Ser Asp
                885                 890                 895

Ser Asp Ser Asp Ser Asp Ser Asp Ser Asp Ser Asp Ser Asp Ser Asp
            900                 905                 910

Ser Asp Ser Asp Ser Asp Ser Asp Ser Asp Ser Asp Ser Asp Ser Asp
        915                 920                 925

Ser Asp Ser Asp Ser Asp Ser Asp Ser Asp Ser Asp Ser Asp Ser Asp
    930                 935                 940

Ser Asp Ser Asp Ser Asp Ser Asp Ser Asp Ser Asp Ser Asp Ser Asp
```

```
                    945                 950                 955                 960
Ser Asp Ser Asp Ser Asp Ser Asp Ser Asp Ser Asp Ser Asp
                    965                 970                 975
Ser Asp Ser Asp Ser Asp Ser Asp Ser Asp Ser Asp Ser Asp
                    980                 985                 990
Ser Asp Ser Asp Ser Asp Ser Asp  Ser Asp Ser Asp Ser  Asp Ser Asp
                    995                 1000                1005
Ser Asp  Ser Asp Ser Asp Ser  Asp Ser Asp Ser Asp  Ser Asp Ser
         1010                 1015                1020
Asp Ser  Asp Ser Asp Ser Asp  Ser Asp Ser Asp Ser  Asp Ser Asp
         1025                 1030                1035
Ser Asp  Ser Asp Ala Gly Lys  His Thr Pro Val Lys  Pro Met Ser
         1040                 1045                1050
Thr Thr  Lys Asp His His Asn  Lys Ala Lys Ala Leu  Pro Glu Thr
         1055                 1060                1065

<210> SEQ ID NO 9

<400> SEQUENCE: 9

000

<210> SEQ ID NO 10
<211> LENGTH: 304
<212> TYPE: PRT
<213> ORGANISM: Staphylococcus aureus

<400> SEQUENCE: 10

Ala Thr Glu Ala Thr Asn Ala Thr Asn Asn Gln Ser Thr Gln Val Ser
1               5                   10                  15

Gln Ala Thr Ser Gln Pro Ile Asn Phe Gln Val Gln Lys Asp Gly Ser
            20                  25                  30

Ser Glu Lys Ser His Met Asp Asp Tyr Met Gln His Pro Gly Lys Val
        35                  40                  45

Ile Lys Gln Asn Asn Lys Tyr Tyr Phe Gln Thr Val Leu Asn Asn Ala
    50                  55                  60

Ser Phe Trp Lys Glu Tyr Lys Phe Tyr Asn Ala Asn Asn Gln Glu Leu
65                  70                  75                  80

Ala Thr Thr Val Val Asn Asp Asn Lys Lys Ala Asp Thr Arg Thr Ile
                85                  90                  95

Asn Val Ala Val Glu Pro Gly Tyr Lys Ser Leu Thr Thr Lys Val His
            100                 105                 110

Ile Val Val Pro Gln Ile Asn Tyr Asn His Arg Tyr Thr Thr His Leu
        115                 120                 125

Glu Phe Glu Lys Ala Ile Pro Thr Leu Ala Asp Ala Lys Pro Asn
    130                 135                 140

Asn Val Lys Pro Val Gln Pro Lys Pro Ala Gln Pro Lys Thr Pro Thr
145                 150                 155                 160

Glu Gln Thr Lys Pro Val Gln Pro Lys Val Glu Lys Val Lys Pro Thr
                165                 170                 175

Val Thr Thr Thr Ser Lys Val Glu Asp Asn His Ser Thr Lys Val Val
            180                 185                 190

Ser Thr Asp Thr Thr Lys Asp Gln Thr Lys Thr Gln Thr Ala His Thr
        195                 200                 205

Val Lys Thr Ala Gln Thr Ala Gln Glu Gln Asn Lys Val Gln Thr Pro
    210                 215                 220
```

```
Val Lys Asp Val Ala Thr Ala Lys Ser Glu Ser Asn Asn Gln Ala Val
225                 230                 235                 240

Ser Asp Asn Lys Ser Gln Gln Thr Asn Lys Val Thr Lys His Asn Glu
            245                 250                 255

Thr Pro Lys Gln Ala Ser Lys Ala Lys Glu Leu Pro Lys Thr Gly Leu
        260                 265                 270

Thr Ser Val Asp Asn Phe Ile Ser Thr Val Ala Phe Ala Thr Leu Ala
        275                 280                 285

Leu Leu Gly Ser Leu Ser Leu Leu Phe Lys Arg Lys Glu Ser Lys
        290                 295                 300

<210> SEQ ID NO 11
<211> LENGTH: 278
<212> TYPE: PRT
<213> ORGANISM: Staphylococcus aureus

<400> SEQUENCE: 11

Ala Thr Glu Ala Thr Asn Ala Asn Asn Gln Ser Thr Gln Val Ser
1               5                   10                  15

Gln Ala Thr Ser Gln Pro Ile Asn Phe Gln Val Gln Lys Asp Gly Ser
            20                  25                  30

Ser Glu Lys Ser His Met Asp Asp Tyr Met Gln His Pro Gly Lys Val
        35                  40                  45

Ile Lys Gln Asn Asn Lys Tyr Tyr Phe Gln Thr Val Leu Asn Asn Ala
    50                  55                  60

Ser Phe Trp Lys Glu Tyr Lys Phe Tyr Asn Ala Asn Asn Gln Glu Leu
65                  70                  75                  80

Ala Thr Thr Val Val Asn Asp Asn Lys Lys Ala Asp Thr Arg Thr Ile
                85                  90                  95

Asn Val Ala Val Glu Pro Gly Tyr Lys Ser Leu Thr Thr Lys Val His
            100                 105                 110

Ile Val Val Pro Gln Ile Asn Tyr Asn His Arg Tyr Thr Thr His Leu
        115                 120                 125

Glu Phe Glu Lys Ala Ile Pro Thr Leu Ala Asp Ala Ala Lys Pro Asn
130                 135                 140

Asn Val Lys Pro Val Gln Pro Lys Pro Ala Gln Pro Lys Thr Pro Thr
145                 150                 155                 160

Glu Gln Thr Lys Pro Val Gln Pro Lys Val Glu Lys Val Lys Pro Thr
                165                 170                 175

Val Thr Thr Thr Ser Lys Val Glu Asp Asn His Ser Thr Lys Val Val
            180                 185                 190

Ser Thr Asp Thr Thr Lys Asp Gln Thr Lys Thr Gln Thr Ala His Thr
        195                 200                 205

Val Lys Thr Ala Gln Thr Ala Gln Glu Gln Asn Lys Val Gln Thr Pro
210                 215                 220

Val Lys Asp Val Ala Thr Ala Lys Ser Glu Ser Asn Asn Gln Ala Val
225                 230                 235                 240

Ser Asp Asn Lys Ser Gln Gln Thr Asn Lys Val Thr Lys His Asn Glu
            245                 250                 255

Thr Pro Lys Gln Ala Ser Lys Ala Lys Glu Leu Pro Lys Thr Gly Leu
        260                 265                 270

Thr Ser Val Asp Asn Phe
        275
```

<210> SEQ ID NO 12
<211> LENGTH: 605
<212> TYPE: PRT
<213> ORGANISM: Staphylococcus aureus

<400> SEQUENCE: 12

```
Ala Ala Glu Glu Thr Gly Gly Thr Asn Thr Glu Ala Gln Pro Lys Thr
1               5                   10                  15

Glu Ala Val Ala Ser Pro Thr Thr Ser Glu Lys Ala Pro Glu Thr
            20                  25                  30

Lys Pro Val Ala Asn Ala Val Ser Val Ser Asn Lys Glu Val Glu Ala
            35                  40                  45

Pro Thr Ser Glu Thr Lys Glu Ala Lys Glu Val Lys Glu Val Lys Ala
        50                  55                  60

Pro Lys Glu Thr Lys Glu Val Lys Pro Ala Ala Lys Ala Thr Asn Asn
65                  70                  75                  80

Thr Tyr Pro Ile Leu Asn Gln Glu Leu Arg Glu Ala Ile Lys Asn Pro
                85                  90                  95

Ala Ile Lys Asp Lys Asp His Ser Ala Pro Asn Ser Arg Pro Ile Asp
            100                 105                 110

Phe Glu Met Lys Lys Lys Asp Gly Thr Gln Gln Phe Tyr His Tyr Ala
        115                 120                 125

Ser Ser Val Lys Pro Ala Arg Val Ile Phe Thr Asp Ser Lys Pro Glu
    130                 135                 140

Ile Glu Leu Gly Leu Gln Ser Gly Gln Phe Trp Arg Lys Phe Glu Val
145                 150                 155                 160

Tyr Glu Gly Asp Lys Lys Leu Pro Ile Lys Leu Val Ser Tyr Asp Thr
                165                 170                 175

Val Lys Asp Tyr Ala Tyr Ile Arg Phe Ser Val Ser Asn Gly Thr Lys
            180                 185                 190

Ala Val Lys Ile Val Ser Ser Thr His Phe Asn Asn Lys Glu Glu Lys
        195                 200                 205

Tyr Asp Tyr Thr Leu Met Glu Phe Ala Gln Pro Ile Tyr Asn Ser Ala
    210                 215                 220

Asp Lys Phe Lys Thr Glu Glu Asp Tyr Lys Ala Glu Lys Leu Leu Ala
225                 230                 235                 240

Pro Tyr Lys Lys Ala Lys Thr Leu Glu Arg Gln Val Tyr Glu Leu Asn
                245                 250                 255

Lys Ile Gln Asp Lys Leu Pro Glu Lys Leu Lys Ala Glu Tyr Lys Lys
            260                 265                 270

Lys Leu Glu Asp Thr Lys Lys Ala Leu Asp Glu Gln Val Lys Ser Ala
        275                 280                 285

Ile Thr Glu Phe Gln Asn Val Gln Pro Thr Asn Glu Lys Met Thr Asp
    290                 295                 300

Leu Gln Asp Thr Lys Tyr Val Val Tyr Glu Ser Val Glu Asn Asn Glu
305                 310                 315                 320

Ser Met Met Asp Thr Phe Val Lys His Pro Ile Lys Thr Gly Met Leu
                325                 330                 335

Asn Gly Lys Lys Tyr Met Val Met Glu Thr Thr Asn Asp Asp Tyr Trp
            340                 345                 350

Lys Asp Phe Met Val Glu Gly Gln Arg Val Arg Thr Ile Ser Lys Asp
        355                 360                 365

Ala Lys Asn Asn Thr Arg Thr Ile Ile Phe Pro Tyr Val Glu Gly Lys
    370                 375                 380
```

```
Thr Leu Tyr Asp Ala Ile Val Lys Val His Val Lys Thr Ile Asp Tyr
385                 390                 395                 400

Asp Gly Gln Tyr His Val Arg Ile Val Asp Lys Glu Ala Phe Thr Lys
            405                 410                 415

Ala Asn Thr Asp Lys Ser Asn Lys Lys Glu Gln Gln Asp Asn Ser Ala
            420                 425                 430

Lys Lys Glu Ala Thr Pro Ala Thr Pro Ser Lys Pro Thr Pro Ser Pro
            435                 440                 445

Val Glu Lys Glu Ser Gln Lys Gln Asp Ser Gln Lys Asp Asp Asn Lys
450                 455                 460

Gln Leu Pro Ser Val Glu Lys Glu Asn Asp Ala Ser Ser Glu Ser Gly
465                 470                 475                 480

Lys Asp Lys Thr Pro Ala Thr Lys Pro Thr Lys Gly Glu Val Glu Ser
            485                 490                 495

Ser Ser Thr Thr Pro Thr Lys Val Val Ser Thr Thr Gln Asn Val Ala
            500                 505                 510

Lys Pro Thr Thr Ala Ser Ser Lys Thr Thr Lys Asp Val Val Gln Thr
            515                 520                 525

Ser Ala Gly Ser Ser Glu Ala Lys Asp Ser Ala Pro Leu Gln Lys Ala
530                 535                 540

Asn Ile Lys Asn Thr Asn Asp Gly His Thr Gln Ser Gln Asn Asn Lys
545                 550                 555                 560

Asn Thr Gln Glu Asn Lys Ala Lys Ser Leu Pro Gln Thr Gly Glu Glu
            565                 570                 575

Ser Asn Lys Asp Met Thr Leu Pro Leu Met Ala Leu Leu Ala Leu Ser
            580                 585                 590

Ser Ile Val Ala Phe Val Leu Pro Arg Lys Arg Lys Asn
            595                 600                 605

<210> SEQ ID NO 13
<211> LENGTH: 430
<212> TYPE: PRT
<213> ORGANISM: Staphylococcus aureus

<400> SEQUENCE: 13

Thr Asn Thr Glu Ala Gln Pro Lys Thr Glu Ala Val Ala Ser Pro Thr
1               5                   10                  15

Thr Thr Ser Glu Lys Ala Pro Glu Thr Lys Pro Val Ala Asn Ala Val
            20                  25                  30

Ser Val Ser Asn Lys Glu Val Glu Ala Pro Thr Ser Glu Thr Lys Glu
        35                  40                  45

Ala Lys Glu Val Lys Glu Val Lys Ala Pro Lys Glu Thr Lys Glu Val
    50                  55                  60

Lys Pro Ala Ala Lys Ala Thr Asn Asn Thr Tyr Pro Ile Leu Asn Gln
65                  70                  75                  80

Glu Leu Arg Glu Ala Ile Lys Asn Pro Ala Ile Lys Asp Lys Asp His
                85                  90                  95

Ser Ala Pro Asn Ser Arg Pro Ile Asp Phe Glu Met Lys Lys Lys Asp
            100                 105                 110

Gly Thr Gln Gln Phe Tyr His Tyr Ala Ser Ser Val Lys Pro Ala Arg
        115                 120                 125

Val Ile Phe Thr Asp Ser Lys Pro Glu Ile Glu Leu Gly Leu Gln Ser
    130                 135                 140

Gly Gln Phe Trp Arg Lys Phe Glu Val Tyr Glu Gly Asp Lys Lys Leu
145                 150                 155                 160
```

Pro Ile Lys Leu Val Ser Tyr Asp Thr Val Lys Asp Tyr Ala Tyr Ile
                165                 170                 175

Arg Phe Ser Val Ser Asn Gly Thr Lys Ala Val Lys Ile Val Ser Ser
            180                 185                 190

Thr His Phe Asn Asn Lys Glu Glu Lys Tyr Asp Tyr Thr Leu Met Glu
        195                 200                 205

Phe Ala Gln Pro Ile Tyr Asn Ser Ala Asp Lys Phe Lys Thr Glu Glu
    210                 215                 220

Asp Tyr Lys Ala Glu Lys Leu Leu Ala Pro Tyr Lys Lys Ala Lys Thr
225                 230                 235                 240

Leu Glu Arg Gln Val Tyr Glu Leu Asn Lys Ile Gln Asp Lys Leu Pro
                245                 250                 255

Glu Lys Leu Lys Ala Glu Tyr Lys Lys Leu Glu Asp Thr Lys Lys
            260                 265                 270

Ala Leu Asp Glu Gln Val Lys Ser Ala Ile Thr Glu Phe Gln Asn Val
        275                 280                 285

Gln Pro Thr Asn Glu Lys Met Thr Asp Leu Gln Asp Thr Lys Tyr Val
    290                 295                 300

Val Tyr Glu Ser Val Glu Asn Asn Glu Ser Met Met Asp Thr Phe Val
305                 310                 315                 320

Lys His Pro Ile Lys Thr Gly Met Leu Asn Gly Lys Lys Tyr Met Val
                325                 330                 335

Met Glu Thr Thr Asn Asp Asp Tyr Trp Lys Asp Phe Met Val Glu Gly
            340                 345                 350

Gln Arg Val Arg Thr Ile Ser Lys Asp Ala Lys Asn Thr Arg Thr
        355                 360                 365

Ile Ile Phe Pro Tyr Val Glu Gly Lys Thr Leu Tyr Asp Ala Ile Val
    370                 375                 380

Lys Val His Val Lys Thr Ile Asp Tyr Asp Gly Gln Tyr His Val Arg
385                 390                 395                 400

Ile Val Asp Lys Glu Ala Phe Thr Lys Ala Asn Thr Asp Lys Ser Asn
                405                 410                 415

Lys Lys Glu Gln Gln Asp Asn Ser Ala Lys Lys Glu Ala Thr
            420                 425                 430

<210> SEQ ID NO 14

<400> SEQUENCE: 14

000

<210> SEQ ID NO 15

<400> SEQUENCE: 15

000

<210> SEQ ID NO 16
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
 50                  55                  60

Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Ala Ala Ala Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Ile Asp Arg Ser Glu Arg Tyr Lys Ile Asp Trp Glu Lys
        275                 280                 285

Glu Glu Met Thr Asn
    290

<210> SEQ ID NO 17
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
 50                  55                  60

Tyr Arg Val Tyr Ser Glu Glu Gly Ala Asn Lys Ser Gly Leu Ala Trp

```
                65                  70                  75                  80
        Pro Ser Ala Phe Lys Val Gln Leu Gln Leu Pro Asp Asn Glu Val Ala
                        85                  90                  95

Gln Ile Ser Asp Tyr Tyr Pro Arg Asn Ser Ile Asp Thr Lys Glu Tyr
                        100                 105                 110

Met Ser Thr Leu Thr Tyr Gly Phe Asn Gly Asn Val Thr Gly Asp Asp
                        115                 120                 125

Thr Gly Lys Ile Gly Gly Leu Ile Gly Ala Asn Val Ser Ile Gly His
                130                 135                 140

Thr Leu Lys Tyr Val Gln Pro Asp Phe Lys Thr Ile Leu Glu Ser Pro
        145                 150                 155                 160

Thr Asp Lys Lys Val Gly Trp Lys Val Ile Phe Asn Asn Met Val Asn
                        165                 170                 175

Gln Asn Ala Gly Pro Tyr Asp Arg Asp Ser Trp Asn Pro Val Tyr Gly
                        180                 185                 190

Asn Gln Leu Phe Met Lys Thr Arg Asn Gly Ser Met Lys Ala Ala Asp
                        195                 200                 205

Asn Phe Leu Asp Pro Asn Lys Ala Ser Ser Leu Leu Ser Ser Gly Phe
                210                 215                 220

Ser Pro Asp Phe Ala Thr Val Ile Thr Met Asp Arg Lys Ala Ser Lys
        225                 230                 235                 240

Gln Gln Thr Asn Ile Asp Val Ile Tyr Glu Arg Val Arg Asp Asp Tyr
                        245                 250                 255

Gln Leu His Trp Thr Ser Thr Asn Trp Lys Gly Thr Asn Thr Lys Asp
                        260                 265                 270

Lys Trp Ile Asp Arg Ser Ser Glu Arg Tyr Lys Ile Asp Trp Glu Lys
                        275                 280                 285

Glu Glu Met Thr Asn
                        290

<210> SEQ ID NO 18
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ala Asp Ser Asp Ile Asn Ile Lys Thr Gly Thr Thr Asp Ile Gly Ser
        1               5                   10                  15

Asn Thr Thr Val Lys Thr Gly Asp Leu Val Thr Tyr Asp Lys Glu Asn
                        20                  25                  30

Gly Met His Lys Lys Val Phe Tyr Ser Phe Ile Asp Asp Lys Asn His
                        35                  40                  45

Asn Lys Lys Leu Leu Val Ile Arg Thr Lys Gly Thr Ile Ala Gly Gln
                50                  55                  60

Tyr Arg Val Tyr Ser Glu Glu Gly Ala Asn Lys Ser Gly Leu Ala Trp
        65                  70                  75                  80

Pro Ser Ala Phe Lys Val Gln Leu Gln Leu Pro Asp Asn Glu Val Ala
                        85                  90                  95

Gln Ile Ser Asp Tyr Tyr Pro Arg Asn Ser Ile Asp Thr Lys Glu Tyr
                        100                 105                 110

Met Ser Thr Leu Thr Tyr Gly Phe Asn Gly Asn Val Thr Gly Asp Asp
                        115                 120                 125
```

```
Thr Gly Lys Ile Gly Gly Leu Ile Gly Ala Asn Val Ser Ile Gly His
            130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Ala Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Ile Asp Arg Ser Ser Glu Arg Tyr Lys Ile Asp Trp Glu Lys
        275                 280                 285

Glu Glu Met Thr Asn
    290

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 19

Leu Pro Xaa Thr Gly
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Tyr Thr Phe Thr Asp Tyr Val Asp
1               5

<210> SEQ ID NO 21
<211> LENGTH: 179
<212> TYPE: PRT
<213> ORGANISM: Rhizobium sp.

<400> SEQUENCE: 21

Met Ile Ile Thr Ser Leu Tyr Ala Thr Phe Gly Thr Ile Ala Asp Gly
1               5                   10                  15

Arg Arg Thr Ser Gly Gly Lys Thr Met Ile Arg Thr Asn Ala Val Ala
            20                  25                  30
```

```
Ala Leu Val Phe Ala Val Ala Thr Ser Ala Leu Ala Phe Asp Ala Ser
        35                  40                  45

Asn Phe Lys Asp Phe Ser Ser Ile Ala Ser Ala Ser Ser Ser Trp Gln
 50                  55                  60

Asn Gln Ser Gly Ser Thr Met Ile Ile Gln Val Asp Ser Phe Gly Asn
 65                  70                  75                  80

Val Ser Gly Gln Tyr Val Asn Arg Ala Gln Gly Thr Gly Cys Gln Asn
                 85                  90                  95

Ser Pro Tyr Pro Leu Thr Gly Arg Val Asn Gly Thr Phe Ile Ala Phe
                100                 105                 110

Ser Val Gly Trp Asn Ser Thr Glu Asn Cys Asn Ser Ala Thr Gly
            115                 120                 125

Trp Thr Gly Tyr Ala Gln Val Asn Gly Asn Asn Thr Glu Ile Val Thr
        130                 135                 140

Ser Trp Asn Leu Ala Tyr Glu Gly Gly Ser Gly Pro Ala Ile Glu Gln
145                 150                 155                 160

Gly Gln Asp Thr Phe Gln Tyr Val Pro Thr Thr Glu Asn Lys Ser Leu
                165                 170                 175

Leu Lys Asp

<210> SEQ ID NO 22
<211> LENGTH: 44
<212> TYPE: PRT
<213> ORGANISM: Rhizobium sp.

<400> SEQUENCE: 22

Met Ile Ile Thr Ser Leu Tyr Ala Thr Phe Gly Thr Ile Ala Asp Gly
  1               5                  10                  15

Arg Arg Thr Ser Gly Gly Lys Thr Met Ile Arg Thr Asn Ala Val Ala
                 20                  25                  30

Ala Leu Val Phe Ala Val Ala Thr Ser Ala Leu Ala
            35                  40

<210> SEQ ID NO 23
<211> LENGTH: 19
<212> TYPE: PRT
<213> ORGANISM: Escherichia coli

<400> SEQUENCE: 23

Met Lys Lys Ile Trp Leu Ala Leu Ala Gly Leu Val Leu Ala Phe Ser
  1               5                  10                  15

Ala Ser Ala

<210> SEQ ID NO 24
<211> LENGTH: 23
<212> TYPE: PRT
<213> ORGANISM: Escherichia coli

<400> SEQUENCE: 24

Met Lys Lys Ile Trp Leu Ala Leu Ala Gly Leu Val Leu Ala Phe Ser
  1               5                  10                  15

Ala Ser Ala Ala Gln Asp Pro
                 20

<210> SEQ ID NO 25
<211> LENGTH: 17
<212> TYPE: PRT
<213> ORGANISM: Unknown
<220> FEATURE:
```

<223> OTHER INFORMATION: Description of Unknown:
      Signal sequence

<400> SEQUENCE: 25

Met Lys Lys Val Ala Ala Phe Val Ala Leu Ser Leu Leu Met Ala Gly
1               5                   10                  15

Cys

<210> SEQ ID NO 26
<211> LENGTH: 19
<212> TYPE: PRT
<213> ORGANISM: Unknown
<220> FEATURE:
<223> OTHER INFORMATION: Description of Unknown:
      Signal sequence

<400> SEQUENCE: 26

Met Lys Lys Ile Trp Leu Ala Leu Ala Gly Leu Val Leu Ala Phe Ser
1               5                   10                  15

Ala Ser Ala

<210> SEQ ID NO 27
<211> LENGTH: 23
<212> TYPE: PRT
<213> ORGANISM: Unknown
<220> FEATURE:
<223> OTHER INFORMATION: Description of Unknown:
      Signal sequence

<400> SEQUENCE: 27

Met Ala Pro Phe Glu Pro Leu Ala Ser Gly Ile Leu Leu Leu Leu Trp
1               5                   10                  15

Leu Ile Ala Pro Ser Arg Ala
            20

<210> SEQ ID NO 28
<211> LENGTH: 17
<212> TYPE: PRT
<213> ORGANISM: Unknown
<220> FEATURE:
<223> OTHER INFORMATION: Description of Unknown:
      Signal sequence

<400> SEQUENCE: 28

Met Lys Lys Val Ala Ala Phe Val Ala Leu Ser Leu Leu Met Ala Gly
1               5                   10                  15

Cys

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Met Lys Lys Val Ala Ala Phe Val Ala Leu Ser Leu Leu Met Ala Gly
1               5                   10                  15

Cys

<210> SEQ ID NO 30
<211> LENGTH: 4
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 30

Ala Gln Asp Pro
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Val Ser Asp Pro
1

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 32

His His His His His His
1               5

<210> SEQ ID NO 33
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Gly Gly Gly Ser Ser Ser Val Asp Lys Leu Ala Ala Ala Leu Glu
1               5                   10                  15

His His His His His His
            20

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Val Asp Lys Leu Ala Ala Ala Leu Glu
1               5

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

```
Gly Gly Gly Gly Ser Ser Ser Val Asp Lys Leu Ala Ala Ala Leu Glu
1               5                   10                  15
```

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

```
Val Asp Lys Leu Ala Ala Ala Leu Glu His His His His His
1               5                   10
```

<210> SEQ ID NO 37
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Gly Gly Gly Gly Ser Ser Ser Val Asp Lys Leu Ala Ala Ala Leu Glu
1               5                   10                  15

His His His His His His
            20
```

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Gly Ser Pro Gly Ile Ser Gly Gly Gly Gly Ile Leu Glu
1               5                   10
```

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Met Lys Lys Val Ala Ala Phe Val Ala Leu Ser Leu Leu Met Ala Gly
1               5                   10                  15

Cys
```

<210> SEQ ID NO 40
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

```
Met Asn Ser Lys Lys Leu Cys Cys Ile Cys Val Leu Phe Ser Leu Leu
1               5                   10                  15
```

```
Ala Gly Cys Ala Ser
            20

<210> SEQ ID NO 41
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Met Arg Tyr Ser Lys Leu Thr Met Leu Ile Pro Cys Ala Leu Leu Leu
1               5                   10                  15

Ser Ala Cys

<210> SEQ ID NO 42
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Met Phe Val Thr Ser Lys Lys Met Thr Ala Ala Val Leu Ala Ile Thr
1               5                   10                  15

Leu Ala Met Ser Leu Ser Ala Cys
            20

<210> SEQ ID NO 43
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Met Ile Lys Arg Val Leu Val Val Ser Met Val Gly Leu Ser Leu Val
1               5                   10                  15

Gly Cys

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Val Ser Asp Pro
1

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Gln Asp Pro
1
```

```
<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Arg or Leu
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (6)..(6)
<223> OTHER INFORMATION: Tyr or Trp

<400> SEQUENCE: 46

Asp Xaa Ala Xaa Pro Xaa
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Arg or Leu
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (7)..(7)
<223> OTHER INFORMATION: Tyr or Trp

<400> SEQUENCE: 47

Cys Asp Xaa Ala Xaa Pro Xaa Cys Gly
1               5

<210> SEQ ID NO 48
<211> LENGTH: 23
<212> TYPE: PRT
<213> ORGANISM: Unknown
<220> FEATURE:
<223> OTHER INFORMATION: Description of Unknown:
      Signal sequence

<400> SEQUENCE: 48

Met Ala Pro Phe Glu Pro Leu Ala Ser Gly Ile Leu Leu Leu Leu Trp
1               5                   10                  15

Leu Ile Ala Pro Ser Arg Ala
            20

<210> SEQ ID NO 49
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 49

Pro Glu Pro
1

<210> SEQ ID NO 50
<211> LENGTH: 24
<212> TYPE: PRT
<213> ORGANISM: Unknown
<220> FEATURE:
<223> OTHER INFORMATION: Description of Unknown:
      Signal sequence

<400> SEQUENCE: 50

Met Lys Lys Ile Met Leu Val Ile Thr Leu Ile Leu Val Ser Pro Ile
1               5                   10                  15

Ala Gln Gln Thr Glu Ala Lys Asp
            20

<210> SEQ ID NO 51
<211> LENGTH: 29
<212> TYPE: PRT
<213> ORGANISM: Unknown
<220> FEATURE:
<223> OTHER INFORMATION: Description of Unknown:
      Signal sequence

<400> SEQUENCE: 51

Met Lys Lys Lys Ile Ile Ser Ala Ile Leu Met Ser Thr Val Ile Leu
1               5                   10                  15

Ser Ala Ala Ala Pro Leu Ser Gly Val Tyr Ala Asp Thr
            20                  25

<210> SEQ ID NO 52
<211> LENGTH: 31
<212> TYPE: PRT
<213> ORGANISM: Unknown
<220> FEATURE:
<223> OTHER INFORMATION: Description of Unknown:
      Signal sequence

<400> SEQUENCE: 52

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val
            20                  25                  30

<210> SEQ ID NO 53
<211> LENGTH: 29
<212> TYPE: PRT
<213> ORGANISM: Unknown
<220> FEATURE:
<223> OTHER INFORMATION: Description of Unknown:
      Signal sequence

<400> SEQUENCE: 53

Met Asn Met Lys Lys Ala Thr Ile Ala Ala Thr Ala Gly Ile Ala Val
1               5                   10                  15

Thr Ala Phe Ala Ala Pro Thr Ile Ala Ser Ala Ser Thr
            20                  25

<210> SEQ ID NO 54
<211> LENGTH: 54
<212> TYPE: PRT
<213> ORGANISM: Unknown
<220> FEATURE:
```

<223> OTHER INFORMATION: Description of Unknown:
      Signal sequence

<400> SEQUENCE: 54

Met Gln Lys Thr Arg Lys Glu Arg Ile Leu Glu Ala Leu Gln Glu Glu
1               5                   10                  15

Lys Lys Asn Lys Lys Ser Lys Lys Phe Lys Thr Gly Ala Thr Ile Ala
            20                  25                  30

Gly Val Thr Ala Ile Ala Thr Ser Ile Thr Val Pro Gly Ile Glu Val
        35                  40                  45

Ile Val Ser Ala Asp Glu
        50

<210> SEQ ID NO 55
<211> LENGTH: 28
<212> TYPE: PRT
<213> ORGANISM: Unknown
<220> FEATURE:
<223> OTHER INFORMATION: Description of Unknown:
      Signal sequence

<400> SEQUENCE: 55

Met Lys Lys Leu Lys Met Ala Ser Cys Ala Leu Val Ala Gly Leu Met
1               5                   10                  15

Phe Ser Gly Leu Thr Pro Asn Ala Phe Ala Glu Asp
            20                  25

<210> SEQ ID NO 56
<211> LENGTH: 31
<212> TYPE: PRT
<213> ORGANISM: Unknown
<220> FEATURE:
<223> OTHER INFORMATION: Description of Unknown:
      Signal sequence

<400> SEQUENCE: 56

Met Ala Lys Lys Phe Asn Tyr Lys Leu Pro Ser Met Val Ala Leu Thr
1               5                   10                  15

Leu Val Gly Ser Ala Val Thr Ala His Gln Val Gln Ala Ala Glu
            20                  25                  30

<210> SEQ ID NO 57
<211> LENGTH: 59
<212> TYPE: PRT
<213> ORGANISM: Unknown
<220> FEATURE:
<223> OTHER INFORMATION: Description of Unknown:
      Signal sequence

<400> SEQUENCE: 57

Met Thr Asp Lys Lys Ser Glu Asn Gln Thr Glu Lys Thr Glu Thr Lys
1               5                   10                  15

Glu Asn Lys Gly Met Thr Arg Arg Glu Met Leu Lys Leu Ser Ala Val
            20                  25                  30

Ala Gly Thr Gly Ile Ala Val Gly Ala Thr Gly Leu Gly Thr Ile Leu
        35                  40                  45

Asn Val Val Asp Gln Val Asp Lys Ala Leu Thr
        50                  55

<210> SEQ ID NO 58
<211> LENGTH: 53
<212> TYPE: PRT
<213> ORGANISM: Unknown

```
<220> FEATURE:
<223> OTHER INFORMATION: Description of Unknown:
      Signal sequence

<400> SEQUENCE: 58

Met Ala Tyr Asp Ser Arg Phe Asp Glu Trp Val Gln Lys Leu Lys Glu
1               5                   10                  15

Glu Ser Phe Gln Asn Asn Thr Phe Asp Arg Arg Lys Phe Ile Gln Gly
                20                  25                  30

Ala Gly Lys Ile Ala Gly Leu Gly Leu Gly Leu Thr Ile Ala Gln Ser
            35                  40                  45

Val Gly Ala Phe Gly
    50
```

MULTIPLE ANTIGEN PRESENTING SYSTEM (MAPS)-BASED *STAPHYLOCOCCUS AUREUS* VACCINE, IMMUNOGENIC COMPOSITION, AND USES THEREOF

CROSS-REFERENCE TO RELATED APPLICATIONS

This application is a 35 U.S.C. § 371 National Phase Entry Application of International Application No. PCT/US2018/024810 filed Mar. 28, 2018, which designates the U.S. and claims benefit of priority to U.S. 62/477,618 filed Mar. 28, 2017, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Apr. 25, 2019, is named 701039-088361-PCT_SL.txt and is 82,807 bytes in size.

FIELD OF THE INVENTION

The present invention relates to molecular genetics, immunology, and microbiology. The present application is generally directed to compositions and methods for preparation of immunogenic compositions. More specifically, an embodiment of the present invention provides for an immunogenic composition comprising at least one immunogenic *Staphylococcus aureus* protein or peptide antigen attached to an immunogenic polysaccharide. In some embodiments, this complex can be used as an immunogenic composition, such as a vaccine, to confer a synergistic humoral and cellular immune response; and in some embodiments, elicits synergistic antibody and/or B-cell response and also in some embodiments, a T-cell mediated protection against *S. aureus* infection and colonization and carriage.

BACKGROUND OF INVENTION

*Staphylococcus aureus* (SA) is an important Gram-positive bacterium that causes a wide range of infections in both healthy and compromised individuals. SA is one of the leading causes of community- and hospital-acquired bacterial infections and postsurgical wound infections, resulting in prolonged hospital stay and significantly increased healthcare cost. Staphylococcal bacteremia is associated with high mortality (about 20-40% in adults) even after appropriate antibiotic treatment. Skin and soft tissue infection (SSTI) is a common chronic SA infection with frequent recurrence. Depending on the severity and depth of the infection, SSTI may represent as scalded skin syndrome, boils, impetigo, cellulitis, abscess, fasciitis or myonecrosis. SA is also a cause of invasive disease, including meningitis, endocarditis, osteomyelitis, pneumonia, sepsis and toxic shock syndrome. SA colonizes about 20% of the human population persistently and up to 80% transiently, serving as a reservoir for future infection and transmission. The treatment of SA infection includes surgical procedure, antibiotics, or a combination of both. However, the effectiveness of antibiotic treatment has been severely impacted by the rapid emergence of multi-drug resistant strains (Methicillin-resistant SA, MRSA, as well as Vancomycin-intermediate strains, or VISA) in both community-acquired (CA-) and hospital-acquired (HA-) infections in the past two decades.

Humans are the natural reservoirs for *Staphylococcus aureus* (*S. aureus*). Healthy individuals can be colonized by *S. aureus* on the skin, in the nares and the throat either persistently (10-35%), intermittently (20-75%) or be in a non-carriage state (5-70%) with no associated disease. See Vandenbergh et al, J. Clin. Micro. 37:3133-3140 (1999). Disease subsequently occurs when individuals become immunocompromised due to breaches in immune barriers, such as during surgery, placement of indwelling catheters or other devices, trauma, or wounds. The resulting *S. aureus* infection can cause a wide range of diseases that range from mild skin infections to endocarditis, osteomyelitis, bacteremia, sepsis, and other forms of disease with accompanying high mortality rates. The large human reservoir enhances opportunity for evolution and spread of adapted pathogenic clonal types.

Invasive staphylococcal infections from the Gram positive cocci *S. aureus* and *S. epidermidis* are of particular concern because they are an increasing public health problem worldwide. Specifically, *S. aureus* is responsible for the majority of hospital-acquired (nosocomial) infections, and its prevalence in community-onset infections is increasing. For example, the incidence of invasive methicillin-resistant *S. aureus* (MRSA) was estimated at 31.8 per 100,000 persons, including 18,650 deaths in the United States in 2005. See Klevens R. M. et al, JAMA, 298: 1763-71 (2007). Staphylococcal diseases have seen a dramatic increase in the last 20 years; this increase parallels the use of intravascular devices and invasive procedures. The rise in disease incidence is made more troubling because of the parallel rise of antibiotic resistance; therefore, there is an urgent need for immunogenic compositions for use in vaccines or to elicit polyclonal or monoclonal antibodies to confer passive immunity as a means to prevent or treat staphylococcal infection and associated diseases.

A vaccine against SA would represent a very attractive alternative. Vaccines provide prevention of and treatment for a variety of diseases, including microorganism infection, viral infection, and cancers. Success of polysaccharide-based vaccines and passive immunization for the prevention of colonization or disease has demonstrated the importance of capsular antibodies, in particular in controlling disease caused by *S. pneumoniae*. Further, studies in both animals and humans demonstrate that antibodies elicited from pneumococcal vaccination can protect against nasopharyngeal (NP) pneumococcal colonization, which precedes pneumococcal disease.

If successful, a SA vaccine could provide broad, long-term benefit to the population via both direct and herd immunities. Efforts in the early SA vaccine development have focused on generating antibodies to various polysaccharide or protein antigens, including the capsular polysaccharides, the extracellular polysaccharides, the toxins and the surface proteins. The strategy of taking a combination of capsular polysaccharides and/or proteins has been successfully used against many human pathogens, such as *Haemophilus influenzae* type b, *Streptococcus pneumoniae*, *Neisseria meningitidis* (including most recently serogroup B), pertussis. The same approach has been attempted for vaccines for SA. However, unfortunately, to date, all the vaccine candidates for SA, which include use of SA polysaccharides and proteins in vaccines, or antibodies directed against these antigens, have failed in clinical trials. This is not expected considering that there was clear demonstration of efficacy of these vaccines in various animal models of invasive SA infections.

Given this failure, there remains a need to improve the efficacy of SA vaccines, particularly to prevent infection and/or colonization and carriage.

SUMMARY OF THE INVENTION

The present invention provides for an immunogenic multiple antigen presenting system (MAPS) comprising an immunogenic polysaccharide, and attached to the immunogenic polysaccharide via an affinity binding pair, at least one *Staphylococcus aureus* (SA) antigen. Such a *Staphylococcus aureus*-MAPS (SA-MAPS) composition as disclosed herein is useful for the production of immunogenic compositions, such as those useful in vaccines, as well as for treatment.

In some embodiments, the SA-MAPS immunogenic composition as disclosed herein generates an immune response in a subject, preferably an antibody response and a B-cell and/or T-cell response. In some embodiments, the SA-MAPS immunogenic composition as disclosed herein generates a CD8+ T-cell response, a CD4+ T-cell response or a CD8+/CD4+ T-cell response. The inventors demonstrate that mice immunized with or administered a SA-MAPS immunogenic composition as disclosed responded to SA antigens and produced significant amount of IFN-γ, IL-17A and IL-22, demonstrating that the SA-MAPS composition can generate of Th1, Th2, Th17 and Th22 responses. Accordingly, in some embodiments, a SA-MAPS immunogenic composition as disclosed herein generates a T-cell response and, more specifically, any one or more of a Th1, Th2, Th17 and Th22 response to a SA peptide or protein present in the SA-MAPS composition. In some embodiments, a SA-MAPS immunogenic composition as disclosed herein generates an anti-polysaccharide antibody response and/or a B-cell and/or T-cell, e.g., Th1/Th2/Th17/Th22 response. In some embodiments, the immune response elicited by the SA-MAPS immunogenic composition as disclosed herein is an antibody or B cell response to at least one antigenic polysaccharide, and an antibody or B cell response and a CD4+ and/or CD8+ T cell response, including Th1, Th2, Th17 or Th22 responses, or a CD8+ T cell response.

In some embodiments, a SA-MAPS immunogenic composition as disclosed herein elicits an immune response that results in activation of INF-γ, IL-17A, IL-17F, IL-21 or IL-22 producing cells, or produces INF-γ, IL-17A and IL-22 producing cells. This is important in that the SA-MAPS immunogenic composition presents a major advantage by eliciting two forms of immunity—that is, a conventional humoral (B-cell dependent) immune response to an immunogenic polysaccharide and SA-antigens, as well as a T-cell response and, more specifically, any one or more of Th17, Th1, Th2 or Th22 responses to a SA peptide or protein present in the SA-MAPS composition. Moreover, in some embodiments, the SA-MAPS immunogenic composition as disclosed herein can enhance specific B-cell or T-cell responses by modifying the protein/polysaccharide ratio, complex size, or by incorporating specific co-stimulatory factor, such as TLR2/4 ligands, etc., into the composition.

In particular, the present invention is relates to compositions comprising an immunogenic polysaccharide, at least one *Staphylococcus aureus* protein or peptide antigen; and at least one complementary affinity-molecule pair comprising (i) a first affinity molecule that associates with the immunogenic polysaccharide, and (ii) a complementary affinity molecule that associates with the *Staphylococcus aureus* protein or peptide antigen, such that the first and complementary affinity molecules serve as an indirect link between the immunogenic polysaccharide and SA protein or peptide antigens. Such a system allows for a modular immunogenic composition, where one or more SA protein or peptide antigens can be attached to the immunogenic polysaccharide in a modular fashion, allowing for flexibility in the number and type of SA antigens attached to immunogenic polysaccharide. Accordingly, the immunogenic polysaccharide can attach at least 1, or at least 2, or a plurality of the same, or different SA protein or peptide antigens. In some embodiments, the immunogenic polysaccharide is antigenic, and in some embodiments, the immunogenic polysaccharide is Type 5 (CP5) or Type 8 (CP8), or a combination of Type 5 or Type 8 capsular polysaccharide from *Staphylococcus aureus*, or can be a pneumococcal capsular polysaccharide, e.g., Type 1 (CP1) capsular polysaccharide from *S. pneumoniae*.

*Staphylococcus aureus* (SA) is a major cause of morbidity and mortality worldwide. Vaccine development against SA has been challenging, likely due to the complexity of pathogenesis and an incomplete understanding of protective immune mechanisms. The inventors previously developed a vaccine platform referred to the Multiple-Antigen-Presenting-System (MAPS), as disclosed in US patent Application 2014/0154287, which is incorporated herein in its entirety by reference, which enables the induction of broad adaptive immune responses. Herein, the inventors have developed and optimized the system for the treatment and prevention of infection from *Staphylococcus aureus*. Herein, the inventors have used a SA-specific MAPS immunogenic composition which comprises 6 different SA peptide antigens to demonstrate that B- and T-cell mediated immune mechanisms contribute differentially to host defense against SA in models of skin necrosis, skin abscess, invasive disease or mucosal colonization. In particular, immunization with a conventional subunit vaccine (i.e., a mixture of individual SA antigens not attached to a scaffold or polysaccharide), which induces solely humoral responses, or passive transfer of rabbit anti-SA sera protected mice against sepsis and dermonecrosis infection, but had no impact on skin abscess infection or gastrointestinal colonization by SA, against which antigen-specific T-cell immunity was both necessary and sufficient for protection. T-cell immunity also contributed to protection in the sepsis and dermonecrosis models, particularly when combined with antibody responses. Taken together, the inventors have demonstrated that both humoral and cellular immunity are important for host defense against SA. Herein, the inventors have demonstrated a SA-MAPS immunogenic composition as a novel vaccine to elicit multipronged adaptive responses, and is highly valuable in the development of effective and broadly protective vaccines against SA.

In some embodiments, the SA-MAPS comprises at least one or more SA antigens, where the SA antigen is a antigenic protein or polypeptide selected from any of the group of: hemolysin (Hl) (e.g., hemolysin α or Hla), Clumping factor A (ClfA), Clumping factor B (ClfB), serine-aspirate repeat protein D (SdrD), Iron regulator surface protein A (IsdA) and Iron regulator surface protein B (IsdB). In some embodiments, the SA-MAPS immunogenic composition as disclosed herein comprises one or more peptide or polypeptide fragments of these proteins, as long as the fragment is antigenic, and/or comprises one or more epitopes to induce an immune response. Exemplary fragments can be, for example, but are not limited to Hla209(27-319), ClfA (221-559), ClfB (203-542), SdrD (246-682), IsdA (47-324), IsdB (48-447). In some embodiments, a SA-MAPS immunogenic composition as disclosed herein comprises at least 2, or at least 3, or at least 4, or at least 5, or all 6 peptide or polypeptide SA-antigens of Hla209(27-319), ClfA (221-559), ClfB (203-542), SdrD (246-682), IsdA (47-324), IsdB (48-447), or proteins or peptides of at least 85% sequence identity thereto. In some embodiments, any of the above listed SA antigens can be substituted for a different SA peptide or polypeptide antigen known to one of ordinary skill in the art. Exemplary SA antigens can be any peptide or polypeptide comprising at least part of the serine-aspirate repeat protein E (SdrE) protein, Leukotoxin D (LukD) protein, or Leukotoxin E (LukE) protein, provided that the any peptide or polypeptide is immunogenic, or is antigenic. Other SA antigens can be used, and are disclosed herein.

The SA-MAPS immunogenic composition as disclosed herein can elicit both humoral and cellular responses to one or multiple SA antigens at the same time. The SA-MAPS immunogenic compositions provide for a long-lasting memory response, potentially protecting a subject from future infection. This allows for a single SA-MAPS immunogenic composition that raise a high titer of functional anti-SA polysaccharide antibodies, and is similar or compares favorably with the antibody level induced by conventional conjugate vaccine. Moreover, there is no restriction to specific immunogenic polysaccharide used in the MAPS construct, which is typically a SA capsular polysaccharide or other bacterial capsular or noncapsular polysaccharide, or the various SA antigen peptide or polypeptides used in SA-MAPS conjugate to generate a robust anti-polysaccharide antibody response. Additionally, the strong antibody response as well as Th17/Th1 and/or Th22 responses are specific to multiple SA protein antigens presented via the SA-MAPS composition. This is important in that the SA-MAPS immunogenic composition presents a major advantage by eliciting two forms of immunity—that is, a conventional immune response to an immunogenic polysaccharide and SA-antigens, as well as a T-cell response and, more specifically, any one or more of Th17, Th1, Th2 or Th22 responses to a SA peptide or protein present in the SA-MAPS composition. Moreover, the SA-MAPS immunogenic composition as disclosed herein provides a potential to enhance specific B-cell or T-cell responses by modifying the protein/polysaccharide ratio, complex size, or by incorporating specific co-stimulatory factor, such as TLR2/4 ligands, etc., into the composition.

Accordingly, the SA-MAPS immunogenic composition as disclosed herein uses an affinity-pair method to conjugate the SA antigens to the immunogenic polysaccharide, therefore enabling a modular approach that is easy and highly flexible for the preparation of a Staphylococcus aureus vaccine composition. The SA-MAPS immunogenic composition is highly specific and stable; it can remain in the cold for months and retain its potency. The assembly process is simple enough to ensure high reproducibility; there are only a few steps required, which reduces the risk of lot-to-lot variation, of great industrial advantage. The SA-MAPS immunogenic composition assembly is highly efficient (over 95%), even at low concentrations of protein and polysaccharide (such as 0.1 mg/ml); this is a major advantage, because inefficiencies in conjugate manufacture (typically efficiencies are in the <50% range) represent a major hurdle and reason for the high cost of vaccines. For formulation: it is easy to adjust the composition and physical properties of the final product. The protein: polysaccharide ratio in the complex is adjustable; with moderate biotinylation of polymer, protein: polysaccharide can be 10:1 (w/w) or more; conversely, the ratio can be 1:10 or less if such is the interest based on immunological goals. Additionally, the size of the immunogenic MAPS composition can be adjusted by the choice of immunogenic polysaccharide size. The methods of making the SA-MAPS provide for ease in combining SA protein antigens and immunogenic polysaccharide with little modification, and allows the generation of a multivalent SA-MAPS composition by loading multiple SA peptide or protein antigens onto single immunogenic construct. As such, the SA-MAPS immunogenic composition as disclosed herein can be used to decrease the number of vaccines required to immunize a subject against Staphylococcus aureus, in particular, different strains of Staphylococcus aureus.

In some embodiments, the SA-MAPS immunogenic compositions as disclosed herein can be used to protect or treat a human susceptible to S. aureus infection, by means of administering the immunogenic compositions via a systemic, dermal or mucosal route or be used to generate a polyclonal or monoclonal antibody preparation that could be used to confer passive immunity on another subject. These administrations can include injection via the intramuscular, intraperitoneal, intradermal or subcutaneous routes; or via mucosal administration to the oral/alimentary, respiratory or genitourinary tracts. In one embodiment, intranasal administration is used for the treatment or prevention of nasopharyngeal carriage of S. aureus, thus attenuating infection at its earliest stage. In some embodiments, the SA-MAPS immunogenic compositions as disclosed herein may also be used to generate antibodies that are functional as measured by the killing of bacteria in either an animal efficacy model or via an opsonophagocytic killing assay.

In some embodiments, aspects of the invention disclosed herein relate to a SA-MAPS immunogenic composition comprising an immunogenic polysaccharide, at least one S. aureus peptide or polypeptide antigen, and at least one complementary affinity-molecule pair comprising: (a) a first affinity molecule associated with the immunogenic polysaccharide, and (b) a complementary affinity molecule associated with the at least S. aureus peptide or polypeptide antigen, where the first affinity molecule associates with the complementary affinity molecule to link the S. aureus peptide or polypeptide antigen and the immunogenic polysaccharide.

In some embodiments, the S. aureus peptide or polypeptide antigen is selected from any one or a combination of SA antigens selected from: hemolysin (Hl), Clumping factor A (ClfA), Clumping factor B (ClfB), serine-aspirate repeat protein D (SdrD), serine-aspirate repeat protein E (SdrE), Iron regulator surface protein A (IsdA), Iron regulator surface protein B (IsdB), Leukotoxin D (LukD), and/or Leukotoxin E (LukE). In some embodiments, the SA-MAPS composition comprises a hemolysin (Hl) S. aureus antigen and at least one additional S. aureus antigen selected from: Clumping factor A (ClfA), Clumping factor B (ClfB), serine-aspirate repeat protein D (SdrD), serine-aspirate repeat protein E (SdrE), Iron regulator surface protein A (IsdA), Iron regulator surface protein B (IsdB), Leukotoxin D (LukD), or Leukotoxin E (LukE).

In some embodiments, the SA-MAPS composition comprises a hemolysin (Hl) S. aureus antigen and at least two, or at least 3, or at least 4, or at least 5 or more additional S. aureus antigen selected from any of the group comprising: Clumping factor A (ClfA), Clumping factor B (ClfB), serine-aspirate repeat protein D (SdrD), serine-aspirate repeat protein E (SdrE), Iron regulator surface protein A (IsdA), Iron regulator surface protein B (IsdB), Leukotoxin D (LukD), or Leukotoxin E (LukE). In some embodiments, the SA-MAPS composition comprises a hemolysin α (Hla) antigen, and a Clumping factor A (ClfA) antigen, and a Clumping factor B (ClfB) antigen, and a serine-aspirate repeat protein D (SdrD) antigen, and a Iron regulator surface protein A (IsdA) antigen, and an Iron regulator surface protein B (IsdB) antigen.

In some embodiments, the SA-MAPS composition comprises S. aureus antigens Hla209 (27-319), ClfA (221-559), ClfB (203-542), SdrD (246-682), IsdA (47-324) and IsdB (48-447).

In some embodiments, the SA-MAPS composition comprises a Hl antigen is a α-hemolysin (Hla), a β-hemolysin (Hlb) or a γ-hemolysin (Hl-gamma) from S. aureus, for example, a wildtype Hla (WT Hla) SA antigen or a Hla SA antigen with a reduced hemolytic activity or is a non-hemolytic Hla protein. In some embodiments, the SA-MAPS composition comprises a Hla antigen with a reduced hemolytic activity comprises amino acids of SEQ ID NO: 14 (i.e., wt-Hla), SEQ ID NO: 15, SEQ ID NO: 17 or SEQ ID NO: 18 or a polypeptide with at least 85% sequence identity thereto. In some embodiments, a SA-MAPS composition as disclosed herein comprises a Hla antigen with a reduced hemolytic activity that has amino acids of SEQ ID NO: 16 or a polypeptide with at least 85% sequence identity thereto. (i.e., Hla209 (27-319)).

In some embodiments, a SA-MAPS composition as disclosed herein comprises a ClfA antigen comprises at least SEQ ID NO: 3 or a polypeptide with at least 85% sequence identity to SEQ ID NO: 3 (i.e., aa 221-559 of ClfA). In some embodiments, a SA-MAPS composition as disclosed herein comprises a ClfA antigen that is a fragment of at least 30 amino acids of SEQ ID NO: 2 or a polypeptide of at least 30 amino acids that has at least 85% sequence identity to a portion of SEQ ID NO: 2. (i.e., ClfA (40-899))

In some embodiments, a SA-MAPS composition as disclosed herein comprises aClfB antigen which comprises at least SEQ ID NO: 5 or a polypeptide with at least 85% sequence identity to SEQ ID NO: 5 (i.e., ClfB (203-542)). In some embodiments, a SA-MAPS composition as disclosed herein comprises a ClfB antigen that is a fragment of at least 30 amino acids of SEQ ID NO: 4 or a polypeptide of at least 30 amino acids that has at least 85% sequence identity to a portion of SEQ ID NO: 4 (i.e., a fragment of ClfB protein).

In some embodiments, a SA-MAPS composition as disclosed herein comprises a SdrD antigen which comprises at least SEQ ID NO: 7 or a polypeptide with at least 85% sequence identity to SEQ ID NO: 7 (i.e., SdrD (246-682)). In some embodiments, a SA-MAPS composition as disclosed herein comprises a SdrD antigen which is a fragment of at least 30 amino acids of SEQ ID NO:6 or a polypeptide of at least 30 amino acids that has at least 85% sequence identity to a portion of SEQ ID NO: 6. (i.e., a fragment of aa 31-1281 (mature) of SdrD protein).

In some embodiments, a SA-MAPS composition as disclosed herein comprises a SdrE SA antigen which comprises a fragment of at least 30 amino acids of SEQ ID NO:8 or a polypeptide of at least 30 amino acids that has at least 85% sequence identity to a portion of SEQ ID NO: 8 (i.e., a fragment ofs maure protein of SdrE)

In some embodiments, a SA-MAPS composition as disclosed herein comprises a IsdA SA-antigen which comprises at least SEQ ID NO: 11 or a polypeptide with at least 85% sequence identity to SEQ ID NO: 11 (i.e., IsdA (47-324)). In some embodiments, a SA-MAPS composition as disclosed herein comprises a IsdA SA antigen which comprises a fragment of at least 30 amino acids of SEQ ID NO:10 or a polypeptide of at least 30 amino acids that has at least 85% sequence identity to a portion of SEQ ID NO: 10 (i.e., a fragment of aa 47-316 (mature) IsdA protein).

In some embodiments, a SA-MAPS composition as disclosed herein comprises a IsdB SA-antigen which comprises at least SEQ ID NO: 13 or a polypeptide with at least 85% sequence identity to SEQ ID NO: 13 (i.e., IsdB (48-477)). In some embodiments, a SA-MAPS composition as disclosed herein comprises a IsdB SA antigen which comprises a fragment of at least 30 amino acids of SEQ ID NO:12 or a polypeptide of at least 30 amino acids that has at least 85% sequence identity to a portion of SEQ ID NO: 12 (i.e., a fragment of aa 47-613 (mature) IsdB protein).

In some embodiments, a SA-MAPS composition as disclosed herein comprises a first affinity molecule which is biotin or a derivative or mimic molecule thereof, for example, but not limited to, a biotin derivative, lipoic acid, HABA (hydroxyazobenzene-benzoic acid) or/and dimethyl-HABA or an amine-PEG3-biotin ((+)-biotinylation-3-6, 9-trixaundecanediamine).

In some embodiments, a SA-MAPS composition as disclosed herein comprises a complementary affinity molecule which is a biotin-binding protein, or an avidin-like protein, for example, but not limited to, any one or a combination of rhizavidin, avidin, streptavidin, or a homologue or derivative thereof. In some embodiments, a SA-MAPS composition as disclosed herein comprises a complementary affinity molecule which is rhizavidin, and comprises amino acids of SEQ ID NO: 1, or 85% sequence identity to amino acids of SEQ ID NO: 1.

In some embodiments, a SA-MAPS composition as disclosed herein comprises a S. aureus antigen as a fusion protein comprising the S. aureus antigen fused to a complementary affinity binding molecule. In alternative embodiments, the first affinity molecule is cross-linked to the immunogenic polysaccharide.

In some embodiments, a SA-MAPS composition as disclosed herein comprises a first affinity molecule is cross-linked to the immunogenic polysaccharide using a cross-linking reagent selected from any in the group consisting of: CDAP (1-cyano-4-dimethylaminopyridinium tetrafluoroborate); EDC (1-Ethyl-3-[3-dimethylaminopropyl]carbodiimide hydrochloride); sodium cyanoborohydride; cyanogen bromide; and ammonium bicarbonate/iodoacetic acid. In some embodiments, the first affinity molecule is cross-linked to carboxyl, hydroxyl, amino, phenoxyl, hemiacetal, and mecapto functional groups of the immunogenic polysaccharide. In some embodiments, the first affinity molecule is covalently bonded to the immunogenic polysaccharide.

In some embodiments, a SA-MAPS composition as disclosed herein comprises a first affinity molecule and complementary affinity molecule pair, which can be selected from a group consisting of: biotin/biotin-binding protein, antibody/antigen, enzyme/substrate, receptor/ligand, metal/metal-binding protein, carbohydrate/carbohydrate binding protein, lipid/lipid-binding protein, His tag/His tag-binding substance. In some embodiments, wherein the antigen is non-covalently attached, or covalently attached to the complementary affinity molecule.

In some embodiments, a secretion signal peptide is located at the N-terminal of the avidin-like protein, e.g., but not limited to a secretion signal sequence that comprises at least MKKIWLALAGLVLAFSASA (SEQ ID NO: 23) or MKKIWLALAGLVLAFSASAAQDP (SEQ ID NO: 24) or an amino acid sequence having at least 85% identity thereof. In some embodiments, a flexible linker peptide is also attached to the antigen, wherein the flexible linker peptide attaches the antigen to the complementary affinity molecule.

In some embodiments, a SA-MAPS composition as disclosed herein comprises an immunogenic polysaccharide is purified from living organisms or is a synthetic immunogenic polysaccharide, for example, where the living organism is selected from the group consisting of: bacteria, archaea, eukaryotic cells, fungi, insects, plants, animals, or chimeras thereof.

In some embodiments, a SA-MAPS composition as disclosed herein comprises at least 3 *S. aureus* peptide or polypeptide antigens, or at least 5 *S. aureus* peptide or polypeptide antigens, or between 2-10 *S. aureus* peptide or polypeptide antigens, or between 10-15 *S. aureus* peptide or polypeptide antigens, or between 15-20 *S. aureus* peptide or polypeptide antigens, or between 20-50 *S. aureus* peptide or polypeptide antigens, or between 50-100 *S. aureus* peptide or polypeptide antigens, or more than 100 *S. aureus* peptide or polypeptide antigens.

In some embodiments, a SA-MAPS composition as disclosed herein comprises an immunogenic polysaccharide is selected from a polysaccharide from the group consisting of: *S. aureus*, Vi polysaccharide, pneumococcal capsular polysaccharides, pneumococcal cell wall polysaccharide, *Haemophilus influenzae* Type b polysaccharide, Meningococcal polysaccharide, 0-antigens from Gram-negative bacteria and other bacterial capsular or cell wall polysaccharides. In some embodiments, a SA-MAPS composition as disclosed herein comprises an immunogenic polysaccharide selected from type 1 capsular polysaccharide (CP1) of *Streptococcus pneumoniae*, type 5 capsular polysaccharide (CP5) of *S. aureus* or type 8 capsular polysaccharide (CP8) of *S. aureus*.

In some embodiments, a SA-MAPS composition as disclosed herein, further comprises at least one co-stimulation factor associated to the immunogenic polysaccharide, e.g., a co-stimulation factor is selected from the group consisting of: Toll like receptor ligand or agonists, NOD ligand or agonists, or activator/agonists of the inflammasome. In some embodiments, the co-stimulation factor is attached to immunogenic polysaccharide directly, or via a complementary affinity-molecule pair comprising: a first affinity molecule which associates with the immunogenic polysaccharide, and a complementary affinity molecule which associates with the co-stimulation factor, wherein the first affinity molecule associates with the complementary affinity molecule to link the co-stimulatory factor to the immunogenic polysaccharide.

In some embodiments, a SA-MAPS composition as disclosed herein is used to elicit an immune response to *S. aureus* in a subject, for example, where the immune response is any of or a combination of: (i) an antibody or B-cell response, (ii) an antibody or B-cell response and T-cell response, (iii) an immune response to at least one immunogenic polysaccharide and at least one peptide or polypeptide *S. aureus* antigen, (iv) a CD4+ T cell response, including Th1, Th2, or Th17 or Th22 response, or a CD8+ T cell response, or CD4+ and CD8+ T cell response, (v) an antibody or B cell response to at least one antigenic polysaccharide and a CD4+ T cell response, including Th1, Th2, or Th17 or Th22 response, or a CD8+ T cell response, or CD4+/CD8+ T cell response to at least one peptide or polypeptide antigen, (vi) an antibody or B cell response to at least one antigenic polysaccharide, and an antibody or B cell response and a CD4+ T cell response, including Th1, Th2, Th17 or Th22 responses, or a CD8+ T cell response, or CD4+/CD8+ T cell response to at least one peptide or polypeptide antigen, (vii) results in activation of INF-γ, IL-17A or IL-22 producing cells, or INF-γ, IL-17A and IL-22 producing cells, (viii) an antibody or B-cell response against the *S. aureus* antigen which associates with the immunogenic polysaccharide.

In some embodiments, a SA-MAPS composition as disclosed herein, further comprises at least one adjuvant.

In some embodiments, a SA-MAPS composition as disclosed herein is used in a diagnostic for exposure to a pathogen or immune threat. In some embodiments, a SA-MAPS composition as disclosed herein is used in preventing infection by *S. aureus*. In some embodiments, a SA-MAPS composition as disclosed herein is used for preventing colonization of a subject by *S. aureus*.

Another aspect of the technology disclosed herein relates to a method for inducing an immune response in a subject to *S. aureus*, comprising administering to the subject a SA-MAPS composition as disclosed herein. For example, the SA-MAPS composition as disclosed herein is used to induce an immune response in a subject to *S. aureus*, where the immune response is, for example, any of or a combination of: (i) an antibody or B-cell response, (ii) an antibody or B-cell response and T-cell response, (iii) an immune response to at least one immunogenic polysaccharide and at least one peptide or polypeptide *S. aureus* antigen, (iv) a CD4+ T cell response, including Th1, Th2, or Th17 or Th22 response, or a CD8+ T cell response, or CD4+ and CD8+ T cell response, (v) an antibody or B cell response to at least one antigenic polysaccharide and a CD4+ T cell response, including Th1, Th2, or Th17 or Th22 response, or a CD8+ T cell response, or CD4+/CD8+ T cell response to at least one peptide or polypeptide antigen, (vi) an antibody or B cell response to at least one antigenic polysaccharide, and an antibody or B cell response and a CD4+ T cell response, including Th1, Th2, Th17 or Th22 responses, or a CD8+ T cell response, or CD4+/CD8+ T cell response to at least one peptide or polypeptide antigen, (vii) results in activation of INF-γ, IL-17A or IL-22 producing cells, or INF-γ, IL-17A and IL-22 producing cells, (viii) an antibody or B-cell response against the *S. aureus* antigen which associates with the immunogenic polysaccharide.

Another aspect of the technology disclosed herein relates to a method of vaccinating a mammal against at least one antigen-bearing pathogen, the method comprising administering to the mammal a SA-MAPS composition as disclosed herein. In some embodiments, the subject or mammal is a human. In alternative embodiments, the subject or mammal is an agricultural or non-domestic animal, or a domestic animal.

In some embodiments, a SA-MAPS composition as disclosed herein is administered via subcutaneous, intranasal, intradermal, or intra muscular injection, or via transdermal skin patch.

Another aspect of the technology disclosed herein relates to a fusion protein comprising a rhizavidin protein and at least one *S. aureus* peptide or polypeptide antigen, wherein the rhizavidin protein comprises amino acids of SEQ ID NO: 1, or 85% sequence identity to amino acids of SEQ ID NO: 1, and the *S. aureus* peptide or polypeptide comprises a fragment of at least 20 amino acids of a protein selected from any of: haemolysin (Hl), Clumping factor A (ClfA), Clumping factor B (ClfB), serine-aspirate repeat protein D (SdrD), serine-aspirate repeat protein E (SdrE), Iron regulator surface protein A (IsdA), Iron regulator surface protein B (IsdB), Leukoptoxin D (LukD), or Leukoptoxin E (LukE). In some embodiments, a fusion protein as disclosed herein comprises a *S. aureus* peptide selected from any of Hla209 (27-319), ClfA (221-559), ClfB (203-542), SdrD (246-682), IsdA (47-324) and IsdB (48-447).

Another aspect of the technology disclosed herein relates to a fusion protein comprising a rhizavidin protein and an *S. aureus* peptide or polypeptide antigen, wherein the rhizavidin protein comprises amino acids of SEQ ID NO: 1, or 85% sequence identity to amino acids of SEQ ID NO: 1, and the *S. aureus* peptide or polypeptide comprises a non-hemolytic variant of a Hla protein (i.e. Rhavi-Hla209). In some embodiments, a non-haemolytic variant of a Hla protein comprises at least SEQ ID NO: 16 or a protein of at least 20 amino acids that has at least 85% sequence identity to SEQ ID NO: 16. (i.e., Hla209(aa 27-319).

Another aspect of the technology disclosed herein relates to a fusion protein comprising a rhizavidin protein and an *S. aureus* peptide or polypeptide antigen, wherein the rhizavidin protein comprises amino acids of SEQ ID NO: 1, or 85% sequence identity to amino acids of SEQ ID NO: 1, and the *S. aureus* peptide or polypeptide comprises a fragment of at least 20 amino acids of a Clumping factor A (ClfA) protein (i.e. Rhavi-ClfA). In some embodiments, a ClfA protein comprises at least SEQ ID NO: 3 or a protein of at least 20 amino acids that has at least 85% sequence identity to SEQ ID NO: 3 (i.e., ClfA (221-559)).

Another aspect of the technology disclosed herein relates to a fusion protein comprising a rhizavidin protein and an *S. aureus* peptide or polypeptide antigen, wherein the rhizavidin protein comprises amino acids of SEQ ID NO: 1, or 85% sequence identity to amino acids of SEQ ID NO: 1, and the *S. aureus* peptide or polypeptide comprises a fragment of at least 20 amino acids of a Clumping factor B (ClfB) protein (i.e., Rhavi-ClfB). In some embodiments, a ClfB protein comprises at least SEQ ID NO: 5 or a protein of at least 20 amino acids that has at least 85% sequence identity to SEQ ID NO: 5. (i.e., ClfB (203-542)).

Another aspect of the technology disclosed herein relates to a fusion protein comprising a rhizavidin protein and an *S. aureus* peptide or polypeptide antigen, wherein the rhizavidin protein comprises amino acids of SEQ ID NO: 1, or 85% sequence identity to amino acids of SEQ ID NO: 1, and the *S. aureus* peptide or polypeptide comprises a fragment of at least 20 amino acids of a serine-aspirate repeat protein D (SdrD) protein (i.e. Rhavi-SdrD). In some embodiments, a SdrD protein comprises at least SEQ ID NO: 7 or a protein of at least 20 amino acids that has at least 85% sequence identity to SEQ ID NO: 7 (i.e., SdrD (246-682)).

Another aspect of the technology disclosed herein relates to a fusion protein comprising a rhizavidin protein and an *S. aureus* peptide or polypeptide antigen, wherein the rhizavidin protein comprises amino acids of SEQ ID NO: 1, or 85% sequence identity to amino acids of SEQ ID NO: 1, and the *S. aureus* peptide or polypeptide comprises a fragment of at least 20 amino acids of a serine-aspirate repeat protein D (SdrE) protein (i.e. Rhavi-SdrE). In some embodiments, a SdrE protein comprises at least SEQ ID NO: 8 or a protein of at least 20 amino acids that has at least 85% sequence identity to SEQ ID NO: 8.

Another aspect of the technology disclosed herein relates to a fusion protein comprising a rhizavidin protein and an *S. aureus* peptide or polypeptide antigen, wherein the rhizavidin protein comprises amino acids of SEQ ID NO: 1, or 85% sequence identity to amino acids of SEQ ID NO: 1, and the *S. aureus* peptide or polypeptide comprises a fragment of at least 20 amino acids of Iron regulator surface protein A (IsdA), protein (i.e. Rhavi-IsdA). In some embodiments, a IsdA protein comprises at least SEQ ID NO: 11 or a protein of at least 20 amino acids that has at least 85% sequence identity to SEQ ID NO: 11 (i.e., IsdA (47-324).

Another aspect of the technology disclosed herein relates to a fusion protein comprising a rhizavidin protein and an *S. aureus* peptide or polypeptide antigen, wherein the rhizavidin protein comprises amino acids of SEQ ID NO: 1, or 85% sequence identity to amino acids of SEQ ID NO: 1, and the *S. aureus* peptide or polypeptide comprises a fragment of at least 20 amino acids of Iron regulator surface protein B (IsdB), protein (i.e. Rhavi-IsdB). In some embodiments, a IsdB protein comprises at least SEQ ID NO: 13 or a protein of at least 20 amino acids that has at least 85% sequence identity to SEQ ID NO: 13 (i.e., IsdB (48-477)).

Another aspect of the technology disclosed herein relates to a kit comprising: (a) a container comprising an immunogenic polysaccharide cross-linked with a plurality of first affinity molecules; and (b) a container comprising a complementary affinity molecule which associates with the first affinity molecule, wherein the complementary affinity molecule associates with at least one *S. aureus* antigen. In some embodiments, a kit can further comprise any one or more of: (i) a means or agent to attach the complementary affinity molecule to the antigen, (ii) at least one co-stimulation factor, (iii) a cross-linking reagent which can be selected from the group consisting of: CDAP (1-cyano-4-dimethyl-aminopyridinium tetrafluoroborate), EDC (1-Ethyl-3-[3-di-methylaminopropyl] carbodiimide hydrochloride), sodium cyanoborohydride, cyanogen bromide, or ammonium bicarbonate/iodoacetic acid for linking the co-factor to the polysaccharide, (iv) a container comprising an expression vector for expressing an antigen-affinity molecule fusion protein, for example, an expression vector that can optionally comprise a sequence for a linker peptide, wherein the expression vector can expresses an antigen-affinity molecule fusion protein comprising a linker peptide between the antigen and the affinity molecule, and/or (v) one or more of a fusion protein as disclosed herein, wherein the fusion protein is selected from any of: (i) a fusion protein comprising a the C-terminal of SEQ ID NO: 1 (or a protein of at least 80% or 85% or more sequence identity thereto) is fused to any of hemolysin (Hl) (e.g., hemolysin a or Hla209), Clumping factor A (ClfA), Clumping factor B (ClfB), serine-aspirate repeat protein D (SdrD), Iron regulator surface protein A (IsdA) and Iron regulator surface protein B (IsdB), or fragments thereof, or (ii) a fusion protein comprising a the C-terminal of SEQ ID NO: 1 (or a protein of at least 80% or 85% or more sequence identity thereto) fused to any one of: Hla209(27-319), ClfA (221-559), ClfB (203-542), SdrD (246-682), IsdA (47-324), IsdB (48-447) or proteins or peptides having at least 85% sequence identity thereto, or (iii) a fusion protein selected from any of Rhavi-HLA209-ClfA, Rhivi-HLA209-ClfB, Rhivi-HLA209-SdrD, Rhavi-HLA209-IsdA, Rhavi-HLA209-IsdB, Rhavi-ClfA-ClfB, Rhavi-ClfA-SdrD, Rhavi-ClfA-IsdA; Rhavi-ClfA-IsdB; Rhavi-ClfB-SdrD; Rhavi-ClfB-IsdA; Rhavi-ClfB-IsdB, Rhavi-SdrD-IsdA; Rhavi-SdrD-IsdB; Rhavi-IsdA-IsdB, where CLFA=CLFA protein or a fragment thereof, e.g., ClfA (221-559), CLFB=ClfB protein or a fragment thereof, e.g., ClfB (203-542), SDRD=SdrD protein or a fragment thereof, e.g., SdrD (246-682), ISDA=IsdA protein or a fragment thereof, e.g., IsdA (47-324); ISDB=IsdB protein or a fragment thereof, e.g., IsdB (48-477); HLA209=Hla protein with the 209 mutation, or a fragment thereof, e.g., Hla209 (27-319).

Accordingly, one aspect of the present invention relates to an immunogenic composition comprising a polymer, at least one protein or peptide antigen, and at least one complementary affinity-molecule pair, where the complementary affinity-molecule pair comprises a first affinity molecule that associates with the polymer and a complementary affinity molecule that associates with the protein or peptide antigen, so that when the first affinity molecule associates with the complementary affinity molecule, it indirectly links the antigen to the polymer.

Provided herein also is a method of vaccinating a subject, e.g., a mammal, e.g., a human with the immunogenic compositions as disclosed herein, the method comprising administering a vaccine composition comprising a SA-MAPS composition as disclosed herein to the subject.

DESCRIPTION OF THE DRAWINGS

FIG. 1A shows hemolytic activity of wild type (WT) Hla, Hla209 mutant and their rhizavidin (rhavi) fusions. One HU was defined as the activity that causes 50% hemolysis of 1% rabbit red blood cells in PBS (pH7.5) after 30 min incubation at 37° C. and expressed per 1 mg/ml. Fusion with rhizavidin significantly reduced the hemolytic activity of WT Hla. Symbols represent mean±SEM. FIG. 1B shows schematics of SA-Mix and SA-MAPS vaccine. SA-Mix vaccine contains six *S. aureus* antigens mixed at equal molar ratio. SA-MAPS complex was prepared by coupling rhavi fusion antigens with a biotinylated pneumococcal type-1 capsular polysaccharide (SP PS1 or CP1). FIG. 1C shows results of SDS-PAGE of the purified SA-MAPS complex. MAPS complexes were treated with reducing-SDS sample buffer at room temperature (RT) or at 100° C. (Boil) for 10 min before applied to SDS-PAGE. The affinity coupling between rhavi-fusion antigens and biotinylated PS in MAPS complexes was retained after SDS-treatment unless the sample was boiled.

FIG. 2A is a histogram of antigen-specific IgG titer of C57BL/6 mice (n=10 per group) after three subcutaneous immunizations with SA-Mix or SA-MAPS vaccine. Control group received adjuvant alone (Alum). Immunization of mice with SA-MAPS induced significantly higher titer of IgG antibody to each target antigen than what was induced by SA-Mix. FIG. 2B shows that IFNγ, IL-17A and IL22 production, indicative of antigen-specific T-cell responses after SA-Mix or SA-MAPS. SA-MAPS but not SA-Mix eliciting antigen-specific T-cell responses. a.u., arbitrary unit. Bars represent Geometric means +/−95% CI. *, $P<0.05$; , $P<0.01$; *, $P<0.001$.

FIG. 3A (left) shows a Kaplan-Maher survival curve after vaccination with either SA-Mix or SA-MAPS, and demonstrated that SA-MAPS protected animals from sepsis infection of *S. aureus*. Moreover, FIG. 3A (right) shows that mice that received SA-MAPS vaccine had delayed onset illness compared to the control group or the group that received SA-Mix. FIG. 3B and FIG. 3C shows area of lesion after mice are vaccinated with SA-Mix or SA-MAPS, with SA-MAPS reducing the incidence (FIG. 3C) and the extent (FIG. 3B) of dermonecrosis after skin infection with *S. aureus*. FIG. 3B (left) shows area of lesion of mice immunized with SA-MAPS (closed square), SA-Mix (closed triangle) as compared to Alum controls (open square). Inset of FIG. 3B (left) is a representative picture of dermonecrotic lesion (black arrow) after *S. aureus* infection. FIG. 3B (right) is a histogram showing that vaccination with SA-MAPS (closed squares) but not with SA-Mix (closed triangles) protected against skin abscess formation caused by *S. aureus*. Symbols represent Mean surface area±SEM. FIG. 3D shows the CFU of bacteria recovered from skin abscesses on day 4 after infection. FIG. 3E shows CFU with SA-Mix (closed triangles) or SA-MAPS (closed squares), as compared to the control Alum group (open squares), and demonstrates that significantly fewer animals that received SA-MAPS vaccine developed skin abscess after inoculation. FIG. 3E (inset) are representative picture of skin abscess of SA-MAPS (top) or SA-Mix (bottom) (arrows). Bars indicated Geometric means. Dashed line indicated the detection limit (22.5 CFU).

FIG. 4A shows CFU per gram of feces of C57BL/6 mice (n=5) inoculated intranasally with $5\times10^7$ CFU of USA300 LAC$^{strep}$ strain. Fecal pellets were collected on days 1 (D1), 4 (D4), 7 (D7) and 11 (D11) after inoculation. Stable SA colonization is apparent between days 4 and 11 post-inoculation. FIGS. 4B and 4C show that vaccination with SA-MAPS, but not with SA-Mix, significantly reduced the density of GI colonization of SA over time. FIG. 4B shows the CFU of bacteria recovered from fecal samples. FIG. 4C shows the percentage of CFU on day-7 (D7) post inoculation as compared to CFU on day-1 (D1) post inoculation. Bars represent Geometric means. Dashed lines indicated the detection limit (40 CFU). N.S, not significant; **, $P<0.01$.

FIG. 6A is a histogram of antigen-specific IgF and shows that immunization of μMT$^{-/-}$ (B-cell deficient) mice with SA-MAPS elicited no IgG antibodies. FIG. 6B shows levels of IFNγ, IL-17 and IL-22 production after immunization of μMT$^{-/-}$ (B-cell deficient) mice with SA-MAPS, showing normal T-cell responses to *S. aureus* antigens. Bars represent Geometric mean +95% CI. FIG. 6C shows the generation of antigen-specific T cell immunity slightly delays onset of illness, but does not provide significant protection. FIG. 6D shows antigen-specific T cell immunity provided partial protection against dermonecrosis, especially in the early stage of the infection. Symbols represent Mean±SEM. FIGS. 6E and 6F show that in the absence of antibodies, SA MAPS provides protection against abscess formation during skin infection (FIG. 6E) and accelerates clearance of GI colonization of *S. aureus* (FIG. 6F). Bars represent Geometric means. Dashed lines indicated the detection limit (22.5 CFU for abscess infection and 40 CFU for GI colonization model). N.S, not significant; *, $P<0.05$; ***, $P<0.001$.

DETAILED DESCRIPTION OF THE INVENTION

Figure 1A:
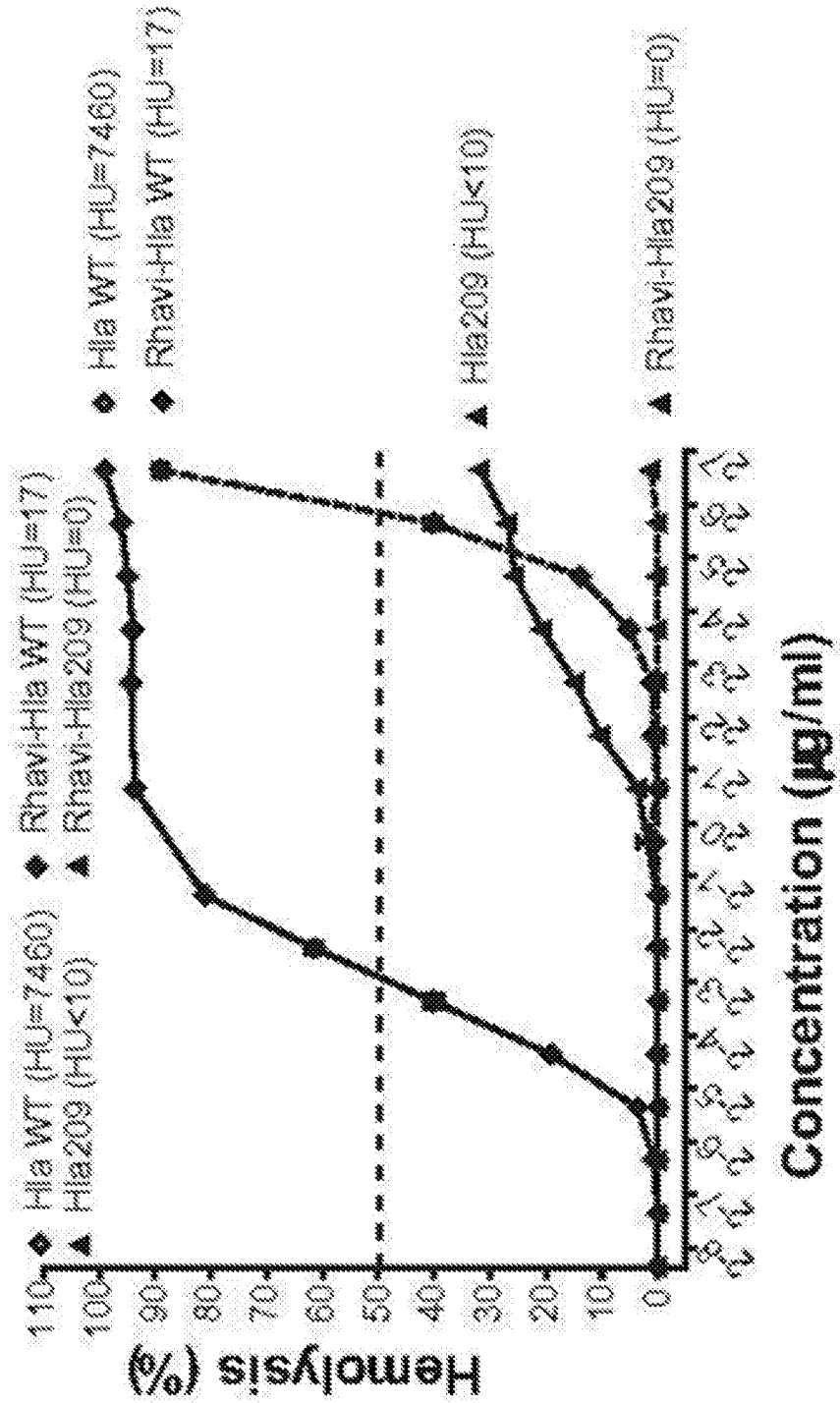
FIGS. 1A-1C show the preparation of SA-Mix and SA-MAPS vaccines.

The present invention relates immunogenic compositions and compositions comprising an immunogenic complex that comprises at least one *Staphylococcus aureus* antigen, or multiple *Staphylococcus aureus* antigens, attached to an immunogenic polysaccharide scaffold for use in eliciting an immune response (both a cellular and humoral immune response) to each of the SA antigens attached to the immunogenic polysaccharide and to the immunogenic polysaccharide, when administered to a subject.

More specifically, disclosed herein is an immunogenic Multiple Antigen Presenting System (MAPS) comprising an immunogenic polysaccharide, and attached to the immunogenic polysaccharide via an affinity binding pair, at least one *Staphylococcus aureus* (SA) antigen. Such a *Staphylococcus aureus*-MAPS (SA-MAPS) composition as disclosed herein is useful for the production of immunogenic compositions, such as those useful in vaccines, as well as for treatment. The SA-MAPS immunogenic composition as disclosed herein stimulates a humoral and cellular immune response: it can generate anti-polysaccharide antibody and the B-cell and T-cell, e.g., Th1/Th17 responses to multiple *Staphylococcus aureus* (SA) antigen using single SA-MAPS immunogenic construct. A combination of B- and T-cell immunity to *Staphylococcus aureus* will be a useful vaccine strategy against *Staphylococcus aureus* invasive diseases, as well as from mild skin infections to endocarditis, dermonecrosis, osteomyelitis, bacteremia, sepsis, and other forms of disease associated with *Staphylococcus aureus*.

The inventors previously developed a vaccine platform referred to the Multiple-Antigen-Presenting-System (MAPS), as disclosed in US patent Application 2014/0154287, which is incorporated herein in its entirety by reference, which enables the induction of broad adaptive immune responses. Herein, the inventors have developed and optimized the system for the treatment and prevention of infection from *Staphylococcus aureus*.

In particular, the inventors have generated a SA-MAPS immunogenic composition comprising an immunogenic polysaccharide (typically SA CP5, CP8 or *S. pneumoniae* CP1, or other PS or variants or combinations thereof), at least one *Staphylococcus aureus* protein or peptide antigen; and at least one complementary affinity-molecule pair comprising (i) a first affinity molecule that associates with the immunogenic polysaccharide, and (ii) a complementary affinity molecule that associates with the *Staphylococcus aureus* protein or peptide antigen, such that the first and complementary affinity molecules serve as an indirect link between the immunogenic polysaccharide and SA protein or peptide antigens. Such a system allows for a modular immunogenic composition, where one or more SA protein or peptide antigens can be attached to the immunogenic polysaccharide in a modular fashion, allowing for flexibility in the number and type of SA antigens attached to immunogenic polysaccharide. Accordingly, the immunogenic polysaccharide can attach at least 1, or at least 2, or a plurality of the same or different SA protein or peptide antigens. In some embodiments, the immunogenic polysaccharide is antigenic, and in some embodiments, the immunogenic polysaccharide is Type 5 (CP5) or Type 8 (CP8), or a combination of Type 5 or Type 8 capsular polysaccharide from *Staphylococcus aureus*, or can be a pneumococcal capsular polysaccharide, e.g., Type 1 (CP1) capsular polysaccharide from *S. pneumoniae*.

Herein, the inventors have used a SA-specific MAPS immunogenic composition which comprises 6 different SA peptide antigens to demonstrate that B- and T-cell mediated immune mechanisms contribute differentially to host defense against SA in models of skin necrosis, skin abscess, invasive disease or mucosal colonization.

In some embodiments, the SA-MAPS comprises at least one or more SA antigens, where the SA antigen is an antigenic protein or polypeptide selected from any of the group of: hemolysin (Hl) (e.g., hemolysin α or Hla), Clumping factor A (ClfA), Clumping factor B (ClfB), serine-aspirate repeat protein D (SdrD), Iron regulator surface protein A (IsdA) and Iron regulator surface protein B (IsdB). In some embodiments, the SA-MAPS immunogenic composition as disclosed herein comprises one or more peptide or polypeptide fragments of these proteins, as long as the fragment is antigenic, and/or comprises one or more epitopes to induce an immune response. Exemplary fragments can be, for example, but are not limited to Hla209 (27-319), ClfA (221-559), ClfB (203-542), SdrD (246-682), IsdA (47-324), IsdB (48-447). In some embodiments, a SA-MAPS immunogenic composition as disclosed herein comprises at least 2, or at least 3, or at least 4, or at least 5, or all 6 peptide or polypeptide SA-antigens of Hla209(27-319), ClfA (221-559), ClfB (203-542), SdrD (246-682), IsdA (47-324), IsdB (48-447), or proteins or peptides of at least 85% sequence identity thereto. In some embodiments, any of the above listed SA antigens can be substituted for a different SA peptide or polypeptide antigen known to one of ordinary skill in the art. Exemplary SA antigens can be any peptide or polypeptide comprising at least part of the serine-aspirate repeat protein E (SdrE) protein, Leukotoxin D (LukD) protein, or Leukotoxin E (LukE) protein, provided that the any peptide or polypeptide is immunogenic, or is antigenic. Other SA antigens can be used, and are disclosed herein.

Accordingly, the embodiments herein provide for an immunogenic composition and methods useful for raising an immune response to *Staphylococcus aureus* in a subject, which can be used on its own or in conjunction or admixture with essentially any existing vaccine approaches.

*Staphylococcus aureus* Multiple-Antigen Presenting System (SA-MAPS)

While it is envisioned that the SA-MAPS immunogenic composition as disclosed herein comprises immunogenic polysaccharides from *Staphylococcus aureus*, the SA-MAPS can use immunogenic polysaccharides from a variety of different bacterial cells. In some embodiments, the immunogenic polysaccharide is for example, but not limited to, Type 5 (CP5) or Type 8 (CP8), or a combination of Type 5 or Type 8 capsular polysaccharide from *Staphylococcus aureus*, or can be a pneumococcal capsular polysaccharide, e.g., Type 1 (CP1) capsular polysaccharide from *S. pneumoniae*, or other capsular or noncaspular PS. In some embodiments, the polysaccharide is a capsular polysaccharide. In some embodiments, the polysaccharide is not a capsular polysaccharide (i.e., a noncapsular PS). With the different combinations of immunogenic polysaccharides and different combinations of SA peptide or polypeptide antigens, the SA-MAPS composition is a flexible and versatile composition that can be designed and manufactured to elicit a particular, broad spectrum immune response to *Staphylococcus aureus*. Table 1 provides a simple example guide for envisioning the flexibility of SA-MAPS embodiments.

Table 1 shows the versatility of the SA-MAPS platform: SA-MAPS comprises an antigenic polysaccharide backbone and at least one SA-antigen, and optionally one or more non-SA antigens. The antigenic or immunogenic polysaccharide backbone can be a synthetic or antigenic polysaccharide from *Staphylococcus aureus* or alternatively a different pathogen (exemplary antigenic polysaccharides are listed in the last column). A SA-MAPS composition can comprise at least one SA-antigen (exemplary SA antigens are listed), and can optionally comprise non-SA antigens.

TABLE 1

| SA-MAPS | Immunogenic polymer backbone: | Immunogenic polysaccharide | synthetic | Pneumococcal capsular PS (e.g., CP1 from Type 1 serotypes) |
| --- | --- | --- | --- | --- |
| | | | From pathogen | Pneumococcal cell wall PS (various serotypes) |
| | | Other immunogenic polysaccharides from viruses etc. | | *Salmonella typhi* Vi *Staphylococcus aureus* capsular PS (e.g., CP5, CP8 from Type 5 and Type 8 serotypes) |
| | Antigens: | SA-Antigens | e.g., Hla209, ClfA, ClfB, SdrD, IsdA, IsdB etc. | *Haemophilus influenzae* Type b (Hib) PS, other Haemophili *Streptococcus* PS (Group A or Group B) Meningoccus PS Antrax PS |
| | | Non-SA antigens | Bacterial proteins/toxins Viral proteins Cancer antigens Plant toxins | Enteric pathogens pseudomonas Fungal pathogens (*Cryptococcus*, other) Glycoproteins from viruses |

Polysaccharides

One component of the SA-MAP immunogenic composition as disclosed herein is a "backbone," typically an antigenic or immunogenic polysaccharide (PS), and can comprise additional elements that do not negatively impact the antigenic polysaccharide's function of (i) inducing an immune response to the polysaccharide and (ii) presenting the associated SA-antigen(s) to the immune system in immunogenic fashion. In some embodiments, the immunogenic polysaccharide is a synthetic polysaccharide.

It is envisioned that the polysaccharide used in the SA-MAPS composition is immunogenic, that is, it helps induce a specific immune response, and herein is referred to as an "immunogenic polysaccharide" or "antigenic polysaccharide". The specific immune response recognizes the particular immunogenic PS and provides a unique response to the immunogenic complex as opposed to a different immunogenic complex. As explained herein, the response includes both a humoral and cell-mediated response.

In some embodiments, the immunogenic polysaccharide is a naturally occurring polysaccharide, e.g., a polysaccharide derived or purified from bacterial cells, and can be, for example, a capsular or noncaspular PS. In some embodiments, the immunogenic polysaccharide is derived or purified from eukaryotic cells, e.g., fungi, insect or plant cells. In yet other embodiments, the immunogenic polysaccharide is derived from mammalian cells, such as virus-infected cells or cancer cells. In general, such immunogenic polysaccharides are well known in the art and are encompassed for use in the methods and compositions as disclosed herein.

Staphylococcal microorganisms capable of causing invasive disease generally also are capable of producing a capsule polysaccharide (CP) that encapsulates the bacterium and enhances its resistance to clearance by the host innate immune system. The CP serves to cloak the bacterial cell in a protective capsule that renders the bacteria resistant to phagocytosis and intracellular killing. Bacteria lacking a capsule are more susceptible to phagocytosis. Capsular polysaccharides are frequently an important virulence factor for many bacterial pathogens, including *Haemophilus influenzae, Streptococcus pneumoniae* and Group B *streptococci*. In some embodiments, an immunogenic polysaccharide for use in the SA-MAPS immunogenic composition as disclosed herein is a polysaccharide or oligosaccharide from Gram-positive bacteria, for example, a *Staphlococcus aureus* capsular polysaccharide.

Type 5 and Type 8 Polysaccharides from *S. aureus*

Most strains of *S. aureus* that cause infection in man contain either Type 5 or Type 8 polysaccharides. Approximately 60% of human strains are Type 8 and approximately 30% are Type 5. The structures of Type 5 and Type 8 capsular polysaccharide antigens are described in Moreau et al Carbohydrate Res. 201; 285 (1990) and Fournier et al Infect. Immun. 45; 87 (1984). Both have FucNAcp in their repeat unit as well as ManNAcA which can be used to introduce a sulfhydryl group.

Recently (Jones Carbohydrate Research 340, 1097-1106 (2005)) NMR spectroscopy revised the structures of the capsular polysaccharides to:

Type 5→4)-β-D-ManNAcA-(1→4)-α-L-FucNAc (3OAc)-(1→3)-β-D-FucNAc-(1→Type 8→3)-β-D-ManNAcA(4OAc)-(1→3)-α-L-FucNAc(1→3)-α-D-FucNAc (1→

Polysaccharides may be extracted from the appropriate strain of *S. aureus* using methods well known to the skilled man, for instance as described in U.S. Pat. No. 6,294,177 or Infection and Immunity (1990) 58(7); 2367, Fournier et al. (1984), supra; Fournier et al. (1987) Ann. Inst. Pasteur/Microbiol. 138:561-567; US Patent Application Publication No. 2007/0141077; and Int'l Patent Application Publication No. WO 00/56357; each of which is incorporated herein by reference as if set forth in its entirety). For example, ATCC 12902 is a Type 5 *S. aureus* strain and ATCC 12605 is a Type 8 *S. aureus* strain. In addition, they can be produced using synthetic protocols. Moreover, serotype 5 or 8 capsular polysaccharide can be recombinant produced using genetic engineering procedures also known to one of ordinary skill in the art (see, Sau et al. (1997) Microbiology 143:2395-2405; and U.S. Pat. No. 6,027,925; each of which is incorporated herein by reference as if set forth in its entirety).

One *S. aureus* strain that can be used to obtain isolated serotype 8 capsular polysaccharide is *S. aureus* R2 PFESA0286. This strain was selected by flow cytometry with rabbit anti-serotype 8 polysaccharide antibodies after cultivation of *S. aureus* PFESA0286 (American Type Culture Collection; Manassas, Va.: ATCC Accession No. 495: 25) in Modified Frantz Broth. Two populations, R1 and R2, were observed during flow cytometry. R1 and R2 were purified and re-cultured. R2 yielded a serotype 8 capsular polysaccharide. Flow cytometric analysis showed a homogenous fluorescence intensity. As such, R2 was selected for serotype 8 capsular polysaccharide production.

One *S. aureus* strain that can be used to obtain isolated serotype 5 capsular polysaccharide is *S. aureus* PFESA0266. This strain produces serotype 5 capsular polysaccharide during growth, and production peaks when cells are in a stationary phase. Other *S. aureus* type 5 or type 8 strains can be used to make the respective polysaccharides that are obtained either from established culture collections or clinical specimens.

In some embodiments, a Becker or Newman *S. aureus* strain can be used to obtain isolated serotype 5 capsular polysaccharide (CP5). In some embodiments, the Newman *S. aureus* strain can be used to obtain isolated serotype 5 capsular polysaccharide (CP5).

In some embodiments, a Becker or Newman *S. aureus* strain can be used to obtain isolated serotype 8 capsular polysaccharide (CP8). In some embodiments, the Becker *S. aureus* strain can be used to obtain isolated serotype 8 capsular polysaccharide (CP8).

Polysaccharides are of native size or alternatively may be sized, for instance by microfluidisation, ultrasonic irradiation or by chemical treatment. The invention also covers oligosaccharides derived from the type 5 and 8 polysaccharides from *S. aureus*.

In some embodiments, an immunogenic polysaccharide for use in the SA-MAPS complex as disclosed herein can comprises a Type 5 (CP5), or Type 8 (CP8) capsular polysaccharides (CP), or any of the polysaccharides or oligosaccharides or lipopolysaccharides from *Staphylococcus aureus*. In some embodiments, an immunogenic polysaccharide for use in the SA-MAPS complex as disclosed herein can comprises a capsular polysaccharide from a non-typeable (NT) SA strain, e.g., a cell wall surface antigen 336 (Type 336) or a polyribitol phosphate N-acetylglucosamine, which resembles cell wall teichoic acid. Type 336 isolates do not express capsule but do express cell surface polysaccharide or the 336 polysaccharide (336PS), which resembles *S. aureus* cell wall teichoic acid (Ma, J., et al., 2004. Evaluation of serotypes of *Staphylococcus aureus* strains used in the production of a bovine mastitis bacterin. J. Dairy. Sci. 87:178-182 14, 17; O'Brien, et al., 2000. Production of antibodies to *Staphylococcus aureus* serotypes 5, 8, and 336 using poly(dl-lactide-co-glycolide) microspheres. J. Dairy Sci. 83:1758-1766).

In some embodiments, an immunogenic polysaccharide for use in the SA-MAPS complex as disclosed herein can comprises a capsular polysaccharide (CP) from a methicillin-resistant *S. aureus* (MRSA), including hospital-acquired MRSA (HA-MRSA), or community-acquired MRSA (CA-MRSA) or any polysaccharides or oligosaccharides or lipopolysaccharides from MRSA, e.g., e.g., any one or more of a CP5, or CP8 from HA-MSSA and/or CA-MRSA. In alternative embodiments, an immunogenic polysaccharide for use in the SA-MAPS complex as disclosed herein can comprises a capsular polysaccharide (CP) from a methicillin-sensitive *S. aureus* (MSSA), e.g., any one or more of a CP5, or CP8 from MSSA.

In some embodiments, an immunogenic polysaccharide for use in the SA-MAPS complex as disclosed herein can comprise more than one type of polysaccharide. For example, an immunogenic polysaccharide for use in the SA-MAPS complex as disclosed herein can comprise a portion of polysaccharide A (e.g., Type 5 from SA), and the remaining portion of polysaccharide B (Type 8 from SA). The antigenic polysaccharide does not need to be from the same organism, e.g., for example an immunogenic polysaccharide for use in the SA-MAPS complex as disclosed herein can comprise a portion of polysaccharide A (e.g., Type 5 or Type 8 from SA), and the remaining portion of polysaccharide B (e.g., a pneumococcus polysaccharide or other bacterial capsular PS or noncapsular PS). There is no limit to the amount of different types of immunogenic polysaccharides which can be used in a single MAPS backbone entity. In some embodiments, where the immunogenic polysaccharide for use in the SA-MAPS complex as disclosed herein is a branched polymer, the chain polysaccharide can be polysaccharide A, and the branches can be at least 1 or at least 2 or at least 3 or more different antigenic polysaccharides.

In some embodiments, the immunogenic polysaccharide for use in the SA-MAPS complex as disclosed herein is a branched polymer. In some embodiments, an immunogenic polysaccharide for use in the SA-MAPS complex as disclosed herein is a single chain polymer.

In some embodiments, the immunogenic polysaccharide for use in the SA-MAPS complex as disclosed herein comprises at least 10 carbohydrate repeating units, or at least 20, or at least 50, or at least 75, or at least 100, or at least 150, or at least 200, or at least 250, or at least 300, or at least 350, or at least 400, or at least 450, or at least 500, or more than 500 repeating units, inclusive.

In one aspect of the invention, the immunogenic polysaccharide (PS) for use in the SA-MAPS complex as disclosed herein can have a molecular mass of <500 kDa or >500 kDa. In another aspect of the invention, the PS has a molecular mass of <70 kDa. In some embodiments, an immunogenic polysaccharide for use in the SA-MAPS complex as disclosed herein is a large molecular weight polymer, e.g., a polymer can be of an average molecular weight of between about 425-500 kDa, inclusive, for example, at least 300 kDa, or at least 350 kDa, or at least 400 kDa, or at least 425 kDa, or at least 450 kDa, or at least 500 kDa or greater than 500 kDa, inclusive, but typically less than 500 kDa. In some embodiments, an immunogenic polysaccharide for use in the SA-MAPS complex as disclosed herein can be a small molecular weight polymer, e.g., a polymer can be of an average molecular weight of between about 60 kDA to about 90 kDa, for example, at least 50 kDa, or at least 60 kDa, or at least 70 kDa, or at least 80 kDa, or at least 90 kDa, or at least 100 kDa, or greater than 100 kDa, inclusive, but generally less than about 120 kDa.

In some embodiments, the immunogenic polysaccharide for use in the SA-MAPS complex as disclosed herein is harvested and purified from a natural source; and in other embodiments, the polysaccharide is synthetic. Methods to produce synthetic polymers, including synthetic polysaccharides, are known to persons of ordinary skill and are encompassed in the compositions and methods as disclosed herein.

In some embodiments, a type 5 and/or type 8 capsular polysaccharide or oligosaccharide included in a SA-MAPS immunogenic compositions as disclosed herein has a molecular weight of between 20 kDa and 1000 kDa. In some embodiments, the type 5 and/or type 8 and/or type 1 capsular polysaccharide or oligosaccharide of a SA-MAPS immunogenic compositions as disclosed herein has a molecular weight of between 200 kDa and 5000 kDa, or a molecular weight range of between 70 kDa and 300 kDa, or a molecular weight range of between 500 kDa and 2500 kDa.

High molecular weight capsular polysaccharides are able to induce certain antibody immune responses due to a higher valence of the epitopes present on the antigenic surface. The isolation of "high molecular weight capsular polysaccharides" is contemplated for use in the compositions and methods of the present invention. In some embodiments, high molecular weight serotype 5 or 8 capsular polysaccharide can be isolated and purified ranging from 20 kDa to 1000 kDa in molecular weight. In one embodiment, high molecular weight serotype 5 or 8 capsular polysaccharide can be isolated and purified ranging from 50 kDa to 700 kDa in molecular weight, or ranging from 50 kDa to 300 kDa in molecular weight, or ranging from 70 kDa to 300 kDa, or ranging from 90 kDa to 250 kDa, or ranging from 90 kDa to 150 kDa in molecular weight, or ranging from 90 kDa to 120 kDa in molecular weight, or ranging from 80 kDa to 120 kDa in molecular weight. In some embodiments, a type 5 and/or type 8 capsular polysaccharide or oligosaccharide included in a SA-MAPS immunogenic compositions as disclosed herein has a high molecular weight of any of 70 kDa to 100 kDa in molecular weight; 70 kDa to 110 kDa in molecular weight; 70 kDa to 120 kDa in molecular weight; 70 kDa to 130 kDa in molecular weight; 70 kDa to 140 kDa in molecular weight; 70 kDa to 150 kDa in molecular weight; 70 kDa to 160 kDa in molecular weight; 80 kDa to 110 kDa in molecular weight; 80 kDa to 120 kDa in molecular weight; 80 kDa to 130 kDa in molecular weight; 80 kDa to 140 kDa in molecular weight; 80 kDa to 150 kDa in molecular weight; 80 kDa to 160 kDa in molecular weight; 90 kDa to 110 kDa in molecular weight; 90 kDa to 120 kDa in molecular weight; 90 kDa to 130 kDa in molecular weight; 90 kDa to 140 kDa in molecular weight; 90 kDa to 150 kDa in molecular weight; 90 kDa to 160 kDa in molecular weight; 100 kDa to 120 kDa in molecular weight; 100 kDa to 130 kDa in molecular weight; 100 kDa to 140 kDa in molecular weight; 100 kDa to 150 kDa in molecular weight; 100 kDa to 160 kDa in molecular weight; and similar desired molecular weight ranges. Any whole number integer within any of the above ranges is contemplated as an embodiment of the invention.

In one embodiment, the conjugate has a molecular weight of between about 50 kDa and about 5000 kDa in molecular weight. In one embodiment, the conjugate has a molecular weight of between about 200 kDa and about 5000 kDa in molecular weight. In one embodiment, the immunogenic conjugate has a molecular weight of between about 500 kDa and about 2500 kDa. In one embodiment, the immunogenic conjugate has a molecular weight of between about 500 kDa and about 2500 kDa. In one embodiment, the immunogenic conjugate has a molecular weight of between about 600 kDa and about 2800 kDa. In one embodiment, the immunogenic conjugate has a molecular weight of between about 700 kDa and about 2700 kDa. In one embodiment, the immunogenic conjugate has a molecular weight of between about 1000 kDa and about 2000 kDa; between about 1800 kDa and about 2500 kDa; between about 1100 kDa and about 2200 kDa; between about 1900 kDa and about 2700 kDa; between about 1200 kDa and about 2400 kDa; between about 1700 kDa and about 2600 kDa; between about 1300 kDa and about 2600 kDa; between about 1600 kDa and about 3000 kDa. Any whole number integer within any of the above ranges is contemplated as an embodiment of the SA-MAPS immunogenic composition as disclosed herein.

In one embodiment, the serotype 5 or 8 capsular polysaccharide has a degree of O-acetylation between 10-100%. In one embodiment, the degree of O-acetylation is between 50-100%. In one embodiment, the degree of O-acetylation is between 75-100%. In one embodiment, the immunogenic conjugate generates an antibody that is functional as measured by killing bacteria in either an animal efficacy model or via an opsonophagocytic killing assay.

Most clinical isolates of *S. aureus* are encapsulated with either serotypes 5 or 8. Type 5 (CP5) and type 8 (CP8) capsular polysaccharides (CPs) have similar tri-saccharide repeating units comprised of N-acetyl mannosaminuronic acid, N-acetyl L-fucosamine, and N-acetyl D-fucosamine. See Fournier, J. M. et al., Infect. Immun. 45:97-93 (1984) and Moreau, M., et al, Carbohydrate Res. 201:285-297 (1990). The two CPs, which have the same sugars, but differ in the sugar linkages and in sites of O-acetylation, each produce serologically distinct patterns of immunoreactivity. CP5 and CP8 are serologically distinct, and this can be attributed to differences in the linkages between the sugars and in the sites of O-acetylation.

In some embodiments, a type 5 and/or 8 capsular polysaccharide or oligosaccharide included in a SA-MAPS immunogenic compositions as disclosed herein can be O-acetylated. In an embodiment, the degree of O-acetylation of type 5 capsular polysaccharide or oligosaccharide is 10-100%, 20-100%, 30-100%, 40-100%, 50-100%. 60-100%, 70-100%, 80-100%, 90-100%, 50-90%, 60-90%, 70-90% or 80-90%. In an embodiment, the degree of O-acetylation of type 8 capsular polysaccharide or oligosaccharide is 10-100%, 20-100%, 30-100%, 40-100%, 50-100%. 60-100%, 70-100%, 80-100%, 90-100%, 50-90%, 60-90%, 70-90% or 80-90%. In an embodiment, the degree of O-acetylation of type 5 and type 8 capsular polysaccharides or oligosaccharides is 10-100%, 20-100%, 30-100%, 40-100%, 50-100%. 60-100%, 70-100%, 80-100%, 90-100%, 50-90%, 60-90%, 70-90% or 80-90%.

The degree of O-acetylation of the polysaccharide or oligosaccharide can be determined by any method known in the art, for example, by proton NMR (Lemercinier and Jones 1996, Carbohydrate Research 296; 83-96, Jones and Lemercinier 2002, J Pharmaceutical and Biomedical analysis 30; 1233-1247, WO 05/033148 or WO 00/56357). A further commonly used method is that described by Hestrin (1949) J. Biol. Chem. 180; 249-261.

O-acetyl groups can be removed by hydrolysis, for example by treatment with a base such as anhydrous hydrazine (Konadu et al 1994; Infect. Immun. 62; 5048-5054) or treatment with 0.1N NaOH for 1-8 hours. In order to maintain high levels of O-acetylation on type 5 and/or 8 polysaccharide or oligosaccharide, treatments which would lead to hydrolysis of the O-acetyl groups are minimized. For example, treatment at extremes of pH are minimized.

The SA-MAPS immunogenic compositions as disclosed herein comprises, of consists essentially of either type 5 or type 8 polysaccharide or a conjugate of type 5 or type 8 polysaccharide. In some embodiments, the SA-MAPS immunogenic compositions as disclosed herein comprise PNAG, or type 5 or type 8 polysaccharides from *S. aureus*, where each or all can be between 30% and 100% O-acetylated.

In some embodiments, the serotype 5 and/or 8 capsular polysaccharides of the SA-MAPS immunogenic composition as disclosed herein are used to generate antibodies that are functional as measured by the killing of bacteria in an animal efficacy model or an opsonophagocytic killing assay that demonstrates that the antibodies kill the bacteria. Such functionality may not be observed using an assay that monitors the generation of antibodies alone, which is not indicative of the importance of O-acetylation in efficacy.

Capsule Epidemiology

The association of particular capsule serotypes with disease is possible through monitoring of clinical isolates. Of the eight different serotypes of *S. aureus* identified (Karakawa and Vann (1982) only serotypes 1 and 2 are heavily encapsulated, and these are rarely isolated. See Capsular Polysaccharides of *Staphylococcus aureus*, p. 285-293, In J. B. Robbins, J. C. Hill and J. C. Sadoff (ed.), Seminars in infectious disease, vol. 4, Bacterial Vaccines. Thieme Stratton, Inc. New York). Surveys have shown that approximately 85-90% of *S. aureus* clinical isolates express CP5 or CP8 (Arbeit R D, et al., Diagn. Microbiol. Infect. Dis. (1984) April; 2(2):85-91; Karakawa W W, et al., J. Clin. Microbiol. (1985) September; 22(3):445-7; Essawi T, et al., Trop. Med. Int. Health. (1998) July; 3(7):576-83; Na'was T, et al., J. Clin. Microbiol. (1998) 36(2):414-20. Most of CP5 and CP8 non-typeable strains are genetically type 5 or type 8 containing mutations in cap5/8 locus (Cocchiaro, Gomez et al., (2006), Mol. Microbiol. February 59(3):948-960). Capsulation for some strains is lost rapidly within few passages in vitro which is due to a repressive effect of high phosphate concentration in media used in clinical diagnosis on capsule production. It was also reported that non-capsulated isolates recover capsule expression after passing through cows. See Opdebeck, J. P. et al., J. Med. Microbiol. 19:275-278 (1985). Some non-typeable strains become capsule positive under appropriate growth conditions.

CP5 and CP8 Structure

The repeat unit of both CP5 and CP8 is comprised of 2-acetamido-2-deoxy-D-mannuronic acid, 2-acetamido-2-deoxy-L-fucose and 2-acetamido-2-deoxy-D-fucose. See C. Jones et al., Carbohydr. Res. 340:1097-1106 (2005). Although CP5 and CP8 have the same sugar composition, they have been demonstrated to be immunologically distinct. They differ in glycosidic linkages and site of O-acetylation of uronic acid. Strain dependent incomplete N-acetylation of one of the FucNAc residues was observed. See Tzianabos et al., PNAS V98: 9365 (2001).

It is important that the *S. aureus* Capsule Polysaccharide (CP) used in the SA-MAPS immunogenic composition as disclosed herein is immunogenic. The molecular weight of the *S. aureus* capsule polysaccharides is an important consideration, as a high molecular weight capsule polysaccharide can induce certain antibody immune responses due to a higher valency of the epitopes present on the antigenic surface. In some embodiments, a CP8 or CP5 used in a SA-MAPS immunogenic composition as disclosed herein is a high molecular weight capsule polysaccharide type 5 and type 8.

Poly N-Acetylated Glucosamine (PNAG)

PNAG is a polysaccharide intercellular adhesion and is composed of a polymer of β-(1→6)-linked glucosamine, optionally substituted with N-acetyl and/or O-succinyl constituents. This polysaccharide is present in both *S. aureus* and *S. epidermidis* and can be isolated from either source (Joyce et al 2003, Carbohydrate Research 338; 903; Maira-Litran et al 2002, Infect. Imun. 70; 4433). For example, PNAG may be isolated from *S. aureus* strain MN8m (WO 04/43407). The preparation of dPNAG is described in WO 04/43405.

The polysaccharide previously known as poly-N-succinyl-β-(1→6)-glucosamine (PNSG) was recently shown not to have the expected structure since the identification of N-succinylation was incorrect (Maira-Litran et al 2002, Infect. Imun. 70; 4433). Therefore, the polysaccharide formally known as PNSG and now found to be PNAG is also encompassed by the term PNAG.

PNAG may be of different sizes varying from over 400 kDa to between 75 and 400 kDa to between 10 and 75 kDa to oligosaccharides composed of up to 30 repeat units (of (β-(1→6)-linked glucosamine, optionally substituted with N-acetyl and O-succinyl constituents). Any size of PNAG polysaccharide or oligosaccharide may be used in an immunogenic composition of the invention, for example a size of over 40 kDa can be used. Sizing may be achieved by any method known in the art, for instance by microfluidisation, ultrasonic irradiation or by chemical cleavage (WO 03/53462, EP497524, EP497525).

Size ranges of PNAG are for example 40-400 kDa, 50-350 kDa, 40-300 kDa, 60-300 kDa, 50-250 kDa and 60-200 kDa.

PNAG can have different degree of acetylation due to substitution on the amino groups by acetate. PNAG produced in vitro is almost fully substituted on amino groups (95-100%). Alternatively, a deacetylated PNAG can be used having less than 50%, 40%, 30%, 20%, 10% or 5% N-acetylation. Use of a deacetylated PNAG allows opsonic killing of Gram positive bacteria, optionally *S. aureus* and/or *S. epidermidis* (WO 04/43405). In an embodiment, the PNAG has a size between 40 kDa and 300 kDa and is deacetylated so that less than 50%, 40%, 30%, 20%, 10% or 5% of amino groups are N acetylated.

In an embodiment, the PNAG is not O-succinylated or is O-succinylated on less than 25, 20, 15, 10, 5, 2, 1 or 0.1% of residues.

The term deacetylated PNAG (dPNAG) refers to a PNAG polysaccharide or oligosaccharide in which less than 50%, 40%, 30%, 20%, 10% or 5% of the amino groups are acetylated.

As used herein, the term PNAG encompasses both acetylated and deacetylated forms of the saccharide.

In an embodiment, PNAG is deacetylated to form dPNAG, by chemically treating the native polysaccharide. For example, the native PNAG is treated with a basic solution such that the pH rises to above 10. For instance, the PNAG is treated with 0.1-5M, 0.2-4M, 0.3-3M, 0.5-2M, 0.75-1.5M or 1M NaOH, KOH or NH4OH. Treatment is for at least 10 or 30 minutes, or 1, 2, 3, 4, 5, 10, 15 or 20 hours at a temperature of 20-100, 25-80, 30-60 or 30-50 or 35-45° C. dPNAG may be prepared as described in WO 04/43405.

*S. aureus* 336 Antigen

In an embodiment, the SA-MAPS immunogenic composition as disclosed herein can comprise the *S. aureus* 336 antigen described in U.S. Pat. No. 6,294,177, which is incorporated herein in its entirety by reference. The 336 antigen comprises β-linked hexosamine, contains no O-acetyl groups and specifically binds to antibodies to *S. aureus* Type 336 deposited under ATCC 55804.

In an embodiment, the 336 antigen is a polysaccharide which is of native size or alternatively may be sized, for instance by microfluidisation, ultrasonic irradiation or by chemical treatment. The invention also covers oligosaccharides derived from the 336 antigen. The 336 antigen, where included in the immunogenic composition of the invention is optionally conjugated to a carrier protein as described below or are alternatively unconjugated.

Other Immunogenic Polysaccharides

In some embodiments, an immunogenic polysaccharide for use in the SA-MAPS complex as disclosed herein a polysaccharide or oligosaccharide that is not a *S. aureus* polysaccharide. For example, in some embodiments an immunogenic polysaccharide for use in the SA-MAPS complex as disclosed herein can be a pneumococcal polysaccharide, e.g., a capsular polysaccharide from *Streptococcus pneumoniae* from any of the over 93 serotypes of pneumococcus that have been identified to date, for example, including but not limited to serotypes 1, 2, 3, 4, 5, 6A, 6B, 6C, 6D, 7F, 8, 9N, 9V, 10A, 11A, 12F, 14, 15B, 17F, 18C, 19A, 19F, 20, 22F, 23F, and 33F. Additional pneumococcal serotypes may be identified and included in the present SA-MAPS immunogenic composition as described herein. More than one pneumococcal polysaccharide can be included as the polymer backbone of the present immunogenic compositions or in a vaccine comprising the present SA-MAPS composition. In some embodiments, an immunogenic polysaccharide for use in the SA-MAPS complex as disclosed herein is Type 1 capsular polysaccharide (CP1) from *Streptococcus Pneumoniae*.

In some embodiments, an immunogenic polysaccharide for use in the SA-MAPS complex as disclosed herein can comprises *N. meningitidis* capsular polysaccharides from at least one, two, three or four of the serogroups A, C, W, W135, or Y. In some embodiments, an immunogenic polysaccharide for use in the SA-MAPS complex as disclosed herein is selected from the group consisting of: *Salmonella typhi* Vi capsular polysaccharide, pneumococcal capsular polysaccharides, pneumococcal cell wall polysaccharide, *Haemophilus influenzae* Type b (Hibb) capsular polysaccharide, *Haemophili* polysaccharide, Meningococcal polysaccharide, polysaccharides or oligosaccharides from Gram-positive bacteria (e.g., *Staphylococcus aureus* capsular polysaccharide, *Bacillus anthracis* polysaccharide), *Streptococcus* polysaccharides (e.g., Gp A and Gp B), Pseudomonas polysaccharide, fungal polysaccharides (e.g., cryptococcys polysaccharides), viral polysaccharides (e.g., glycoprotein) and other bacterial capsular or cell wall polysaccharides. In some embodiments, an immunogenic polysaccharide is selected from any of the following, dextran, Vi polysaccharide of *Salmonella typhi*, pneumococcal capsular polysaccharide, pneumococcal cell wall polysaccharide (CWPS), meningococcal polysaccharide, *Haemophilus influenzae* type b polysaccharide, or any another polysaccharide of viral, prokaryotic, or eukaryotic origin.

In some embodiments, an immunogenic polysaccharide for use in the SA-MAPS complex as disclosed herein is selected from the group consisting of: *Salmonella typhi* Vi capsular polysaccharides, pneumococcal capsular polysaccharides, pneumococcal cell wall polysaccharides, *Haemophilus influenzae* Type b (Hib) polysaccharides, *Haemophili* polysaccharides, Meningococcal polysaccharides, polysaccharides or oligosaccharides or lipopolysaccharides from Gram-positive bacteria (e.g., *Staphylococcus aureus* capsular polysaccharides, *Bacillus anthracis* polysaccharides), *Streptococcus* polysaccharides (e.g., Gp A and Gp B), Pseudomonas polysaccharides, polysaccharides or oligosaccharides or lipopolysaccharides from Gram-negative bacteria, other bacterial capsular or cell wall polysaccharides, fungal polysaccharides (e.g., cryptococcus polysaccharides), viral polysaccharides (e.g., glycoprotein), or polysaccharides derived from cancer cells.

In some embodiments, an immunogenic polysaccharide for use in the SA-MAPS complex as disclosed herein consists of or comprises an antigenic sugar moiety. For example, in some embodiments, a polysaccharide for use in the methods and immunogenic compositions as disclosed herein is a Vi polysaccharide of *Salmonella typhi*. The Vi capsular polysaccharide has been developed against bacterial enteric infections, such as typhoid fever. Robbins et al., 150 J. Infect. Dis. 436 (1984); Levine et al., 7 Baillieres Clin. Gastroenterol. 501 (1993). Vi is a polymer of α-1→4-galacturonic acid with an N acetyl at position C-2 and variable O-acetylation at C-3. The virulence of *S. typhi* correlates with the expression of this molecule. Sharma et al., 101 PNAS 17492 (2004). The Vi polysaccharide vaccine of *S. typhi* has several advantages: Side effects are infrequent and mild, a single dose yields consistent immunogenicity and efficacy. Vi polysaccharide may be reliably standardized by physicochemical methods verified for other polysaccharide vaccines, Vi is stable at room temperature and it may be administered simultaneously with other vaccines without affecting immunogenicity and tolerability. Azze et al., 21 Vaccine 2758 (2003).

Thus, the Vi polysaccharide of *S. typhi* may be cross-linked to a first affinity molecule as disclosed herein, for attaching at least one antigen to the polysaccharide. In some embodiments, the antigen can be from the same or from another organism, such that the resulting immunogenic composition confers at least some level of immunity against one pathogen, or two different pathogens: if the antigen confers protection against pneumococcus, an immunogenic composition where the polymer scaffold is a Vi polysaccharide can raise an immunogenic response against both *S. typhi* and pneumococci. Other examples include combining sugars from encapsulated bacteria (such as meningococcus, *S. aureus*, pneumococcus, Hib, etc.) and tuberculosis antigens, to provide an immunogenic composition that raises an immune response against two different pathogens.

In some embodiments, a polysaccharide for use in the SA-MAPS complex as disclosed herein is a capsular polysaccharide (CP) or oligosaccharide. In some embodiments, a polysaccharide for use in the SA-MAPS complex as disclosed herein is a noncapsular polysaccharide or oligosaccharide.

Other immunogenic polysaccharide (PS) for use in the SA-MAPS complex as disclosed herein can include bacterial cell wall polysaccharides (CWPS), or carbohydrate antigens of cancers.

In some embodiments, an immunogenic polysaccharide for use in the SA-MAPS complex as disclosed herein that can serve as a backbone for one or more SA-antigens or non-SA antigen types are exemplified in Table 2:

TABLE 2

Example immunogenic polysaccharides for the SA-MAPS backbone and associated example antigens

| Polysaccharide | | Protein Antigens | |
|---|---|---|---|
| | | Number of antigens | Antigen origins |
| Dextran | D90 (60-90 KD) | Two | *Staphylococcus aureus* |
| | D150 (150 KD) | Three | *Staphylococcus aureus* |
| | D270 (270 KD) | Three | *Staphylococcus aureus* |
| | D500 (425-575 KD) | two; three; six | *Staphylococcus aureus* |
| Pneumococcal capsular polysaccharide | Serotype 1 | one, two, three, five | pneumococcus, tuberculosis, *Staphylococcus aureus* |
| | Serotype 3 | Five | pneumococcus, tuberculosis, *Staphylococcus aureus* |
| | Serotype 5 | one; two; three; five | pneumococcus, tuberculosis, *Staphylococcus aureus* |
| | Serotype 6B | Two | Pneumococcus, *Staphylococcus aureus* |
| | Serotype 7 | Three | Pneumococcus, *Staphylococcus aureus* |
| | Serotype 14 | one; two; three; five | pneumococcus, tuberculosis |
| | Serotype 19 | Three | Pneumococcus, *Staphylococcus aureus* |
| *Staphylococcus aureus* | Serotype 5 | one; two; three; five, six | *Staphylococcus aureus* |
| | Serotype 8 | one; two; three; five, six | *Staphylococcus aureus* |
| | PNAG | one; two; three; five, six | *Staphylococcus aureus* |
| | *S. aureus* 336 antigen | one; two; three; five, six | *Staphylococcus aureus* |
| Pneumococcal cell wall polysaccharide | | Five | Pneumococcus, *Staphylococcus aureus* |
| *S. typhi* Vi polysaccharide | | Five | Pneumococcus, *Staphylococcus aureus* |

In some embodiments, an immunogenic polysaccharide for use in the SA-MAPS complex as disclosed herein can comprise additional polymers, for example, polyethylene glycol-based polymers, poly(ortho ester) polymers, polyacryl carriers, PLGA, polyethylenimine (PEI), polyamidoamine (PAMAM) dendrimers, β-amino ester polymers, polyphosphoester (PPE), liposomes, polymerosomes, nucleic acids, phosphorothioated oligonucleotides, chitosan, silk, polymeric micelles, protein polymers, virus particles, virus-like-particles (VLPs) or other micro-particles. See, e.g., El-Sayed et al., *Smart Polymer Carriers for Enhanced Intracellular Delivery of Therapeutic Molecules*, 5 Exp. Op. Biol. Therapy, 23 (2005). Biocompatible polymers developed for nucleic acid delivery may be adapted for use as a backbone herein. See, e.g., BIOCOMPATIBLE POL. NUCL. ACID. DELIV. (Domb et al., eds., John Wiley & Sons, Inc. Hoboken, N.J., 2011).

For example, VLPs resemble viruses, but are non-infectious because they do not contain any viral genetic material. The expression, including recombinant expression, of viral structural proteins, such as envelope or capsid components, can result in the self-assembly of VLPs. VLPs have been produced from components of a wide variety of virus families including Parvoviridae (e.g., adeno-associated virus), Retroviridae (e.g., HIV), and Flaviviridae (e.g., Hepatitis B or C viruses). VLPs can be produced in a variety of cell culture systems including mammalian cell lines, insect cell lines, yeast, and plant cells. Recombinant VLPs are particularly advantageous because the viral component can be fused to recombinant antigens as described herein.

*S. aureus* Antigens

It is well recognized that any single animal model of SA infection is unlikely to adequately represent the pathophysiology of disease in humans; therefore, evaluation of any potential candidate in several models would appear prudent. At the same time, the large number of virulence factors (including polysaccharides, surface proteins, and secreted toxins produced by SA, may provide credence to the idea that multiple, genetically conserved antigens should be included in a candidate vaccine. Finally, a closer examination of mechanisms of immunity to SA in humans may also provide clues for an effective vaccine strategy. Indeed, while humoral immunity plays a leading role in host defense against many bacterial or viral pathogens, it is unlikely that antibodies are the only or even the primary factor for resistance to SA. Patients with B-cell deficiencies do not appear to be at significantly increased risk of SA infections, and individuals with high levels of pre-existing SA-specific antibodies can still get infected by SA. On the other hand, a growing body of literature now suggests that T-cell immunity, the other arm of acquired host defense, plays a critical role in SA defense. Indeed, individuals with suppressed or impaired cellular immunity, caused by high dose prednisone therapy, HIV infection, defective interferon-γ (IFN-γ) production, defective interleukin-17 (IL-17) production, are at very high risk for SA infection and recurrence. Moreover, in murine models, IFN-γ or IL-17A/F deficiency has been shown to induce hyper-susceptibility to SA skin infections, and IL-17A deficiency in mice is also associated with prolonged nasal carriage of SA. Therefore, the inventors have developed a SA-MAPS immunogenic composition that induces both B- and T-cell acquired immunes responses in the organism may provide optimal protection against this organism.

Herein, the inventors have generated a SA-MAPS immunogenic composition comprising containing several conserved SA antigens to elicit a broad range of immune responses. More specifically, the inventors demonstrate a vaccine platform, referred herein as the *Staphylococcus aureus* Multiple-Antigen-Presenting-System (SA-MAPS), which comprises an immunogenic polysaccharide with affinity-coupled complexes of SA antigens that can induce broad B- and T-cell responses. The immune response generated with the SA-MAPS vaccine was compared to a multi-component SA subunit vaccine using a conventional approach (i.e., immunization with purified proteins alone, and not attached to an immunogenic polysaccharide). The inventors demonstrated the immunogenicity of these two vaccines (the antigens alone, or antigens as part of the SA-MAPS complex) in mice, compared their protective efficacy in SA sepsis infection, dermonecrosis infection, skin abscess infection and gastrointestinal (GI) colonization models, and finally, studied the role of antigen-specific antibodies and T-cell immunity against different types of SA infection or colonization An immunogenic SA antigen for use in the immunogenic compositions and methods described herein can be any SA antigen, including, but not limited to pathogenic peptides, toxins, toxoids, subunits thereof, or combinations thereof. In some embodiments, a SA antigen, which in some embodiments, is fused to the complementary affinity molecule, e.g., a biotin-binding protein such as rhizavidin as disclosed herein, can be any SA. antigen, peptide, polypeptide, polysaccharide, expressed by *Staphylococcus aureus* bacterium.

In some embodiments, the SA-MAPS comprises at least one or more SA antigens, where the SA antigen is an antigenic protein or polypeptide, and can be selected from any of the group of: hemolysin (HI) (e.g., hemolysin a or Hla), Clumping factor A (ClfA), Clumping factor B (ClfB), serine-aspirate repeat protein D (SdrD), Iron regulator surface protein A (IsdA) and Iron regulator surface protein B (IsdB), or a an antigenic fragment or portion thereof. In some embodiments, the SA-MAPS immunogenic composition as disclosed herein comprises one or more peptide or polypeptide fragments of these proteins, as long as the protein fragment is antigenic, and/or comprises one or more epitopes to induce an immune response.

Exemplary SA antigens for use in the SA-MAPS composition as disclosed herein can be, for example, but are not limited to: Hla209(27-319), ClfA (221-559), ClfB (203-542), SdrD (246-682), IsdA (47-324), IsdB (48-447).

In some embodiments, a SA-MAPS immunogenic composition as disclosed herein comprises at least 2, or at least 3, or at least 4, or at least 5, or all 6 peptide or polypeptide SA-antigens of Hla209(27-319), ClfA (221-559), ClfB (203-542), SdrD (246-682), IsdA (47-324), IsdB (48-447), or proteins or peptides of at least 85% sequence identity thereto. It is envisioned that any of the above listed SA antigens can be substituted for a different SA peptide or polypeptide antigen known to one of ordinary skill in the art. Exemplary SA antigens can be any peptide or polypeptide comprising at least part of the serine-aspirate repeat protein E (SdrE) protein, Leukotoxin D (LukD) protein, or Leukotoxin E (LukE) protein, provided that the any peptide or polypeptide is immunogenic, or is antigenic. Other SA antigens can be used, and are disclosed herein.

Non-Hemolytic Hemolysin α (Hla)

Hemolysin α (Hla) is a secreted pore-forming toxin and an essential virulence factor of MRSA in a mouse model of *S. aureus* pneumonia. The level of Hla expression by independent *S. aureus* strains directly correlates with their virulence. In some embodiments, the SA antigen is a non-hemolytic Hla, e.g., Hla(209) as disclosed herein.

Hemolysins are exotoxins produced by bacteria that cause lysis of red blood cells. While highly immunogenic, their use in vaccines is limited because they cause lysis of red blood cells. Accordingly, in another aspect, provided herein are variants of *Staphylococcus aureus* alpha-hemolysin (Hla) as the SA antigen for use in the SA-MAPS composition as disclosed herein, as well as it in a fusion construct with biotin-binding protein and its uses. These variants, designated herein as "mHla," have substantially non-hemolytic, i.e., have substantially low hemolytic activity. As used herein, the phrase "substantially non-hemolytic" means an inability to lyse red blood cells at equivalent titers of wild-type Hla. The term "wild-type Hla" is accorded the usual definition associated with such phrase, i.e., Hla that is naturally secreted by a capable bacterial source. "Wild-type Hla," by definition, does not include, e.g., Hla fusion products derived via recombinant DNA techniques. In some embodiments, hemolytic activity of mHla is at least 5%, at least 10%, at least 15%, at least 20%, at least 20%, at least 30%, at least 30%, at least 35%, least 40%, at least 45%, at least 50%, at least 55%, at least 60%, at least 65%, at least 70%, at least 75%, at least 80%, at least 85%, at least 90%, at least 95% lower than an equivalent titers of wild-type Hla. In some embodiments, the mHla has no detectable hemolytic activity. The inventors have also discovered that hemolytic activity of mHla can be further reduced by linking the mHla with a biotin-binding protein, e.g., a rhizavidin biotin-binding protein as disclosed herein. Accordingly, the present disclosure also describes fusion proteins comprising an mHla protein and a biotin-binding protein.

In some embodiments, a mHla is where the tripeptide DRD209-211 is substituted with a tri-alanine peptide (AAA) in the wild-type Hla, and is referred to herein as Hla209 and comprises the following amino acid sequence:

(SEQ ID NO: 16)
ADSDINIKTGTTDIGSNTTVKTGDLVTYDKENGMHKKVFYSFIDDKNHNKK

LLVIRTKGTIAGQYRVYSEEGANKSGLAWPSAFKVQLQLPDNEVAQISDYY

PRNSIDTKEYMSTLTYGFNGNVTGDDTGKIGGLIGANVSIGHTLKYVQPDF

KTILESPTDKKVGWKVIFNNMVNQNWGPYAAASWNPVYGNQLFMKTRNGSM

KAADNFLDPNKASSLLSSGFSPDFATVITMDRKASKQQTNIDVIYERVRDD

YQLHWTSMWKGTNTKDKWIDRSSERYKIDWEKEEMTN;

In some embodiments, a SA antigen for use in a SA-MAPS immunogenic composition as disclosed herein comprises SEQ ID NO: 16, or a protein or peptide fragment of at least 50 amino acids of SEQ ID NO: 16, or a protein or peptide having at least 85% amino acid identity to SEQ ID NO: 16, where Asp-Arg-Asp (DRD) is mutated to Ala-Ala-Ala (AAA).

In another embodiment, a non-hemolytic Hla can be created where residue W205 or W213 is substituted with alanine (A), and comprise the following sequences, respectively:

Hla W205A:

(SEQ ID NO: 17)
ADSDINIKTGTTDIGSNTTVKTGDLVTYDKENGMHKKVFYSFIDDKNHNKK

LLVIRTKGTIAGQYRVYSEEGANKSGLAWPSAFKVQLQLPDNEVAQISDYY

PRNSIDTKEYMSTLTYGFNGNVTGDDTGKIGGLIGANVSIGHTLKYVQPDF

KTILESPTDKKVGWKVIFNNMVNQNAGPYDRDSWNPVYGNQLFMKTRNGSM

-continued
KAADNFLDPNKASSLLSSGFSPDFATVITMDRKASKQQTNIDVIYERVRDD

YQLHWTSTNWKGTNTKDKWIDRSSERYKIDWEKEEMTN;

In some embodiments, a SA antigen for use in a SA-MAPS immunogenic composition as disclosed herein comprises SEQ ID NO: 17, or a protein or peptide fragment of at least 50 amino acids of SEQ ID NO: 17, or a protein or peptide having at least 85% amino acid identity to SEQ ID NO: 17, where amino acid W205 is mutated to Ala (W205A).

Hla W213A:

(SEQ ID NO: 18)
ADSDINIKTGTTDIGSNTTVKTGDLVTYDKENGMHKKVFYSFIDDKNHNKK

LLVIRTKGTIAGQYRVYSEEGANKSGLAWPSAFKVQLQLPDNEVAQISDYY

PRNSIDTKEYMSTLTYGFNGNVTGDDTGKIGGLIGANVSIGHTLKYVQPDF

KTILESPTDKKVGWKVIFNNMVNQNWGPYDRDSANPVYGNQLFMKTRNGSM

KAADNFLDPNKASSLLSSGFSPDFATVITMDRKASKQQTNIDVIYERVRDD

YQLHWTSTNWKGTNTKDKWIDRSSERYKIDWEKEEMTN;

In some embodiments, a SA antigen for use in a SA-MAPS immunogenic composition as disclosed herein comprises SEQ ID NO: 18, or a protein or peptide fragment of at least 50 amino acids of SEQ ID NO: 18, or a protein or peptide having at least 85% amino acid identity to SEQ ID NO: 18, where amino acid W205 is mutated to Ala (W213A).

A non-toxic non-hemolytic mHla protein can be expressed and purified in an E. coli expression system, and the mutants can be made by point mutation using quick change mutagenesis by a person of ordinary skill in the art. For example, the nucleotide sequence of a nucleic acid encoding the wild-type Hla can be changed to replace a given amino acid in the wild-type Hla to another amino acid.

In some embodiments, the Hla variants described herein, e.g., mHla, such as, Hla209 are ligands for Toll Like Receptors (TLRs), and as such can be used as TLR ligands. For example, the mHla variants can be used in a SA-MAPS immunogenic composition as disclosed herein can induce TLR2 stimulation, e.g., for inducing immunogenicity to other antigens/pathogens.

In some embodiments, a SA-MAPS immunogenic composition as disclosed herein comprising a mHla SA antigen can elicit an immunological response—local or systemic. The response can, but need not, be protective. Accordingly, a non-hemolytic mutant of Hla described herein can be as an antigen, adjuvant, or a co-stimulator in an immunological, immunogenic, or vaccine composition.

In some embodiments, the antigenic protein is a non-hemolytic Hla described herein.

In some embodiments, the non-hemolytic Hla protein is a fusion protein comprising a biotin-binding protein and a non-hemolytic Hla described herein.

In alternative embodiments, the Hla antigen is a mutant mHla of H35L (referred to as SEQ ID NO: 5 in US patent application 2011/0274720 which is incorporated herein in its entirety by reference), which cannot form pores (Menzies, B. E., et al., 1996. Passive immunization with antiserum to a nontoxic alpha-toxin mutant from *Staphylococcus aureus* is protective in a murine model. Infect Immun 64:1839-41; Jursch, R., et al., 1994. Histidine residues near the N terminus of staphylococcal alpha-toxin as reporters of regions that are critical for oligomerization and pore formation. Infect Immun 62(6): 2249-56), was shown to generate antigen-specific immunoglobulin G responses and to afford protection against staphylococcal pneumonia. Transfer of Hla-specific antibodies protects naive animals against *S. aureus* challenge and prevents the injury of human lung epithelial cells during infection (Bubeck Wardenburg, J., A. M. Palazzolo-Ballance, M. Otto, O, Schneewind, and F. R. DeLeo. 2008. Panton-Valentine leukocidin is not a virulence determinant in murine models of community-associated methicillin-resistant *Staphylococcus aureus* disease. J Infect Dis 198:1166-70). To be used as a vaccine, the H35L mutation in Hla is required to eliminate toxicity of the protein (Menzies, B. E., and D. S. Kernodle. 1994. Site-directed mutagenesis of the alpha-toxin gene of *Staphylococcus aureus*: role of histidines in toxin activity in vitro and in a murine model. Infect Immun 62:1843-7).

In one embodiment, a SA-MAPS composition may include a polypeptide, peptide, or protein that is or is at least 70%, 75%, 80%, 85%, 90%, 95%, 96%, 97%, 98%, or 99% identical or similar to a mHla protein. In certain aspects the mHla protein will have all, or part of the amino acid sequence of SEQ ID NO: 16, e.g., will comprise at least 50, or at least 60, or at least 70, or at least 80, or at least 90, or at least 100, or at least 120, or at least 140, or at least 160, or at least 180, or at least 200, or at least 220 or at least 240, or at least 260, or at least 280 amino acids of SEQ ID NO: 16. In one embodiment, a SA antigen of the SA-MAPS immunogenic composition is a polypeptide, peptide, or protein that is or is at least 70%, 75%, 80%, 85%, 90%, 95%, 96%, 97%, 98%, or 99% identical or similar to SEQ ID NO: 16.

The term "Hla protein" refers to a protein that includes isolated wild-type Hla polypeptides from *staphylococcus* bacteria and segments thereof, as well as variants that stimulate an immune response against *staphylococcus* bacteria Hla proteins.

Clumping Factor A (ClfA)

Clumping factor A (ClfA) is a *S. aureus* surface protein associated with binding to host matrix proteins via a fibrinogen binding site, and is functions as a cell wall-associated adhesin protein that mediates staphylococcal binding to fibrinogen and platelets. It is expressed on the cell surface of the bacterium, where it is thought to promote pathogenesis by binding to the fibrinogen and fibrin that is deposited at the site of tissue damage. ClfA is well conserved, and even the most diverse form (~85% identity) exhibits extensive cross-reactivity to both monoclonal and polyclonal antibodies.

ClfA is a member of a family of proteins containing the carboxyl terminal LPXTG (SEQ ID NO: 19) motif that enables the protein to become covalently linked to the cell surface. ClfA also belongs to another family of proteins (Microbial Surface Components Recognizing Adhesive Matrix Molecule, or MSCRAMMs) that are associated with binding host proteins such as fibrinogen (bound by ClfA), the fibronectin binding proteins (FnbA and FnbB), the collagen binding protein (Cna) and others. These proteins all share the amino terminal signal sequence that mediates transport to the cell surface. The MSCRAMMs also include an A-domain that is the functional region containing the active site for ligand binding (e.g., fibrinogen, fibronectin, elastin, keratin). The A-domain is followed by a region composed of serine aspartate repeats (SD repeat), which is thought to span the peptidoglycan layer. The SD repeat is followed by a membrane-spanning region that includes the LPXTG (SEQ ID NO: 19) motif for covalent linkage of the protein to peptidoglycan. ClfA is described in U.S. Pat. No. 6,008,341.

Thus, ClfA is a reasonable candidate for a component of a vaccine against *S. aureus*. However, given the structural instability of ClfA, a formulation of ClfA is problematic since it can readily degrade over time in storage.

Full-length ClfA comprises several regions and domains: an N-terminal secretory domain ("S" domain); followed by a ligand-binding A region, which contains three domains (N1, N2, which contains an EF-hand motif, and N3); followed by an R region, which contains serine-aspartate dipeptide repeats; followed by a cell wall-binding region ("W" region) containing an LPXTG motif; a hydrophobic membrane-spanning domain ("M" region); and a charged C-terminus ("C" region) containing positively charged amino acids. The N1 region contains a protease-sensitive site. Much of the instability of ClfA is attributed to the clipping of ClfA at N1, which results in fragments containing N1 and N2N3.

The structure and function of ClfA is disclosed in U.S. Patent Application Publication No. 2007/0087014A1 (Pavliak et al, Apr. 19, 2007), and U.S. Pat. No. 6,008,341 which are incorporated herein by reference in their entirety.

ClfA contains a protease resistant domain which is used for immunization. Passive immunization of mice with anti-ClfA and anti CP5 antibodies effectively sterilized mammary glands in mammary gland infection model (Tuchscherr, L. P., F. R. Buzzola, L. P. Alvarez, J. C. Lee, and D. O. Sordelli. 2008. Antibodies to capsular polysaccharide and clumping factor A prevent mastitis and the emergence of unencapsulated and small-colony variants of *Staphylococcus aureus* in mice. Infect Immun 76: 5738-44).

The ligand binding region of ClfA comprising N1N2N3 of the A domain spans amino acids 40-559. The N domains of ClfA have been assigned as follows: N1 encompasses residues 45-220; N2 encompasses residues 229-369; and N3 encompasses residues 370-559. See Deivanayagam et al. EMBO J. 21:6660-6672 (2002). For ease of reference the N1N2N3 domains may be referred to as N123, likewise N2N3 may be referred to as N23. In preparations of recombinant N1N2N3, the N1 domain has been found to be protease sensitive and is easily cleaved or hydrolyzed to leave the N2N3 as a stable ligand binding recombinant fragment. See Deivanayagam et al. EMBO J. 21:6660-6672 (2002). The crystal structure of the fibrinogen binding N2N3 fragment of ClfA A domain, revealed that both N2 and N3 are dominated by anti-parallel beta strands. In addition to the anti-parallel beta strands, the N2 domain contains a single turn alpha helix and two $3_{10}$ helices and the N3 domain contains three $3_{10}$ helices. See Deivanayagam et al. EMBO J. 21:6660-6672 (2002). Sequence alignment of N2 and N3 reveals only 13% sequence identity and 36% sequence similarity over their lengths. See Deivanayagam et al. EMBO J. 21:6660-6672 (2002). The topology of the N2 and N3 domains are similar to the classic IgG fold and have been proposed to be novel variants of the IgG fold. See Deivanayagam et al. EMBO J. 21:6660-6672 (2002).

ClfA Sequence: The gene for clumping factor protein A, designated ClfA, has been cloned, sequenced and analyzed in detail at the molecular level (McDevitt et al., Mol. Microbiol. 11: 237-248 (1994); McDevitt et al., Mol. Microbiol. 16:895-907 (1995)).

In some embodiments, the ClfA antigen for use in the SA-MAPS immunogenic composition as disclosed herein comprises a polypeptide or peptide comprising at least part of SEQ ID NO: 2, which corresponds to the full length ClfA mature protein from *S. aureus* strain USA300 (without the signal sequence).

```
                                           (SEQ ID NO: 2)
SENSVTQSDSASNESKSNDSSSVSAAPKTDDTNVSDTKTSSNTNNGETSVA

QNPAQQETTQSSSTNATTEETPVTGEATTTTNQANTPATTQSSNTNAEEL

VNQTSNETTFNDTNTVSSVNSPQNSTNAENVSTTQDTSTEATPSNNESAPQ

STDASNKDVVNQAVNTSAPRMRAFSLAAVAADAPAAGTDITNQLTNVTVGI

DSGTTVYPHQAGYVKLNYGFSVPNSAVKGDTFKITVPKELNLNGVTSTAKV

PPIMAGDQVLANGVIDSDGNVIYTFTDYVNTKDDVKATLTMPAYIDPENVK

KTGNVTLATGIGSTTANKTVLVDYEKYGKEYNLSIKGTIDQIDKTNNTYRQ

TTYVNPSGDNVIAPVLTGNLKPNTDSNALIDQQNTSIKVYKVDNAADLSES

YFVNPENFEDVTNSVNITFPNPNQYKVEFNTPDDQITTPYIVVVNGHIDPN

SKGDLALRSTLYGYNSNIIWRSMSWDNEVAFNNGSGSGDGIDKPVVPEQPD

EPGEIEPIPEDSDSDPGSDSGSDSNSDSGSDSGSDSTSDSGSDSASDSDSA

SDSDSASDSDSASDSDSASDSDSDNDSDSDSDSDSDSDSDSDSDSDSDSDS

DSDSDSDSDSDSDSDSDSDSDSDSDSDSDSDSDSDSDSDSDSDSDSDSDSD

SDSDSDSDSDSDSDSDSDSDSDSDSDSDSDSDSDSDSDSDSDSDSDSDSDS

DSDSDSDSDSDSASDSDSDSDSDSDSDSDSDSDSDSDSDSDSDSDSDSDSD

SDSESDSDSESDSDSDSDSDSDSDSDSDSDSASDSDSGSDSDSSSDSDS

ESDSNSDSESGSNNNVVPPNSPKNGTNASNKNEAKDSKEPLPDTGSEDEAN

TSLIWGLLASIGSLLLFRRKKENKDKK
```

In some embodiments, the ClfA antigen for use in the SA-MAPS immunogenic composition as disclosed herein is ClfA (221-559) (SEQ ID NO: 3), or a fragment or protein of at least 85% amino acid sequence identity thereto. SEQ ID NO: 3 has the following amino acid sequence:

```
                                            (SEQ ID NO: 3)
VAADAPAAGT DITNQLTNVT VGIDSGTTVY PHQAGYVKLN

YGFSVPNSAV KGDTFKITVP KELNLNGVTS TAKVPPIMAG

DQVLANGVID SDGNVIYTFT DYVNTKDDVK ATLTMPAYID

PENVKKTGNV TLATGIGSTT ANKTVLVDYE KYGKFYNLSI

KGTIDQIDKT NNTYRQTIYV NPENFEDVTN SVNITFPNPN

QYKVEFNTPD DQITTPYIVV VNGHIDPNSK GDLALRSTLY

GYNSNIIWRS MSWDNEVAFN NGSGSGDGID KPVVPEQPDE

PGEIEPIPE
```

In one embodiment, a SA-MAPS composition may include a polypeptide, peptide, or protein that is or is at least 70%, 75%, 80%, 85%, 90%, 95%, 96%, 97%, 98%, or 99% identical or similar to a ClfA of SEQ ID NO: 2 or SEQ ID NO: 3. In certain aspects a ClfA antigen peptide or polypeptide will have all, or part of the amino acid sequence of SEQ ID NO: 3, e.g., will comprise at least 50, or at least 60, or at least 70, or at least 80, or at least 90, or at least 100, or at least 120, or at least 140, or at least 160, or at least 180, or at least 200, or at least 220 or at least 240 amino acids of SEQ ID NO: 2 or SEQ ID NO: 3. In one embodiment, a ClfA antigen peptide or polypeptide present in the SA-MAPS immunogenic composition is a polypeptide, peptide, or protein that is or is at least 70%, 75%, 80%, 85%, 90%, 95%, 96%, 97%, 98%, or 99% identical or similar to SEQ ID NO: 2.

In alternative embodiments, a ClfA antigen for use in the SA-MAPS immunogenic composition as disclosed herein is a protein or peptide having an amino acid sequence of ClfA from 111 *S. aureus* disease-causing isolates disclosed in Table 10 of U.S. Pat. No. 8,568,735, which is incorporated herein in its entirety by reference. In some embodiments, a ClfA antigen for use in the SA-MAPS immunogenic composition as disclosed herein is a ClfA variant of SEQ ID NO: 61-108, or a mutant ClfA from *S. aureus* strain PFESA0237 of SEQ ID NO: 130, 131 and 123 as disclosed in U.S. Pat. No. 8,568,735, and are encompassed for use in the SA-MAPS immunogenic composition as disclosed herein.

The amino acid sequence of the full length (including the signal sequence) wild type ClfA from *S. aureus* strain PFESA0237 is disclosed as SEQ ID NO: 130 in U.S. Pat. No. 8,568,735. SEQ ID NO: 130 has a tyrosine at position 338, which is changed to an alanine in the mutated form of ClfA (mClfA). The full length gene encoding the wild type ClfA from *S. aureus* strain PFESA0237, comprising the N123 region, the repeat region and the anchor region is disclosed as SEQ ID NO: 131 in U.S. Pat. No. 8,568,735, and the amino acid sequence of the mClfA (Y338A) id disclosed as SEQ ID NO: 123 in U.S. Pat. No. 8,568,735. However, it should be noted that the change from a tyrosine to an alanine, which occurs in the wild type ClfA at position 338 of SEQ ID NO: 130, and which is designated as Y338A, is shown in the mutated form of ClfA, in SEQ ID NO: 123 at position 310. Furthermore, the mutated form of ClfA shown in the amino acid sequence of SEQ ID NO: 123 is the mature form of ClfA without the signal sequence, thus accounting for the difference in position of this mutation between SEQ ID NO: 130 and SEQ ID NO: 123.

The term "ClfA protein" refers to a protein that includes isolated wild-type ClfA polypeptides from *staphylococcus* bacteria and segments thereof, as well as variants that stimulate an immune response against *staphylococcus* bacteria ClfA proteins.

Clumping Factor B (ClfB)

Clumping factor B (ClfB) is a *S. aureus* protein having fibrinogen binding activity and triggers *S. aureus* to form clumps in the presence of plasma. ClfB is an MSCRAMM protein and displays the characteristic MSCRAMM domain organization including an A-domain that is the functional region containing the active site for ligand binding (e.g., fibrinogen, fibronectin, elastin, keratin). The A-domain is followed by a region composed of serine aspartate repeats (SD repeat), which is thought to span the peptidoglycan layer. The SD repeat is followed by a membrane-spanning region that includes the LPXTG (SEQ ID NO: 19) motif for covalent linkage of the protein to peptidoglycan. ClfB is described in WO 99/27109 and in U.S. Pat. Nos. 6,680,195 and 8,568,735, which are incorporated herein in their entirety by reference.

The internal organization of ClfB N-terminal A domain is very similar organization as found in ClfB. The A domain is composed of three subdomains N1, N2, and N3. The ligand binding region of ClfB comprising N1N2N3 of the A domain (FIG. 1) spans amino acids 44-585. For ease of reference the N1N2N3 domains may be referred to as N123, likewise N2N3 may be referred to as N23. The N domains of ClfB have been assigned as follows: N1 encompasses residues 44-197; N2 encompasses residues 198-375; and N3 encompasses residues 375-585. In ClfA, the crystal structure of the A domain was found to have a unique version of the immunoglobulin fold and by analogy the same may be speculated to be the case for ClfB. See Deivanayagam et al., EMBO J. 21:6660-6672 (2002). Even though organization of the A domains of ClfB and ClfA are similar, sequence identity is only 26%, See Ni Eidhin et al., Mol. Microbiol. 30:245-257 (2002).

ClfB Sequence: The gene encoding ClfB is classified as a core adhesion gene. In some embodiments, the ClfB antigen for use in the SA-MAPS immunogenic composition as disclosed herein comprises a polypeptide or peptide comprising at least part of SEQ ID NO: 4, which corresponds to the full length ClfB mature protein from *S. aureus* strain USA300 (without the signal sequence).

```
                                              (SEQ ID NO: 4)
SEQSNDTTQSSKNNASADSEKNNMIETPQLNTTANDTSDISANTNSANVDS

TTKPMSTQTSNTTTTEPASTNETPQPTAIKNQATAAKMQDQTVPQEANSQV

DNKTTNDANSIATNSELKNSQTLDLPQSSPQTISNAQGTSKPSVRTRAVRS

LAVAEPVVNAADAKGTNVNDKVTASNFKLEKTTFDPNQSGNTFMAANFTVT

DKVKSGDYFTAKLPDSLTGNGDVDYSNSNNTMPIADIKSTNGDVVAKATYD

ILTKTYTFVFTDYVNNKENINGQFSLPLFTDRAKAPKSGTYDANINIADEM

FNNKITYNYSSPIAGIDKPNGANISSQIIGVDTASGQNTYKQTVFVNPKQR

VLGNTWVYIKGYQDKIEESSGKVSATDTKLRIFEVNDISKLSDSYYADPND

SNLKEVTDQFKNRIYYEHPNVASIKFGDITKTYVVLVEGHYDNTGKNLKTQ

VIQENVDPVTNRDYSIFGWNNENVVRYGGGSADGDSAVNPKDPTPGPPVDP

EPSPDPEPEPSPDPDPDSDSDSDSGSDSDSGSDSDSESDSDSDSDSDSDSD

SDSESDSDSESDSDSDSDSDSDSDSDSDSDSDSDSDSDSDSDSDSESDSDS

ESDSESDSDSDSDSDSDSDSDSDSDSDSDSDSDSDSDSDSDSDSDSDSDSD

SDSDSDSDSDSDSDSDSDSDSDSDSDSDSDSDSDSDSDSDSDSDSDSDSDS

DSDSDSDSDSDSDSDSDSDSDSDSDSDSDSDSDSDSDSDSDSDSDSDSDSD

SDSDSDSDSDSDSDSRVTPPNNEQKAPSNPKGEVNHSNKVSKQHKTDAL

PETGDKSENTNATLFGAMALLGSLLLFRKRKQDHKEKA
```

In some embodiments, the ClfB antigen for use in the SA-MAPS immunogenic composition as disclosed herein is ClfB (203-542) (SEQ ID NO: 5), or a fragment or protein of at least 85% amino acid sequence identity thereto. SEQ ID NO: 5 has the following amino acid sequence:

```
                                              (SEQ ID NO: 5)
PVVNAADAKGTNVNDKVTASNFKLEKTTFDPNQSGNTFMAANFTVTDKVKS

GDYFTAKLPDSLTGNGDVDYSNSNNTMPIADIKSTNGDVVAKATYDILTKT

YTFVFTDYVNNKENINGQFSLPLFTDRAKAPKSGTYDANINIADEMFNNKI

TYNYSSPIAGIDKPNGANISSQIIGVDTASGQNTYKQTVFVNPKQRVLGNT

WVYIKGYQDKIEESSGKVSATDTKLRIFEVNDISKLSDSYYADPNDSNLKE

VTDQFKNRIYYEHPNVASIKFGDITKTYVVLVEGHYDNTGKNLKTQVIQEN

VDPVTNRDYSIFGWNNENVVRYGGGSADGDSAVN
```

In one embodiment, a SA-MAPS composition may include a polypeptide, peptide, or protein that is or is at least 70%, 75%, 80%, 85%, 90%, 95%, 96%, 97%, 98%, or 99% identical or similar to a ClfB of SEQ ID NO: 4 or SEQ ID NO: 5. In certain aspects a ClfB antigen peptide or polypeptide will have all, or part of the amino acid sequence of SEQ ID NO: 5, e.g., will comprise at least 50, or at least 60, or at least 70, or at least 80, or at least 90, or at least 100, or at least 120, or at least 140, or at least 160, or at least 180, or at least 200, or at least 220 or at least 240 amino acids of SEQ ID NO: 4 or SEQ ID NO: 5. In one embodiment, a ClfB antigen peptide or polypeptide present in the SA-MAPS immunogenic composition is a polypeptide, peptide, or protein that is or is at least 70%, 75%, 80%, 85%, 90%, 95%, 96%, 97%, 98%, or 99% identical or similar to SEQ ID NO: 5.

In alternative embodiments, a ClfB antigen for use in the SA-MAPS immunogenic composition as disclosed herein is a protein or peptide having an amino acid sequence of one the ClfB proteins sequenced from 92 strains of *S. aureus* associated with multiple disease states, which are disclosed in Table 11 of U.S. Pat. No. 8,568,735. Other ClfB antigens not identified herein are disclosed encompassed for use in the SA-MAPS immunogenic composition, provided they are antigenic.

The term "ClfB protein" refers to a protein that includes isolated wild-type ClfB polypeptides from *staphylococcus* bacteria and segments thereof, as well as variants that stimulate an immune response against *staphylococcus* bacteria ClfB proteins.

Serine-Aspirate Repeat Protein D (SdrD)

SdrD Sequence: In some embodiments, the SdrD antigen for use in the SA-MAPS immunogenic composition as disclosed herein comprises a polypeptide or peptide comprising at least part of SEQ ID NO: 6, which corresponds to the full length SdrD mature protein (aa53-1831) from *S. aureus* strain USA300 (without the signal sequence).

```
                                          (SEQ ID NO: 6)
AESTNKELNEATTSASDNQSSDKVDMQQLNQEDNTKNDNQKEMVSSQGNET

TSNGNKLIEKESVQSTTGNKVEVSTAKSDEQASPKSTNEDLNTKQTISNQE

ALQPDLQENKSVVNVQPTNEENKKVDAKTESTTLNVKSDAIKSNDETLVDN

NSNSNNENNADIILPKSTAPKRLNTRMRIAAVQPSSTEAKNVNDLITSNTT

LTVVDADKNNKIVPAQDYLSLKSQITVDDKVKSGDYFTIKYSDTVQVYGLN

PEDIKNIGDIKDPNNGETIATAKHDTANNLITYTFTDYVDRFNSVQMGINY

SIYMDADTIPVSKNDVEFNVTIGNTTTKTTANIQYPDYVVNEKNSIGSAFT

ETVSHVGNKENPGYYKQTIYVNPSENSLTNAKLKVQAYHSSYPNNIGQINK

DVTDIKIYQVPKGYTLNKGYDVNTKELTDVTNQYLQKITYGDNNSAVIDEG

NADSAYVVMVNTKFQYTNSESPTLVQMATLSSTGNKSVSTGNALGFTNNQS

GGAGQEVYKIGNYVWEDTNKNGVQELGEKGVGNVTVTVFDNNTNTKVGEAV

TKEDGSYLIPNLPNGDYRVEFSNLPKGYEVTPSKQGNNEELDSNGLSSVIT

VNGKDNLSADLGIYKPKYNLGDYVWEDTNKNGIQDQDEKGISGVTVTLKDE

NGNVLKTVTTDADGKYKFTDLDNGNYKVEFTTPEGYTPTTVTSGSDIEKDS

NGLTTTGVINGADNMTLDSGFYKTPKYNLGNYVWEDTNKDGKQDSTEKGIS

GVTVTLKNENGEVLQTTKTDKDGKYQFTGLENGTYKVEFETPSGYTPTQVG

SGTDEGIDSNGTSTTGVIKDKDNDTIDSGFYKPTYNLGDYVWEDTNKNGVQ

DKDEKGISGVTVTLKDENDKVLKTVTTDENGKYQFTDLNNGTYKVEFETPS

GYTPTSVTSGNDTEKDSNGLTTTGVIKDADNMTLDSGFYKTPKYSLGDYVW
```

```
-continued
YDSNKDGKQDSTEKGIKDVKVTLLNEKGEVIGTTKTDENGKYCEDNLDSGK

YKVIFEKPAGLTQTGTNTTEDDKDADGGEVDVTITDHDDFTLDNGYYEEET

SDSDSDSDSDSDSDSDRDSDSDSDSDSDSDSDSDSDSDSDSDSDRDSDSDS

DSDSDSDSDSDSDSDSDSDSDSDSDSDSDSDSDSDSDSDSDSDSDSDSDSD

SDSDSDSDSDSDSDSDSDSDSDSDSDSDSDSDSDSDSDSDSDSDSDSDSDS

DSDSDSDSDSDSDSDSDSDSDSDSDSDSDSDSDSDSDSDSDSDAGKHTP

VKPMSTTKDHHNKAKALPETGNENSGSNNATLFGGLFAALGSLLLFGRRKK

QNK
```

In some embodiments, the SdrD antigen for use in the SA-MAPS immunogenic composition as disclosed herein is SdrD (246-682) (SEQ ID NO: 7), or a fragment or protein of at least 85% amino acid sequence identity thereto. SEQ ID NO: 7 has the following amino acid sequence:

```
                                          (SEQ ID NO: 7)
NVNDLITSNTTLTVVDADKNNKIVPAQDYLSLKSQITVDDKVKSGDYFTIK

YSDTVQVYGLNPEDIKNIGDIKDPNNGETIATAKHDTANNLITYTFTDYVD

RFNSVQMGINYSIYMDADTIPVSKNDVEFNVTIGNTTTKTTANIQYPDYVV

NEKNSIGSAFTETVSHVGNKENPGYYKQTIYVNPSENSLTNAKLKVQAYHS

SYPNNIGQINKDVTDIKIYQVPKGYTLNKGYDVNTKELTDVTNQYLQKITY

GDNNSAVIDFGNADSAYVVMVNTKFQYTNSESPTLVQMATLSSTGNKSVST

GNALGFTNNQSGGAGQEVYKIGNYVWEDTNKNGVQELGEKGVGNVTVTVFD

NNTNTKVGEAVTKEDGSYLIPNLPNGDYRVEFSNLPKGYEVTPSKQGNNEE

LDSNGLSSVITVNGKDNLSADLGIYKPKY
```

In one embodiment, a SA-MAPS composition may include a polypeptide, peptide, or protein that is or is at least 70%, 75%, 80%, 85%, 90%, 95%, 96%, 97%, 98%, or 99% identical or similar to a SdrD of SEQ ID NO: 6 or SEQ ID NO: 7. In certain aspects a SdrD antigen peptide or polypeptide will have all, or part of the amino acid sequence of SEQ ID NO: 7, e.g., will comprise at least 50, or at least 60, or at least 70, or at least 80, or at least 90, or at least 100, or at least 120, or at least 140, or at least 160, or at least 180, or at least 200, or at least 220 or at least 240 amino acids of SEQ ID NO: 6 or SEQ ID NO: 7. In one embodiment, a SdrD antigen peptide or polypeptide present in the SA-MAPS immunogenic composition is a polypeptide, peptide, or protein that is or is at least 70%, 75%, 80%, 85%, 90%, 95%, 96%, 97%, 98%, or 99% identical or similar to SEQ ID NO: 7.

The term "SdrD protein" refers to a protein that includes isolated wild-type SdrD polypeptides from *staphylococcus* bacteria and segments thereof, as well as variants that stimulate an immune response against *staphylococcus* bacteria SdrD proteins.

In some embodiments, other SdrD antigens can be used in the SA-MAPS composition as disclosed herein, e.g., SdrD antigenic proteins or peptides derived from various species of organisms, some of which include the following SdrD from *S. aureus*: strain USA300 FPR3757 (protein accession number SAUSA300_0547); strain NCTC8325 (protein accession number SAOUHSC_00545): strain MW2 (protein accession number MW0517); strain MSSA476 (protein accession number SAS0520; and strain Mu50 (protein accession number SAV0562).

Iron Regulator Surface Protein A (IsdA)

IsdA Sequence: In some embodiments, the IsdA antigen for use in the SA-MAPS immunogenic composition as disclosed herein comprises a polypeptide or peptide comprising at least part of SEQ ID NO: 10, which corresponds to the full length IsdA mature protein (aa 47-350) from *S. aureus* strain USA300 (without the signal sequence).

```
                                       (SEQ ID NO: 10)
ATEATNATNNQSTQVSQATSQPINFQVQKDGSSEKSHMDDYMQHPGKVIKQ

NNKYYFQTVLNNASFWKEYKFYNANNQELATTVVNDNKKADTRTINVAVEP

GYKSLTTKVHIVVPQINYNHRYTTHLEFEKAIPTLADAAKPNNVKPVQPKP

AQPKTPTEQTKPVQPKVEKVKPTVTTTSKVEDNHSTKVVSTDTTKDQTKTQ

TAHTVKTAQTAQEQNKVQTPVKDVATAKSESNNQAVSDNKSQQTNKVTKHN

ETPKQASKAKELPKTGLTSVDNFISTVAFATLALLGSLSLLLFKRKESK
```

In some embodiments, the IsdA antigen for use in the SA-MAPS immunogenic composition as disclosed herein is IsdA (47-324) (SEQ ID NO: 11), or a fragment or protein of at least 85% amino acid sequence identity thereto. SEQ ID NO: 11 has the following amino acid sequence:

```
                                       (SEQ ID NO: 11)
ATEATNATNNQSTQVSQATSQPINFQVQKDGSSEKSHMDDYMQHPGKVIKQ

NNKYYFQTVLNNASFWKEYKFYNANNQELATTVVNDNKKADTRTINVAVEP

GYKSLTTKVHIVVPQINYNHRYTTHLEFEKAIPTLADAAKPNNVKPVQPKP

AQPKTPTEQTKPVQPKVEKVKPTVTTTSKVEDNHSTKVVSTDTTKDQTKTQ

TAHTVKTAQTAQEQNKVQTPVKDVATAKSESNNQAVSDNKSQQTNKVTKHN

ETPKQASKAKELPKTGLTSVDNF
```

In one embodiment, a SA-MAPS composition may include a polypeptide, peptide, or protein that is or is at least 70%, 75%, 80%, 85%, 90%, 95%, 96%, 97%, 98%, or 99% identical or similar to a IsdA of SEQ ID NO: 10 or SEQ ID NO: 11. In certain aspects a IsdA antigen peptide or polypeptide will have all, or part of the amino acid sequence of SEQ ID NO: 11, e.g., will comprise at least 50, or at least 60, or at least 70, or at least 80, or at least 90, or at least 100, or at least 120, or at least 140, or at least 160, or at least 180, or at least 200, or at least 220 or at least 240 amino acids of SEQ ID NO: 10 or SEQ ID NO: 11. In one embodiment, a IsdA antigen peptide or polypeptide present in the SA-MAPS immunogenic composition is a polypeptide, peptide, or protein that is or is at least 70%, 75%, 80%, 85%, 90%, 95%, 96%, 97%, 98%, or 99% identical or similar to SEQ ID NO: 11.

The term "IsdA protein" refers to a protein that includes isolated wild-type IsdA polypeptides from *staphylococcus* bacteria and segments thereof, as well as variants that stimulate an immune response against *staphylococcus* bacteria IsdA proteins.

Iron Regulator Surface Protein B (IsdB)

In some embodiments, a SA antigen for use in the SA-MAPS composition as disclosed herein is the *S. aureus* surface protein iron surface determinant B (IsdB). This MSCRAMM was described by Mazmanian et al. (Mazmanian, S K et al. Proc. Natl. Acad. Sci., USA 99:2293-2298 (2002)) and it has subsequently been tested and shown to be effective as a vaccine candidate in a murine model of infection and a rhesus macaque immunogenicity study by Kuklin, et al. (Kuklin, N A, et al. Infection and Immunity, Vol. 74, No. 4, 2215-2223, (2006)).

IsdB Sequence: In some embodiments, the IsdB antigen for use in the SA-MAPS immunogenic composition as disclosed herein comprises a polypeptide or peptide comprising at least part of SEQ ID NO: 12, which corresponds to the full length IsdB mature protein (aa 41-652) from *S. aureus* strain USA300 (without the signal sequence).

```
                                       (SEQ ID NO: 12)
AAEETGGTNTEAQPKTEAVASPTTTSEKAPETKPVANAVSVSNKEVEAPTS

ETKEAKEVKEVKAPKETKEVKPAAKATNNTYPILNQELREAIKNPAIKDKD

HSAPNSRPIDFEMKKKDGTQQFYHYASSVKPARVIFTDSKPEIELGLQSGQ

FWRKFEVYEGDKKLPIKLVSYDTVKDYAYIRFSVSNGTKAVKIVSSTHFNN

KEEKYDYTLMEFAQPIYNSADKFKTEEDYKAEKLLAPYKKAKTLERQVYEL

NKIQDKLPEKLKAEYKKKLEDTKKALDEQVKSAITEFQNVQPTNEKMTDLQ

DTKYVVYESVENNESMMDTFVKHPIKTGMLNGKKYMVMETTNDDYWKDFMV

EGQRVRTISKDAKNNTRTIIFPYVEGKTLYDAIVKVHVKTIDYDGQYHVRI

VDKEAFTKANTDKSNKKEQQDNSAKKEATPATPSKPTPSPVEKESQKQDSQ

KDDNKQLPSVEKENDASSESGKDKTPATKPTKGEVESSSTTPTKVVSTTQN

VAKPTTASSKTTKDVVQTSAGSSEAKDSAPLQKANIKNTNDGHTQSQNNKN

TQENKAKSLPQTGEESNKDMTLPLMALLALSSIVAFVLPRKRKN
```

In some embodiments, the IsdB antigen for use in the SA-MAPS immunogenic composition as disclosed herein is IsdB (48-477) (SEQ ID NO: 13), or a fragment or protein of at least 85% amino acid sequence identity thereto. SEQ ID NO: 13 has the following amino acid sequence:

```
                                       (SEQ ID NO: 13)
TNTEAQPKTEAVASPTTTSEKAPETKPVANAVSVSNKEVEAPTSETKEAKE

VKEVKAPKETKEVKPAAKATNNTYPILNQELREAIKNPAIKDKDHSAPNSR

PIDFEMKKKDGTQQFYHYASSVKPARVIFTDSKPEIELGLQSGQFWRKFEV

YEGDKKLPIKLVSYDTVKDYAYIRFSVSNGTKAVKIVSSTHFNNKEEKYDY

TLMEFAQPIYNSADKFKTEEDYKAEKLLAPYKKAKTLERQVYELNKIQDKL

PEKLKAEYKKKLEDTKKALDEQVKSAITEFQNVQPTNEKMTDLQDTKYVVY

ESVENNESMMDTFVKHPIKTGMLNGKKYMVMETTNDDYWKDFMVEGQRVRT

ISKDAKNNTRTIIFPYVEGKTLYDAIVKVHVKTIDYDGQYHVRIVDKEAFT

KANTDKSNKKEQQDNSAKKEAT
```

In one embodiment, a SA-MAPS composition may include a polypeptide, peptide, or protein that is or is at least 70%, 75%, 80%, 85%, 90%, 95%, 96%, 97%, 98%, or 99% identical or similar to a IsdB of SEQ ID NO: 12 or SEQ ID NO: 13. In certain aspects a IsdA antigen peptide or polypeptide will have all, or part of the amino acid sequence of SEQ ID NO: 13, e.g., will comprise at least 50, or at least 60, or at least 70, or at least 80, or at least 90, or at least 100, or at least 120, or at least 140, or at least 160, or at least 180, or at least 200, or at least 220 or at least 240 amino acids of SEQ ID NO: 12 or SEQ ID NO: 31. In one embodiment, a IsdB antigen peptide or polypeptide present in the SA-MAPS immunogenic composition is a polypeptide, peptide, or protein that is or is at least 70%, 75%, 80%, 85%, 90%, 95%, 96%, 97%, 98%, or 99% identical or similar to SEQ ID NO: 13.

The term "IsdB protein" refers to a protein that includes isolated wild-type IsdB polypeptides from *staphylococcus* bacteria and segments thereof, as well as variants that stimulate an immune response against *staphylococcus* bacteria IsdB proteins.

In some embodiments, other IsdB antigens can be used in the SA-MAPS composition as disclosed herein, e.g., IsdB antigenic proteins or peptides derived from various species of organisms, some of which include the following IsdB from *S. aureus* strains, including strain MRSA252 (protein accession number CAG40104.1); strain Newman (protein accession number BAF67312.1); strain MSSA476 (protein accession number CAG42837.1); strain Mu3 (protein accession number BAF78003.1); strain RF122 (protein accession number CAI80681.1).

Other SA Antigens

While exemplary SA antigens used in the SA-MAPS composition as disclosed herein can be one or more of, or all 6 of hemolysin (Hl) (e.g., hemolysin α or Hla209), Clumping factor A (ClfA), Clumping factor B (ClfB), serine-aspirate repeat protein D (SdrD), Iron regulator surface protein A (IsdA) and Iron regulator surface protein B (IsdB), or fragments thereof, e.g., Hla209(27-319), ClfA (221-559), ClfB (203-542), SdrD (246-682), IsdA (47-324), IsdB (48-447) or proteins or peptides having at least 85% sequence identity thereto, it is envisioned that any of the above listed SA antigens can be substituted for a different SA peptide or polypeptide antigen known to one of ordinary skill in the art.

For example, in some embodiments, any one or more SA antigens useful in the SA-MAPS composition as disclosed herein include, but are not limited to, a peptide or polypeptide comprising at least part of the serine-aspirate repeat protein E (SdrE) protein, SdrC, Leukotoxin D (LukD) protein, or Leukotoxin E (LukE) protein, provided that the any peptide or polypeptide is immunogenic, or is antigenic. Other SA antigens can be used, and are disclosed herein.

In some embodiments, other SA antigens can be used in the SA-MAPS composition as disclosed herein. For example, the *S. aureus* MntC protein (also known as Protein 305, P305, P305A, and ORF305) is a component of a manganese ABC transporter. This protein is expressed in vivo. *S. aureus* uses manganese as a cofactor for an enzyme that enhances the survival of *S. aureus* in neutraphils. MntC is, therefore, important for the in vivo survival of *S. aureus* during infection. Like ClfA, this protein is also unstable in solution. However, unlike ClfA, which can aggregate, or clip via hydrolysis, the primary mechanism of MntC degradation is deamidation when subject to basic pH and/or temperature around room temperature (about 25° C.) or higher.

In some embodiments SA antigens can be used in the SA-MAPS composition as disclosed herein can be selected from any one or, or a combination of: SdrC, SdrE, MntC/SitC/Saliva Binding Protein, Opp3a, DltA, HtsA, LtaS, SdrH, SrtA, SpA, SBI, beta-hemolysin, fibronectin-binding protein A (fnbA), coagulase, map, Panton-Valentine leukocidin (pvl), gamma-toxin (hlg), ica, immunodominant ABC transporter, RAP, autolysin, laminin receptors, SPOIIIE, SsaA, EbpS, Sasf, SasH, EFB (FIB), FnbB, Npase, EBP, bone sialo binding protein II; aureolysin precursor (AUR)/Sepp1, Cna, TSST-1, mecA, dPNAG, GehD, EbhA, EbhB, SSP-1, SSP-2 HBP, vitronectin binding protein, HarA, Enterotoxin A, Enterotoxin B, Enterotoxin C1, and novel autolysin.

In some embodiments SA antigens can be used in the SA-MAPS composition as disclosed herein can be selected from any one or, or a combination of Opp3a, DltD, HtsA, LtaS, IsdA, IsdC, SdrF, SdrG, SdrH, SrtA, SpA, Shi alpha-hemolysin (hla), beta-hemolysin, fibronectin-binding protein A (fnbA), fibronectin-binding protein B (fnbB), coagulase, Fig, map, Panton-Valentine leukocidin (pvl), alpha-toxin and its variants, gamma-toxin (hlg) and variants, ica, immunodominant ABC transporter, Mg2+ transporter, Ni ABC transporter, RAP, autolysin, laminin receptors, IsaA/PisA, IsaB/PisB, SPOIIIE, SsaA, EbpS, SasA, SasF, SasH, EFB (FIB), SBI, Npase, EBP, bone sialo binding protein II, aureolysin precursor (AUR)/Sepp1, Cna, and fragments thereof such as M55, TSST-1, mecA, poly-N-acetylglucosamine (PNAG/dPNAG) exopolysaccharide, GehD, EbhA, EbhB, SSP-1, SSP-2, HBP, vitronectin binding protein, HarA, EsxA, EsxB, Enterotoxin A, Enterotoxin B. Enterotoxin C1, and novel autolysin.

Bacterial antigens include, but are not limited to (i) a secreted virulence factor, and/or a cell surface protein or peptide, or (ii) a recombinant nucleic acid molecule encoding a secreted virulence factor, and/or a cell surface protein or peptide. The bacterial antigen can include one or more of at least or at most 1, 2, 3, 4, 5, 6, 7, 8, 9, 10, 11, 12, 13, 14, 15, 16, 17, 18, or 19 additional staphylococcal antigen or immunogenic fragment thereof, including, but not limited to FnBpA, FnBpB, LukD (GI:2765304), LukE (GI:2765303), LukF (GI:12231006), SasA, SasD, SasG, SasI, SasK, SpA (and variants thereof), Eap, Ebh, Emp, EsaB, EsaC, EsxA, EsxB, SdrC, SdrE, Coa, Hla (e.g., H35 mutants), IsdC, SasF, vWbp, vWh, 52 kDa vitronectin binding protein (WO 01/60852), Aaa (GenBank CAC80837), Aap (GenBank accession AJ249487), Ant (GenBank accession NP-372518), autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/P isA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein (see PCT publications WO2007/113222, WO2007/113223, WO2006/032472, WO2006/032475, WO2006/032500, each of which is incorporated herein by reference in their entirety).

In some embodimetnts, a SA-antigen for use in the SA-MAPS composition as disclosed herein is a Microbial Surface Components Recognizing Adhesive Matrix Molecule, or MSCRAMMs, which include, but are not limited to: EkeS, DsqA, KesK, KrkN, KrkN2, RkaS, RrkN, and KnkA. These MSCRAMMS are described in WO 02/102829, which is hereby incorporated by reference. Additional MSCRAMMS, identified by GenBank Accession No., include NP_373261.1, NP_373371.1, NP_374246.1, NP_374248.1, NP_374841.1, NP_374866.1, NP_375140.1, NP_375614.1, NP_375615.1, NP_375707.1, NP_375765.1, and NP_375773.1.

In certain aspects, a SA-MAPs composition can comprise a staphylococcal antigen selected from the group consisting of: FnBpA, FnBpB, LukD, LukE, LukF, SasA, SasD, SasG, SasI, SasK, SpA (and variants thereof), Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, vWh and immunogenic fragments thereof.

Some exemplary alternative SA antigens for use in the SA-MAPS immunogenic composition as disclosed herein are discussed below.

Serine-Aspirate Repeat Protein E (SdrE)

The sdr genes are closely linked and tandemly arrayed, accordingly any one of the Sdr proteins (e.g., SdrC, SdrD, SdrE, ClfA, and ClfB) can be used in the SA-MAPS immunogenic composition as disclosed herein. The Sdr proteins characteristically comprise an A region where there is highly conserved amino acid sequence that can be used to derive a consensus TYTFTDYVD (SEQ ID NO: 20) motif. The motif exhibits slight variation between the different proteins. This variation, along with the consensus sequence of the motif is described in U.S. Pat. No. 6,680,195. In the Clf-Sdr proteins, this motif is highly conserved. The motif can be used in immunogenic compositions to impart broad spectrum immunity to bacterial infections, and also can be used as an antigen in the production of monoclonal or polyclonal antibodies. Such an antibody can be used to impart broad spectrum passive immunity.

The Sdr proteins differ from ClfA and ClfB by having two to five additional 110-113 residue repeated sequences (B-motifs) located between region A and the R-region. Each B-motif contains a consensus Ca2+-binding EF-hand loop normally found in eukaryotic proteins. The structural integrity of a recombinant protein comprising the five B-repeats of SdrD was shown by bisANS fluorescence analysis to be Ca2+-dependent, suggesting that the EF-hands are functional. When Ca2+ was removed the structure collapsed to an unfolded conformation. The original structure was restored by addition of Ca2+. The C-terminal R-domains of the Sdr proteins contain 132-170 SD residues. These are followed by conserved wall-anchoring regions characteristic of many surface proteins of Gram positive bacteria.

In the Sdr and Clf proteins this B motif is highly conserved while a degenerate version occurs in fibronectin binding MSCRAMMS, as well as the collagen binding protein Cna. The B motifs, in conjunction with the R regions, are necessary for displaying the ligand-binding domain at some distance from the cell surface. The repeated B motifs are one common denominator of the sub-group of SD repeat proteins described herein. These motifs are found in different numbers in the three Sdr proteins from strain PFESA0237. There are clear distinctions between the individual B motifs. The most conserved units are those located adjacent to the R regions (SdrC B2, SdrD B5 and SdrE B3). They differ from the rest at several sites, especially in the C-terminal half A noteworthy structural detail is that adjacent B repeats are always separated by a proline residue present in the C-terminal region, but a proline never occurs between the last B repeats and the R region. Instead this linker is characterized by a short acidic stretch. These differences are evidence that the end units have a different structural or functional role compared to the other B motifs. The N-terminal B motifs of SdrD and SdrE have drifted apart from the others, and there are numerous amino acid alterations, including small insertions and deletions whereas the remaining internal B motifs are more highly conserved. Note that each of the three Sdr proteins has at least one B motif of each kind.

The C-terminal R-domains of the Sdr proteins contain 132-170 SD residues. These are followed by conserved wall-anchoring regions characteristic of many surface proteins of Gram positive bacteria.

In some embodiments, a SdrE antigen can be used in the SA-MAPS immunogenic composition as disclosed herein, and can comprises a polypeptide or peptide comprising at least part of SEQ ID NO: 8, which corresponds to the full length SdrE mature protein from S. aureus strain USA300 (without the signal sequence).

(SEQ ID NO: 8)
AENTSTENAKQDDATTSDNKEVVSETENNSTTENNSTNPIKKETNTDSQPE

AKKESTSSSTQKQQNNVTATTETKPQNIEKENVKPSTDKTATEDTSVILEE

KKAPNNTNNDVTTKPSTSEPSTSEIQTKPTTPQESTNIENSQPQPTPSKVD

NQVTDATNPKEPVNVSKEELKNNPEKLKELVRNDSNTDHSTKPVATAPTSV

APKRVNAKMRFAVAQPAAVASNNVNDLIKVTKQTIKVGDGKDNVAAAHDGK

DIEYDTEFTIDNKVKKGDTMTINYDKNVIPSDLTDKNDPIDITDPSGEVIA

KGTFDKATKQITYTFTDYVDKYEDIKSRLTLYSYIDKKTVPNETSLNLTFA

TAGKETSQNVTVDYQDPMVHGDSNIQSIFTKLDEDKQTIEQQIYVNPLKKS

ATNTKVDIAGSQVDDYGNIKLGNGSTIIDQNTEIKVYKVNSDQQLPQSNRI

YDFSQYEDVTSQEDNKKSFSNNVATLDFGDINSAYIIKVVSKYTPTSDGEL

DIAQGTSMRTTDKYGYYNYAGYSNFIVTSNDTGGGDGTVKPEEKLYKIGDY

VWEDVDKDGVQGTDSKEKPMANVLVTLTYPDGTTKSVRTDANGHYEFGGLK

DGETYTVKFETPTGYLPTKVNGTTDGEKDSNGSSVTVKINGKDDMSLDTGF

YKEPKYNLGDYVWEDTNKDGIQDANEPGIKDVKVTLKDSTGKVIGTTTTDA

SGKYKFTDLDNGNYTVEFETPAGYTPTVKNTTADDKDSNGLTTTGVIKDAD

NMTLDSGFYKTPKYSLGDYVWYDSNKDGKQDSTEKGIKDVTVTLQNEKGEV

IGTTKTDENGKYRFDNLDSGKYKVIFEKPAGLTQTVTNTTEDDKDADGGEV

DVTITDHDDFTLDNGYFEEDTSDSDSDSDSDSDSDSDSDSDSDSDSDSDSD

SDSDSDSDSDSDSDSDSDSDSDSDSDSDSDSDSDSDSDSDSDSDSDSDSDS

DSDSDSDSDSDSDSDSDSDSDSDSDSDSDSDSDSDSDSDSDSDSDSDSDSD

SDSDSDSDSDSDSDSDSDSDAGKHTPVKPMSTTKDHHNKAKALPET

In some embodiments, a SA-MAPS composition can include a polypeptide, peptide, or protein that is or is at least 70%, 75%, 80%, 85%, 90%, 95%, 96%, 97%, 98%, or 99% identical or similar to a SdrE of SEQ ID NO: 8. In certain aspects a SdrE antigen peptide or polypeptide will have all, or part of the amino acid sequence of SEQ ID NO: 8, e.g., will comprise at least 50, or at least 60, or at least 70, or at least 80, or at least 90, or at least 100, or at least 120, or at least 140, or at least 160, or at least 180, or at least 200, or at least 220 or at least 240 amino acids of SEQ ID NO: 8. In one embodiment, a SdrD antigen peptide or polypeptide present in the SA-MAPS immunogenic composition is a polypeptide, peptide, or protein that is or is at least 70%, 75%, 80%, 85%, 90%, 95%, 96%, 97%, 98%, or 99% identical or similar to SEQ ID NO: 8.

The term "SdrE protein" refers to a protein that includes isolated wild-type SdrE polypeptides from *staphylococcus* bacteria and segments thereof, as well as variants that stimulate an immune response against *staphylococcus* bacteria SdrE proteins.

The term "SdrC protein" refers to a protein that includes isolated wild-type SdrC polypeptides from *staphylococcus* bacteria and segments thereof, as well as variants that stimulate an immune response against *staphylococcus* bacteria SdrC proteins.

LukD, LukE, LukF

In one embodiment, a SA-MAPS composition may include a polypeptide, peptide, or protein that is or is at least 70%, 75%, 80%, 85%, 90%, 95%, 96%, 97%, 98%, or 99% identical or similar to an LukD protein. In certain aspects the LukD protein will have all or part of the amino acid sequence of accession number CAA73668/GI:2765304. The term "LukD protein" refers to a protein that includes isolated wild-type LukD polypeptides from *staphylococcus* bacteria and segments thereof, as well as variants that stimulate an immune response against *staphylococcus* bacteria LukD proteins.

In one embodiment, a SA-MAPS composition may include a polypeptide, peptide, or protein that is or is at least 70%, 75%, 80%, 85%, 90%, 95%, 96%, 97%, 98%, or 99% identical or similar to an LukE protein. In certain aspects the LukE protein will have all or part of the amino acid sequence of accession number CAA73667.1/GI:2765303. The term "LukE protein" refers to a protein that includes isolated wild-type LukE polypeptides from *staphylococcus* bacteria and segments thereof, as well as variants that stimulate an immune response against *staphylococcus* bacteria LukE proteins.

In one embodiment, a SA-MAPS composition may include a polypeptide, peptide, or protein that is or is at least 70%, 75%, 80%, 85%, 90%, 95%, 96%, 97%, 98%, or 99% identical or similar to an LukF protein. In certain aspects the LukF protein will have all or part of the amino acid sequence of accession number AAC60446.1/GI:410007. The term "LukF protein" refers to a protein that includes isolated wild-type LukF polypeptides from *staphylococcus* bacteria and segments thereof, as well as variants that stimulate an immune response against *staphylococcus* bacteria LukF proteins.

S. aureus MntC/SitC/Saliva Binding Protein

In one embodiment, a SA-MAPS composition may include a polypeptide, peptide, or protein that is or is at least 70%, 75%, 80%, 85%, 90%, 95%, 96%, 97%, 98%, or 99% identical or similar to a MntC/SitC/Saliva Binding Protein. MntC/SitC/Saliva Binding Protein is an ABC transporter protein and has homologues in S. epidermidis and S. aureus. It is referred to herein as MntC. This protein is a 32 kDa lipoprotein and is located in the bacterial cell wall. See Sellman et al., and Cockayne et al., Infect. Immun. 66: 3767 (1998). In S. epidermidis, it is a component of an iron-regulated operon. It shows considerable homology to both adhesins including FimA of S. parasanguis, and with lipoproteins of a family of ABC transporters with proven or putative metal iron transport functions. The S. aureus homologue of MntC is known as saliva binding protein and was disclosed in U.S. Pat. No. 5,801,234, which is incorporated herein in its entirety by reference. The protein sequence for the S. aureus homologue of MntC/SitC/Saliva Binding Protein is found in GenBank accession number NP_371155 for strain Mu50, (also known as SAV0631), where the accession number for the nucleotide sequence for the complete genome of strain Mu50 is NC_002758.2 (coordinates 704988-705917).

In alternative embodiments, a MntC antigen for use in the SA-MAPS immunogenic composition as disclosed herein is a protein or peptide having an amino acid sequence of one the MntC proteins disclosed in Table 12 of U.S. Pat. No. 8,568,735, which is incorporated herein in its entirety by reference. Other MntC antigens not identified herein are disclosed encompassed for use in the SA-MAPS immunogenic composition, provided they are antigenic.

S. epidermidis SitC Protein

In one embodiment, a SA-MAPS composition may include a polypeptide, peptide, or protein that is or is at least 70%, 75%, 80%, 85%, 90%, 95%, 96%, 97%, 98%, or 99% identical or similar to a SitC protein. SitC is the S. epidermidis homologue of MntC/SitC/Saliva Binding Protein and was disclosed in Sellman et al. (Sellman et al., Infect. Immun. 2005 October; 73(10): 6591-6600). The protein sequence for SitC is found in GenBank accession number YP_1187886.1 (also known as SERP0290) and is disclosed as SEQ ID NO: 121 in U.S. Pat. No. 8,568,735, which is incorporated herein in its entirety by reference. The accession number for the nucleotide sequence for the complete genome of strain RP62A, is NC_002976 (coordinates 293030-293959). Other candidate SitC molecules may be derived from various species of organisms for use in an immunogenic composition of the invention, some of which include, but are not limited to: all or part of the amino acid sequence of accession number BAE03450.1 (S. haemolyticus, JCSC1435 strain), AA004002.1 (S. epidermidis, strain ATCC 12228); BAE19233.1 (S. saprophyticus, strain ATCC 15305); ABR57162.1 (S. xylosus, strain DSM20267); CAL27186.1 (S. carnosus, strain TM300).

The term "FnBpA protein" refers to a protein that includes isolated wild-type FnBpA polypeptides from *staphylococcus* bacteria and segments thereof, as well as variants that stimulate an immune response against *staphylococcus* bacteria FnBpA proteins.

The term "FnBpB protein" refers to a protein that includes isolated wild-type FnBpB polypeptides from *staphylococcus* bacteria and segments thereof, as well as variants that stimulate an immune response against *staphylococcus* bacteria FnBpB proteins.

The term "SasA protein" refers to a protein that includes isolated wild-type SasA polypeptides from *staphylococcus* bacteria and segments thereof, as well as variants that stimulate an immune response against *staphylococcus* bacteria SasA proteins.

The term "SasD protein" refers to a protein that includes isolated wild-type SasD polypeptides from *staphylococcus* bacteria and segments thereof, as well as variants that stimulate an immune response against *staphylococcus* bacteria SasD proteins.

The term "SasG protein" refers to a protein that includes isolated wild-type SasG polypeptides from *staphylococcus* bacteria and segments thereof, as well as variants that stimulate an immune response against *staphylococcus* bacteria SasG proteins.

The term "SasI protein" refers to a protein that includes isolated wild-type SasI polypeptides from *staphylococcus* bacteria and segments thereof, as well as variants that stimulate an immune response against *staphylococcus* bacteria SasI proteins.

The term "SasK protein" refers to a protein that includes isolated wild-type SasK polypeptides from *staphylococcus* bacteria and segments thereof, as well as variants that stimulate an immune response against *staphylococcus* bacteria SasK proteins.

The term "EsxA protein" refers to a protein that includes isolated wild-type EsxA polypeptides from *staphylococcus* bacteria and segments thereof, as well as variants that stimulate an immune response against *staphylococcus* bacteria EsxA proteins.

The term "EsxB protein" refers to a protein that includes isolated wild-type EsxB polypeptides from *staphylococcus* bacteria and segments thereof, as well as variants that stimulate an immune response against *staphylococcus* bacteria EsxB proteins.

The term "Eap protein" refers to a protein that includes isolated wild-type Eap polypeptides from *staphylococcus* bacteria and segments thereof, as well as variants that stimulate an immune response against *staphylococcus* bacteria Eap proteins.

The term "Ebh protein" refers to a protein that includes isolated wild-type Ebh polypeptides from *staphylococcus* bacteria and segments thereof, as well as variants that stimulate an immune response against *staphylococcus* bacteria Ebh proteins.

The term "Emp protein" refers to a protein that includes isolated wild-type Emp polypeptides from *staphylococcus* bacteria and segments thereof, as well as variants that stimulate an immune response against *staphylococcus* bacteria Emp proteins.

The term "EsaB protein" refers to a protein that includes isolated wild-type EsaB polypeptides from *staphylococcus* bacteria and segments thereof, as well as variants that stimulate an immune response against *staphylococcus* bacteria EsaB proteins.

The term "EsaC protein" refers to a protein that includes isolated wild-type EsaC polypeptides from *staphylococcus* bacteria and segments thereof, as well as variants that stimulate an immune response against *staphylococcus* bacteria EsaC proteins.

The term "Coa protein" refers to a protein that includes isolated wild-type Coa polypeptides from *staphylococcus* bacteria and segments thereof, as well as variants that stimulate an immune response against *staphylococcus* bacteria Coa proteins.

The term "SasF protein" refers to a protein that includes isolated wild-type SasF polypeptides from *staphylococcus* bacteria and segments thereof, as well as variants that stimulate an immune response against *staphylococcus* bacteria SasF proteins.

The term "vWbp protein" refers to a protein that includes isolated wild-type vWbp (von Willebrand factor binding protein) polypeptides from *staphylococcus* bacteria and segments thereof, as well as variants that stimulate an immune response against *staphylococcus* bacteria vWbp proteins.

The term "vWh protein" refers to a protein that includes isolated wild-type vWh (von Willebrand factor binding protein homolog) polypeptides from *staphylococcus* bacteria and segments thereof, as well as variants that stimulate an immune response against *staphylococcus* bacteria vWh proteins.

In certain embodiments, the claimed invention specifically excludes 1, 2, 3, 4, 5, 6, 7, 8, 9, 10 or more of FnBpA, FnBpB, LukD (GI:2765304), LukE (GI:2765303), LukF (GI:12231006), SasA, SasD, SasG, SasI, SasK, SpA (and variants thereof), Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, vWh, 52 kDa vitronectin binding protein (WO 01/60852), Aaa (GenBank CAC80837), Aap (GenBank accession AJ249487), Ant (GenBank accession NP-372518), autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/P isA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein (see PCT publications WO2007/113222, WO2007/113223, WO2006/032472, WO2006/032475, WO2006/032500, each of which is incorporated herein by reference in their entirety). In certain aspects, the bacterial antigen is a staphylococcal antigen. The staphylococcal antigen can be selected from the group consisting of: FnBpA, FnBpB, LukD, LukE, LukF, SasA, SasD, SasG, SasI, SasK, SpA (and variants thereof), Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, vWh and immunogenic fragments thereof. Certain embodiments are directed to an immunogenic composition comprising an isolated Protein A (SpA) specific antibody and a bacterial antigen, wherein the Protein A specific antibody enhances an immune response to the bacterial antigen. In certain aspects, the antibody is a polyclonal antibody, a monoclonal antibody, or an antibody fragment. In still further aspects, the bacterial antigen is comprised in or on a bacterium. The bacteria can be attenuated bacteria, in particular attenuated staphylococcal bacteria.

In certain embodiments a subject is administered a SA-MAPS composition comprising a SA antigen, wherein the SA antigen is Hla209 or any SA antigen selected from any of: FnBpA antigen or immunogenic fragment thereof, FnBpB antigen or immunogenic fragment thereof, LukD antigen or immunogenic fragment thereof, LukE antigen or immunogenic fragment thereof, LukF antigen or immunogenic fragment thereof, SasA antigen or immunogenic fragment thereof, SasD antigen or immunogenic fragment thereof, SasG antigen or immunogenic fragment thereof, SasI antigen or immunogenic fragment thereof, SasK antigen or immunogenic fragment thereof, SpA (and variants thereof) antigen or immunogenic fragment thereof, Eap antigen or immunogenic fragment thereof, Ebh antigen or immunogenic fragment thereof, Emp antigen or immunogenic fragment thereof, EsaB antigen or immunogenic fragment thereof, EsaC antigen or immunogenic fragment thereof, EsxA antigen or immunogenic fragment thereof, EsxB antigen or immunogenic fragment thereof, SdrC antigen or immunogenic fragment thereof, SdrD antigen or immunogenic fragment thereof, SdrE antigen or immunogenic fragment thereof, IsdA antigen or immunogenic fragment thereof, IsdB antigen or immunogenic fragment thereof, ClfA antigen or immunogenic fragment thereof, ClfB antigen or immunogenic fragment thereof, Coa antigen or immunogenic fragment thereof, Hla (e.g., H35 mutants) antigen or immunogenic fragment thereof, IsdC antigen or immunogenic fragment thereof, SasF antigen or immunogenic fragment thereof, vWbp antigen or immunogenic fragment thereof, vWh antigen or immunogenic fragment thereof.

Combinations of SA Antigens Present on the SA-MAPS Immunogenic Composition

In some embodiments, a SA-MAPS complex comprises at least 2 SA antigens, e.g., Hla, such as but not limited to Hla(209) as disclosed herein, and one or more SA antigens selected from a Clumping factor A (ClfA), Clumping factor B (ClfB), serine-aspirate repeat protein D (SdrD), serine-aspirate repeat protein E (SdrE), Iron regulator surface protein A (IsdA), Iron regulator surface protein B (IsdB), Leukotoxin D (LukD), or Leukotoxin E (LukE), or fragments thereof.

In some embodiments, a SA-MAPS immunogenic composition as disclosed herein can comprise all 6 SA antigens selected from: hemolysin (Hl) (e.g., hemolysin α or Hla209), Clumping factor A (ClfA), Clumping factor B (ClfB), serine-aspirate repeat protein D (SdrD), Iron regulator surface protein A (IsdA) and Iron regulator surface protein B (IsdB), or fragments thereof, for example, but not limited to: Hla209(27-319), ClfA (221-559), ClfB (203-542), SdrD (246-682), IsdA (47-324), IsdB (48-447) or proteins or peptides having at least 85% sequence identity thereto. It is envisioned that any of the above listed SA antigens can be substituted for a different SA peptide or polypeptide antigen known to one of ordinary skill in the art.

In alternative embodiments, the SA-MAPS immunogenic compositions as disclosed herein can comprise any SA antigen that elicits an immune response in a subject. In some embodiments, the SA-MAPS composition comprises at least one, or at least 2 SA antigens. In some embodiments, the SA-MAPS immunogenic composition comprises at least 2, or at least 3, or at least 4, or between 2-4, or between 3-5, or between 6-8, or between 8-10 or between 10-12, or between 10-15, or between 15-20 or more than 20 SA protein or polypeptide antigens. In some embodiments, the antigens can be the same, e.g., all ClfA antigens, or a combination of different antigens, e.g., Hla209, ClfA, ClfB etc. In some embodiments, the SA-MAPS composition comprises at least a Hla209 antigen (e.g., Hla209(27-319)) and at least 1 more, or at least 2 more, or at least 3 more or at least 4 more, or at least 5 more SA antigens as disclosed herein.

Exemplary combinations of different SA antigen present on a SA-MAPS immunogenic composition as disclosed herein are shown in Tables 3A-3G.

In particular, Tables 3A-3G show exemplary SA antigens present on SA-MAPS complexes which are useful in the compositions and methods as disclosed herein. Tables 3A-3G have used an exemplary set of 9 SA antigens, and it is envisioned that any of the SA antigens can be substituted for a different SA peptide or polypeptide antigen known to one of ordinary skill in the art. In some embodiments, a SA-MAPS immunogenic composition comprises a combination of 2, 3, 4, 5 or 6 of the exemplary SA antigens selected from hemolysin (Hl) (e.g., hemolysin a or Hla209), Clumping factor A (ClfA), Clumping factor B (ClfB), serine-aspirate repeat protein D (SdrD), Iron regulator surface protein A (IsdA) and Iron regulator surface protein B (IsdB), or fragments thereof, e.g., Hla209(27-319), ClfA (221-559), ClfB (203-542), SdrD (246-682), IsdA (47-324), IsdB (48-447) or proteins or peptides having at least 85% sequence identity thereto. It is noted that reference to LUKD, LUKE and SDRE in Tables 3A-3G are examples of other SA antigens that can be used in place of (i.e., substituted) any of, or in addition to, the exemplary Hla209(27-319), ClfA (221-559), ClfB (203-542), SdrD (246-682), IsdA (47-324), IsdB (48-447) SA antigens.

Table 3B-3G show exemplary combinations of 2, 3, 4, 5, 6, 7, 8 and 9 antigens present in the MAPS complex. HLA209=Hla(209), CLFA=ClfA (221-559), CLFB=ClfB (203-542), SDRD=SdrD (246-682), SDRE=SdrE, ISDA=IsdA (47-324), ISDB=IsdB (48-447), LUKD=LukD, LUKE=LukE.

TABLE 3A

Table 3A: SA-MAPS with at least 1 SA-antigens (9 combinations)

| HLA209 | CLFA | CLFB | SDRD | ISDA | ISDB | SDRE | LUKD | LUKE |
|---|---|---|---|---|---|---|---|---|

TABLE 3B

Table 3B: SA-MAPS with different combinations of 2 SA-antigens (24 combinations)

| | | | | | | | |
|---|---|---|---|---|---|---|---|
| HLA209, CLFA | HLA209, CLFB | HLA209, SDRD | HLA209, ISDA | HLA209, ISDB | HLA209, SDRE | HLA209, LUKD | HLA209, LUKE |
| CLFA, CLFB | CLFA, SDRD | CLFA, ISDA | CLFA, ISDB | CLFA, SDRE | CLFA, LUKD | CLFA, LUKE | CLFB, SDRD |
| CLFB, ISDA | CLFB, ISDB | CLFB, SDRE | CLFB, LUKD | CLFB, LUKE | SDRD, ISDA | SDRD, ISDB | SDRD, SDRE |
| SDRD, LUKD | SDRD, LUKE | ISDA, ISDB | ISDA, SDRE | ISDA, LUKD | ISDA, LUKE | ISDB, SDRE | ISDB, LUKD |
| ISDB, LUKE | SDRE, LUKD | SDRE, LUKE | LUKD, LUKE | | | | |

TABLE 3C

Table 3C: SA-MAPS with different combinations of 3 SA-antigens (84 combinations)

| | | | | | | | |
|---|---|---|---|---|---|---|---|
| HLA209, CLFA, CLFB | HLA209, CLFA, SDRD | HLA209, CLFA, ISDA | HLA209, CLFA, ISDB | HLA209, CLFA, SDRE | HLA209, CLFA, LUKD | HLA209, CLFA, LUKE | HLA209, CLFB, SDRD |
| HLA209, CLFB, ISDA | HLA209, CLFB, ISDB | HLA209, CLFB, SDRE | HLA209, CLFB, LUKD | HLA209, CLFB, LUKE | HLA209, SDRD, ISDA | HLA209, SDRD, ISDB | HLA209, SDRD, SDRE |
| HLA209, SDRD, LUKD | HLA209, SDRD, LUKE | HLA209, ISDA, ISDB | HLA209, ISDA, SDRE | HLA209, ISDA, LUKD | HLA209, ISDA, LUKE | HLA209, ISDB, SDRE | HLA209, ISDB, LUKD |
| HLA209, ISDB, LUKE | HLA209, SDRE, LUKD | HLA209, SDRE, LUKE | HLA209, LUKD, LUKE | CLFA, CLFB, SDRD | CLFA, CLFB, ISDA | CLFA, CLFB, ISDB | CLFA, CLFB, SDRE |
| CLFA, | CLFA, | CLFA, | CLFA, | CLFA, | CLFA, | CLFA, | CLFA, |

TABLE 3C-continued

Table 3C: SA-MAPS with different combinations of 3 SA-antigens (84 combinations)

| | | | | | | | |
|---|---|---|---|---|---|---|---|
| CLFB, | CLFB, | SDRD, | SDRD, | SDRD, | SDRD, | SDRD, | ISDA, |
| LUKD | LUKE | ISDA | ISDB | SDRE | LUKD | LUKE | ISDB |
| CLFA, | CLFA, | CLFA, | CLFA, | CLFA, | CLFA, | CLFA, | CLFA, |
| ISDA, | ISDA, | ISDA, | ISDB, | ISDB, | ISDB, | SDRE, | SDRE, |
| SDRE | LUKD | LUKE | SDRE | LUKD | LUKE | LUKD | LUKE |
| CLFA, | CLFB, | CLFB, | CLFB, | CLFB, | CLFB, | CLFB, | CLFB, |
| LUKD, | SDRD, | SDRD, | SDRD, | SDRD, | SDRD, | ISDA, | ISDA, |
| LUKE | ISDA | ISDB | SDRE | LUKD | LUKE | ISDB | SDRE |
| CLFB, | CLFB, | CLFB, | CLFB, | CLFB, | CLFB, | CLFB, | CLFB, |
| ISDA, | ISDA, | ISDB, | ISDB, | ISDB, | SDRE, | SDRE, | LUKD, |
| LUKD | LUKE | SDRE | LUKD | LUKE | LUKD | LUKE | LUKE |
| SDRD, | SDRD, | SDRD, | SDRD, | SDRD, | SDRD, | SDRD, | SDRD, |
| ISDA, | ISDA, | ISDA, | ISDA, | ISDB, | ISDB, | ISDB, | SDRE, |
| ISDB | SDRE | LUKD | LUKE | SDRE | LUKD | LUKE | LUKD |
| SDRD, | SDRD, | ISDA, | ISDA, | ISDA, | ISDA, | ISDA, | ISDA, |
| SDRE, | LUKD, | ISDB, | ISDB, | ISDB, | SDRE, | SDRE, | LUKD, |
| LUKE | LUKE | SDRE | LUKD | LUKE | LUKD | LUKE | LUKE |
| ISDB, | ISDB, | ISDB, | SDRE, | | | | |
| SDRE, | SDRE, | LUKD, | LUKD, | | | | |
| LUKD | LUKE | LUKE | LUKE | | | | |

TABLE 3D

Table 3D: SA-MAPS with different combinations of 4 SA-antigens (126 combinations)

| | | | | | | | |
|---|---|---|---|---|---|---|---|
| HLA209, | HLA209, | HLA209, | HLA209, | HLA209, | HLA209, | HLA209, | HLA209, |
| CLFA, | CLFA, | CLFA, | CLFA, | CLFA, | CLFA, | CLFA, | CLFA, |
| CLFB, | CLFB, | CLFB, | CLFB, | CLFB, | CLFB, | SDRD, | SDRD, |
| SDRD | ISDA | ISDB | SDRE | LUKD | LUKE | ISDA | ISDB |
| HLA209, | HLA209, | HLA209, | HLA209, | HLA209, | HLA209, | HLA209, | HLA209, |
| CLFA, | CLFA, | CLFA, | CLFA, | CLFA, | CLFA, | CLFA, | CLFA, |
| SDRD, | SDRD, | SDRD, | ISDA, | ISDA, | ISDA, | ISDA, | ISDB, |
| SDRE | LUKD | LUKE | ISDB | SDRE | LUKD | LUKE | SDRE |
| HLA209, | HLA209, | HLA209, | HLA209, | HLA209, | HLA209, | HLA209, | HLA209, |
| CLFA, | CLFA, | CLFA, | CLFA, | CLFA, | CLFB, | CLFB, | CLFB, |
| ISDB, | ISDB, | SDRE, | SDRE, | LUKD, | SDRD, | SDRD, | SDRD, |
| LUKD | LUKE | LUKD | LUKE | LUKE | ISDA | ISDB | SDRE |
| HLA209, | HLA209, | HLA209, | HLA209, | HLA209, | HLA209, | HLA209, | HLA209, |
| CLFB, | CLFB, | CLFB, | CLFB, | CLFB, | CLFB, | CLFB, | CLFB, |
| SDRD, | SDRD, | ISDA, | ISDA, | ISDA, | ISDA, | ISDB, | ISDB, |
| LUKD | LUKE | ISDB | SDRE | LUKD | LUKE | SDRE | LUKD |
| HLA209, | HLA209, | HLA209, | HLA209, | HLA209, | HLA209, | HLA209, | HLA209, |
| CLFB, | CLFB, | CLFB, | CLFB, | SDRD, | SDRD, | SDRD, | SDRD, |
| ISDB, | SDRE, | SDRE, | LUKD, | ISDA, | ISDA, | ISDA, | ISDA, |
| LUKE | LUKD | LUKE | LUKE | ISDB | SDRE | LUKD | LUKE |
| HLA209, | HLA209, | HLA209, | HLA209, | HLA209, | HLA209, | HLA209, | HLA209, |
| SDRD, | SDRD, | SDRD, | SDRD, | SDRD, | ISDA, | ISDA, | ISDA, |
| ISDB, | ISDB, | ISDB, | SDRE, | SDRE, | LUKD, | ISDB, | ISDB, |
| SDRE | LUKD | LUKE | LUKD | LUKE | LUKE | SDRE | LUKD |
| HLA209, | HLA209, | HLA209, | HLA209, | HLA209, | HLA209, | HLA209, | HLA209, |
| ISDA, | ISDA, | ISDA, | ISDA, | ISDB, | ISDB, | ISDB, | SDRE, |
| ISDB, | SDRE, | SDRE, | LUKD, | SDRE, | SDRE, | LUKD, | LUKD, |
| LUKE | LUKD | LUKE | LUKE | LUKD | LUKE | LUKE | LUKE |
| CLFA, | CLFA, | CLFA, | CLFA, | CLFA, | CLFA, | CLFA, | CLFA, |
| CLFB, | CLFB, | CLFB, | CLFB, | CLFB, | CLFB, | CLFB, | CLFB, |
| SDRD, | SDRD, | SDRD, | SDRD, | SDRD, | ISDA, | ISDA, | ISDA, |
| ISDA | ISDB | SDRE | LUKD | LUKE | ISDB | SDRE | LUKD |
| CLFA, | CLFA, | CLFA, | CLFA, | CLFA, | CLFA, | CLFA, | CLFA, |
| CLFB, | CLFB, | CLFB, | CLFB, | CLFB, | CLFB, | CLFB, | SDRD, |
| ISDA, | ISDB, | ISDB, | ISDB, | SDRE, | SDRE, | LUKD, | ISDA, |
| LUKE | SDRE | LUKD | LUKE | LUKD | LUKE | LUKE | ISDB |
| CLFA, | CLFA, | CLFA, | CLFA, | CLFA, | CLFA, | CLFA, | CLFA, |
| SDRD, | SDRD, | SDRD, | SDRD, | SDRD, | SDRD, | SDRD, | SDRD, |
| ISDA, | ISDA, | ISDA, | ISDB, | ISDB, | ISDB, | SDRE, | SDRE, |
| SDRE | LUKD | LUKE | SDRE | LUKD | LUKE | LUKD | LUKE |
| CLFA, | CLFA, | CLFA, | CLFA, | CLFA, | CLFA, | CLFA, | CLFA, |
| SDRD, | ISDA, | ISDA, | ISDA, | ISDA, | ISDA, | ISDA, | ISDA, |
| LUKD, | ISDB, | ISDB, | ISDB, | SDRE, | SDRE, | LUKD, | ISDB, |
| LUKE | SDRE | LUKD | LUKE | LUKD | LUKE | LUKE | LUKD |
| CLFA, | CLFA, | CLFA, | CLFB, | CLFB, | CLFB, | CLFB, | CLFB, |
| ISDB, | ISDB, | SDRE, | SDRD, | SDRD, | SDRD, | SDRD, | SDRD, |
| SDRE, | LUKD, | LUKD, | ISDA, | ISDA, | ISDA, | ISDA, | ISDB, |
| LUKE | LUKE | LUKE | ISDB | SDRE | LUKD | LUKE | SDRE |
| CLFB, | CLFB, | CLFB, | CLFB, | CLFB, | CLFB, | CLFB, | CLFB, |
| SDRD, | SDRD, | SDRD, | SDRD, | SDRD, | ISDA, | ISDA, | ISDA, |

TABLE 3D-continued

Table 3D: SA-MAPS with different combinations of 4 SA-antigens (126 combinations)

| | | | | | | | |
|---|---|---|---|---|---|---|---|
| ISDB, | ISDB, | SDRE, | SDRE, | LUKD, | ISDB, | ISDB, | ISDB, |
| LUKD | LUKE | LUKD | LUKE | LUKE | SDRE | LUKD | LUKE |
| CLFB, | CLFB, | CLFB, | CLFB, | CLFB, | CLFB, | CLFB, | SDRD, |
| ISDA, | ISDA, | ISDA, | ISDB, | ISDB, | ISDB, | SDRE, | ISDA, |
| SDRE, | SDRE, | LUKD, | SDRE, | SDRE, | LUKD, | LUKD, | ISDB, |
| LUKD | LUKE | LUKE | LUKD | LUKE | LUKE | LUKE | SDRE |
| SDRD, | SDRD, | SDRD, | SDRD, | SDRD, | SDRD, | SDRD, | SDRD, |
| ISDA, | ISDA, | ISDA, | ISDA, | ISDA, | ISDB, | ISDB, | ISDB, |
| ISDB, | ISDB, | SDRE, | SDRE, | LUKD, | SDRE, | SDRE, | LUKD, |
| LUKD | LUKE | LUKD | LUKE | LUKE | LUKD | LUKE | LUKE |
| SDRD, | ISDA, | ISDA, | ISDA, | ISDA, | ISDB, | | |
| SDRE, | ISDB, | ISDB, | ISDB, | SDRE, | SDRE, | | |
| LUKD, | SDRE, | SDRE, | LUKD, | LUKD, | LUKD, | | |
| LUKE | LUKD | LUKE | LUKE | LUKE | LUKE | | |

TABLE 3E

Table 3E: SA-MAPS with different combinations of 5 SA-antigens (126 combinations)

| | | | | | | | |
|---|---|---|---|---|---|---|---|
| HLA209, | HLA209, | HLA209, | HLA209, | HLA209, | HLA209, | HLA209, | HLA209, |
| CLFA, | CLFA, | CLFA, | CLFA, | CLFA, | CLFA, | CLFA, | CLFA, |
| CLFB, | CLFB, | CLFB, | CLFB, | CLFB, | CLFB, | CLFB, | CLFB, |
| SDRD, | SDRD, | SDRD, | SDRD, | SDRD, | ISDA | ISDA, | ISDA, |
| ISDA | ISDB | SDRE | LUKD | LUKE | ISDB | SDRE | LUKD |
| HLA209, | HLA209, | HLA209, | HLA209, | HLA209, | HLA209, | HLA209, | HLA209, |
| CLFA, | CLFA, | CLFA, | CLFA, | CLFA, | CLFA, | CLFA, | CLFA, |
| CLFB, | CLFB, | CLFB, | CLFB, | CLFB, | CLFB, | CLFB, | SDRD, |
| ISDA, | ISDB, | ISDB, | ISDB, | SDRE, | SDRE, | LUKD, | ISDA, |
| LUKE | SDRE | LUKD | LUKE | LUKD | LUKE | LUKE | ISDB |
| HLA209, | HLA209, | HLA209, | HLA209, | HLA209, | HLA209, | HLA209, | HLA209, |
| CLFA, | CLFA, | CLFA, | CLFA, | CLFA, | CLFA, | CLFA, | CLFA, |
| SDRD, | SDRD, | SDRD, | SDRD, | SDRD, | SDRD, | SDRD, | SDRD, |
| ISDA, | ISDA, | ISDA, | ISDB, | ISDB, | ISDB, | SDRE, | SDRE, |
| SDRE | LUKD | LUKE | SDRE | LUKD | LUKE | LUKD | LUKE |
| HLA209, | HLA209, | HLA209, | HLA209, | HLA209, | HLA209, | HLA209, | HLA209, |
| CLFA, | CLFA, | CLFA, | CLFA, | CLFA, | CLFA, | CLFA, | CLFA, |
| SDRD, | ISDA, | ISDA, | ISDA, | ISDA, | ISDA, | ISDA, | ISDB, |
| LUKD, | ISDB, | ISDB, | ISDB, | SDRE, | SDRE, | LUKD, | SDRE, |
| LUKE | SDRE | LUKD | LUKE | LUKD | LUKE | LUKE | LUKD |
| HLA209, | HLA209, | HLA209, | HLA209, | HLA209, | HLA209, | HLA209, | HLA209, |
| CLFA, | CLFA, | CLFA, | CLFB, | CLFB, | CLFB, | CLFB, | CLFB, |
| ISDB, | ISDB, | SDRE, | SDRD, | SDRD, | SDRD, | SDRD, | SDRD, |
| SDRE, | LUKD, | LUKD, | ISDA, | ISDA, | ISDA, | ISDA, | ISDB, |
| LUKE | LUKE | LUKE | ISDB | SDRE | LUKD | LUKE | SDRE |
| HLA209, | HLA209, | HLA209, | HLA209, | HLA209, | HLA209, | HLA209, | HLA209, |
| CLFB, | CLFB, | CLFB, | CLFB, | CLFB, | CLFB, | CLFB, | CLFB, |
| SDRD, | SDRD, | SDRD, | SDRD, | SDRD, | ISDA, | ISDA, | ISDA, |
| ISDB, | ISDB, | SDRE, | SDRE, | LUKD, | ISDB, | ISDB, | ISDB, |
| LUKD | LUKE | LUKD | LUKE | LUKE | SDRE | LUKD | LUKE |
| HLA209, | HLA209, | HLA209, | HLA209, | HLA209, | HLA209, | HLA209, | HLA209, |
| CLFB, | CLFB, | CLFB, | CLFB, | CLFB, | CLFB, | CLFB, | SDRD, |
| ISDA, | ISDA, | ISDA, | ISDB, | ISDB, | ISDB, | SDRE, | ISDA, |
| SDRE, | SDRE, | LUKD, | SDRE, | SDRE, | LUKD, | LUKD, | ISDB, |
| LUKD | LUKE | LUKE | LUKD | LUKE | LUKE | LUKE | SDRE |
| HLA209, | HLA209, | HLA209, | HLA209, | HLA209, | HLA209, | HLA209, | HLA209, |
| SDRD, | SDRD, | SDRD, | SDRD, | SDRD, | SDRD, | SDRD, | SDRD, |
| ISDA, | ISDA, | ISDA, | ISDA, | ISDA, | ISDB, | ISDB, | ISDB, |
| ISDB, | ISDB, | SDRE, | SDRE, | LUKD, | SDRE, | SDRE, | LUKD, |
| LUKD | LUKE | LUKD | LUKE | LUKE | LUKD | LUKE | LUKE |
| HLA209, | HLA209, | HLA209, | HLA209, | HLA209, | HLA209, | CLFA, | CLFA, |
| SDRD, | ISDA, | ISDA, | ISDA, | ISDA, | ISDB, | CLFB, | CLFB, |
| SDRE, | ISDB, | ISDB, | ISDB, | SDRE, | SDRE, | SDRD, | SDRD, |
| LUKD, | SDRE, | SDRE, | LUKD, | LUKD, | LUKD, | ISDA, | ISDA, |
| LUKE | LUKD | LUKE | LUKE | LUKE | LUKE | ISDB | SDRE |
| CLFA, | CLFA, | CLFA, | CLFA, | CLFA, | CLFA, | CLFA, | CLFA, |
| CLFB, | CLFB, | CLFB, | CLFB, | CLFB, | CLFB, | CLFB, | CLFB, |
| SDRD, | SDRD, | SDRD, | SDRD, | SDRD, | SDRD, | SDRD, | SDRD, |
| ISDA, | ISDA, | ISDB, | ISDB, | ISDB, | SDRE, | SDRE, | LUKD, |
| LUKD | LUKE | SDRE | LUKD | LUKE | LUKD | LUKE | LUKE |
| CLFA, | CLFA, | CLFA, | CLFA, | CLFA, | CLFA, | CLFA, | CLFA, |
| CLFB, | CLFB, | CLFB, | CLFB, | CLFB, | CLFB, | CLFB, | CLFB, |
| ISDA, | ISDA, | ISDA, | ISDA, | ISDA, | ISDA, | ISDB, | ISDB, |
| ISDB, | ISDB, | ISDB, | SDRE, | SDRE, | LUKD, | SDRE, | SDRE, |
| SDRE | LUKD | LUKE | LUKD | LUKE | LUKE | LUKD | LUKE |
| CLFA, | CLFA, | CLFA, | CLFA, | CLFA, | CLFA, | CLFA, | CLFA, |

TABLE 3E-continued

Table 3E: SA-MAPS with different combinations of 5 SA-antigens (126 combinations)

| | | | | | | | |
|---|---|---|---|---|---|---|---|
| CLFB, | CLFB, | SDRD, | SDRD, | SDRD, | SDRD, | SDRD, | SDRD, |
| ISDB, | SDRE, | ISDA, | ISDA, | ISDA, | ISDA, | ISDA, | ISDA, |
| LUKD, | LUKD, | ISDB, | ISDB, | ISDB, | SDRE, | SDRE, | LUKD, |
| LUKE | LUKE | SDRE | LUKD | LUKE | LUKD | LUKE | LUKE |
| CLFA, | CLFA, | CLFA, | CLFA, | CLFA, | CLFA, | CLFA, | CLFA, |
| SDRD, | SDRD, | SDRD, | SDRD, | ISDA, | ISDA, | ISDA, | ISDA, |
| ISDB, | ISDB, | ISDB, | SDRE, | ISDB, | ISDB, | ISDB, | SDRE, |
| SDRE, | SDRE, | LUKD, | LUKD, | SDRE, | SDRE, | LUKD, | LUKD, |
| LUKD | LUKE | LUKE | LUKE | LUKD | LUKE | LUKE | LUKE |
| CLFA, | CLFB, | CLFB, | CLFB, | CLFB, | CLFB, | CLFB, | CLFB, |
| ISDB, | SDRD, | SDRD, | SDRD, | SDRD, | SDRD, | SDRD, | SDRD, |
| SDRE, | ISDA, | ISDA, | ISDA, | ISDA, | ISDA, | ISDA, | ISDB, |
| LUKD, | ISDB, | ISDB, | ISDB, | SDRE, | SDRE, | LUKD, | SDRE, |
| LUKE | SDRE | LUKD | LUKE | LUKD | LUKE | LUKE | LUKD |
| CLFB, | CLFB, | CLFB, | CLFB, | CLFB, | CLFB, | CLFB, | CLFB, |
| SDRD, | SDRD, | SDRD, | ISDA, | ISDA, | ISDA, | ISDA, | ISDB, |
| ISDB, | ISDB, | SDRE, | ISDB, | ISDB, | ISDB, | SDRE, | SDRE, |
| SDRE, | LUKD, | LUKD, | SDRE, | SDRE, | LUKD, | LUKD, | LUKD, |
| LUKE | LUKE | LUKE | LUKD | LUKE | LUKE | LUKE | LUKE |
| SDRD, | SDRD, | SDRD, | SDRD, | SDRD, | ISDA, | | |
| ISDA, | ISDA, | ISDA, | ISDA, | ISDB, | ISDB, | | |
| ISDB, | ISDB, | ISDB, | SDRE, | SDRE, | SDRE, | | |
| SDRE, | SDRE, | LUKD, | LUKD, | LUKD, | LUKD, | | |
| LUKD | LUKE | LUKE | LUKE | LUKE | LUKE | | |

TABLE 3F

Table 3F: SA-MAPS with different combinations of 6 SA-antigens (84 combinations)

| | | | | | | | |
|---|---|---|---|---|---|---|---|
| HLA209, | HLA209, | HLA209, | HLA209, | HLA209, | HLA209, | HLA209, | HLA209, |
| CLFA, | CLFA, | CLFA, | CLFA, | CLFA, | CLFA, | CLFA, | CLFA, |
| CLFB, | CLFB, | CLFB, | CLFB, | CLFB, | CLFB, | CLFB, | CLFB, |
| SDRD, | SDRD, | SDRD, | SDRD, | SDRD, | SDRD, | SDRD, | SDRD, |
| ISDA, | ISDA, | ISDA, | ISDA, | ISDB, | ISDB, | ISDB, | SDRE, |
| ISDB | SDRE | LUKD | LUKE | SDRE | LUKD | LUKE | LUKD |
| HLA209, | HLA209, | HLA209, | HLA209, | HLA209, | HLA209, | HLA209, | HLA209, |
| CLFA, | CLFA, | CLFA, | CLFA, | CLFA, | CLFA, | CLFA, | CLFA, |
| CLFB, | CLFB, | CLFB, | CLFB, | CLFB, | CLFB, | CLFB, | CLFB, |
| SDRD, | SDRD, | ISDA, | ISDA, | ISDA, | ISDA, | ISDA, | ISDA, |
| SDRE, | LUKD, | ISDB, | ISDB, | ISDB, | SDRE, | SDRE, | LUKD, |
| LUKE | LUKE | SDRE | LUKD | LUKE | LUKD | LUKE | LUKE |
| HLA209, | HLA209, | HLA209, | HLA209, | HLA209, | HLA209, | HLA209, | HLA209, |
| CLFA, | CLFA, | CLFA, | CLFA, | CLFA, | CLFA, | CLFA, | CLFA, |
| CLFB, | CLFB, | CLFB, | SDRD, | SDRD, | SDRD, | SDRD, | SDRD, |
| ISDB, | ISDB, | SDRE, | ISDA, | ISDA, | ISDA, | ISDA, | ISDA, |
| SDRE, | LUKD, | LUKD, | ISDB, | ISDB, | ISDB, | SDRE, | SDRE, |
| LUKD | LUKE | LUKE | SDRE | LUKD | LUKE | LUKD | LUKE |
| HLA209, | HLA209, | HLA209, | HLA209, | HLA209, | HLA209, | HLA209, | HLA209, |
| CLFA, | CLFA, | CLFA, | CLFA, | CLFA, | CLFA, | CLFA, | CLFA, |
| SDRD, | SDRD, | SDRD, | SDRD, | ISDA, | ISDA, | ISDA, | ISDA, |
| ISDA, | ISDB, | ISDB, | ISDB, | SDRE, | ISDB, | ISDB, | ISDB, |
| LUKD, | SDRE, | SDRE, | LUKD, | LUKD, | SDRE, | SDRE, | LUKD, |
| LUKE | LUKD | LUKE | LUKE | LUKE | LUKD | LUKE | LUKE |
| HLA209, | HLA209, | HLA209, | HLA209, | HLA209, | HLA209, | HLA209, | HLA209, |
| CLFA, | CLFA, | CLFB, | CLFB, | CLFB, | CLFB, | CLFB, | CLFB, |
| ISDA, | ISDB, | SDRD, | SDRD, | SDRD, | SDRD, | SDRD, | SDRD, |
| SDRE, | SDRE, | ISDA, | ISDA, | ISDA, | ISDA, | ISDA, | ISDA, |
| LUKD, | LUKD, | ISDB, | ISDB, | ISDB, | SDRE, | SDRE, | LUKD, |
| LUKE | LUKE | SDRE | LUKD | LUKE | LUKD | LUKE | LUKE |
| HLA209, | HLA209, | HLA209, | HLA209, | HLA209, | HLA209, | HLA209, | HLA209, |
| CLFB, | CLFB, | CLFB, | CLFB, | CLFB, | CLFB, | CLFB, | CLFB, |
| SDRD, | SDRD, | SDRD, | SDRD, | SDRD, | ISDA, | ISDA, | ISDA, |
| ISDB, | ISDB, | ISDB, | SDRE, | SDRE, | ISDB, | ISDB, | ISDB, |
| SDRE, | SDRE, | LUKD, | LUKD, | SDRE, | SDRE, | LUKD, | LUKD, |
| LUKD | LUKE | LUKE | LUKE | LUKD | LUKE | LUKE | LUKE |
| HLA209, | HLA209, | HLA209, | HLA209, | HLA209, | HLA209, | HLA209, | CLFA, |
| CLFB, | SDRD, | SDRD, | SDRD, | SDRD, | SDRD, | SDRD, | CLFB, |
| ISDB, | ISDA, | ISDA, | ISDA, | ISDA, | ISDB, | ISDB, | SDRD, |
| SDRE, | ISDB, | ISDB, | ISDB, | SDRE, | SDRE, | SDRE, | ISDA, |
| LUKD, | SDRE, | SDRE, | LUKD, | LUKD, | LUKD, | LUKD, | ISDB, |
| LUKE | LUKD | LUKE | LUKE | LUKE | LUKE | LUKE | SDRE |
| CLFA, | CLFA, | CLFA, | CLFA, | CLFA, | CLFA, | CLFA, | CLFA, |
| CLFB, | CLFB, | CLFB, | CLFB, | CLFB, | CLFB, | CLFB, | CLFB, |
| SDRD, | SDRD, | SDRD, | SDRD, | SDRD, | SDRD, | SDRD, | SDRD, |
| ISDA, | ISDA, | ISDA, | ISDA, | ISDA, | ISDB, | ISDB, | ISDB, |

TABLE 3F-continued

Table 3F: SA-MAPS with different combinations of 6 SA-antigens (84 combinations)

| | | | | | | | |
|---|---|---|---|---|---|---|---|
| ISDB, | ISDB, | SDRE, | SDRE, | LUKD, | SDRE, | SDRE, | LUKD, |
| LUKD | LUKE | LUKD | LUKE | LUKE | LUKD | LUKE | LUKE |
| CLFA, | CLFA, | CLFA, | CLFA, | CLFA, | CLFA, | CLFA, | CLFA, |
| CLFB, | CLFB, | CLFB, | CLFB, | CLFB, | CLFB, | SDRD, | SDRD, |
| SDRD, | ISDA, | ISDA, | ISDA, | ISDA, | ISDB, | ISDA, | ISDA, |
| SDRE, | ISDB, | ISDB, | ISDB, | SDRE, | SDRE, | ISDB, | ISDB, |
| LUKD, | SDRE, | SDRE, | LUKD, | LUKD, | LUKD, | SDRE, | SDRE, |
| LUKE | LUKD | LUKE | LUKE | LUKE | LUKE | LUKD | LUKE |
| CLFA, | CLFA, | CLFA, | CLFA, | CLFB, | CLFB, | CLFB, | CLFB, |
| SDRD, | SDRD, | SDRD, | ISDA, | SDRD, | SDRD, | SDRD, | SDRD, |
| ISDA, | ISDA, | ISDB, | ISDB, | ISDA, | ISDA, | ISDA, | ISDA, |
| ISDB, | SDRE, | SDRE, | SDRE, | ISDB, | ISDB, | ISDB, | SDRE, |
| LUKD, | LUKD, | LUKD, | LUKD, | SDRE, | SDRE, | LUKD, | LUKD, |
| LUKE | LUKE | LUKE | LUKE | LUKD | LUKE | LUKE | LUKE |
| CLFB, | CLFB, | SDRD, | | | | | |
| SDRD, | ISDA, | ISDA, | | | | | |
| ISDB, | ISDB, | ISDB, | | | | | |
| SDRE, | SDRE, | SDRE, | | | | | |
| LUKD, | LUKD, | LUKD, | | | | | |
| LUKE | LUKE | LUKE | | | | | |

TABLE 3G

Table 3G: SA-MAPS with different combinations of 7 SA-antigens (36 combinations)

| | | | | | | | |
|---|---|---|---|---|---|---|---|
| HLA209, | HLA209, | HLA209, | HLA209, | HLA209, | HLA209, | HLA209, | HLA209, |
| CLFA, | CLFA, | CLFA, | CLFA, | CLFA, | CLFA, | CLFA, | CLFA, |
| CLFB, | CLFB, | CLFB, | CLFB, | CLFB, | CLFB, | CLFB, | CLFB, |
| SDRD, | SDRD, | SDRD, | SDRD, | SDRD, | SDRD, | SDRD, | SDRD, |
| ISDA, | ISDA, | ISDA, | ISDA, | ISDA, | ISDA, | ISDB, | ISDB, |
| ISDB, | ISDB, | ISDB, | SDRE, | SDRE, | LUKD, | SDRE, | SDRE, |
| SDRE | LUKD | LUKE | LUKD | LUKE | LUKE | LUKD | LUKE |
| HLA209, | HLA209, | HLA209, | HLA209, | HLA209, | HLA209, | HLA209, | HLA209, |
| CLFA, | CLFA, | CLFA, | CLFA, | CLFA, | CLFA, | CLFA, | CLFA, |
| CLFB, | CLFB, | CLFB, | CLFB, | CLFB, | CLFB, | CLFB, | SDRD, |
| SDRD, | SDRD, | ISDA, | ISDA, | ISDA, | ISDA, | ISDB, | ISDA, |
| ISDB, | SDRE, | ISDB, | ISDB, | ISDB, | SDRE, | SDRE, | ISDB, |
| LUKD, | LUKD, | SDRE, | SDRE, | LUKD, | LUKD, | LUKD, | SDRE, |
| LUKE | LUKE | LUKD | LUKE | LUKE | LUKE | LUKE | LUKD |
| HLA209, | HLA209, | HLA209, | HLA209, | HLA209, | HLA209, | HLA209, | HLA209, |
| CLFA, | CLFA, | CLFA, | CLFA, | CLFA, | CLFB, | CLFB, | CLFB, |
| SDRD, | SDRD, | SDRD, | SDRD, | ISDA, | SDRD, | SDRD, | SDRD, |
| ISDA, | ISDA, | ISDA, | ISDB, | ISDB, | ISDA, | ISDA, | ISDA, |
| ISDB, | ISDB, | SDRE, | SDRE, | SDRE, | ISDB, | ISDB, | ISDB, |
| SDRE, | LUKD, | LUKD, | LUKD, | LUKD, | SDRE, | SDRE, | LUKD, |
| LUKE | LUKE | LUKE | LUKE | LUKE | LUKD | LUKE | LUKE |
| HLA209, | HLA209, | HLA209, | HLA209, | CLFA, | CLFA, | CLFA, | CLFA, |
| CLFB, | CLFB, | CLFB, | SDRD, | CLFB, | CLFB, | CLFB, | CLFB, |
| SDRD, | SDRD, | ISDA, | ISDA, | SDRD, | SDRD, | SDRD, | SDRD, |
| ISDA, | ISDB, | ISDB, | ISDB, | ISDA, | ISDA, | ISDA, | ISDA, |
| SDRE, | SDRE, | SDRE, | SDRE, | ISDB, | ISDB, | ISDB, | SDRE, |
| LUKD, | LUKD, | LUKD, | LUKD, | SDRE, | SDRE, | LUKD, | LUKD, |
| LUKE | LUKE | LUKE | LUKE | LUKD | LUKE | LUKE | LUKE |
| CLFA, | CLFA, | CLFA, | CLFB, | | | | |
| CLFB, | CLFB, | SDRD, | SDRD, | | | | |
| SDRD, | ISDA, | ISDA, | ISDA, | | | | |
| ISDB, | ISDB, | ISDB, | ISDB, | | | | |
| SDRE, | SDRE, | SDRE, | SDRE, | | | | |
| LUKD, | LUKD, | LUKD, | LUKD, | | | | |
| LUKE | LUKE | LUKE | LUKE | | | | |

TABLE 3F

Table 3F: SA-MAPS with different combinations of 8 SA-antigens (9 combinations)

| | | | | | | | | |
|---|---|---|---|---|---|---|---|---|
| HLA209, | HLA209, | HLA209, | HLA209, | HLA209, | HLA209, | HLA209, | HLA209, | CLFA, |
| CLFA, | CLFA, | CLFA, | CLFA, | CLFA, | CLFA, | CLFA, | CLFB, | CLFB, |
| CLFB, | CLFB, | CLFB, | CLFB, | CLFB, | CLFB, | SDRD, | SDRD, | SDRD, |
| SDRD, | SDRD, | SDRD, | SDRD, | SDRD, | ISDA, | ISDA, | ISDA, | ISDA, |

TABLE 3F-continued

Table 3F: SA-MAPS with different combinations of 8 SA-antigens (9 combinations)

| ISDA, | ISDA, | ISDA, | ISDA, | ISDB, | ISDB, | ISDB, | ISDB, | ISDB, |
|---|---|---|---|---|---|---|---|---|
| ISDB, | ISDB, | ISDB, | SDRE, | SDRE, | SDRE, | SDRE, | SDRE, | SDRE, |
| SDRE, | SDRE, | LUKD, | LUKD, | LUKD, | LUKD, | LUKD, | LUKD, | LUKD, |
| LUKD | LUKE | LUKE | LUKE | LUKE | LUKE | LUKE | LUKE | LUKE |

TABLE 3G

Table 3G: an exemplary SA-MAPS with all 9 SA-antigens

HLA209, CLFA, CLFB, SDRD, ISDA, ISDB, SDRE, LUKD, LUKE

It is envisioned that any of the above-identified antigens in Tables 3A-3G can be switched out for a different SA antigen, including a different peptides or polypeptides of ClfA, ClfB, SdrD, SdrE, IsdA, IsdB, LukD, or LukE, or peptides or polypeptides at least 85% sequence identity thereto, or completely different SA antigens. In some embodiments, a SA antigen identified in tables 3A-3G can be substituted or switched out with a non-SA antigen, as disclosed herein.

Accordingly, in some embodiments, an ordinary skilled artisan can substitute any of the antigens listed in Tables 3A-3G with any other SA antigen not listed herein and known to an ordinary skilled artisan, or even substitute a SA antigen listed in Tables 3A-3G with a non-SA antigen.

In addition to one or more *S. aureus* antigens present in the MAPS complex, the MAPS complex may comprise non-*S. aureus* (non-SA) immunogenic antigens, including but not limited to pathogenic peptides, toxins, toxoids, subunits thereof, or combinations thereof (e.g., cholera toxin, tetanus toxoid).

In some embodiments, an antigen is derived (e.g., obtained) from a pathogenic organism. In some embodiments, the antigen is a cancer or tumor antigen, e.g., an antigen derived from a tumor or cancer cell.

In some embodiments, an antigen derived from a pathogenic organism is an antigen associated with an infectious disease; it can be derived from any of a variety of infectious agents, including virus, bacterium, fungus or parasite.

In some embodiments, a target antigen is any antigen associated with a pathology, for example an infectious disease or pathogen, or cancer or an immune disease such as an autoimmune disease. In some embodiments, an antigen can be expressed by any of a variety of infectious agents, including virus, bacterium, fungus or parasite. A target antigen for use in the methods and compositions as disclosed herein can also include, for example, pathogenic peptides, toxins, toxoids, subunits thereof, or combinations thereof (e.g., cholera toxin, tetanus toxoid).

Non-limiting examples of infectious viruses include: Retroviridae; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), Marek's disease virus, herpes viruses); Poxviridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses). The compositions and methods described herein are contemplated for use in treating infections with these viral agents.

Examples of fungal infections that may be addressed by inclusion of antigens in the preaent embodiments include aspergillosis; thrush (caused by *Candida albicans*); cryptococcosis (caused by *Cryptococcus*); and histoplasmosis. Thus, examples of infectious fungi include, but are not limited to, *Cryptococcus neoformans, Histoplasma capsulatum, Coccidioides immitis, Blastomyces dermatitidis, Chlamydia trachomatis, Candida albicans*. Components of these organisms can be included as antigens in the MAPS described herein.

In one aspect of the invention, an non-SA antigen to be used in combination with one or more SA antigens on the MAPS complex is derived from an infectious microbe such as *Bordatella pertussis, Brucella, Enterococci* sp., *Neisseria meningitidis, Neisseria gonorrheae, Moraxella*, typeable or nontypeable *Haemophilus, Pseudomonas, Salmonella, Shigella, Enterobacter, Citrobacter, Klebsiella, E. coli, Helicobacter pylori, Clostridia, Bacteroides, Chlamydiaceae, Vibrio cholera, Mycoplasma, Treponemes, Borelia burgdorferi, Legionella pneumophilia, Mycobacteria* sps (such as *M. tuberculosis, M. avium, M. intracellulare, M. kansaii, M. gordonae, M. leprae*), *Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Leptospira* sps., *Pasturella multocida, Bacteroides* sp., *Fusobacterium nucleatum, Streptobacillus moniliformis, Treponema pallidium, Treponema pertenue*, and *Actinomyces israelli*.

In some embodiments, a non-SA antigen useful in a SA-MAPS complex as disclosed herein is an antigen from an enteric bacterium, or non-enteric gram-negative bacteria. In some embodiments, a non-SA antigen useful in a SA-MAPS complex as disclosed herein can be selected from any of, or a combination of: a pneumococcal antigen, tuberculous antigen, HIV antigen, sesonal or epidemic influenza antigen, pertussis antigen, meningococcal antigen, haemophilus antigen, HPV antigen, *E. coli* antigens, salmonella antigens, enterobacter antigens, acinetobacter pathogen antigens, pseudomona antigens, klebsiella antigens, citrobacter antigens, serratia antigens, *Clostridium difficile* antigens from an enteric bacteria, antigens from non-enteric gram-negative bacteria, toxoids, toxins or toxin portions thereof.

In some embodiments, a non-SA antigen useful in a SA-MAPS complex as disclosed herein is a pneumococcal antigen, a tuberculosis antigen, an anthrax antigen, a HIV antigens, a seasonal or epidemic influenza antigen, a HPV antigen, an Acinetobacter antigens, a-*Clostridium difficile* antigen, an enteric Gram-negative bacterial antigen or non-enteric Gram-negative bacterial antigen, a Gram-positive bacterial antigens, a toxoid, toxin or toxin portion, a fungal antigen, a viral antigen, a cancer antigen or any combinations thereof.

In some embodiments, a non-SA antigen useful in a SA-MAPS complex as disclosed herein is an enteric Gram-negative bacterial antigen, selected from the group of: *E. coli* antigens, *Salmonella* antigens, *Enterobacter* antigens, *Klebsiella* antigens, *Citrobacter* antigens and Serratia antigens, or combinations thereof. In some embodiments, a non-SA antigen useful in a SA-MAPS complex as disclosed herein is a nonenteric Gram-negative bacterial antigens are selected from the group of: *Pertussis* antigens, *Meningococcal* antigens, *Haemophilus* antigens, and *Pseudomonas* antigens or combinations thereof.

Additional parasite pathogens from which antigens can be derived include, for example: *Entamoeba histolytica, Plasmodium falciparum, Leishmania* sp., *Toxoplasma gondii, Rickettsia*, and the *Helminths*.

In some embodiments, a non-SA antigen useful in a SA-MAPS complex as disclosed herein is a truncated pneumococcal PsaA protein, pneumolysin toxoid pneumococcal serine/threonine protein kinase (StkP), pneumococcal serine/threonine protein kinase repeating unit (StkPR), pneumococcal PcsB protein, staphylococcal alpha hemolysin, Mycobacterium tuberculosis mtb protein ESAT-6, *M. tuberculosis* cell wall core antigen, *Chlamydia* CT144, CT242 or CT812 polypeptides or fragments of these, *Chlamydia* DNA gyrase subunit B, *Chlamydia* sulfite synthesis/biphosphate phosphatase, *Chlamydia* cell division protein FtsY, *Chlamydia* methionyl-tRNA synthetase, *Chlamydia* DNA helicase (uvrD), *Chlamydia* ATP synthase subunit I (atpI), or *Chlamydia* metal dependent hydrolase.

In some embodiments, a non-SA antigen useful in a SA-MAPS complex as disclosed herein is an antigen from *Myocobacterium tuberculosis* (TB). One example of a TB antigen is TbH9 (also known as Mtb 39A). Other TB antigens include, but are not limited to, DPV (also known as Mtb8.4), 381, Mtb41, Mtb40, Mtb32A, Mtb64, Mtb83, Mtb9.9A, Mtb9.8, Mtb16, Mtb72f, Mtb59f, Mtb88f, Mtb71f, Mtb46f and Mtb31f, wherein "f" indicates that it is a fusion or two or more proteins.

In some embodiments, a non-SA antigen useful in a SA-MAPS complex as disclosed herein can be derived from a *Chlamydia* species for use in the immunogenic compositions of the present invention. Chlamydiaceae (consisting of *Chlamydiae* and *Chlamydophila*), are obligate intracellular gram-negative bacteria. *Chlamydia trachomatis* infections are among the most prevalent bacterial sexually transmitted infections, and perhaps 89 million new cases of genital chlamydial infection occur each year. The *Chlamydia* of the present invention include, for example, *C. trachomatis, Chlamydophila pneumoniae, C. muridarum, C. suis, Chlamydophila abortus, Chlamydophila psittaci, Chlamydophila caviae, Chlamydophila felis, Chlamydophila pecorum*, and *C. pneumoniae*. Animal models of chlamydial infection have established that T-cells play a critical role both in the clearance of the initial infection and in protection from re-infection of susceptible hosts. Hence, the immunogenic compositions as disclosed herein can be used to provide particular value by eliciting cellular immune responses against chlamydial infection.

More specifically, Chlamydial antigens useful as a non-SA antigen in a SA-MAPS complex as disclosed herein include DNA gyrase subunit B, sulfite synthesis/biphosphate phosphatase, cell division protein FtsY, methionyl-tRNA synthetase, DNA helicase (uvrD); ATP synthase subunit I (atpI) or a metal-dependent hydrolase (U.S. Patent Application Pub. No. 20090028891). Additional *Chlamydia trachomatis* antigens include CT144 polypeptide, a peptide having amino acid residues 67-86 of CT144, a peptide having amino acid residues 77-96 of CT144, CT242 protein, a peptide having amino acids 109-117 of CT242, a peptide having amino acids 112-120 of CT242 polypeptide, CT812 protein (from the pmpD gene), a peptide having amino acid residues 103-111 of the CT812 protein; and several other antigenic peptides from *C. trachomatis*, which are disclosed in US Patent Application: 2014/0154287 and WO 2009/020553. Additionally, *Chlamydia pneumoniae* antigens including homologues of the foregoing polypeptides (see U.S. Pat. No. 6,919,187), can be used as antigens in the immunogenic compositions and methods as disclosed herein.

In some embodiments, an SA or non-SA antigen for use in the SA-MAPS composition can be an intact (i.e., an entire or whole) antigen, or a functional portion of an antigen that comprises more than one epitope. In some embodiments, an antigen is a peptide functional portion of an antigen. By "intact" in this context is meant that the antigen is the full length antigen as that antigen polypeptide occurs in nature. This is in direct contrast to delivery of only a small portion or peptide of the antigen. Delivering an intact antigen to a cell enables or facilitates eliciting an immune response to a full range of epitopes of the intact antigen, rather than just a single or selected few peptide epitopes. Accordingly, the methods and immunogenic compositions described herein encompass intact antigens associated with the polymer for a more sensitive and have higher specificity of immune response as compared to use of a single epitope peptide-based antigen.

Alternatively, in some embodiments, an intact SA antigen can be divided into many parts, depending on the size of the initial antigen. Typically, where a whole antigen is a multimer polypeptide, the whole protein can be divided into sub-units and/or domains where each individual sub-unit or domain of the antigen can be associated with the polymer according to the methods as disclosed herein. Alternatively, in some embodiments, an intact SA antigen can be divided into functional fragments, or parts, of the whole antigen, for example, at least two, or at least 3, or at least 4, or at least 5, or at least 6, or at least 7, or at least 8, or at least 9, or at least 10, or at least 11, or at least 12, or at least 13, or at least 15, or at least 20, or at least 25, or more than 25 portions (e.g., pieces or fragments), inclusive, and where each individual functional fragment of the antigen can be associated with the polymer according to the methods as disclosed herein.

The fragmentation or division of a full length SA antigen polypeptide can be an equal division of the full length antigen polypeptide, or alternatively, in some embodiments, the fragmentation is asymmetrical or unequal. As a non-limiting example, where an antigen is divided into two overlapping fragments, an antigen can be divided into fragments of approximately the same (equal) size, or alternatively one fragment can be about 45% of the whole antigen and the other fragment can be about 65%. As further non-limiting examples, a whole antigen can be divided into a combination of differently sized fragments, for example, where an antigen is divided into two fragments, fragments can be divided into about 40% and about 70%, or about 45% and about 65%; or about 35% and about 75%; or about 25% and about 85%, inclusive, of the whole antigen. Any combination of overlapping fragments of a full length whole antigen is encompassed for use in the generation of a panel of overlapping polypeptides of an antigen. As an illustrative example only, where an antigen is divided into 5 portions, the portions can divided equally (i.e., each overlapping fragment is about 21% to 25% of the entire full length if the antigen) or unequally (i.e., an antigen can be divided into the following five overlapping fragments; fragment 1 is about 25%, fragment 2 is about 5%, fragment 3 is about 35%, fragment 4 is about 10% and fragment 5 is about 25% of the size of the full length antigen, provided each fragment overlaps with at least one other fragment).

Typically, a panel of antigen portions can substantially cover the entire length of the whole (or intact) antigen polypeptide. Accordingly, in some embodiments, an immunogenic composition comprises a polymer with many different, and/or overlapping fragments of the same intact antigen. Overlapping protein fragments of an antigen can be produced much quicker and cheaper, and with increased stability as compared to the use of peptide antigens alone. Further in some embodiments, antigens which are polypeptides larger than simple peptides are preferred as conformation is important for epitope recognition, and the larger antigen polypeptides or fragments will provide a benefit over peptide fragments.

One of ordinary skill in the art can divide a whole antigen into overlapping proteins of an antigen to create a panel of polypeptides of the antigen. By way of an illustrative example only, a SA antigen ClfA can be divided into, for example at least 10 portions to generate a panel of 10 different polypeptides, each comprising a different but overlapping ClfA-specific antigens fragments.

A target antigen for use in the methods and compositions described herein can be expressed by recombinant means, and can optionally include an affinity or epitope tag to facilitate purification, which methods are well-known in the art. Chemical synthesis of an oligopeptide, either free or conjugated to carrier proteins, can be used to obtain antigen of the invention. Oligopeptides are considered a type of polypeptide. An antigen can be expressed as a fusion with a complementary affinity molecule, e.g., but not limited to rhizavidin or a derivative or functional fragment thereof. Alternatively, it is also possible to prepare target antigen and then conjugate it to a complementary affinity molecule, e.g., but not limited to rhizavidin or a derivative or functional fragment thereof.

Polypeptides can also by synthesized as branched structures such as those disclosed in U.S. Pat. Nos. 5,229,490 and 5,390,111. Antigenic polypeptides include, for example, synthetic or recombinant B-cell and T-cell epitopes, universal T-cell epitopes, and mixed T-cell epitopes from one organism or disease and B-cell epitopes from another.

An antigen can be obtained through recombinant means or chemical polypeptide synthesis, as well as antigen obtained from natural sources or extracts, can be purified by means of the antigen's physical and chemical characteristics, such as by fractionation or chromatography. These techniques are well-known in the art.

In some embodiments, an antigen can be solubilized in water, a solvent such as methanol, or a buffer. Suitable buffers include, but are not limited to, phosphate buffered saline $Ca^{2+}/Mg^{2+}$ free (PBS), normal saline (150 mM NaCl in water), and Tris buffer. Antigen not soluble in neutral buffer can be solubilized in 10 mM acetic acid and then diluted to the desired volume with a neutral buffer such as PBS. In the case of antigen soluble only at acid pH, acetate-PBS at acid pH can be used as a diluent after solubilization in dilute acetic acid. Glycerol can be a suitable non-aqueous solvent for use the compositions, methods and kits described herein.

Typically, when designing a protein vaccine against a pathogen, an extracellular protein or one exposed to the environment on a virus is often the ideal candidate as the antigen component in the vaccine. Antibodies generated against that extracellular protein become the first line of defense against the pathogen during infection. The antibodies bind to the protein on the pathogen to facilitate antibody opsonization and mark the pathogen for ingestion and destruction by a phagocyte such as a macrophage. Antibody opsonization can also kill the pathogen by antibody-dependent cellular cytotoxicity. The antibody triggers a release of lysis products from cells such as monocytes, neutrophils, eosinophils, and natural killer cells.

In one embodiment of the invention described herein, antigens for use in the compositions as disclosed herein all wild type proteins, as in the amino acid residues have the sequences found in naturally occurring viruses and have not been altered by selective growth conditions or molecular biological methods.

In one embodiment, the immunogenic compositions described as herein can comprise antigens which are glycosylated proteins. In other words, an antigen of interest can each be a glycosylated protein. In one embodiment of the immunogenic compositions as described herein, antigens, or antigen-fusion polypeptides are O-linked glycosylated. In another embodiment of the immunogenic compositions as described herein, antigens, or antigen-fusion polypeptides are N-linked glycosylated. In yet another embodiment of the immunogenic compositions as described herein, antigens, or antigen-fusion are both O-linked and N-linked glycosylated. In other embodiments, other types of glycosylations are possible, e.g., C-mannosylation. Glycosylation of proteins occurs predominantly in eukaryotic cells. N-glycosylation is important for the folding of some eukaryotic proteins, providing a co-translational and post-translational modification mechanism that modulates the structure and function of membrane and secreted proteins. Glycosylation is the enzymatic process that links saccharides to produce glycans, and attaches them to proteins and lipids. In N-glycosylation, glycans are attached to the amide nitrogen of asparagine side chain during protein translation. The three major saccharides forming glycans are glucose, mannose, and N-acetylglucosamine molecules. The N-glycosylation consensus is Asn-Xaa-Ser/Thr, where Xaa can be any of the known amino acids. O-linked glycosylation occurs at a later stage during protein processing, probably in the Golgi apparatus. In O-linked glycosylation, N-acetyl-galactosamine, O-fucose, O-glucose, and/or N-acetylglucosamine is added to serine or threonine residues. One skilled in the art can use bioinformatics software such as NetNGlyc 1.0 and NetOGlyc Prediction softwares from the Technical University of Denmark to find the N- and O-glycosylation sites in a polypeptide in the present invention. The NetNglyc server predicts N-Glycosylation sites in proteins using artificial neural networks that examine the sequence context of Asn-Xaa-Ser/Thr sequons. The NetNGlyc 1.0 and NetOGlyc 3.1 Prediction software can be accessed at the EXPASY website. In one embodiment, N-glycosylation occurs in the target antigen polypeptide of the fusion polypeptide described herein.

SA-Antigen-Fusion Proteins

In some embodiments, the SA antigen for use in the MAPS complex as disclosed herein is fused to a recombinant biotin-binding protein. In some embodiments, the recombinant biotin-binding protein is a rhizavidin protein. In some embodiments, the Rhizavidin (Rhavi) protein comprises SEQ ID NO: 1 or a protein or polypeptide of at least 85% amino acid sequence identity to SEQ ID NO: 1.

In some embodiments, the recombinant biotin-binding protein comprises an E. coli signal sequence fused to the N-terminus of an amino acid sequence comprising amino acids 45-179 of wild-type Rhizavidin (rhavi) which is as follows:

(SEQ ID NO: 1)
FDASNFKDFSSIASASSSWQNQSGSTMIIQVDSFGNVSGQYVNRAQGTGCQ

NSPYPLTGRVNGTFIAFSVGWNNSTENCNSATGWTGYAQVNGNNTEIVTSW

NLAYEGGSGPAIEQGQDTFQYVPTTENKSLLKD.

In other words, the biotin-binding domain does not comprise (i.e., lacks) lacks amino acids 1-44

(MIITSLYATFGTIADGRRTSGGKTMIRTNAVAALVFAVATSALA,
SEQ ID NO: 22).

In some embodiments, the recombinant biotin-binding protein consists of, or consists essentially of, the amino acid sequence corresponding to amino acids 45-179 of the wild-type Rhizavidin. Amino acid sequence of the wild-type Rhizavidin is:

(SEQ ID NO: 21)
MIITSLYATFGTIADGRRTSGGKTMIRTNAVAALVFAVATSALAFDASNFK

DFSSIASASSSWQNQSGSTMIIQVDSFGNVSGQYVNRAQGTGCQNSPYPLT

GRVNGTFIAFSVGWNNSTENCNSATGWTGYAQVNGNNTEIVTSWNLAYEGG

SGPAIEQGQDTFQYVPTTENKSLLKD.

In some embodiments, the recombinant biotin-binding protein useful in a fusion protein with at least one SA-antigen as disclosed herein comprises an amino acid sequence having at least 50% identity, at least 55% identity, at least 60% identity, at least 65% identity, at least 70% identity, at least 75% identity, at least 80% identity, preferably at least 85% identity, at least 90% identity, at least 95% identity, at least 96% identity, at least 97% identity, at least 98% identity, or at least 99% identity, and more preferably at least 99.3% identity to SEQ ID NO: 1.

A SA-antigen for use in the SA-MAPS composition as disclosed herein can be genetically fused to rhizavidin (rhavi), which is a dimeric biotin-binding protein from Rhizobium etli, according to the methods as disclosed in U.S. Pat. No. 9,499,593 which is incorporated herein in its entirety by reference.

In some embodiments, a biotin-binding protein useful in the SA-MAPS composition as disclosed herein comprises a sequence $X^1$—$X^2$—$X^3$, wherein $X^2$ is a peptide having the amino acid sequence corresponding to amino acids 45-179 of the wild-type Rhizavidin (i.e., SEQ ID NO: 1) and $X^1$ and $X^3$ are independently absent, or a peptide of 1 to about 100 amino acids with the proviso that the N-terminus of $X^1$ does not comprise an amino acid sequence corresponding to N-terminus of amino acids 1-44 of the wild-type Rhizavidin.

In some embodiments, the biotin-binding proteins can comprise a signal peptide conjugated to the N-terminus of the biotin-binding protein, i.e. $X^1$ can comprise a signal peptide. The signal peptide is also called a leader peptide in the N-terminus, which may or may not be cleaved off after the translocation through the membrane. In some embodiments, the E. coli signal sequence is the Dsba signal sequence which comprises at least MKKIWLALAGLV-LAFSASA (SEQ ID NO: 23) or MKKIWLALAGLV-LAFSASAAQDP (SEQ ID NO: 24). In some embodiments, the signal sequence is MKKVAAFVALSLLMAGC (SEQ ID NO: 25). Secretion/signal peptides are described in more detail below. In some embodiments, the signal sequence is MKKIWLALAGLVLAFSASA (SEQ ID NO: 26), MAPFE-PLASGILLLLWLIAPSRA (SEQ ID NO: 27), MKKVAAF-VALSLLMAGC (SEQ ID NO: 28), or a derivative or functional portion thereof. The signal sequence can be fused with the sequence comprising amino acids 45-179 of wild-type rhavi by a flexible peptide linker.

In some embodiments, the biotin-binding protein is a fusion protein with one or more SA-antigens. For example, the C-terminal of SEQ ID NO: 1 (or a protein of at least 80% or 85% or more sequence identity thereto) is fused to at least 1, or at least 2 or at least 3, or at least 4 or more SA-antigens.

In some embodiments, a biotin-binding protein is a fusion protein comprising a C-terminal of SEQ ID NO: 1 (or a protein of at least 80% or 85% or more sequence identity thereto) is fused to any of hemolysin (Hl) (e.g., hemolysin α or Hla209), Clumping factor A (ClfA), Clumping factor B (ClfB), serine-aspirate repeat protein D (SdrD), Iron regulator surface protein A (IsdA) and Iron regulator surface protein B (IsdB), or fragments thereof. In some embodiments, a biotin-binding protein is a fusion protein comprising a the C-terminal of SEQ ID NO: 1 (or a protein of at least 80% or 85% or more sequence identity thereto) fused to any one of: Hla209(27-319), ClfA (221-559), ClfB (203-542), SdrD (246-682), IsdA (47-324), IsdB (48-447) or proteins or peptides having at least 85% sequence identity thereto.

Aspects of the present invention are directed to an isolated recombinant rhizavidin fusion protein comprising SEQ ID NO: 1 (or a protein of at least 80% or 85% or more sequence identity thereto) fused to Hla209(27-319) (Rhavi-Hla209). Aspects of the present invention are directed to an isolated recombinant rhizavidin fusion protein comprising SEQ ID NO: 1 (or a protein of at least 80% or 85% or more sequence identity thereto) fused to ClfA (221-559) (Rhavi-ClfA). Aspects of the present invention are directed to an isolated recombinant rhizavidin fusion protein comprising SEQ ID NO: 1 (or a protein of at least 80% or 85% or more sequence identity thereto) fused to ClfB (203-542) (Rhavi-ClfB). Aspects of the present invention are directed to an isolated recombinant rhizavidin fusion protein comprising SEQ ID NO: 1 (or a protein of at least 80% or 85% or more sequence identity thereto) fused to SdrD (246-682) (Rhavi-SdrD). Aspects of the present invention are directed to an isolated recombinant rhizavidin fusion protein comprising SEQ ID NO: 1 (or a protein of at least 80% or 85% or more sequence identity thereto) fused to IsdA (47-324) (Rhavi-IsdA). Aspects of the present invention are directed to an isolated recombinant rhizavidin fusion protein comprising SEQ ID NO: 1 (or a protein of at least 80% or 85% or more sequence identity thereto) fused to IsdB (48-447) (Rhavi-IsdB).

In some embodiments, a biotin-binding protein is a fusion protein comprising a the C-terminal of SEQ ID NO: 1 (or a protein of at least 80% or 85% or more sequence identity thereto) fused to at least two antigens selected from any one of: Hla209(27-319), ClfA (221-559), ClfB (203-542), SdrD (246-682), IsdA (47-324), IsdB (48-447) or proteins or peptides having at least 85% sequence identity thereto. The SA-antigens may be the same antigens (e.g., SEQ ID NO: 1-A-A), or alternatively different SA antigens (e.g., SEQ ID NO: 1-A-B), where A and B are different SA-antigens. Exemplary Rhizavidin fusion proteins comprising 2 SA-antigens are shown in Table 4.

Table 4. Exemplary Rhizavidin fusion proteins comprising different combinations of 2 SA-antigens. It is noted that the order of the 2 antigens fused to the Rhizavidin protein of SEQ ID NO: 1 (referred to as "Rhavi") or a homologue of at least 80% identity thereto can be in any order, e.g., Rhavi-HLA209-ClfA, or alternatively, Rhavi-ClfA-HLA209, or Hla209-Rhavi-ClfA or ClfA-Rhavi-HLA209, for example.

| |
|---|
| Rhavi-HLA209-CLFA |
| Rhiva-HLA209-CLFB |
| Rhiva-HLA209-SDRD |
| Rhavi-HLA209-ISDA |
| Rhavi-HLA209-ISDB |
| Rhavi-CLFA-CLFB |
| Rhavi-CLFA-SDRD |
| Rhavi-CLFA-ISDA |
| Rhavi-CLFA-ISDB |
| Rhavi-CLFB-SDRD |
| Rhavi-CLFB-ISDA |
| Rhavi-CLFB-ISDB |
| Rhavi-SDRD-ISDA |
| Rhavi-SDRD-ISDB |
| Rhavi-ISDA-ISDB |

CLFA=CLFA protein or a fragment thereof, e.g., ClfA (221-559), CLFB=ClfB protein or a fragment thereof, e.g., ClfB (203-542), SDRD=SdrD protein or a fragment thereof, e.g., SdrD (246-682), ISDA=IsdA protein or a fragment thereof, e.g., IsdA (47-324); ISDB=IsdB protein or a fragment thereof, e.g., IsdB (48-477); HLA209=Hla protein with the 209 mutation, or a fragment thereof, e.g., Hla209 (27-319). It is envisioned that any of the SA antigens in the Rhavi-antigen-antigen fusion proteins shown in Table 4 can be substituted or replaced with any other SA antigen as disclosed herein, or known to one of ordinary skill in the art.

In some embodiments, a rhizavidin fusion protein comprising a SA antigen can comprise a lipidation sequence at the N-terminus, e.g., MKKVAAFVALSLLMAGC (SEQ ID NO: 29) or an amino acid 85% identity thereto.

In some embodiments, a rhizavidin fusion protein comprising a SA antigen can comprise a signal peptide linked to the N-terminus of the biotin-binding domain either directly (e.g., via a bond) or indirectly (e.g., by a linker). In some embodiments, the signal peptide can be linked to the N-terminus of the biotin-binding domain by a peptide linker. The peptide linker sequence can be of any length. For example, the peptide linker sequence can be one, two, three, four, five, six, seven, eight, nine, ten, eleven, twelve, thirteen, fourteen, fifteen or more amino acids in length. In some embodiments, the peptide linker is four amino acids in length.

The peptide linker sequence can comprise any amino acid sequence. For example, the peptide linker can comprise an amino acid sequence which can be cleaved by a signal peptidase. In some embodiments, the peptide linker comprises the amino acid sequence AQDP (SEQ ID NO: 30) or VSDP (SEQ ID NO: 31).

In some embodiments, a rhizavidin fusion protein comprising a SA antigen can be conjugated at its C-terminus to a peptide of 1-100 amino acids. Such peptides at the C-terminus can be used for purification tags, linkers to other domains, and the like. In some embodiments, a rhizavidin fusion protein comprising a SA antigen comprises on its N- or C-terminus one or more (e.g., one, two, three, four, five, six, seven, eight, nine, ten or more) purification tags. Examples of purification tags include, but are not limited to a histidine tag, a c-my tag, a Halo tag, a Flag tag, and the like. In some embodiments, the biotin-binding protein comprises on its C-terminus a histidine tag, e.g. a (His)$_6$ (SEQ ID NO: 32). In some embodiments, a rhizavidin fusion protein comprising a SA antigen for use in the SA-MAPS immunogenic composition as disclosed herein comprises a peptide of amino acid sequence GGGGSSSVDK-LAAALEHHHHHH (SEQ ID NO: 33). This peptide at the C-terminus provides a histidine tag for purification and a place for insertion of other domains, e.g. antigenic domains, in the biotin protein. Further, while Helppolainen et al. (Biochem J., 2007, 405: 397-405) describe expression of Rhizavidin in *E. coli*, there is no teaching or suggestion in Helppolainen et al. for conjugating an additional peptide to the C-terminus of the biotin-binding domain of Rhizavidin.

A purification tag can be conjugated to a rhizavidin fusion protein comprising a SA antigen as disclosed herein by a peptide linker to enhance the probability that the tag is exposed to the outside. The length of the linker can be at least one (e.g., one, two, three, four, five six, seven, eight, nine, ten, eleven, twelve, thirteen, fourteen, or fifteen) amino acid. The linker peptide can comprise any amino acid sequence without limitations. In some embodiments, the linker peptide comprises the amino acid sequence VDK-LAAALE (SEQ ID NO: 34) or GGGGSSSVDKLAAALE (SEQ ID NO: 35). In some embodiments, a rhizavidin fusion protein comprising a SA antigen as disclosed herein can comprise at its C-terminus the amino acid sequence VDK-LAAALEHHHHH (SEQ ID NO: 36) or GGGGSSSVDK-LAAALEHHHHH (SEQ ID NO: 37).

As discussed herein, a rhizavidin fusion protein comprising a SA antigen for use in the SA-MAPS immunogenic composition as disclosed herein consists of amino acids 45-179 of wild-type Rhizavidin.

In some embodiments, rhizavidin fusion protein comprising a SA antigen for use in the SA-MAPS immunogenic composition as disclosed herein can comprise an N-terminal signal sequence as disclosed herein. In some embodiments, the signal sequence is attached to the N-terminal of the complementary affinity molecule as disclosed herein.

In some embodiments, a rhizavidin fusion protein comprising a SA antigen for use in the SA-MAPS immunogenic composition as disclosed herein has a spacer peptide, e.g., a 14-residue spacer (GSPGISGGGGILE) (SEQ ID NO: 38) separating the SA antigen from the rhizavidin protein. The coding sequence of such a short spacer can be constructed by annealing a complementary pair of primers. One of skill in the art can design and synthesize oligonucleotides that will code for the selected spacer. Spacer peptides should generally have non-polar amino acid residues, such as glycine and proline.

Lipidated Rhizavidin Fusion Protein or Biotin-Binding Protein

In another aspect provided herein is a lipidated biotin-binding protein, e.g., a lipidated rhizavidin fusion protein comprising a SA antigen for use in the SA-MAPS immunogenic composition as disclosed herein. As used herein, the term "lipidated biotin-binding protein" refers to a biotin-binding protein that is covalently conjugated with a lipid. The lipid moieties could be a diacyl or triacyl lipid.

In some embodiments, a rhizavidin fusion protein comprising a SA antigen for use in the SA-MAPS immunogenic composition as disclosed herein comprises a lipidation sequence. As used herein, the term "lipidation sequence" refers to an amino acid sequence that facilitates lipidation in bacteria, e.g., E. coli, of a polypeptide carrying the lipidating sequence. The lipidation sequence can be present at the N-terminus or the C-terminus of the protein. The lipidation sequence can be linked to the recombinant biotin-binding protein to form a fusion protein, which is in lipidated form when expressed in E. coli by conventional recombinant technology. In some embodiments, a lipidation sequence is located at the N-terminus of the biotin-binding protein.

Any lipidation sequence known to one of ordinary skill in the art can be used. In some embodiments, the lipidating sequence is MKKVAAFVALSLLMAGC (SEQ ID NO: 39) or a derivative or functional portion thereof. Other exemplary lipidating sequences include, but are not limited to, MNSKKLCCICVLFSLLAGCAS (SEQ ID NO: 40), MRYSKLTMLIPCALLLSAC (SEQ ID NO: 41), MFVTSKKMTAAVLAITLAMSLSAC (SEQ ID NO: 42), MIKRVLVVSMVGLSLVGC (SEQ ID NO: 43), and derivatives or functional portions thereof.

In some embodiments, the lipidation sequence can be fused to a rhizavidin fusion protein comprising a SA antigen via a peptide linker, wherein the peptide linker attaches the lipidating sequence to the biotin-binding protein. In some embodiment, the peptide linker comprises the amino acid sequence VSDP (SEQ ID NO: 44) or AQDP (SEQ ID NO: 45).

In some embodiments, a rhizavidin fusion protein comprising a SA antigen for use in the SA-MAPS immunogenic composition as disclosed herein that is a lipoprotein as described herein have enhanced immunogenicity. Without wishing to be bound by a theory, lipid moieties at the N-terminals of the lipoproteins or lipopeptides contribute to the adjuvant activity. Accordingly, additional embodiments provide immunogenic or vaccine compositions for inducing an immunological response, comprising the isolated biotin-binding lipoprotein, or a suitable vector for in vivo expression thereof, or both, and a suitable carrier, as well as to methods for eliciting an immunological or protective response comprising administering to a host the isolated recombinant biotin-binding lipoprotein, the vector expressing the recombinant biotin-binding lipoprotein, or a composition containing the recombinant lipoprotein or vector, in an amount sufficient to elicit the response.

A SA-MAPS immunogenic composition comprising a rhizavidin fusion protein comprising a SA antigen that is a lipoprotein elicits an immunological response—local or systemic. The response can, but need not, be protective.

Affinity Molecule Pairs

As disclosed herein, a key aspect of the SA-MAPS composition is the attachment of the SA antigens to the immunogenic polysaccharide. As discussed herein, a SA antigen is connected to an immunogenic polysaccharide via a complementary affinity pair. This connecting of the SA antigen to the immunogenic polysaccharide is mediated by the immunogenic polysaccharide being connected to a first affinity molecule, which associates a second (e.g., complementary) affinity molecule, which is attached to the SA antigen. An example complementary affinity pair is biotin and a biotin-binding protein, e.g. biotin and rhizavidin protein or fragment thereof.

Exemplary examples of the affinity complementary affinity pairs for use in the SA-MAPS immunogenic composition include, but without limitation, biotin binding proteins or avidin-like proteins that bind to biotin. For example, where the first affinity binding molecule is biotin (which associates with the polymer), the complementary affinity molecule can be a biotin binding protein or an avidin-like protein or a derivative thereof, e.g., but not limited to, avidin, rhizavidin, or streptavidin or variants, derivatives or functional portions thereof.

In some embodiments, the first affinity binding molecule is biotin, a biotin derivative, or a biotin mimic, for example, but not limited to, amine-PEG3-biotin (((+)-biotinylation-3-6,9-trixaundecanediamine) or a derivative or functional fragment thereof. A specific biotin mimetic has a specific peptide motif containing sequence of $DX_aAX_bPX_c$ (SEQ ID NO: 46), or $CDX_aAX_bPX_cCG$ (SEQ ID NO: 47), where $X_a$ is R or L, $X_b$ is S or T, and $X_c$ is Y or W. These motifs can bind avidin and Neutravidin, but streptavidin. See, e.g., Gaj et al., 56 Prot. Express. Purif 54 (2006). In some embodiments the first affinity binding molecule is lipoic acid or a derivative thereof, or HABA (hydroxyazobenzene-benzoic acid, or dimethyl-HABA).

The linkage of the first affinity molecule to the immunogenic polysaccharide, and the complementary affinity molecule to the SA antigen can be a non-covalent linkage, or a chemical mechanism, for instance covalent binding, affinity binding, intercalation, coordinate binding and complexation. Covalent binding provides for very stable binding, and is particularly well-suited for the present embodiments. Covalent binding can be achieved either by direct condensation of existing side chains or by the incorporation of external bridging molecules.

For example, in some embodiments, a SA antigen can be non-covalently bonded to one of the pairs in a complementary affixing pair. In alternative embodiments, an antigen can be covalently bonded or fused to one of the pairs in a complementary affixing pair. Methods for generation of fusion proteins are well known in the art, and are discussed herein.

In other embodiments, a first affinity binding molecule is linked to the immunogenic polysaccharide by a non-covalent bond, or by a covalent bond. In some embodiments, a cross-linking reagent is used to covalently bond the first affinity binding molecule to the immunogenic polysaccharide as disclosed herein.

In some embodiments, the first affinity binding molecule associates with the complementary affinity molecule by non-covalent bond association as known in the art, including, but not limited to, electrostatic interaction, hydrogen bound, hydrophobic interaction (i.e., van der Waals forces), hydrophilic interactions, and other non-covalent interactions. Other higher order interactions with intermediate moieties are also contemplated.

In some embodiments, the complementary affinity molecule is an avidin-related polypeptide. In specific embodiments, the complementary affinity molecule is rhizavidin, such as recombinant rhizavidin of SEQ ID NO: 1 or a protein having an amino acid that has at least 85% sequence identity to SEQ ID NO:1. In particular, the recombinant rhizavidin is a modified rhizavidin that can be expressed in E. coli with a high yield. The typical yield is >30 mg per liter of E. coli culture. Rhizavidin has a lower sequence homology to egg avidin (22.4% sequence identity and 35.0% similarity) compared with other avidin-like proteins. Use of the modified rhizavidin reduces the risk of the MAPS inducing an egg-related allergic reaction in a subject. Moreover, antibody to recombinant modified rhizavidin has no apparent cross-reactivity to egg avidin (and vice versa).

Additional affinity pairs that may be useful in the methods and compositions described herein include antigen-antibody, metal/ion-metal/ion-binding protein, lipid/lipid binding protein, saccharide/saccharide binding protein, amino acid/peptide/amino acid or peptide binding protein, enzyme-substrate or enzyme-inhibitor, ligand-agonist/receptor, or biotin mimetic. When using alternative affinity pairs, alternative means of attaching the respective polymer and antigen may also be employed, such as in vitro enzymatic reactions rather than genetic fusion. More specifically, antigen-antibody affinity pair provides for a very strong and specific interaction. The antigen can be any epitope including protein, peptide, nucleic acid, lipid, poly/oligosaccharide, ion, etc. The antibody can be any type of immunoglobulin, or the Ag-binding portion of an immunoglobulin, such as a Fab fragment. Regarding metal/ion-metal/ion binding protein, examples include Ni NTA vs. histidine-tagged protein, or Zn vs. Zn binding protein. Regarding lipid/lipid binding protein, examples include cholesterol vs. cholesterol binding protein. Regarding saccharide/saccharide binding protein, examples include maltose vs. maltose binding protein, mannose/glucose/oligosaccharide vs. lectin. Enzyme-substrate/inhibitors include substrates from a wide range of substances, including protein, peptide, amino acid, lipid, sugar, or ions. The inhibitor can be the analog of the real substrate which can generally bind to the enzymes more tightly and even irreversibly. For example, trypsin vs. soy trypsin inhibitor. The inhibitor can be natural or synthetic molecule. Regarding other ligand/agonist-receptor, ligand can be from a wide range of substance, including protein, peptide, amino acid, lipid, sugar, ion, agonist can be the analog of the real ligand. Examples include the LPS vs. TLR4 interaction.

Cross-Linking Reagents

Many bivalent or polyvalent linking agents are useful in coupling at least one or more affinity molecules to the immunogenic polysaccharide of the SA-MAPS immunogenic composition as disclosed herein. For example, representative coupling agents can include organic compounds such as thioesters, carbodiimides, succinimide esters, disocyanates, glutaraldehydes, diazobenzenes and hexamethylene diamines. This listing is not intended to be exhaustive of the various classes of coupling agents known in the art but, rather, is exemplary of the more common coupling agents. See Killen & Lindstrom, 133 J. Immunol. 1335 (1984); Jansen et al., 62 Imm. Rev. 185 (1982); Vitetta et al.

In some embodiments, cross-linking reagents agents described in the literature are encompassed for use in the methods, immunogenic compositions and kits as disclosed herein. See, e.g., Ramakrishnan, et al., 44 Cancer Res. 201 (1984) (describing the use of MBS (M-maleimidobenzoyl-N-hydroxysuccinimide ester)); Umemoto et al., U.S. Pat. No. 5,030,719 (describing the use of a halogenated acetyl hydrazide derivative coupled to an antibody by way of an oligopeptide linker). Particular linkers include: (a) EDC (1-ethyl-3-(3-dimethylamino-propyl) carbodiimide hydrochloride; (b) SMPT (4-succinimidyloxycarbonyl-alpha-methyl-alpha-(2-pyridyl-dithio)-toluene (Pierce Chem. Co., Cat. (21558G); (c) SPDP (succinimidyl-6 [3-(2-pyridyldithio) propionamido] hexanoate (Pierce Chem. Co., Cat #21651G); (d) Sulfo-LC-SPDP (sulfosuccinimidyl 6 [3-(2-pyridyldithio)-propianamide] hexanoate (Pierce Chem. Co. Cat. #2165-G); and (f) sulfo-NHS (N-hydroxysulfo-succinimide: Pierce Chem. Co., Cat. #24510) conjugated to EDC.

The linkages or linking agents described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage can be cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Additional cross linkers for —SH (thiolated CP) to —NH$_2$ linkages include but are not limited to: sulfa-LC-SMPT; sulfo-LC-SMPT (4-sulfosuccinimidyl-6-methyl-a-(2-pyridyldithio)toluamidolhexanoate)); sulfo-KMUS (N[k-maleimidoundecanoyloxylsulfosuccinimide ester); sulfo-LC-SPDP (sulfosuccinimidyl 6-(3'-[2-pyridyldithio]-propionamido)hexanoate) which cleaves by thiols; sulfo-SMPB (sulfosuccinimidyl 4-[p-maleimidophenyl]butyrate); sulfo-SIAB (N-sulfosuccinimidyl[4-iodoacetyl]aminobenzoate); sulfa-EMCS ([N-e-maleimidocaproyloxy]sulfosuccinimide ester); EMCA (N-e-maleimidocaproic acid); sulfo-SMCC (sulfosuccinimidyl 4-[N-maleimidomethyl] cyclohexane-1-carboxylate); sulfo-MBS (m-maleimidobenzoyl-N-hydroxysulfosuccinimide ester); sulfo-GMBS (N4g-maleimidobutyryloxy]sulfosuccinimide ester); BMPA (N-.beta.-maleimidopropionic acid); 2-immunothiolane hydrochloride; 3-(2-pyridyldithio)propionic acid N-succinimidyl ester; 3-malemidopropionic acid N-succinimidyl ester; 4-maleimidobutyric acid N-succinimidyl ester; SMPT (4-succinimidyloxycarbonyl-methyl-a-[2-pyridyldithio]toluene); LC-SMCC (succinimidyl-4-[N-maleimidomethyl]cyclohexane-1-carboxy-[6-amidocaproate-]); KMUA (N-k-maleimidoundecanoic acid); LC-SPDP (succinimidyl 6-(3-[2-pyridyldithio]-propionamido)hexanoate); SMPH (succinimidyl-6-[.beta.-maleimidopropionamido]hexanoate); SMPB (succinimidyl 4-[p-maleimidophenyl]butyrate); SIAB (N-succinimidyl[4-iodoacetyl]aminobenzoate); EMCS ([N-e-Maleimidocaproyloxy]succinimide ester); SMCC (succinimidyl 4-[N-maleimidomethyl]cyclohexane-1-carboxylate); MBS (m-Maleimidobenzoyl-N-hydroxysuccinimide ester); SBAP (succinimidyl 3-[bromoacetamido] propionate); BMPS (N-[.beta.-maleimidopropyloxysuccinimide ester); AMAS N-(a-maleimidoacetoxy)succinimide ester); SIA (N-succinimidyl iodoacetate); and N-succinimidyl (4-iodoacetyl)-aminobenzoate.

The agents can also be crosslinked using crosslinkers for —SH to —OH groups. Such cross linkers include but are not limited to PMPI (N-[p-maleimidophenyl]isocyanate).

Exemplary cross-linking molecules for use in the methods and immunogenic compositions as disclosed herein include, but are not limited to those listed in Tables 5 and 6.

TABLE 5

Exemplary homobifunctional crosslinkers*

| Crosslinking Target | Crosslinker Reactive Groups, Features | Example Products |
|---|---|---|
| Amine-to-Amine | NHS esters | DSG; DSS; BS3; TSAT (trifunctional); Bioconjugate Toolkit Reagent Pairs |
| | NHS esters, PEG spacer | BS(PEG)5; BS(PEG)9 |
| | NHS esters, thiol-cleavable | DSP; DTSSP |
| | NHS esters, misc-cleavable | DST; BSOCOES; EGS; Sulfo-EGS |
| | Imidoesters | DMA; DMP; DMS |
| | Imidoesters, thiol-cleavable | DTBP |
| | Other | DFDNB; THPP (trifunctional); Aldehyde-Activated Dextran Kit |
| Sulfhydryl-to-Sulfhydryl | Maleimides | BMOE; BMB; BMH; TMEA (trifunctional) |
| | Maleimides, PEG spacer | BM(PEG)2; BM(PEG)3 |
| | Maleimides, cleavable | BMDB; DTME |
| | Pyridyldithiols (cleavable) | DPDPB |
| | Other | HBVS (vinylsulfone) |
| Nonselective | Aryl azides | BASED (thiol-cleavable) |

*crosslinking reagents that have the same type of reactive group at either end. Reagents are classified by what chemical groups they cross link (left column) and their chemical composition (middle column). Products are listed in order of increasing length within each cell.

TABLE 6

Exemplary heterobifunctional crosslinkers*

| Crosslinking Targets | Crosslinker Reactive Groups, Features | Example Products |
|---|---|---|
| Amine-to-Sulfhydryl | NHS ester/Maleimide | AMAS; BMPS; GMBS and Sulfo-GMBS; MBS and Sulfo-MBS; SMCC and Sulfo-SMCC; EMCS and Sulfo-EMCS; SMPB and Sulfo-SMPB; SMPH; LC-SMCC; Sulfo-KMUS |
| | NHS ester/Maleimide, PEG spacer | SM(PEG)2; SM(PEG)4; SM(PEG)6; SM(PEG)8; SM(PEG)12; SM(PEG)24 |
| | NHS ester/Pyridyldithiol, cleavable | SPDP; LC-SPDP and Sulfo-LC-SPDP; SMPT; Sulfo-LC-SMPT |
| | NHS esters/Haloacetyl | SIA; SBAP; SIAB; Sulfo-SIAB |
| Amine-to-Nonselective | NHS ester/Aryl Azide | NHS-ASA ANB-NOS Sulfo-HSAB Sulfo-NHS-LC-ASA SANPAH and Sulfo-SANPAH |
| | NHS ester/Aryl Azide, cleavable | Sulfo-SFAD; Sulfo-SAND; Sulfo-SAED |
| | NHS ester/Diazirine | SDA and Sulfo-SDA; LC-SDA and Sulfo-LC-SDA |
| | NHS ester/Diazirine, cleavable | SDAD and Sulfo-SDAD |
| Amine-to-Carboxyl | Carbodiimide | DCC; EDC |
| Sulfhydryl-to-Nonselective | Pyridyldithiol/Aryl Azide | APDP |
| Sulfhydryl-to-Carbohydrate | Maleimide/Hydrazide | BMPH; EMCH; MPBH; KMUH |
| | Pyridyldithiol/Hydrazide | BMPH; EMCH; MPBH; KMUH |
| Carbohydrate-to-Nonselective | Hydrazide/Aryl Azide | ABH |
| Hydroxyl-to-Sulfhydryl | Isocyanate/Maleimide | PMPI |
| Amine-to-DNA | NHS ester/Psoralen | SPB |

*crosslinking reagents that have the different reactive groups at either end. Reagents are classified by what chemical groups they cross link (left column) and their chemical composition (middle column). Products are listed in order of increasing length within each cell.

Co-Stimulatory Factor

In some embodiments, an immunogenic composition comprising the SA-MAPS as disclosed herein comprises at least one co-stimulatory molecule. In some embodiments, the co-stimulatory factor is cross-linked to the immunogenic polysaccharide. In some embodiments, the co-stimulatory factor is associated to the immunogenic polysaccharide by a complementary affinity pair similar to how the SA antigen is associated with the immunogenic polysaccharide. In some embodiments, where the complementary affinity pair which links the co-stimulatory factor to the immunogenic polysaccharide is the same, or a different complementary affinity pair which links the SA antigen to the immunogenic polysaccharide.

In some embodiments, at least one, or at least 2, or at least 3, or at least 5, or at least 10, or at least 15, or at least 20, or at least 50, or at least 100, or more than about 100, inclusive, co-stimulatory factors can be associated with the immunogenic polysaccharide as disclosed herein. In some embodiments, the co-stimulatory factors can be the same co-stimulator factor, or they can be a variety of different co-stimulatory factors associated with the immunogenic polysaccharide.

In some embodiments, the co-stimulator factor is a ligand/agonist of Toll like receptors, e.g., but not limited to TLR1, TLR2, TLR3, TLR4, TLR5, TLR6, TLR7, TLR8, TLR9, TLR10, TLR11, etc. In some embodiments, a co-stimulator factor is a NOD ligand/agonist, or an activator/agonist of the inflammasome. Without wishing to be bound by theory, the inflammasome is a multiprotein oligomer consisting of caspase 1, PYCARD, NALP and sometimes caspase 5 or caspase 11 and promotes the maturation of inflammatory cytokines interleukin 1-β and interleukin 18.

In some embodiments, a co-stimulator factor is a cytokine. In some embodiments, a cytokine is selected from the group consisting of: GM-CSF; IL-1α; IL-1β; IL-2; IL-3; IL-4; IL-5; IL-6; IL-7; IL-8; IL-10; IL-12; IL-23; IFN-α; IFN-β; IFN-γ; MIP-1α; MIP-1β; TGF-β; TNFα, and TNFβ. In some embodiments, the co-stimulatory factor is an adjuvant, which may be associated with the polymer, as just discussed, or may be added to the MAPS composition prior to or concurrent with administration to a subject. Adjuvants are further described elsewhere herein.

Production of SA Antigens and SA Antigens Fused to the Complementary Affinity Molecule Recombinant proteins may be conveniently expressed and purified by a person skilled in the art, or by using commercially available kits, for example PROBOND™ Purification System (Invitrogen Corp., Carlsbad, Calif.). In some embodiments, recombinant antigens can be synthesized and purified by protein purification methods using bacterial expression systems, yeast expression systems, baculovirus/insect cell expression system, mammalian cell expression systems, or transgenic plant or animal systems as known to persons of ordinary skill in the art.

The fusion polypeptides as described herein, e.g., a SA antigen fused to a rhizavidin protein of SEQ ID NO: 1 (e.g., Rhavi-Hla209(27-319), Rhavi-ClfA (221-559), Rhavi-ClfB (203-542), Rhavi-SdrD (246-682), Rhavi-IsdA (47-324), Rhavi-IsdB (48-447)) can all be synthesized and purified by protein and molecular methods that are well known to one skilled in the art. Molecular biology methods and recombinant heterologous protein expression systems are used. For example, recombinant protein can be expressed in bacteria, mammalian, insect, yeast, or plant cells; or in transgenic plant or animal hosts.

In one embodiment, provided herein is an isolated polynucleotide encoding a fusion polypeptide or a non-fusion polypeptide described herein. Conventional polymerase chain reaction (PCR) cloning techniques can be used to construct a chimeric or fusion coding sequence encoding a fusion polypeptide as described herein. A coding sequence can be cloned into a general purpose cloning vector such as pUC19, pBR322, pBLUESCRIPT® vectors (Stratagene, Inc.) or pCR TOPO® (Invitrogen). The resultant recombinant vector carrying the nucleic acid encoding a polypeptide as described herein can then be used for further molecular biological manipulations such as site-directed mutagenesis to create a variant fusion polypeptide as described herein or can be subcloned into protein expression vectors or viral vectors for protein synthesis in a variety of protein expression systems using host cells selected from the group consisting of mammalian cell lines, insect cell lines, yeast, bacteria, and plant cells.

Each PCR primer should have at least 15 nucleotides overlapping with its corresponding templates at the region to be amplified. The polymerase used in the PCR amplification should have high fidelity such as PfuULTRA® polymerase (Stratagene) for reducing sequence mistakes during the PCR amplification process. For ease of ligating several separate PCR fragments together, for example in the construction of a fusion polypeptide, and subsequently inserting into a cloning vector, the PCR primers should also have distinct and unique restriction digestion sites on their flanking ends that do not anneal to the DNA template during PCR amplification. The choice of the restriction digestion sites for each pair of specific primers should be such that the fusion polypeptide coding DNA sequence is in-frame and will encode the fusion polypeptide from beginning to end with no stop codons. At the same time the chosen restriction digestion sites should not be found within the coding DNA sequence for the fusion polypeptide. The coding DNA sequence for the intended polypeptide can be ligated into cloning vector pBR322 or one of its derivatives, for amplification, verification of fidelity and authenticity of the chimeric coding sequence, substitutions/or specific site-directed mutagenesis for specific amino acid mutations and substitutions in the polypeptide.

Alternatively, the coding DNA sequence for the polypeptide can be PCR cloned into a vector using for example, the TOPO® cloning method comprising topoisomerase-assisted TA vectors such as pCR®-TOPO, pCR®-Blunt II-TOPO, pENTR/D-TOPO®, and pENTR/SD/D-TOPO® (Invitrogen, Inc., Carlsbad, Calif.). Both pENTR/D-TOPO®, and pENTR/SD/D-TOPO® are directional TOPO entry vectors which allow the cloning of the DNA sequence in the 5'→3' orientation into a GATEWAY® expression vector. Directional cloning in the 5'→3' orientation facilitates the unidirectional insertion of the DNA sequence into a protein expression vector such that the promoter is upstream of the 5' ATG start codon of the fusion polypeptide coding DNA sequence, enabling promoter driven protein expression. The recombinant vector carrying the coding DNA sequence for the fusion polypeptide can be transfected into and propagated in general cloning E. coli such as XL1Blue, SURE® (STRATAGENE®) and TOP-10 cells (Invitrogen).

One skilled in the art would be able to clone and ligate the coding region of the antigen of interest with the coding region of the complementary affinity molecule to construct a chimeric coding sequence for a fusion polypeptide comprising the antigen or a fragment thereof and the complementary affinity molecule of a derivative thereof using specially designed oligonucleotide probes and polymerase chain reaction (PCR) methodologies that are well known in the art. One skilled in the art would also be able to clone and ligate the chimeric coding sequence for a fusion protein into a selected vector, e.g., bacterial expression vector, an insect expression vector or baculovirus expression vector. The coding sequences of antigen and the target antigen polypeptide or fragment thereof should be ligated in-frame and the chimeric coding sequence should be ligated downstream of the promoter, and between the promoter and the transcription terminator. Subsequent to that, the recombinant vector is transfected into regular cloning E. coli, such as XL1Blue. Recombinant E. coli harboring the transfer vector DNA is then selected by antibiotic resistance to remove any E. coli harboring non-recombinant plasmid DNA. The selected transformant E. coli are grown and the recombinant vector DNA can be subsequently purified for transfection into S. frugiperda cells.

In some embodiments, the SA antigens as disclosed herein can comprise a signal peptide for translocation into periplasmic space of bacteria. The signal peptide is also called a leader peptide in the N-terminus, which may or may not be cleaved off after the translocation through the membrane. One example of a signal peptide is MKKIWLA-LAGLVLAFSASA (SEQ ID NO: 23) as disclosed herein. Another signal sequence is MAPFEPLASGILLLL-WLIAPSRA (SEQ ID NO: 48). Other examples of signal peptides can be found at SPdb, a Signal Peptide Database, which is found at the world wide web site of "proline.bic.nus.edu.sg/spdb/".

In some embodiments, where the antigen is fused to a complementary affinity protein, the signal sequence can be located at the N-terminal of the complementary affinity protein. For example, if an antigen is fused to an avidin-like protein, the signal sequence can be located at the N-terminal of the complementary affinity protein. In some embodiments, the signal sequence is cleaved off from the complementary affinity protein before the complementary affinity protein associates with the first affinity molecule.

In some embodiments, a SA antigen and/or complementary affinity protein as described herein lacks a signal sequence.

The polypeptides described herein can be expressed in a variety of expression host cells e.g., bacteria, yeasts, mammalian cells, insect cells, plant cells, algal cells such as *Chlamadomonas*, or in cell-free expression systems. In some embodiments the nucleic acid can be subcloned from the cloning vector into a recombinant expression vector that is appropriate for the expression of fusion polypeptide in bacteria, mammalian, insect, yeast, or plant cells or a cell-free expression system such as a rabbit reticulocyte expression system. Some vectors are designed to transfer coding nucleic acid for expression in mammalian cells, insect cells and year in one single recombination reaction. For example, some of the GATEWAY® (Invitrogen) destination vectors are designed for the construction of baculovirus, adenovirus, adeno-associated virus (AAV), retrovirus, and lentiviruses, which upon infecting their respective host cells, permit heterologous expression of fusion polypeptides in the appropriate host cells. Transferring a gene into a destination vector is accomplished in just two steps according to manufacturer's instructions. There are GATEWAY® expression vectors for protein expression in insect cells, mammalian cells, and yeast. Following transformation and selection in *E. coli*, the expression vector is ready to be used for expression in the appropriate host.

Examples of other expression vectors and host cells are the strong CMV promoter-based pcDNA3.1 (Invitrogen) and pCINEO vectors (Promega) for expression in mammalian cell lines such as CHO, COS, HEK-293, Jurkat, and MCF-7; replication incompetent adenoviral vector vectors pADENO-X™, pAd5F35, pLP-ADENO™-X-CMV (CLONTECH®), pAd/CMV/V5-DEST, pAd-DEST vector (Invitrogen) for adenovirus-mediated gene transfer and expression in mammalian cells; pLNCX2, pLXSN, and pLAPSN retrovirus vectors for use with the RETRO-X™ system from Clontech for retroviral-mediated gene transfer and expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells; adenovirus-associated virus expression vectors such as pAAV-MCS, pAAV-IRES-hrGFP, and pAAV-RC vector (Stratagene) for adeno-associated virus-mediated gene transfer and expression in mammalian cells; BACpak6 baculovirus (Clontech) and pFASTBAC™ HT (Invitrogen) for the expression in *S. frugiperda* 9 (Sf9), Sf11, Tn-368 and BTI-TN-5B4-1 insect cell lines; pMT/BiP/V5-His (Invitrogen) for the expression in *Drosophila schneider* S2 cells; *Pichia* expression vectors pPICZα, pPICZ, pFLDα and pFLD (Invitrogen) for expression in *P. pastoris* and vectors pMETα and pMET for expression in *P. methanolica*; pYES2/GS and pYD1 (Invitrogen) vectors for expression in yeast *S. cerevisiae*.

Recent advances in the large scale expression heterologous proteins in *Chlamydomonas reinhardtii* are described. Griesbeck., 34 Mol. Biotechnol. 213 (2006); Fuhrmann, 94 Methods Mol Med. 191 (2006). Foreign heterologous coding sequences are inserted into the genome of the nucleus, chloroplast and mitochondria by homologous recombination. The chloroplast expression vector p64 carrying the most versatile chloroplast selectable marker aminoglycoside adenyl transferase (aadA), which confer resistance to spectinomycin or streptomycin, can be used to express foreign protein in the chloroplast. The biolistic gene gun method can be used to introduce the vector in the algae. Upon its entry into chloroplasts, the foreign DNA is released from the gene gun particles and integrates into the chloroplast genome through homologous recombination.

Also included in the invention are complementary affinity molecule fused to an antigen. In some embodiments, the fusion construct can also optionally comprise purification tags, and/or secretion signal peptides. These fusion proteins may be produced by any standard method. For example, for production of a stable cell line expressing an antigen-complementary affinity molecule fusion protein, PCR-amplified antigen nucleic acids may be cloned into the restriction site of a derivative of a mammalian expression vector. For example, KA, which is a derivative of pcDNA3 (Invitrogen) contains a DNA fragment encoding an influenza virus hemagglutinin tag (HA). Alternatively, vector derivatives encoding other tags, such as c-myc or poly Histidine tags, can be used. The antigen-complementary affinity molecule fusion expression construct may be co-transfected, with a marker plasmid, into an appropriate mammalian cell line (e.g., COS, HEK293T, or NIH 3T3 cells) using, for example, LIPOFECTAMINE™ (Gibco-BRL, Gaithersburg, Md.) according to the manufacturer's instructions, or any other suitable transfection technique known in the art. Suitable transfection markers include, for example, β-galactosidase or green fluorescent protein (GFP) expression plasmids or any plasmid that does not contain the same detectable marker as the antigen-complementary affinity molecule fusion protein. The fusion protein expressing cells can be sorted and further cultured, or the tagged antigen-complementary affinity molecule fusion protein can be purified. In some embodiments, an antigen-complementary affinity molecule fusion protein is amplified with a signal peptide. In alternative embodiments, a cDNA encoding an antigen-complementary affinity molecule fusion protein can be amplified without the signal peptide and subcloned into a vector (pSecTagHis) having a strong secretion signal peptide. In another example, antigen-complementary affinity molecule fusion protein can have an alkaline phosphatase (AP) tag, or a histadine (His) tag for purification. Any method known to persons of ordinary skill in the art for protein purification of the antigen and/or antigen-complementary affinity molecule fusion protein is encompassed for use in the methods of the invention.

In some embodiments, any of the polypeptides described herein is produced by expression from a recombinant baculovirus vector. In another embodiment, any of the polypeptides described herein is expressed by an insect cell. In yet another embodiment, any of the polypeptides described herein is isolated from an insect cell. There are several benefits of protein expression with baculovirus in insect cells, including high expression levels, ease of scale-up, production of proteins with posttranslational modifications, and simplified cell growth. Insect cells do not require $CO_2$ for growth and can be readily adapted to high-density suspension culture for large-scale expression. Many of the post-translational modification pathways present in mammalian systems are also utilized in insect cells, allowing the production of recombinant protein that is antigenically, immunogenically, and functionally similar to the native mammalian protein.

Baculoviruses are DNA viruses in the family Baculoviridae. These viruses are known to have a narrow host-range that is limited primarily to Lepidopteran species of insects (butterflies and moths). The baculovirus *Autographa californica* Nuclear Polyhedrosis Virus (AcNPV), which has become the prototype baculovirus, replicates efficiently in susceptible cultured insect cells. AcNPV has a double-stranded closed circular DNA genome of about 130,000 base-pairs and is well characterized with regard to host range, molecular biology, and genetics. The Baculovirus Expression Vector System (BEVS) is a safe and rapid method for the abundant production of recombinant proteins in insect cells and insects. Baculovirus expression systems are powerful and versatile systems for high-level, recombinant protein expression in insect cells. Expression levels up to 500 mg/1 have been reported using the baculovirus expression system, making it an ideal system for high-level expression. Recombinant baculoviruses that express foreign genes are constructed by way of homologous recombination between baculovirus DNA and chimeric plasmids containing the gene sequence of interest. Recombinant viruses can be detected by virtue of their distinct plaque morphology and plaque-purified to homogeneity.

Recombinant fusion proteins described herein can be produced in insect cells including, but not limited to, cells derived from the *Lepidopteran* species *S. frugiperda*. Other insect cells that can be infected by baculovirus, such as those from the species *Bombyx mori, Galleria mellanoma, Trichplusia ni*, or *Lamanthria dispar*, can also be used as a suitable substrate to produce recombinant proteins described herein. Baculovirus expression of recombinant proteins is well known in the art. See U.S. Pat. Nos. 4,745,051; 4,879,236; 5,179,007; 5,516,657; 5,571,709; 5,759,809. It will be understood by those skilled in the art that the expression system is not limited to a baculovirus expression system. What is important is that the expression system directs the N-glycosylation of expressed recombinant proteins. The recombinant proteins described herein can also be expressed in other expression systems such as Entomopox viruses (the poxviruses of insects), cytoplasmic polyhedrosis viruses (CPV), and transformation of insect cells with the recombinant gene or genes constitutive expression. A good number of baculovirus transfer vectors and the corresponding appropriately modified host cells are commercially available, for example, pAcGP67, pAcSECG2TA, pVL1392, pVL1393, pAcGHLT, and pAcAB4 from BD Biosciences; pBAC-3, pBAC-6, pBACgus-6, and pBAC-surf-1 from NOVAGEN®, and pPolh-FLAG and pPolh-MAT from SIGMA ALDRICH®.

The region between the promoter and the transcriptional terminator can have multiple restriction enzyme digestion sites for facilitating cloning of the foreign coding sequence, in this instance, the coding DNA sequence for an antigen polypeptide, and a complementary affinity molecule. Additional sequences can be included, e.g., signal peptides and/or tag coding sequences, such as His-tag, MAT-Tag, FLAG tag, recognition sequence for enterokinase, honeybee melittin secretion signal, beta-galactosidase, glutathione 5-transferase (GST) tag upstream of the MCS for facilitating the secretion, identification, proper insertion, positive selection of recombinant virus, and/or purification of the recombinant protein.

Standard techniques known to those of skill in the art can be used to introduce mutations (to create amino acid substitutions in an antigen polypeptide sequence of the fusion polypeptide described herein, e. g., in the antigen in the nucleotide sequence encoding the fusion polypeptide described herein, including, for example, site-directed mutagenesis and PCR-mediated mutagenesis. Preferably, the variant fusion polypeptide has less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions, inclusive, relative to the fusion polypeptides described herein.

Certain silent or neutral missense mutations can also be made in the DNA coding sequence that do not change the encoded amino acid sequence or the capability to promote transmembrane delivery. These types of mutations are useful to optimize codon usage, or to improve recombinant protein expression and production.

Specific site-directed mutagenesis of a coding sequence for the fusion polypeptide in a vector can be used to create specific amino acid mutations and substitutions. Site-directed mutagenesis can be carried out using, e. g., the QUICKCHANGE® site-directed mutagenesis kit from Stratagene according to the manufacturer's instructions.

In one embodiment, described herein are expression vectors comprising the coding DNA sequence for the polypeptides described herein for the expression and purification of the recombinant polypeptide produced from a protein expression system using host cells selected from, e.g., bacteria, mammalian, insect, yeast, or plant cells. The expression vector should have the necessary 5' upstream and 3' downstream regulatory elements such as promoter sequences, ribosome recognition and TATA box, and 3' UTR AAUAAA transcription termination sequence for efficient gene transcription and translation in its respective host cell. The expression vector is, preferably, a vector having the transcription promoter selected from a group consisting of CMV (cytomegalovirus) promoter, RSV (Rous sarcoma virus) promoter, β-actin promoter, SV40 (simian virus 40) promoter and muscle creatine kinase promoter, and the transcription terminator selected from a group consisting of SV40 poly(A) and BGH terminator; more preferably, an expression vector having the early promoter/enhancer sequence of cytomegalovirus and the adenovirus tripartite leader/intron sequence and containing the replication orgin and poly(A) sequence of SV40. The expression vector can have additional coding regions, such as those encoding, for example, 6X-histidine, V5, thioredoxin, glutathione-S-transferase, c-Myc, VSV-G, HSV, FLAG, maltose binding peptide, metal-binding peptide, HA and "secretion" signals (Honeybee melittin, □ α-factor, PHO, Bip), which can be incorporated into the expressed fusion polypeptide. In addition, there can be enzyme digestion sites incorporated after these coding regions to facilitate their enzymatic removal if they are not needed. These additional nucleic acids are useful for the detection of fusion polypeptide expression, for protein purification by affinity chromatography, enhanced solubility of the recombinant protein in the host cytoplasm, and/or for secreting the expressed fusion polypeptide out into the culture media or the spheroplast of the yeast cells. The expression of the fusion polypeptide can be constitutive in the host cells or it can be induced, e.g., with copper sulfate, sugars such as galactose, methanol, methylamine, thiamine, tetracycline, infection with baculovirus, and (isopropyl-beta-D-thiogalactopyranoside) IPTG, a stable synthetic analog of lactose.

In another embodiment, the expression vector comprising a polynucleotide described herein is a viral vector, such as adenovirus, adeno-associated virus (AAV), retrovirus, and lentivirus vectors, among others. Recombinant viruses provide a versatile system for gene expression studies and therapeutic applications.

In some embodiments, the fusion polypeptides described herein are expressed from viral infection of mammalian cells. The viral vectors can be, for example, adenovirus, adeno-associated virus (AAV), retrovirus, and lentivirus. A simplified system for generating recombinant adenoviruses is presented by He et al., 95 PNAS 2509 (1998). The gene of interest is first cloned into a shuttle vector, e.g., pAdTrack-CMV. The resultant plasmid is linearized by digesting with restriction endonuclease PmeI, and subsequently cotransformed into E. coli. BJ5183 cells with an adenoviral backbone plasmid, e.g. pADEASY-1 of Stratagene's ADEASY™ Adenoviral Vector System. Recombinant adenovirus vectors are selected for kanamycin resistance, and recombination confirmed by restriction endonuclease analyses. Finally, the linearized recombinant plasmid is transfected into adenovirus packaging cell lines, for example HEK 293 cells (E1-transformed human embryonic kidney cells) or 911 (E1-transformed human embryonic retinal cells). Fallaux, et al. 7 Human Gene Ther. 215 (1996). Recombinant adenovirus are generated within the HEK 293 cells.

Recombinant lentivirus has the advantage of delivery and expression of fusion polypeptides in dividing and non-dividing mammalian cells. The HIV-1 based lentivirus can effectively transduce a broader host range than the Moloney Leukemia Virus (MoMLV)-based retroviral systems. Preparation of the recombinant lentivirus can be achieved using, for example, the pLenti4N5-DEST™, pLenti6/V5-DEST™ or pLenti vectors together with VIRAPOWER™ Lentiviral Expression systems from Invitrogen, Inc.

Recombinant adeno-associated virus (rAAV) vectors are applicable to a wide range of host cells including many different human and non-human cell lines or tissues. rAAVs are capable of transducing a broad range of cell types and transduction is not dependent on active host cell division. High titers, >$10^8$ viral particle/ml, are easily obtained in the supernatant and $10^{11}$-$10^{12}$ viral particle/ml with further concentration. The transgene is integrated into the host genome so expression is long term and stable.

Large scale preparation of AAV vectors is made by a three-plasmid cotransfection of a packaging cell line: AAV vector carrying the coding nucleic acid, AAV RC vector containing AAV rep and cap genes, and adenovirus helper plasmid pDF6, into 50×150 mm plates of subconfluent 293 cells. Cells are harvested three days after transfection, and viruses are released by three freeze-thaw cycles or by sonication.

AAV vectors can be purified by two different methods depending on the serotype of the vector. AAV2 vector is purified by the single-step gravity-flow column purification method based on its affinity for heparin. Auricchio et. al., 12 Human Gene Ther. 71 (2001); Summerford & Samulski, 72 J. Virol. 1438 (1998); Summerford & Samulski, 5 Nat. Med. 587 (1999). AAV2/1 and AAV2/5 vectors are currently purified by three sequential CsCl gradients.

Without wishing to be bound to theory, when proteins are expressed by a cell, including a bacterial cell, the proteins are targeted to a particular part in the cell or secreted from the cell. Thus, protein targeting or protein sorting is the mechanism by which a cell transports proteins to the appropriate positions in the cell or outside of it. Sorting targets can be the inner space of an organelle, any of several interior membranes, the cell's outer membrane, or its exterior via secretion. This delivery process is carried out based on information contained in the protein itself. Correct sorting is crucial for the cell; errors can lead to diseases.

With some exceptions, bacteria lack membrane-bound organelles as found in eukaryotes, but they may assemble proteins onto various types of inclusions such as gas vesicles and storage granules. Also, depending on the species of bacteria, bacteria may have a single plasma membrane (Gram-positive bacteria), or both an inner (plasma) membrane and an outer cell wall membrane, with an aqueous space between the two called the periplasm (Gram-negative bacteria). Proteins can be secreted into the environment, according to whether or not there is an outer membrane. The basic mechanism at the plasma membrane is similar to the eukaryotic one. In addition, bacteria may target proteins into or across the outer membrane. Systems for secreting proteins across the bacterial outer membrane may be quite complex and play key roles in pathogenesis. These systems may be described as type I secretion, type II secretion, etc.

In most Gram-positive bacteria, certain proteins are targeted for export across the plasma membrane and subsequent covalent attachment to the bacterial cell wall. A specialized enzyme, sortase, cleaves the target protein at a characteristic recognition site near the protein C-terminus, such as an LPXTG motif (SEQ ID NO: 19) (where X can be any amino acid), then transfers the protein onto the cell wall. A system analogous to sortase/LPXTG, having the motif PEP-CTERM (SEQ ID NO: 49), termed exosortase/PEP-CTERM, is proposed to exist in a broad range of Gram-negative bacteria.

Proteins with appropriate N-terminal targeting signals are synthesized in the cytoplasm and then directed to a specific protein transport pathway. During, or shortly after its translocation across the cytoplasmic membrane, the protein is processed and folded into its active form. Then the translocated protein is either retained at the periplasmic side of the cell or released into the environment. Since the signal peptides that target proteins to the membrane are key determinants for transport pathway specificity, these signal peptides are classified according to the transport pathway to which they direct proteins. Signal peptide classification is based on the type of signal peptidase (SPase) that is responsible for the removal of the signal peptide. The majority of exported proteins are exported from the cytoplasm via the general "Secretory (Sec) pathway". Most well known virulence factors (e.g. exotoxins of *Staphylococcus aureus*, protective antigen of *Bacillus anthracis*, lysteriolysin 0 of *Listeria monocytogenes*) that are secreted by Gram-positive pathogens have a typical N-terminal signal peptide that would lead them to the Sec-pathway. Proteins that are secreted via this pathway are translocated across the cytoplasmic membrane in an unfolded state. Subsequent processing and folding of these proteins takes place in the cell wall environment on the trans-side of the membrane. In addition to the Sec system, some Gram-positive bacteria also contain the Tat-system that is able to translocate folded proteins across the membrane. Pathogenic bacteria may contain certain special purpose export systems that are specifically involved in the transport of only a few proteins. For example, several gene clusters have been identified in mycobacteria that encode proteins that are secreted into the environment via specific pathways (ESAT-6) and are important for mycobacterial pathogenesis. Specific ATP-binding cassette (ABC) transporters direct the export and processing of small antibacterial peptides called bacteriocins. Genes for endolysins that are responsible for the onset of bacterial lysis are often located near genes that encode for holin-like proteins, suggesting that these holins are responsible for endolysin export to the cell wall. Wooldridge, BACT. SECRETED PROTS: SECRETORY MECHS. & ROLE IN PATHOGEN. (Caister Academic Press, 2009)

In some embodiments, the signal sequence useful in the present invention is OmpA Signal sequence, however any signal sequence commonly known by persons of ordinary skill in the art which allows the transport and secretion of antimicrobial agents outside the bacteriophage infected cell are encompassed for use in the present invention.

Signal sequence that direct secretion of proteins from bacterial cells are well known in the art, for example as disclosed in International application WO 2005/071088. For example, one can use some of the non-limited examples of signal peptide shown in Table 7, which can be attached to the amino-terminus or carboxyl terminus of the antimicrobial peptide (Amp) or antimicrobial polypeptide to be expressed by the antimicrobial-agent engineered bacteriophage, e.g., AMP-engineered bacteriophage. Attachment can be via fusion or chimera composition with selected antigen or antigen-complementary affinity molecule fusion protein resulting in the secretion from the bacterium infected with the antimicrobial-agent engineered bacteriophage, e.g. AMP-engineered bacteriophage.

established molecular adhesion properties can be reversibly fused to the protein of choice. With the appropriate ligand, the protein can be selectively adsorbed to a purification column and then freed from the column in a relatively pure form. The fused protein is then removed by enzymatic activity. Finally, the protein of choice can be purified using affinity or immunoaffinity columns.

After the protein is expressed in the host cells, the host cells can be lysed to liberate the expressed protein for purification. Methods of lysing the various host cells are featured in "Sample Preparation-Tools for Protein Research" EMD Bioscience and in the Current Protocols in Protein Sciences (CPPS). An example purification method is affinity chromatography such as metal-ion affinity chromatograph using nickel, cobalt, or zinc affinity resins for histidine-tagged fusion polypeptides. Methods of purifying histidine-tagged recombinant proteins are described by Clontech using their TALON® cobalt resin and by NOVAGEN® in their pET system manual, 10th edition. Another preferred purification strategy is immuno-affinity chromatography, for example, anti-myc antibody conjugated resin can be used to affinity purify myc-tagged fusion polypeptides. When appropriate protease recognition sequences are

TABLE 7

Example signal peptides to direct secretion of a protein or peptide antigen or antigen-complementary affinity molecule fusion protein of a bacterial cell

| Secretion Pathway | Signal Peptide Amino Acid sequence ($NH_2$–$CO_2$) | Gene | Genus/Species |
|---|---|---|---|
| secA1 | MKKIMLVITLILVSPIAQQTEAKD (SEQ ID NO: 50) | Hly (LLO) | Listeria monocytogenes |
|  | MKKKIISAILMSTVILSAAAPLSGVYADT (SEQ ID NO: 51) | Usp45 | Lactococcus lactis |
|  | MKKRKVLIPLMALSTILVSSTGNLEVIQAEV (SEQ ID NO: 52) | Pag (protective antigen) | Bacillus anthracis |
| secA2 | MNMKKATIAATAGIAVTAFAAPTIASAST (SEQ ID NO: 53) | Iap (invasion-associated protein p60) | Listeria monocytogenes |
|  | MQKTRKERILEALQEEKKNKKSKKFKTGATIAGVTAIATSITVPGIEVIVSADE (SEQ ID NO: 54) | NamA lmo2691 (autolysin) | Listeria monocytogenes |
|  | MKKLKMASCALVAGLMFSGLTPNAFAED (SEQ ID NO: 55) | *BA_0281 (NLP/P60 family) | Bacillus anthracis |
|  | MAKKFNYKLPSMVALTLVGSAVTAHQVQAAE (SEQ ID NO: 56) | * atl (autolysin) | Staphylococcus aureus |
| Tat | MTDKKSENQTEKTETKENKGMTRREMLKLSAVAGTGIAVGATGLGTILNVVDQVDKALT (SEQ ID NO: 57) | lmo0367 | Listeria monocytogenes |
|  | MAYDSRFDEWVQKLKEESFQNNTFDRRKFIQGAGKIAGLGLGLTIAQSVGAFG (SEQ ID NO: 58) | PhoD (alkaline phosphatase) | Bacillus subtillis |

The polypeptides as described herein, e.g., antigens or antigen-complementary affinity molecule fusion protein can be expressed and purified by a variety methods known to one skilled in the art, for example, the fusion polypeptides described herein can be purified from any suitable expression system. Fusion polypeptides can be purified to substantial purity by standard techniques, including selective precipitation with such substances as ammonium sulfate; column chromatography, immunopurification methods, and others; which are well-known in the art. See, e.g., Scopes, PROTEIN PURIFICATION: PRINCIPLES & PRACTICE (1982); U.S. Pat. No. 4,673,641.

A number of procedures can be employed when recombinant proteins are purified. For example, proteins having present, fusion polypeptides can be cleaved from the histidine or myc tag, releasing the fusion polypeptide from the affinity resin while the histidine-tags and myc-tags are left attached to the affinity resin.

Standard protein separation techniques for purifying recombinant and naturally occurring proteins are well known in the art, e.g., solubility fractionation, size exclusion gel filtration, and various column chromatography.

Solubility fractionation: Often as an initial step, particularly if the protein mixture is complex, an initial salt fractionation can separate many of the unwanted host cell proteins (or proteins derived from the cell culture media) from the protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size exclusion filtration: The molecular weight of the protein of choice can be used to isolate it from proteins of greater and lesser size using ultrafiltration through membranes of different pore size (for example, AMICON® or MILLIPORE® membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column chromatography: The protein of choice can also be separated from other proteins on the basis of its size, net surface charge, hydrophobicity, and affinity for ligands. In addition, antibodies raised against recombinant or naturally occurring proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech). For example, an antigen polypeptide can be purified using a PA63 heptamer affinity column. Singh et al., 269, J. Biol. Chem. 29039 (1994).

In some embodiments, a combination of purification steps comprising, for example: (a) ion exchange chromatography, (b) hydroxyapatite chromatography, (c) hydrophobic interaction chromatography, and (d) size exclusion chromatography can be used to purify the fusion polypeptides described herein.

Cell-free expression systems are also contemplated. Cell-free expression systems offer several advantages over traditional cell-based expression methods, including the easy modification of reaction conditions to favor protein folding, decreased sensitivity to product toxicity and suitability for high-throughput strategies such as rapid expression screening or large amount protein production because of reduced reaction volumes and process time. The cell-free expression system can use plasmid or linear DNA. Moreover, improvements in translation efficiency have resulted in yields that exceed a milligram of protein per milliliter of reaction mix. Commercially available cell-free expression systems include the TNT coupled reticulocyte lysate Systems (Promega) which uses rabbit reticulocyte-based in vitro system.
Determining the Efficacy of a SA-MAPS Immunogenic Composition:

The effectiveness of a SA-MAPS immunogenic composition as disclosed herein can be measured either by proliferation assays, by cytolytic assays, such as chromium release assays to measure the ability of a T-cell to lyse its specific target cell, or by measuring the levels of B-cell activity by measuring the levels of circulating antibodies specific for the antigen in serum. An immune response may also be detected by measuring the serum levels of antigen specific antibody induced following administration of the antigen, and more specifically, by measuring the ability of the antibodies so induced to enhance the opsonophagocytic ability of particular white blood cells, as described herein. The level of protection of the immune response may be measured by challenging the immunized host with the antigen that has been administered. For example, if the antigen to which an immune response is desired is a bacterium, the level of protection induced by the immunogenic amount of the antigen is measured by detecting the percent survival or the percent mortality after challenge of the animals with the bacterial cells. In one embodiment, the amount of protection may be measured by measuring at least one symptom associated with the bacterial infection, e.g., a fever associated with the infection. The amount of each of the antigens in the multi-antigen or multi-component vaccine or immunogenic compositions will vary with respect to each of the other components and can be determined by methods known to the skilled artisan. Such methods would include procedures for measuring immunogenicity and/or in vivo efficacy. In certain embodiments, the term "about" leans within 20%, preferably within 10%, and more preferably within 5%.

In some embodiments, the invention further provides antibodies and antibody compositions which bind specifically and selectively to the SA-MAPS immunogenic composition as disclosed herein. In some embodiments, antibodies are generated upon administration of a SA-MAPS immunogenic composition as disclosed herein to a subject. In some embodiments, the antibodies of the present invention are functional as measured by killing bacteria in either an animal efficacy model or via an opsonophagocytic killing assay. In some embodiments, the antibodies of the invention confer passive immunity to a subject. The present invention further provides polynucleotide molecules encoding an antibody or antibody fragment of the invention, and a cell, cell line (such as hybridoma cells or other engineered cell lines for recombinant production of antibodies) or a transgenic animal that produces an antibody or antibody composition of the invention, using techniques well-known to those of skill in the art.

Antibodies or antibody compositions of the invention may be used in a method of treating or preventing a Staphylococcal infection, disease or condition associated with a *Staphylococcus* sp. in a subject, the method comprising generating a polyclonal or monoclonal antibody preparation, and using said antibody or antibody composition to confer passive immunity to the subject. Antibodies of the invention may also be useful for diagnostic methods, e.g., detecting the presence of or quantifying the levels of CP5, CP8 or a conjugate thereof.

Several animal models known in the art may be used to assess the efficacy of any one of the SA-MAPS immunogenic composition as disclosed herein. For example:

Passive Murine Sepsis Model: Mice are passively immunized intraperitoneally (i.p.) with SA-MAPS immunogenic composition as disclosed herein. The mice are challenged 24 hours later with a lethal dose of *S. aureus*. The bacterial challenge is administered intravenously (i.v. or i.p.) ensuring that any survival could be attributed to the specific in vivo interaction of the antibody with the bacteria. The bacterial challenge dose is determined to be the dose required to achieve lethal sepsis of approximately 20% of the unimmunized control mice. Statistical evaluation of survival studies can be carried out by Kaplan-Meier analysis.

Active Immunization and Challenge Model: In this model, mice are actively immunized subcutaneously (s.c.) with a SA-MAPS immunogenic composition as disclosed herein at 0, 3 and 6 weeks (or a similar schedule known to those skilled in the art) and challenged with S. aureus at week 8 (or other similar schedule known to those skilled in the art) by the intravenous or intraperitoneal route. The bacterial challenge dose is calibrated to achieve approximately 20% survival in the control group over a 14 day period. Statistical evaluation of survival studies can be carried out by Kaplan-Meier analysis.

Passive Infectious Endocarditis Model: A passive immunization model for infectious endocarditis (IE) caused by S. aureus has previously been used to show that ClfA can induce protective immunity. See, Vernachio et al. (2006) Antmicro. Agents & Chemo. 50:511-518. In this model of IE, rabbits or rats are used to simulate clinical infections that include a central venous catheter, bacteremia, and hematogenous seeding to distal organs. Catheterized rabbits or rats with sterile aortic valve vegetations are administered a SA-MAPS immunogenic composition as disclosed herein. After 24 hours, the animals are challenged i.v. with heterologous staphylococcal strains or a MRSA strain. Then 48 hours after challenge, cardiac vegetations, kidneys and blood are harvested and cultured. The frequency of staphylococcal infection in cardiac valve vegetations, kidneys, and blood is then measured. In one study, when animals were challenged with either MRSE ATCC 35984 or MRSA PFESA0003, significant reductions in infection rate were shown using either the polyclonal antibody preparation or the monoclonal antibody to ClfA. See, Vernachio et al., supra.

Passive Infectious Endocarditis Model: The infectious endocarditis model has also been adapted for active immunization studies. Rabbits or rats are immunized intramuscularly (i.m.) with a SA-MAPS immunogenic composition as disclosed herein and challenged with aureus two weeks later via the i.v. route.

Pyelonephritis Model: In the pyelonephritis model, mice are immunized on weeks 0, 3 and 6 (or a similar schedule known to those skilled in the art) with a SA-MAPS immunogenic composition as disclosed herein. On week 8, the animals are challenged by, e.g., i.p. injection of, e.g., $1.7 \times 10^8$ cfu S. aureus PFESA0266. After 48 hours, the kidneys and/or other tissues are harvested and cultured. Finally, colony forming units of challenge bacteria are enumerated in the kidneys and/or other tissues. This model evaluates systemic dissemination in the animal.

Monitoring Functional Antibodies Using Opsonophagocytic Killing Assays: Differentiated effector cells from a cell line (e.g. HL60s) or polymorphonuclear cells (PMNs) isolated from donor human blood using LYMPHOLYTE™-poly solution (Cedarlane laboratories limited, Ontario, Canada) as per manufacturer's protocol can be used for this assay. Effector cells were resuspended in assay buffer (Modified Eagle's media containing 1% bovine serum albumin) at approximately $2 \times 10^7$ cells/ml concentration and placed in 37° C. incubator until ready to use. S. aureus strain PFESA0266 was grown overnight on tryptic soy agar plates. Bacterial cells were scraped, washed twice and resuspended in assay buffer containing 5% glycerol to an $OD^{600=1}$, which equals to approximately $5.times.10^8$ cfu/ml concentration. One ml aliquots of the bacterial suspension were frozen and stored at −40° C. until ready to use. Frozen bacterial suspension were thawed and adjusted to a concentration of $10 \times 10^6$ cfu/ml in assay buffer and placed on ice. The assay was performed using a sterile 96 deep well 1 ml polypropylene plates. Two fold serial dilutions of antibody samples (50 µl) were prepared and followed by addition of 300 µl of assay buffer to the antibody mix. Bacteria were added (50 µl) to the plates and placed on a rotary shaker at 4° C. for 30 minutes. The opsonization step was followed by addition of 50 µl of human complement (1% final concentration). Finally, 50 µl of effector cells ($10 \times 10^7$ cells/ml concentration) were added to the plate and the suspension mixed well by repeated pipetting. A 50 µl aliquot of the suspension was 10 fold serially diluted in sterile 1% saponin solution, vortexed to minimize bacterial clumping and plated on tryptic soy agar in duplicate. The assay plate was incubated at 37° C. for 1 hour with continuous mixing using rotisserie style shaker. At the end of the incubation a 50 µl aliquot of suspension was 10 fold serially diluted in sterile 1% saponin solution, mixed by vortexing to minimize bacterial clumping and plated on tryptic soy agar in duplicate. The percentage killing was calculated by determining the ratio of the number of cfu surviving at 60 minutes in wells with bacteria, antibodies, complement and effector cells to the number of cfu surviving in tubes lacking antibodies but containing bacteria, complement and effector cells. Controls containing bacteria, complement, and sera were included to adjust for any reduction in cfu due to clumping.

Complement Adsorption: Serum from human donors adsorbed against S. aureus strains PFESA0266, PFESA0286 and PFESA0270 can be used as a source of complement in the assay. S. aureus strains were grown overnight on TSA plates at 37° C. Cells were scraped from the plate and resuspended in sterile PBS. Bacterial cells were centrifuged at 10,000 rpm for 10 minutes at 4° C. and cell pellet was resuspended in human serum for adsorption. Serum was incubated with bacteria on a nutator at 4° C. for 30 minutes. Cells were centrifuged, serum transferred to another tube containing bacteria and the adsorption step repeated again for 30 minutes. Finally, the cells were centrifuged and the serum passed through a 0.2 micron filter before 0.5 ml aliquots were frozen down in liquid nitrogen.

Method II—OPA Using HL-60 Cells: HL-60 cells were differentiated According to S. Romero-Steiner, et al., Clin Diagn Lab Immunol 4 (4) (1997), pp. 415-422. Harvested HL-60 cells were resuspended in assay buffer (Modified Eagle's media containing 1% bovine serum albumin) at approximately $10.sup.8$ cells/nil and placed in 37° C. incubator until ready to use. S. aureus was grown overnight on tryptic soy agar plates. Bacterial cells were scraped, washed twice and resuspended in assay buffer containing 5% glycerol to an $OD^{600=1}$, which equals to approximately $5 \times 10^8$ cfu/ml. One ml aliquots of the bacterial suspension were frozen and stored at −40° C. until ready to use. Frozen bacterial suspension were thawed and adjusted to a concentration of $10 \times 10^6$ cfu/ml in assay buffer and placed on ice. The assay was performed using a sterile 96 deep well 1 ml polypropylene plates. Two fold serial dilutions of monoclonal antibody samples (25 µl) were prepared and followed by addition of 150 µl of assay buffer to the antibody suspension. Bacteria were added (25 µl) to the plates and placed on a rotary shaker at 4° C. for 30 minutes followed by addition of 25 µl of human complement (1% final concentration). Finally, 25 µl of HL-60 cells ($10 \times 10^7$ cells/ml) were added to the plate and the suspension mixed well by repeated pipetting. A 25 µl aliquot of the suspension was 10 fold serially diluted in sterile 1% saponin solution, mixed by vortexing to minimize bacterial clumping and plated on tryptic soy agar in duplicates. The assay plate was incubated at 37° C. for 1 hour with continuous mixing using rotisserie style shaker. At the end of incubation a 25 µl aliquot of suspension was 10 fold serially diluted in sterile 1% saponin solution, mixed by vortexing to and plated on tryptic soy agar in duplicate. The percentage killing was calculated by determining the ratio of the number of cfu surviving at 60 minutes in wells with bacteria, antibodies, complement and HL-60 cells to the number of cfu surviving in tubes lacking antibodies but containing bacteria, complement and HL-60 cells. Controls containing bacteria complement and mAb was included to adjust for any reduction in cfu due to clumping.

Formulations of an Immune Composition and Methods of Use

Specific embodiments of the present invention provide for use of the SA-MAPS immunogenic compositions as disclosed herein to elicit an immune response to *S. aureus* in an animal. More specifically, the compositions elicit both humoral and cellular immunity, and in many instance mucosal immunity. Embodiments of the present invention provide at least partial protection from or partial improvement after infection by, in particular, *S. aureus*.

In one embodiment, provided herein is a method of vaccinating a mammal comprising administering the SA-MAPS immunogenic composition comprising at least one, or multiple SA antigens attached to an immunogenic polysaccharide for use in eliciting an immune response to the one or more antigens attached to the polymer when administered to a subject. In some embodiments, the immune response is a humoral and/or cellular immune response.

Accordingly, one aspect of the present invention relates to methods to elicit an immune response in a subject, comprising administering to the subject a SA-MAPS immunogenic composition comprising at least one type of immunogenic polysaccharide (e.g., CP5, CP8, a CP5-CP8 conjugate, pneumococcal PS1(CP 1) etc., at least one SA antigen, and at least one complementary affinity-molecule pair comprising (i) a first affinity molecule which associates with the immunogenic polysaccharide, and (ii) a complementary affinity molecule which associates with the SA antigen, to attach the SA antigen to the immunogenic polysaccharide, (e.g., the first affinity molecule associates with the complementary affinity molecule to link the SA antigen to the immunogenic polysaccharide).

Accordingly, one aspect of the present invention relates to methods to elicit a humoral and/or cellular immunity to multiple SA antigens at the same time, e.g., where the immunogenic composition administered to the subject comprises an immunogenic polysaccharide comprising at least 1, or at least 2, or a more, e.g., a plurality of the same or different SA antigens.

One aspect of the present invention relates to a method of immunization or vaccinating a subject, e.g., a bird or a mammal, e.g., a human against *S. aureus* comprising administering a SA-MAPS immune composition as disclosed herein comprising at least one SA antigen derived from one or more pathogens. In some embodiments, a subject can be immunized against at least 1, or at least 2, or at least 2, or at least 3, or at least 5, or at least 10, or at least 15, or at least about 20, or at least 50, or at least about 100, or more than 100 different SA antigens at the same time, where the immunogenic polysaccharide of the SA-MAPS immunogenic composition has different SA antigens attached.

In some embodiments, a subject can be administered several different SA-MAPS immunogenic compositions as disclosed herein, for example, a subject can be administered a SA-MAPS composition comprising an immunogenic polysaccharide with a SA antigen, or a plurality of SA antigens, e.g., antigens A, B, C, and D etc., and also administered a SA-MAPS composition comprising an immunogenic polysaccharide comprising a different SA antigen, or a different set of SA antigens, e.g., antigens W, X, Y, and Z etc. Alternatively, a subject can be administered a SA-MAPS composition comprising a immunogenic polysaccharide A (e.g., CP5) with an SA antigen, or a plurality of SA antigens, e.g., antigens A, B, C, and D, etc., and also administered a SA-MAPS composition comprising a immunogenic polysaccharide B (e.g. CP8) comprising the same e.g., antigens A, B, C, and D etc., or a different set of antigens. It is envisioned that the present invention provides a method for the immunization of a subject with as many SA antigens as desired, e.g., with a variety of different immunogenic complexes as described herein, to enable immunization with as many as 100 or more antigens.

In one embodiment, the SA-MAPS immunogenic compositions as described herein comprise a pharmaceutically acceptable carrier. In another embodiment, the SA-MAPS immunogenic composition described herein is formulated for administering to a bird, mammal, or human, as or in a vaccine. Suitable formulations can be found in, for example, Remington's Pharmaceutical Sciences (2006), or Introduction to Pharmaceutical Dosage Forms (4th ed., Lea & Febiger, Philadelphia, 1985).

In one embodiment, the SA-MAPS immunogenic compositions as described herein comprise pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. For all administrations, conventional depot forms are suitably used. Such forms include, for example, microcapsules, nano-capsules, liposomes, plasters, inhalation forms, nose sprays, sublingual tablets, and sustained release preparations. For examples of sustained release compositions, see U.S. Pat. Nos. 3,773, 919, 3,887,699, EP 58,481A, EP 158,277A, Canadian Patent No. 1176565; Sidman et al., 22 Biopolymers 547 (1983); Langer et al., 12 Chem. Tech. 98 (1982). The proteins will usually be formulated at a concentration of about 0.1 mg/ml to 100 mg/ml per application per patient.

In one embodiment, other ingredients can be added to vaccine formulations, including antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

In some embodiments, the SA-MAPS immunogen composition as disclosed herein is administered with at least one adjuvant or an immune modulator, or both. Adjuvants are a heterogeneous group of substances that enhance the immunological response against an antigen that is administered simultaneously. In some instances, adjuvants improve the immune response so that less vaccine is needed. Adjuvants serve to bring the antigen—the substance that stimulates the specific protective immune response—into contact with the immune system and influence the type of immunity produced, as well as the quality of the immune response (magnitude or duration). Adjuvants can also decrease the toxicity of certain antigens; and provide solubility to some vaccine components. Almost all adjuvants used today for enhancement of the immune response against antigens are particles or form particles together with the antigen. In the book VACCINE DESIGN—SUBUNIT & ADJUVANT APPROACH (Powell & Newman, Eds., Plenum Press, 1995), many known adjuvants are described both regarding their immunological activity and regarding their chemical characteristics. The type of adjuvants that do not form particles are a group of substances that act as immunological signal substances and that under normal conditions consist of the substances that are formed by the immune system as a consequence of the immunological activation after administration of particulate adjuvant systems.

Adjuvants for immunogenic compositions and vaccines are well known in the art. Examples include, but not limited to, monoglycerides and fatty acids (e. g. a mixture of mono-olein, oleic acid, and soybean oil); mineral salts, e.g., aluminium hydroxide and aluminium or calcium phosphate gels; oil emulsions and surfactant based formulations, e.g., MF59 (microfluidised detergent stabilized oil-in-water emulsion), QS21 (purified saponin), AS02 [SBAS2] (oil-in-water emulsion+MPL+QS-21), MPL-SE, Montanide ISA-51 and ISA-720 (stabilised water-in-oil emulsion); particulate adjuvants, e.g., virosomes (unilamellar liposomal vehicles incorporating influenza haemagglutinin), AS04 ([SBAS4] Al salt with MPL), ISCOMS (structured complex of saponins and lipids), polylactide co-glycolide (PLG); microbial derivatives (natural and synthetic), e.g., monophosphoryl lipid A (MPL), Detox (MPL+M. Phlei cell wall skeleton), AGP [RC-529] (synthetic acylated monosaccharide), Detox-PC, DC_Chol (lipoidal immunostimulators able to self-organize into liposomes), OM-174 (lipid A derivative), CpG motifs (synthetic oligonucleotides containing immunostimulatory CpG motifs), or other DNA structures, modified LT and CT (genetically modified bacterial toxins to provide non-toxic adjuvant effects); endogenous human immunomodulators, e.g., hGM-CSF or hIL-12 (cytokines that can be administered either as protein or plasmid encoded), Immudaptin (C3d tandem array), MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Alum, and MF59 and inert vehicles, such as gold particles. Additional adjuvants are known in the art, see, e.g., U.S. Pat. No. 6,890,540; U.S. Patent Pub. No. 2005/0244420; PCT/SE97/01003.

Additional suitable adjuvants used to enhance an immune response of the SA-MAPS composition as disclosed herein further include, without limitation, MPL™ (3-O-deacylated monophosphoryi lipid A, Corixa; Hamilton, Mont.), which is described in U.S. Pat. No. 4,912,094. Also suitable for use as adjuvants are synthetic lipid A analogs or aminoalkyl glucosamine phosphate compounds (AGP), or derivatives or analogs thereof, which are available from Corixa, and those that are described in U.S. Pat. No. 6,113,918. One such AGP is 2-[(R)-3-Tetradecanoyloxytetradecanoylamino]ethyl 2-Deoxy-4-O-phosphono-3-O-[(R)-3-tetradecanoyoxytetradecanoyl]-2-[(R1-3-t-etradecanoyloxytetradecanoyl-amino]-b-D-glucopyranoside, which is also known as 529 (formerly known as RC529). This 529 adjuvant is formulated as an aqueous form (AF) or as a stable emulsion (SE).

Still other adjuvants include muramyl peptides, such as N-acetyl-muramyl-L-threonyl-D-isoglutamine (thr-MDP), N-acetyl-normuramyl-L-alanine-2-(1'-2' dipalmitoyl-sn-glycero-hydroxyphosphoryloxy)-ethylamine (MTP-PE); oil-in-water emulsions, such as MF59 (U.S. Pat. No. 6,299,884) (containing 5% Squalene, 0.5% polysorbate 80, and 0.5% Span 85 (optionally containing various amounts of MTP-PE) formulated into submicron particles using a microfluidizer such as Model 110Y microfluidizer (Microluidics, Newton, Mass.)), and SAF (containing 10% Squalene, 0.4% polysorbate 80, 5% pluronic-blocked polymer L121, and thr-MDP, either microfluidized into a submicron emulsion or vortexed to generate a larger particle size emulsion); incomplete Freund's adjuvant (IFA); aluminum salts (alum), such as aluminum hydroxide, aluminum phosphate, aluminum sulfate; Amphigen; Avridine; L121/squalene; D-lactide-polylactide/glycoside; pluronic polyols; killed Bordetella; saponins, such as Stimulon™ QS-21 (Antigenics, Framingham, Mass.), described in U.S. Pat. No. 5,057,540, Iscomatrix® (CSL Limited, Parkville, Australia), described in U.S. Pat. No. 5,254,339, and immunostimulating complexes (ISCOMS); Mycobacterium tuberculosis; bacterial lipopolysaccharides; synthetic polynucleotides such as oligonucleotides containing a CpG motif (e.g., U.S. Pat. No. 6,207,646); IC-31 (Intercell AG, Vienna, Austria), described in EP Patent No. 1,296,713 and 1,326,634; a pertussis toxin (PT) or mutant thereof a cholera toxin or mutant thereof (e.g., U.S. Pat. Nos. 7,285,281, 7,332,174, 7,361,355 and 7,384,640); or an E. coli heat-labile toxin (LT) or mutant thereof, particularly LT-K63, LT-R72 (e.g., U.S. Pat. Nos. 6,149,919, 7,115,730 and 7,291,588).

In some embodiments, the SA-MAPS immunogen composition as disclosed herein is administered with at least one immune modulator. An "immunomodulator" or "immune modulator" is an agent that perturb or alter the immune system, such that either up-regulation or down-regulation of humoral and/or cell-mediated immunity is observed. In one embodiment, up-regulation of the humoral and/or cell-mediated arms of the immune system is provided. Examples of certain immunomodulators include, e.g., an adjuvant or cytokine, or Iscomatrix™ (CSL Limited; Parkville, Australia), described in U.S. Pat. No. 5,254,339 among others. Non-limiting examples of adjuvants that can be used in the immunogenic composition of the present invention include the RIBI adjuvant system (Ribi Inc.; Hamilton, Mont.), alum, mineral gels such as aluminum hydroxide gel, oil-in-water emulsions, water-in-oil emulsions such as, e.g., Freund's complete and incomplete adjuvants, Block copolymer (CytRx; Atlanta, Ga.), QS-21 (Cambridge Biotech Inc.; Cambridge, Mass.), SAF-M (Chixon; Emeryville, Calif.), Amphigen™ adjuvant, saponin, Quil A or other saponin fraction, monophosphoryl lipid A, and Avridine lipid-amine adjuvant. Non-limiting examples of oil-in-water emulsions useful in the immunogenic composition of the invention include modified SEAM62 and SEAM 1/2 formulations. Modified SEAM62 is oil-in-water emulsion containing 5% (v/v) squalene (Sigma), 1% (v/v) Span® 85 Detergent (ICI Surfactants), 0.7% (v/v) polysorbate 80 detergent (ICI Surfactants), 2.5% (v/v) ethanol, 200 mcg/ml Quil A, 100 mcg/ml cholesterol, and 0.5% (v/v) lecithin. Modified SEAM 1/2 is an oil-in-water emulsion comprising 5% (v/v) squalene, 1% (v/v) Span® 85 Detergent, 0.7% v/v) polysorbate 80 detergent, 2.5% (v/v) ethanol, 100 mcg/ml Quil A, and 50 mcg/ml cholesterol. Other "immunomodulators" that can be included in the immunogenic composition include, e.g., one or more interleukins, interferons, or other known cytokines or chemokines. In one embodiment, the adjuvant may be a cyclodextrin derivative or a polyanionic polymer, such as those described in U.S. Pat. Nos. 6,165,995 and 6,610,310, respectively. It is to be understood that the immunomodulator and/or adjuvant to be used will depend on the subject to which the immunogenic composition will be administered, the route of injection and the number of injections to be given.

In some embodiments, the SA-MAPS immunogen composition as disclosed herein is administered with at least one immune modulator. A number of cytokines or lymphokines have been shown to have immune modulating activity, and thus may be useful in a manner the same or similar to adjuvants, including, but not limited to, the interleukins 1-.alpha., 1-.beta., 2, 4, 5, 6, 7, 8, 10, 12 (see, e.g., U.S. Pat. No. 5,723,127), 13, 14, 15, 16, 17 and 18 (and its mutant forms); the interferons-α, β and γ; granulocyte-macrophage colony stimulating factor (GM-CSF) (see, e.g., U.S. Pat. No. 5,078,996 and ATCC Accession Number 39900); macrophage colony stimulating factor (M-CSF); granulocyte colony stimulating factor (G-CSF); and the tumor necrosis factors a and (3. Still other adjuvants that are useful with the immunogenic compositions described herein include chemokines, including without limitation, MCP-1, MfP-1.alpha., MIP-1.beta., and RANTES; adhesion molecules, such as a selectin, e.g., L-selectin, P-selectin and E-selectin; mucin-like molecules, e.g., CD34, GlyCAM-1 and Mad-CAM-1; a member of the integrin family such as LFA-1, VLA-1, Mac-1 and p150.95; a member of the immunoglobulin superfamily such as PECAM, ICAMs, e.g., ICAM-1, ICAM-2 and ICAM-3, CD2 and LFA-3; co-stimulatory molecules such as B7-1, B7-2, CD40 and CD40L; growth factors including vascular growth factor, nerve growth factor, fibroblast growth factor, epidermal growth factor, PDGF, BL-1, and vascular endothelial growth factor; receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6; and Caspases, including ICE.

In some embodiments an adjuvant is a particulate and can have a characteristic of being slowly biodegradable. Care must be taken to ensure that that the adjuvant do not form toxic metabolites. Preferably, in some embodiments, such adjuvants can be matrices used are mainly substances originating from a body. These include lactic acid polymers, poly-amino acids (proteins), carbohydrates, lipids and biocompatible polymers with low toxicity. Combinations of these groups of substances originating from a body or combinations of substances originating from a body and biocompatible polymers can also be used. Lipids are the preferred substances since they display structures that make them biodegradable as well as the fact that they are a critical element in all biological membranes.

In one embodiment, the immunogenic compositions as described herein for administration must be sterile for administration to a subject. Sterility is readily accomplished by filtration through sterile filtration membranes (e.g., 0.2 micron membranes), or by gamma irradiation.

In some embodiments, the immunogenic compositions described herein further comprise pharmaceutical excipients including, but not limited to biocompatible oils, physiological saline solutions, preservatives, carbohydrate, protein, amino acids, osmotic pressure controlling agents, carrier gases, pH-controlling agents, organic solvents, hydrophobic agents, enzyme inhibitors, water absorbing polymers, surfactants, absorption promoters and anti-oxidative agents. Representative examples of carbohydrates include soluble sugars such as hydropropyl cellulose, carboxymethyl cellulose, sodium carboxyl cellulose, hyaluronic acid, chitosan, alginate, glucose, xylose, galactose, fructose, maltose, saccharose, dextran, chondroitin sulfate, etc. Representative examples of proteins include albumin, gelatin, etc. Representative examples of amino acids include glycine, alanine, glutamic acid, arginine, lysine, and their salts. Such pharmaceutical excipients are well-known in the art.

In some embodiments, the immunogenic MAPS composition is administered in combination with other therapeutic ingredients including, e.g., γ-interferon, cytokines, chemotherapeutic agents, or anti-inflammatory, or anti-viral agents. In some embodiments, the immunogenic composition as disclosed herein can be administered with one or more co-stimulatory molecules and/or adjuvants as disclosed herein.

In some embodiments, the immunogenic composition is administered in a pure or substantially pure form, but may be administered as a pharmaceutical composition, formulation or preparation. Such formulation comprises MAPS described herein together with one or more pharmaceutically acceptable carriers and optionally other therapeutic ingredients. Other therapeutic ingredients include compounds that enhance antigen presentation, e.g., gamma interferon, cytokines, chemotherapeutic agents, or anti-inflammatory agents. The formulations can conveniently be presented in unit dosage form and may be prepared by methods well known in the pharmaceutical art. For example, Plotkin and Mortimer, in VACCINES (2nd ed., W. B. Saunders Co., 1994) describes vaccination of animals or humans to induce an immune response specific for particular pathogens, as well as methods of preparing antigen, determining a suitable dose of antigen, and assaying for induction of an immune response.

Formulations of the SA-MAPS compositions as disclosed herein suitable for intravenous, intramuscular, intranasal, oral, sublingual, vaginal, rectal, subcutaneous, or intraperitoneal administration conveniently comprise sterile aqueous solutions of the active ingredient with solutions which are preferably isotonic with the blood of the recipient. Such formulations may be conveniently prepared by dissolving solid active ingredient in water containing physiologically compatible substances such as sodium chloride (e.g., 0.1 M-2.0 M), glycine, and the like, and having a buffered pH compatible with physiological conditions to produce an aqueous solution, and rendering the solution sterile. These may be present in unit or multi-dose containers, for example, sealed ampoules or vials.

Liposomal suspensions can also be used as pharmaceutically acceptable carriers. These can be prepared according to methods known to those skilled in the art, for example, as described in U.S. Pat. No. 4,522,811.

Formulations for an intranasal delivery are described in U.S. Pat. Nos. 5,427,782; 5,843,451; 6,398,774.

The formulations of the SA-MAPS compositions as disclosed herein can incorporate a stabilizer. Illustrative stabilizers are polyethylene glycol, proteins, saccharide, amino acids, inorganic acids, and organic acids which may be used either on their own or as admixtures. Two or more stabilizers may be used in aqueous solutions at the appropriate concentration and/or pH. The specific osmotic pressure in such aqueous solution is generally in the range of 0.1-3.0 osmoses, preferably in the range of 0.80-1.2. The pH of the aqueous solution is adjusted to be within the range of pH 5.0-9.0, preferably within the range of pH 6-8.

In certain embodiments, a formulation of the invention which is compatible with parenteral administration comprises one or more non-ionic surfactants, including but not limited to polyoxyethylene sorbitan fatty acid esters, Polysorbate-80 (Tween 80), Polysorbate-60 (Tween 60), Polysorbate-40 (Tween 40) and Polysorbate-20 (Tween 20), polyoxyethylene alkyl ethers, including but not limited to Brij 58, Brij 35, as well as others such as Triton X-100; Triton X-114, NP40, Span 85 and the Pluronic series of non-ionic surfactants (e. g., Plutonic 121), with preferred components Polysorbate-80 at a concentration from about 0.001% to about 2% (with up to about 0.25% being preferred) or Polysorbate-40 at a concentration from about 0.001% to 1% (with up to about 0.5% being preferred).

In certain embodiments, a formulation of the SA-MAPS compositions as disclosed herein comprises one or more additional stabilizing agents suitable for parenteral administration, e.g., a reducing agent comprising at least one thiol (—SH) group (e.g., cysteine, N-acetyl cysteine, reduced glutathione, sodium thioglycolate, thiosulfate, monothioglycerol, or mixtures thereof). Alternatively, or optionally, preservative-containing immunogenic composition formulations of the invention may be further stabilized by removing oxygen from storage containers, protecting the formulation from light (e.g., by using amber glass containers).

Preservative-containing immunogenic composition formulations of the SA-MAPS composition may comprise one or more pharmaceutically acceptable carriers or excipients, which includes any excipient that does not itself induce an immune response. Suitable excipients include but are not limited to macromolecules such as proteins, saccharides, polylactic acids, polyglycolic acids, polymeric amino acids, amino acid copolymers, sucrose (Paoletti et al, 2001, Vaccine, 19:2118), trehalose, lactose and lipid aggregates (such as oil droplets or liposomes). Such carriers are well known to the skilled artisan. Pharmaceutically acceptable excipients are discussed, e.g., in Gennaro, 2000, Remington: The Science and Practice of Pharmacy, 20.sup.th edition, ISBN: 0683306472.

In some embodiments, SA-MAPS compositions as disclosed herein may be lyophilized or in aqueous form, i.e. solutions or suspensions. Liquid formulations may advantageously be administered directly from their packaged form and are thus ideal for injection without the need for reconstitution in aqueous medium as otherwise required for lyophilized compositions of the invention.

When oral preparations are desired, the immunogenic compositions can be combined with typical carriers, such as lactose, sucrose, starch, talc magnesium stearate, crystalline cellulose, methyl cellulose, carboxymethyl cellulose, glycerin, sodium alginate or gum arabic among others.

In some embodiments, the SA-MAPS immunogenic compositions as described herein can be administered intravenously, intranasally, intramuscularly, subcutaneously, intraperitoneally, sublingually, vaginal, rectal or orally. In some embodiments, the route of administration is oral, intranasal, subcutaneous, or intramuscular. In some embodiments, the route of administration is intranasal administration.

Vaccination can be conducted by conventional methods. For example, a SA-MAPS immunogenic composition as disclosed herein can be used in a suitable diluent such as saline or water, or complete or incomplete adjuvants. The immunogenic composition can be administered by any route appropriate for eliciting an immune response. The SA-MAPS immunogenic composition can be administered once or at periodic intervals until an immune response is elicited. Immune responses can be detected by a variety of methods known to those skilled in the art, including but not limited to, antibody production, cytotoxicity assay, proliferation assay and cytokine release assays. For example, samples of blood can be drawn from the immunized mammal, and analyzed for the presence of antibodies against the antigens of the immunogenic composition by ELISA (see de Boer et. al., 115 Arch Virol. 147 (1990) and the titer of these antibodies can be determined by methods known in the art.

The precise dose of the SA-MAPS to be employed in the formulation will also depend on the route of administration and should be decided according to the judgment of the practitioner and each patient's circumstances. For example, a range of 25 µg-900 µg total protein can be administered monthly for three months.

Packaging and Dosage Forms

In some embodiments, the SA-MAPS immunogenic compositions as disclosed herein may be packaged in unit dose or multi-dose form (e.g. 2 doses, 4 doses, or more). For multi-dose forms, vials are typically but not necessarily preferred over pre-filled syringes. Suitable multi-dose formats include but are not limited to: 2 to 10 doses per container at 0.1 to 2 mL per dose. In certain embodiments, the dose is a 0.5 mL dose. See, e.g., International Patent Application WO2007/127668, which is incorporated by reference herein.

In some embodiments, the SA-MAPS immunogenic compositions as disclosed herein can be presented in vials or other suitable storage containers, or may be presented in pre-filled delivery devices, e.g., single or multiple component syringes, which may be supplied with or without needles. A syringe typically but need not necessarily contains a single dose of the preservative-containing immunogenic composition of the invention, although multi-dose, pre-filled syringes are also envisioned. Likewise, a vial may include a single dose but may alternatively include multiple doses.

Effective dosage volumes can be routinely established, but a typical dose of the composition for injection has a volume of 0.5 mL. In certain embodiments, the dose is formulated for administration to a human subject. In certain embodiments, the dose is formulated for administration to an adult, teen, adolescent, toddler or infant (i.e., no more than one year old) human subject and may in preferred embodiments be administered by injection.

Ultimately, the attending physician will decide the amount of the SA-MAPS immunogenic composition or vaccine composition to administer to particular individuals. As with all immunogenic compositions or vaccines, the immunologically effective amounts of the immunogens (e.g., the immunogenic polysaccharide and the SA antigens) must be determined empirically. Factors to be considered include the immunogenicity of the composition as a whole (e.g., it is important to note that the SA antigens induce a greater immune response when present in a SA-MAPS complex as compared to the mixture of the SA antigens alone (not complexed), the presence of an adjuvant or co-stimulant as disclosed herein, routes of administrations and the number of immunizing dosages to be administered. Such factors are known in the vaccine art and it is well within the skill of immunologists to make such determinations without undue experimentation.

Liquid immunogenic compositions of the SA-MAPS immunogenic compositions as disclosed herein are also suitable for reconstituting other immunogenic compositions which are presented in lyophilized form. Where an immunogenic composition is to be used for such extemporaneous reconstitution, in some embodiment, the present invention provides a kit with two or more vials, two or more ready-filled syringes, or one or more of each, with the contents of the syringe being used to reconstitute the contents of the vial prior to injection, or vice versa.

Alternatively, in some embodiments, the SA-MAPS immunogenic compositions as disclosed herein may be lyophilized and reconstituted, e.g., using one of a multitude of methods for freeze drying well known in the art to form dry, regular shaped (e.g., spherical) particles, such as micropellets or microspheres, having particle characteristics such as mean diameter sizes that may be selected and controlled by varying the exact methods used to prepare them. In some embodiments, the SA-MAPS immunogenic compositions as disclosed herein may further comprise an adjuvant which may optionally be prepared with or contained in separate dry, regular shaped (e.g., spherical) particles such as micropellets or microspheres. In some embodiments, the SA-MAPS immunogenic compositions as disclosed herein are present in a kit comprising a first component that includes a stabilized, dry SA-MAPS immunogenic composition as disclosed herein, optionally further comprising one or more preservatives, and a second component comprising a sterile, aqueous solution for reconstitution of the first component. In certain embodiments, the aqueous solution comprises one or more preservatives, and may optionally comprise at least one adjuvant (see, e.g., WO2009/109550 (incorporated herein by reference).

In yet another embodiment, a container of the multi-dose format is selected from one or more of the group consisting of, but not limited to, general laboratory glassware, flasks, beakers, graduated cylinders, fermentors, bioreactors, tubings, pipes, bags, jars, vials, vial closures (e.g., a rubber stopper, a screw on cap), ampoules, syringes, dual or multi-chamber syringes, syringe stoppers, syringe plungers, rubber closures, plastic closures, glass closures, cartridges and disposable pens and the like. The container of the present invention is not limited by material of manufacture, and includes materials such as glass, metals (e.g., steel, stainless steel, aluminum, etc.) and polymers (e.g., thermoplastics, elastomers, thermoplastic-elastomers). In a particular embodiment, the container of the format is a 5 mL Schott Type I glass vial with a butyl stopper. The skilled artisan will appreciate that the format set forth above is by no means an exhaustive list, but merely serve as guidance to the artisan with respect to the variety of formats available for the present invention. Additional formats contemplated for use in the present invention may be found in published catalogues from laboratory equipment vendors and manufacturers such as United States Plastic Corp. (Lima, Ohio), VWR.

Kits

The present invention also provides for kits for producing a SA-MAPS immunogenic composition as disclosed herein which is useful for an investigator to tailor an immunogenic composition with their preferred SA antigens, e.g., for research purposes to assess the effect of a SA antigen, or a combination of SA antigens on immune response. Such kits can be prepared from readily available materials and reagents. For example, such kits can comprise any one or more of the following materials: a container comprising an immunogenic polysaccharide, cross-linked with a plurality of first affinity molecules; and a container comprising a complementary affinity molecule which associates with the first affinity molecule, wherein the complementary affinity molecule associates with a SA antigen.

In another embodiment, the kit can comprise a container comprising an immunogenic polysaccharide, a container comprising a plurality of first affinity molecules, and a container comprising a cross-linking reagent for cross-linking the first affinity molecules to the immunogenic polysaccharide.

In some embodiments, the kit further comprises a means to attach the complementary affinity molecule to the antigen, where the means can be by a cross-linking reagent or by some intermediary fusion protein. In some embodiments, the kit can comprise at least one co-stimulation factor which can be added to the polymer. In some embodiments, the kit comprises a cross-linking reagent, for example, but not limited to, CDAP (1-cyano-4-dimethylaminopyridinium tetrafluoroborate), EDC (1-Ethyl-3-[3-dimethylaminopropyl] carbodiimide hydrochloride), sodium cyanoborohydride; cyanogen bromide; ammonium bicarbonate/iodoacetic acid for linking the co-factor to the polymer.

A variety of kits and components can be prepared for use in the methods described herein, depending upon the intended use of the kit, the particular target antigen and the needs of the user.

In one embodiment, a SA-MAPS immunogenic composition or vaccine composition as described herein, when administered to mice, can provoke an immune response that prevents a disease symptom in at least 20% of animals challenged with 5 $LD_{50}$ of the immunogenic composition comprising antigens to which the disease symptom is prevented. Methods of vaccination and challenging an immunized animal are known to one skilled in the art. For example, a 10 µg aliquot of an immunogenic composition or vaccine composition as disclosed herein can be prepared in 100 µl PBS and/or with addition of alum adjuvants or incomplete Freund's adjuvant and injected subcutaneously per mouse per vaccination. Alternatively, parenteral, intraperitoneal and footpad injections can be used. Volumes of footpad injections are reduced to 50 µl. Mice can be immunized with an immunogenic composition or vaccine composition as disclosed herein on three separate occasions with several days, e.g., 14 days interval in between.

Efficacy of vaccination can be tested by challenge with the pathogen, e.g., *S. aureus*, or by the method disclosed herein. Seven days after the last dose of an immunogenic composition, the immunized mice are challenged intranasally with a pathogenic organism from which the antigen was derived. Ether anaesthetized mice (10 g to 12 g) can be infected intranasally with 50 µl of PBS-diluted allantoic fluid containing 5 $LD_{50}$ of the pathogenic organism. Protection can be measured by monitoring animal survival and body weight, which is assessed throughout an observation period of 21 days. Severely affected mice are euthanized. One $LD_{50}$ of A/Mallard/Pennsylvania/10218/84 is equal to 100-1000 the Tissue Culture Infectious Dose50 (TCID50) assay.

Definitions:

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

As used herein and in the claims, the singular forms include the plural reference and vice versa unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about." It is further to be understood that all base sizes or amino acid sizes, and all molecular weight or molecular mass values, given for nucleic acids or polypeptides are approximate, and are provided for description.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

The term "immunogenic" as used herein means an ability of an antigen (or an epitope of the antigen), such as a bacterial capsular polysaccharide or a conjugate immunogenic composition comprising the bacterial capsular polysaccharide and a polypeptide or peptide antigen, to elicit an immune response in a host such as a mammal, either humorally or cellularly mediated, or both.

The term "immunogenic composition" used herein is defined as a composition capable of eliciting an immune response, such as an antibody or cellular immune response, or both, when administered to a subject. The immunogenic compositions as disclosed herein may or may not be immunoprotective or therapeutic. When the immunogenic compositions as disclosed herein prevent, ameliorate, palliate or eliminate disease from the subject, then the immunogenic composition may optionally be referred to as a vaccine. As used herein, however, the term immunogenic composition is not intended to be limited to vaccines.

Accordingly, an "immunogenic composition" as used herein means any immunogenic polysaccharide conjugated to one or more first affinity molecules, where the first affinity molecule is bound to a complementary affinity molecule that is fused to, or otherwise attached to at least one *S. aureus* peptide or polypeptide antigen, whereby both the immunogenic polysaccharide and the *S. aureus* peptide or polypeptide antigen, each, serve as antigens or antigenic determinant (i.e., epitopes) of the immunogenic composition to elicit an immune response. That is, the immunogenic composition induces a more robust immune response than each of the components alone (i.e., the immunogenic polysaccharide alone, or one or more of the *S. aureus* peptide or polypeptide antigens alone (i.e., a mixture of one or more of the *S. aureus* peptide or polypeptide antigens that are not in a complex or conjugated to the polysaccharide). The immunogenic composition may serve to sensitize the host by the presentation of one or more of the *S. aureus* peptide or polypeptide antigens in association with MHC molecules at a cell surface. In addition, antigen-specific T-cells or antibodies can be generated to allow for the future protection of an immunized host. Immunogenic composition thus can protect the host from one or more symptoms associated with infection by the *S. aureus*, or may protect the host from death due to the infection with *S. aureus*. In some embodiments, the SA-MAPS immunogenic compositions as disclosed herein can also be used to generate polyclonal or monoclonal antibodies, which may be used to confer passive immunity to a subject. In some embodiments, the SA-MAPS immunogenic compositions as disclosed herein can also be used to generate antibodies that are functional as measured by the killing of bacteria in either an animal efficacy model or via an opsonophagocytic killing assay.

The term "antigen" generally refers to a biological molecule, usually a protein or polypeptide, peptide, polysaccharide or conjugate in an immunogenic composition, or immunogenic substance that can stimulate the production of antibodies or T-cell responses, or both, in an animal, including compositions that are injected or absorbed into an animal. The immune response may be generated to the whole molecule (i.e., such as the SA-MAPS immunogenic composition, or to the whole immunogenic polysaccharide, or the whole peptide or polypeptide antigen), or to a various portions of the molecule (e.g., an epitope or hapten within a part of the SA-MAPS immunogenic composition, or to the whole immunogenic polysaccharide, or the whole peptide or polypeptide antigen). The term may be used to refer to an individual molecule or to a homogeneous or heterogeneous population of antigenic molecules. An antigen is recognized by antibodies, T-cell receptors or other elements of specific humoral and/or cellular immunity. The term "antigen" also includes all related antigenic epitopes. Epitopes of a given antigen can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by, e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715; each of which is incorporated herein by reference as if set forth in its entirety. Similarly, conformational epitopes may be identified by determining spatial conformation of amino acids such as by, e.g., x-ray crystallography and 2-dimensional nuclear magnetic resonance. See, e.g., Epitope Mapping Protocols, supra. Furthermore, for purposes of the present invention, "antigen" also can be used to refer to a protein that includes modifications, such as deletions, additions and substitutions (generally conservative in nature, but they may be non-conservative), to the native sequence, so long as the protein maintains the ability to elicit an immunological response. These modifications may be deliberate, as through site-directed mutagenesis, or through particular synthetic procedures, or through a genetic engineering approach, or may be accidental, such as through mutations of hosts, which produce the antigens. Furthermore, the antigen can be derived, obtained, or isolated from a microbe, e.g., a bacterium, or can be a whole organism. Similarly, an oligonucleotide polynucleotide, which expresses an antigen, such as in nucleic acid immunization applications, is also included in the definition. Synthetic antigens are also included, e.g., polyepitopes, flanking epitopes, and other recombinant or synthetically derived antigens (Bergmann et al. (1993) Eur. J. Immunol. 23:2777 2781; Bergmann et al. (1996) J. Immunol. 157: 3242-3249; Suhrbier (1997) Immunol. Cell Biol. 75:402 408; Gardner et al. (1998) 12th World AIDS Conference, Geneva, Switzerland, Jun. 28 to Jul. 3, 1998). In some embodiments, an antigen is a peptide or a polypeptide, e.g., a *S. aureus* peptide or a polypeptide, or immunogenic polysaccharide and in other embodiments, it can be any chemical or moiety, e.g., a carbohydrate, that elicits an immune response directed against the substance.

An "immune response" to an antigen or immunogenic composition is the development in a subject of a humoral and/or a cell-mediated immune response to molecules present in the antigen or vaccine composition of interest. For purposes of the present invention, a "humoral immune response" is an antibody-mediated immune response and involves the induction and generation of antibodies that recognize and bind with some affinity for the antigen in the immunogenic composition of the invention, while a "cell-mediated immune response" is one mediated by T-cells and/or other white blood cells. A "cell-mediated immune response" is elicited by the presentation of antigenic epitopes in association with Class I or Class II molecules of the major histocompatibility complex (MHC), CD1 or other non-classical MHC-like molecules. This activates antigen-specific CD4+ T helper cells or CD8+cytotoxic lymphocyte cells ("CTLs"). CTLs have specificity for peptide antigens that are presented in association with proteins encoded by classical or non-classical MHCs and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide or other antigens in association with classical or non-classical MHC molecules on their surface. A "cell-mediated immune response" also refers to the production of cytokines, chemokines and other such molecules produced by activated T-cells and/or other white blood cells, including those derived from CD4+ and CD8+ T-cells. The ability of a particular antigen or composition to stimulate a cell-mediated immunological response may be determined by a number of assays, such as by lymphoproliferation (lymphocyte activation) assays, CTL cytotoxic cell assays, by assaying for T-lymphocytes specific for the antigen in a sensitized subject, or by measurement of cytokine production by T cells in response to re-stimulation with antigen. Such assays are well known in the art. See, e.g., Erickson et al. (1993) J. Immunol. 151:4189-4199; and Doe et al. (1994) Eur. J. Immunol. 24:2369-2376.

The term "treatment" (including variations thereof, e.g., "treat" or "treated") as used herein means any one or more of the following: (i) the prevention of infection or re-infection, as in a traditional vaccine, (ii) the reduction in the severity of, or, in the elimination of symptoms, and (iii) the substantial or complete elimination of the pathogen or disorder in question. Hence, treatment may be effected prophylactically (prior to infection) or therapeutically (following infection). In the present invention, prophylactic treatment is the preferred mode. According to a particular embodiment of the present invention, compositions and methods are provided that treat, including prophylactically and/or therapeutically immunize, a host animal against a microbial infection (e.g., a bacterium such as *Staphylococcus*). The methods of the present invention are useful for conferring prophylactic and/or therapeutic immunity to a subject. The methods of the present invention can also be practiced on subjects for biomedical research applications.

The term "mammal" as used herein means a human or non-human animal. More particularly, mammal refers to any animal classified as a mammal, including humans, domestic and farm animals, and zoo, sports and pet companion animals such as a household pet and other domesticated animal including, but not limited to, cattle, sheep, ferrets, swine, horses, rabbits, goats, dogs, cats, and the like. In some embodiments, a companion animal is a dog or cat. Preferably, the mammal is human.

The term an "immunogenic amount," and "immunologically effective amount," both of which are used interchangeably herein, refers to the amount of the antigen or immunogenic composition sufficient to elicit an immune response, either a cellular (T-cell) or humoral (B-cell or antibody) response, or both, as measured by standard assays known to one skilled in the art. The "immunogenic amount" of a particular immunogenic composition is generally dosed based on total immunogenic polysaccharide and attached or associated SA peptide or polypeptide antigens. For example, an SA-MAPS immunogenic composition as disclosed herein will have at least about 80% or more of, e.g., a serotype 5 or 8 capsular polysaccharide with attached SA-antigens via the affinity binding pair. Accordingly, in some embodiments, a SA-MAPS immunogenic composition as disclosed herein can have 20%, or less, free immunogenic (e.g. CP5 or CP8 or a CP5/CP8 conjugate) polysaccharide, and as such, a 100 mcg dose can have about 80 mcg of immunogenic polysaccharide-antigen SA-MAPS complex and about 20 mcg, or less, of a non-conjugated immunogenic polysaccharide. In some embodiments, the dose of the SA-antigens associated with the immunogenic polysaccharide is important and considered when calculating the dose of a SA-MAPS composition to administer to a subject. The amount of SA-MAPS complex can vary depending upon the number and types of the attached SA antigens, the immunogenic polysaccharide (e.g., the staphylococcal serotype) as well as any associated co-stimulants as disclosed herein, as well as route of administration, subject and disease to be treated. Generally, each SA-MAPS dose will comprise 0.1 to 100 mcg of an immunogenic polysaccharide and attached SA antigens, particularly 0.1 to 10 mcg, and more particularly 1 to 10 mcg.

The amount of a SA-MAPS immunogenic composition as disclosed herein can vary depending upon the staphylococcal serotype. Generally, each dose will comprise 0.1 to 100 mcg of immunogenic polysaccharide, particularly 0.1 to 10 mcg, and more particularly 1 to 10 mcg. The "immunogenic amount" of the different polysaccharide components in the immunogenic composition, may diverge and each may comprise 1 mcg, 2 mcg, 3 mcg, 4 mcg, 6 mcg, 6 mcg, 7 mcg, 8 mcg, 9 mcg, 10 mcg, 15 mcg, 20 mcg, 30 mcg, 40 mcg, 50 mcg, 60 mcg, 70 mcg, 80 mcg, 90 mcg, or about 100 mcg of any particular polysaccharide antigen.

*S. aureus* "invasive disease" is the isolation of bacteria from a normally sterile site, where there is associated clinical signs/symptoms of disease. Normally sterile body sites include blood, CSF, pleural fluid, pericardial fluid, peritoneal fluid, joint/synovial fluid, bone, internal body site (lymph node, brain, heart, liver, spleen, vitreous fluid, kidney, pancreas, ovary) or other normally sterile sites. Clinical conditions characterizing invasive diseases include bacteremia, pneumonia, cellulitis, osteomyelitis, endocarditis, septic shock and more.

The term "associates" as used herein refers to the linkage of two or more molecules by non-covalent or covalent bonds. In some embodiments, where linking of two or more molecules occurs by a covalent bond, the two or more molecules can be fused together, or cross-linked together. In some embodiments, where linking of two or more molecules occurs by a non-covalent bond, the two or more molecules can form a complex.

The term "complex" as used herein refers to a collection of two or more molecules, connected spatially by means other than a covalent interaction; for example, they can be connected by electrostatic interactions, hydrogen bound or by hydrophobic interactions (i.e., van der Waals forces).

The term "cross-linked" as used herein refers to a covalent bond formed between a polymer chain and a second molecule. The term "cross-linking reagent" refers to an entity or agent which is an intermediate molecule to catalyze the covalent linkage of a polymer with an entity, e.g., first affinity molecule or co-stimulatory factor.

As used herein, the term "fused" means that at least one protein or peptide is physically associated with a second protein or peptide. In some embodiments, fusion is typically a covalent linkage, however, other types of linkages are encompassed in the term "fused" include, for example, linkage via an electrostatic interaction, or a hydrophobic interaction and the like. Covalent linkage can encompass linkage as a fusion protein or chemically coupled linkage, for example via a disulfide bound formed between two cysteine residues.

As used herein, the term "fusion polypeptide" or "fusion protein" means a protein created by joining two or more polypeptide sequences together. The fusion polypeptides encompassed in this invention include translation products of a chimeric gene construct that joins the DNA sequences encoding one or more antigens, or fragments or mutants thereof, with the DNA sequence encoding a second polypeptide to form a single open-reading frame. In other words, a "fusion polypeptide" or "fusion protein" is a recombinant protein of two or more proteins which are joined by a peptide bond or via several peptides. In some embodiments, the second protein to which the antigens are fused to is a complementary affinity molecule which is capable of interacting with a first affinity molecule of the complementary affinity pair.

The terms "polypeptide" and "protein" may be used interchangeably to refer to a polymer of amino acid residues linked by peptide bonds, and for the purposes of the claimed invention, have a typical minimum length of at least 25 amino acids. The term "polypeptide" and "protein" can encompass a multimeric protein, e.g., a protein containing more than one domain or subunit. The term "peptide" as used herein refers to a sequence of peptide bond-linked amino acids containing less than 25 amino acids, e.g., between about 4 amino acids and 25 amino acids in length. Proteins and peptides can be composed of linearly arranged amino acids linked by peptide bonds, whether produced biologically, recombinantly, or synthetically and whether composed of naturally occurring or non-naturally occurring amino acids, are included within this definition. Both full-length proteins and fragments thereof greater than 25 amino acids are encompassed by the definition of protein. The terms also include polypeptides that have co-translational (e.g., signal peptide cleavage) and post-translational modifications of the polypeptide, such as, for example, disulfide-bond formation, glycosylation, acetylation, phosphorylation, lipidation, proteolytic cleavage (e.g., cleavage by metalloproteases), and the like. Furthermore, as used herein, a "polypeptide" refers to a protein that includes modifications, such as deletions, additions, and substitutions (generally conservative in nature as would be known to a person in the art) to the native sequence, as long as the protein maintains the desired activity. These modifications can be deliberate, as through site-directed mutagenesis, or can be accidental, such as through mutations of hosts that produce the proteins, or errors due to PCR amplification or other recombinant DNA methods.

By "signal sequence" is meant a nucleic acid sequence which, when operably linked to a nucleic acid molecule, facilitates secretion of the product (e.g., protein or peptide) encoded by the nucleic acid molecule. In some embodiments, the signal sequence is preferably located 5' to the nucleic acid molecule.

As used herein, the term "N-glycosylated" or "N-glycosylation" refers to the covalent attachment of a sugar moiety to asparagine residues in a polypeptide. Sugar moieties can include but are not limited to glucose, mannose, and N-acetylglucosamine. Modifications of the glycans are also included, e.g., siaylation.

An "antigen presenting cell" or "APC" is a cell that expresses the Major Histocompatibility complex (MHC) molecules and can display foreign antigen complexed with MHC on its surface. Examples of antigen presenting cells are dendritic cells, macrophages, B-cells, fibroblasts (skin), thymic epithelial cells, thyroid epithelial cells, glial cells (brain), pancreatic beta cells, and vascular endothelial cells.

The term "functional portion" or "functional fragment" as used in the context of a "functional portion of an antigen" refers to a portion of the antigen or antigen polypeptide that mediates the same effect as the full antigen moiety, e.g., elicits an immune response in a subject, or mediates an association with other molecule, e.g., comprises at least on epitope.

A "portion" of a target antigen as that term is used herein will be at least 3 amino acids in length, and can be, for example, at least 6, at least 8, at least 10, at least 14, at least 16, at least 17, at least 18, at least 19, at least 20 or at least 25 amino acids or greater, inclusive.

The terms "Cytotoxic T Lymphocyte" or "CTL" refers to lymphocytes which induce death via apoptosis or other mechanisms in targeted cells. CTLs form antigen-specific conjugates with target cells via interaction of TCRs with processed antigen (Ag) on target cell surfaces, resulting in apoptosis of the targeted cell. Apoptotic bodies are eliminated by macrophages. The term "CTL response" is used to refer to the primary immune response mediated by CTL cells.

The term "cell mediated immunity" or "CMI" as used herein refers to an immune response that does not involve antibodies or complement but rather involves the activation of, for example, macrophages, natural killer cells (NK), antigen-specific cytotoxic T-lymphocytes (T-cells), T-helper cells, neutrophils, and the release of various cytokines in response to a target antigen. Stated another way, CMI refers to immune cells (such as T cells and other lymphocytes) which bind to the surface of other cells that display a target antigen (such as antigen presenting cells (APC)) and trigger a response. The response may involve either other lymphocytes and/or any of the other white blood cells (leukocytes) and the release of cytokines. Cellular immunity protects the body by: (i) activating antigen-specific cytotoxic T-lymphocytes (CTLs) that are able to destroy body cells displaying epitopes of foreign antigen on their surface, such as virus-infected cells and cells with intracellular bacteria; (2) activating macrophages and NK cells, enabling them to destroy intracellular pathogens; and (3) stimulating cells to secrete a variety of cytokines or chemokines that influence the function of other cells such as T cells, macrophages or neutrophils involved in adaptive immune responses and innate immune responses.

The term "immune cell" as used herein refers to any cell which can release a cytokine, chemokine or antibody in response to a direct or indirect antigenic stimulation. Included in the term "immune cells" herein are lymphocytes, including natural killer (NK) cells, T-cells (CD4+ and/or CD8+ cells), B-cells, macrophages; leukocytes; dendritic cells; mast cells; monocytes; and any other cell which is capable of producing a cytokine or chemokine molecule in response to direct or indirect antigen stimulation. Typically, an immune cell is a lymphocyte, for example a T-cell lymphocyte.

A "protective" immune response refers to the ability of an immunogenic composition as disclosed herein to elicit an immune response, either humoral or cell mediated, or both, which serves to protect a subject from an infection. The protection provided need not be absolute, i.e., the infection need not be totally prevented or eradicated, if there is a statistically significant improvement compared with a control population of subjects, e.g. infected animals not administered the vaccine or immunogenic composition. Protection may be limited to mitigating the severity or rapidity of onset of symptoms of the infection. In general, a "protective immune response" would include the induction of an increase in antibody levels specific for a particular antigen in at least 50% of subjects, including some level of measurable functional antibody responses to each antigen. In particular situations, a "protective immune response" could include the induction of a two-fold increase in antibody levels or a fourfold increase in antibody levels specific for a particular antigen in at least 50% of subjects, including some level of measurable functional antibody responses to each antigen. In certain embodiments, opsonising antibodies correlate with a protective immune response. Thus, protective immune response may be assayed by measuring the percent decrease in the bacterial count in an opsonophagocytosis assay, for instance those described below. Preferably, there is a decrease in bacterial count of at least 10%, 25%, 50%, 65%, 75%, 80%, 85%, 90%, 95% or more.

The term "cytokine" as used herein refers to a molecule released from an immune cell in response to stimulation with an antigen. Examples of such cytokines include, but are not limited to: GM-CSF; IL-1α; IL-1β; IL-2; IL-3; IL-4; IL-5; IL-6; IL-7; IL-8; IL-10; IL-12; IL-17A, IL-17F, or other members of the IL-17 family, IL-22, IL-23, IFN-α; IFN-β; IFN-γ; MIP-1α; MIP-1β; TGF-β; TNFα, or TNFβ. The term "cytokine" does not include antibodies.

The term "subject" as used herein refers to any animal in which it is useful to elicit an immune response. The subject can be a wild, domestic, commercial or companion animal such as a bird or mammal. The subject can be a human. Although in one embodiment of the invention it is contemplated that the immunogenic compositions as disclosed herein can also be suitable for the therapeutic or preventative treatment in humans, it is also applicable to warm-blooded vertebrates, e.g., mammals, such as non-human primates, (particularly higher primates), sheep, dog, rodent (e.g., mouse or rat), guinea pig, goat, pig, cat, rabbits, cows, and non-mammals such as chickens, ducks, or turkeys. In another embodiment, the subject is a wild animal, for example a bird such as for the diagnosis of avian flu. In some embodiments, the subject is an experimental animal or animal substitute as a disease model. The subject may be a subject in need of veterinary treatment, where eliciting an immune response to an antigen is useful to prevent a disease and/or to control the spread of a disease, for example SIV, STL1, SFV, or in the case of live-stock, hoof and mouth disease, or in the case of birds Marek's disease or avian influenza, and other such diseases.

As used herein, the term "pathogen" refers to an organism or molecule that causes a disease or disorder in a subject. For example, pathogens include but are not limited to viruses, fungi, bacteria, parasites, and other infectious organisms or molecules therefrom, as well as taxonomically related macroscopic organisms within the categories algae, fungi, yeast, protozoa, or the like.

The term "wild type" refers to the naturally-occurring, normal polynucleotide sequence encoding a protein, or a portion thereof, or protein sequence, or portion thereof, respectively, as it normally exists in vivo.

The term "mutant" refers to an organism or cell with any change in its genetic material, in particular a change (i.e., deletion, substitution, addition, or alteration) relative to a wild-type polynucleotide sequence or any change relative to a wild-type protein sequence. The term "variant" may be used interchangeably with "mutant". Although it is often assumed that a change in the genetic material results in a change of the function of the protein, the terms "mutant" and "variant" refer to a change in the sequence of a wild-type protein regardless of whether that change alters the function of the protein (e.g., increases, decreases, imparts a new function), or whether that change has no effect on the function of the protein (e.g., the mutation or variation is silent).

The term "pharmaceutically acceptable" refers to compounds and compositions which may be administered to mammals without undue toxicity. The term "pharmaceutically acceptable carriers" excludes tissue culture medium. Exemplary pharmaceutically acceptable salts include but are not limited to mineral acid salts such as hydrochlorides, hydrobromides, phosphates, sulfates, and the like, and the salts of organic acids such as acetates, propionates, malonates, benzoates, and the like. Pharmaceutically acceptable carriers are well-known in the art.

It will be appreciated that proteins or polypeptides often contain amino acids other than the 20 amino acids commonly referred to as the 20 naturally occurring amino acids, and that many amino acids, including the terminal amino acids, can be modified in a given polypeptide, either by natural processes such as glycosylation and other post-translational modifications, or by chemical modification techniques which are well known in the art. Known modifications which can be present in polypeptides of the present invention include, but are not limited to, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formulation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

As used herein, the terms "homologous" or "homologues" are used interchangeably, and when used to describe a polynucleotide or polypeptide, indicate that two polynucleotides or polypeptides, or designated sequences thereof, when optimally aligned and compared, for example using BLAST, version 2.2.14 with default parameters for an alignment are identical, with appropriate nucleotide insertions or deletions or amino-acid insertions or deletions, typically in at least 70% of the nucleotides of the nucleotides for high homology. For a polypeptide, there should be at least 30% of amino acid identity in the polypeptide, or at least 50% for higher homology. The term "homolog" or "homologous" as used herein also refers to homology with respect to structure. Determination of homologs of genes or polypeptides can be easily ascertained by the skilled artisan. When in the context with a defined percentage, the defined percentage homology means at least that percentage of amino acid similarity. For example, 85% homology refers to at least 85% of amino acid similarity.

As used herein, the term "heterologous" reference to nucleic acid sequences, proteins or polypeptides mean that these molecules are not naturally occurring in that cell. For example, the nucleic acid sequence coding for a fusion antigen polypeptide described herein that is inserted into a cell, e.g. in the context of a protein expression vector, is a heterologous nucleic acid sequence.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Where necessary or desired, optimal alignment of sequences for comparison can be conducted by any variety of approaches, as these are well-known in the art.

The term "variant" as used herein may refer to a polypeptide or nucleic acid that differs from the naturally occurring polypeptide or nucleic acid by one or more amino acid or nucleic acid deletions, additions, substitutions or side-chain modifications, yet retains one or more specific functions or biological activities of the naturally occurring molecule. Amino acid substitutions include alterations in which an amino acid is replaced with a different naturally-occurring or a non-conventional amino acid residue. Such substitutions may be classified as "conservative," in which case an amino acid residue contained in a polypeptide is replaced with another naturally occurring amino acid of similar character either in relation to polarity, side chain functionality or size. Substitutions encompassed by variants as described herein may also be "non conservative," in which an amino acid residue which is present in a peptide is substituted with an amino acid having different properties (e.g., substituting a charged or hydrophobic amino acid with alanine), or alternatively, in which a naturally-occurring amino acid is substituted with a non-conventional amino acid. Also encompassed within the term "variant," when used with reference to a polynucleotide or polypeptide, are variations in primary, secondary, or tertiary structure, as compared to a reference polynucleotide or polypeptide, respectively (e.g., as compared to a wild-type polynucleotide or polypeptide).

The term "substantially similar," when used in reference to a variant of an antigen or a functional derivative of an antigen as compared to the original antigen means that a particular subject sequence varies from the sequence of the antigen polypeptide by one or more substitutions, deletions, or additions, but retains at least 50%, or higher, e.g., at least 60%, 70%, 80%, 90% or more, inclusive, of the function of the antigen to elicit an immune response in a subject. In determining polynucleotide sequences, all subject polynucleotide sequences capable of encoding substantially similar amino acid sequences are considered to be substantially similar to a reference polynucleotide sequence, regardless of differences in codon sequence. A nucleotide sequence is "substantially similar" to a given antigen nucleic acid sequence if: (a) the nucleotide sequence hybridizes to the coding regions of the native antigen sequence, or (b) the nucleotide sequence is capable of hybridization to nucleotide sequence of the native antigen under moderately stringent conditions and has biological activity similar to the native antigen protein; or (c) the nucleotide sequences are degenerate as a result of the genetic code relative to the nucleotide sequences defined in (a) or (b). Substantially similar proteins will typically be greater than about 80% similar to the corresponding sequence of the native protein.

Variants can include conservative or non-conservative amino acid changes, as described below. Polynucleotide changes can result in amino acid substitutions, additions, deletions, fusions and truncations in the polypeptide encoded by the reference sequence. Variants can also include insertions, deletions or substitutions of amino acids, including insertions and substitutions of amino acids and other molecules) that do not normally occur in the peptide sequence that is the basis of the variant, for example but not limited to insertion of ornithine which do not normally occur in human proteins. "Conservative amino acid substitutions" result from replacing one amino acid with another that has similar structural and/or chemical properties. Conservative substitution tables providing functionally similar amino acids are well known in the art. For example, the following six groups each contain amino acids that are conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W). See, e.g., Creighton, PROTEINS (W. H. Freeman & Co., 1984).

The choice of conservative amino acids may be selected based on the location of the amino acid to be substituted in the peptide, for example if the amino acid is on the exterior of the peptide and exposed to solvents, or on the interior and not exposed to solvents. Selection of such conservative amino acid substitutions is within the skill of one of ordinary skill in the art. Accordingly, one can select conservative amino acid substitutions suitable for amino acids on the exterior of a protein or peptide (i.e. amino acids exposed to a solvent). These substitutions include, but are not limited to the following: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

Alternatively, one can also select conservative amino acid substitutions suitable for amino acids on the interior of a protein or peptide (i.e., the amino acids are not exposed to a solvent). For example, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, LF polypeptides including non-conservative amino acid substitutions are also encompassed within the term "variants." As used herein, the term "non-conservative" substitution refers to substituting an amino acid residue for a different amino acid residue that has different chemical properties. Non-limiting examples of non-conservative substitutions include aspartic acid (D) being replaced with glycine (G); asparagine (N) being replaced with lysine (K); and alanine (A) being replaced with arginine (R).

The term "derivative" as used herein refers to proteins or peptides which have been chemically modified, for example by ubiquitination, labeling, pegylation (derivatization with polyethylene glycol) or addition of other molecules. A molecule is also a "derivative" of another molecule when it contains additional chemical moieties not normally a part of the molecule. Such moieties can improve the molecule's solubility, absorption, biological half-life, etc. The moieties can alternatively decrease the toxicity of the molecule, or eliminate or attenuate an undesirable side effect of the molecule, etc. Moieties capable of mediating such effects are disclosed in REMINGTON'S PHARMACEUTICAL SCIENCES (21st ed., Tory, ed., Lippincott Williams & Wilkins, Baltimore, Md., 2006).

The term "functional" when used in conjunction with "derivative" or "variant" refers to a protein molecule which possesses a biological activity that is substantially similar to a biological activity of the entity or molecule of which it is a derivative or variant. "Substantially similar" in this context means that the biological activity, e.g., antigenicity of a polypeptide, is at least 50% as active as a reference, e.g., a corresponding wild-type polypeptide, e.g., at least 60% as active, 70% as active, 80% as active, 90% as active, 95% as active, 100% as active or even higher (i.e., the variant or derivative has greater activity than the wild-type), e.g., 110% as active, 120% as active, or more, inclusive.

The term "recombinant" when used to describe a nucleic acid molecule, means a polynucleotide of genomic, cDNA, viral, semisynthetic, and/or synthetic origin, which, by virtue of its origin or manipulation, is not associated with all or a portion of the polynucleotide sequences with which it is associated in nature. The term recombinant as used with respect to a peptide, polypeptide, protein, or recombinant fusion protein, means a polypeptide produced by expression from a recombinant polynucleotide. The term recombinant as used with respect to a host cell means a host cell into which a recombinant polynucleotide has been introduced. Recombinant is also used herein to refer to, with reference to material (e.g., a cell, a nucleic acid, a protein, or a vector) that the material has been modified by the introduction of a heterologous material (e.g., a cell, a nucleic acid, a protein, or a vector).

The term "vectors" refers to a nucleic acid molecule capable of transporting or mediating expression of a heterologous nucleic acid to which it has been linked to a host cell; a plasmid is a species of the genus encompassed by the term "vector." The term "vector" typically refers to a nucleic acid sequence containing an origin of replication and other entities necessary for replication and/or maintenance in a host cell. Vectors capable of directing the expression of genes and/or nucleic acid sequence to which they are operatively linked are referred to herein as "expression vectors". In general, expression vectors of utility are often in the form of "plasmids" which refer to circular double stranded DNA molecules which, in their vector form are not bound to the chromosome, and typically comprise entities for stable or transient expression or the encoded DNA. Other expression vectors that can be used in the methods as disclosed herein include, but are not limited to plasmids, episomes, bacterial artificial chromosomes, yeast artificial chromosomes, bacteriophages or viral vectors, and such vectors can integrate into the host's genome or replicate autonomously in the particular cell. A vector can be a DNA or RNA vector. Other forms of expression vectors known by those skilled in the art which serve the equivalent functions can also be used, for example self replicating extrachromosomal vectors or vectors which integrates into a host genome. Preferred vectors are those capable of autonomous replication and/or expression of nucleic acids to which they are linked.

The term "reduced" or "reduce" or "decrease" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least t 50%, or least 60%, or least 70%, or least 80%, at least 90% or more, up to and including a 100% decrease (i.e., absent level as compared to a reference sample), or any decrease between 10-100% as compared to a reference level, as that term is defined herein.

The term "low" as used herein generally means lower by a statically significant amount; for the avoidance of doubt, "low" means a statistically significant value at least 10% lower than a reference level, for example a value at least 20% lower than a reference level, at least 30% lower than a reference level, at least 40% lower than a reference level, at least 50% lower than a reference level, at least 60% lower than a reference level, at least 70% lower than a reference level, at least 80% lower than a reference level, at least 90% lower than a reference level, up to and including 100% lower than a reference level (i.e., absent level as compared to a reference sample).

The terms "increased" or "increase" as used herein generally mean an increase by a statically significant amount; such as a statistically significant increase of at least 10% as compared to a reference level, including an increase of at least 20%, at least 30%, at least 40%, at least 50%, at least 60%, at least 70%, at least 80%, at least 90%, at least 100% or more, inclusive, including, for example at least 2-fold, at least 3-fold, at least 4-fold, at least 5-fold, at least 10-fold increase or greater as compared to a reference level, as that term is defined herein.

The term "high" as used herein generally means a higher by a statically significant amount relative to a reference; such as a statistically significant value at least 10% higher than a reference level, for example at least 20% higher, at least 30% higher, at least 40% higher, at least 50% higher, at least 60% higher, at least 70% higher, at least 80% higher, at least 90% higher, at least 100% higher, inclusive, such as at least 2-fold higher, at least 3-fold higher, at least 4-fold higher, at least 5-fold higher, at least 10-fold higher or more, as compared to a reference level.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment of the invention.

Although the foregoing invention has been described in some detail by way of illustration and example for purposes of clarity of understanding it will be readily apparent to one of ordinary skill in the art in light of the teachings of this invention that certain changes and modifications may be made thereto without departing from the spirit or scope of the appended claims. The following is meant to be illustrative of the present invention; however, the practice of the invention is not limited or restricted in any way by the examples.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Some embodiments of the technology described herein can be defined according to any of the following numbered paragraphs:

1. An immunogenic composition comprising an immunogenic polysaccharide, at least one *S. aureus* peptide or polypeptide antigen, and at least one complementary affinity-molecule pair comprising: a first affinity molecule associated with the immunogenic polysaccharide, and a complementary affinity molecule associated with the at least *S. aureus* peptide or polypeptide antigen, wherein the first affinity molecule associates with the complementary affinity molecule to link the *S. aureus* peptide or polypeptide antigen and the immunogenic polysaccharide.
2. The immunogenic composition of paragraph 1, wherein at least one *S. aureus* peptide or polypeptide antigen is selected from any of the group comprising: hemolysin (Hl), Clumping factor A (ClfA), Clumping factor B (ClfB), serine-aspirate repeat protein D (SdrD), serine-aspirate repeat protein E (SdrE), Iron regulator surface protein A (IsdA), Iron regulator surface protein B (IsdB), Leukotoxin D (LukD), or Leukotoxin E (LukE).
3. The immunogenic composition of paragraph 1, wherein the immunogenic composition comprises a hemolysin (Hl) *S. aureus* antigen and at least one additional *S. aureus* antigen selected from any of the group comprising: Clumping factor A (ClfA), Clumping factor B (ClfB), serine-aspirate repeat protein D (SdrD), serine-aspirate repeat protein E (SdrE), Iron regulator surface protein A (IsdA), Iron regulator surface protein B (IsdB), Leukotoxin D (LukD), or Leukotoxin E (LukE).
4. The immunogenic composition of paragraph 1, wherein the immunogenic composition comprises a hemolysin (Hl) *S. aureus* antigen and at least two or more additional *S. aureus* antigen selected from any of the group comprising: Clumping factor A (ClfA), Clumping factor B (ClfB), serine-aspirate repeat protein D (SdrD), serine-aspirate repeat protein E (SdrE), Iron regulator surface protein A (IsdA), Iron regulator surface protein B (IsdB), Leukotoxin D (LukD), or Leukotoxin E (LukE).
5. The immunogenic composition of paragraph 4, wherein the immunogenic composition comprises a hemolysin a (Hla) antigen, and a Clumping factor A (ClfA) antigen, and a Clumping factor B (ClfB) antigen, and a serine-aspirate repeat protein D (SdrD) antigen, and a Iron regulator surface protein A (IsdA) antigen, and an Iron regulator surface protein B (IsdB) antigen.
6. The immunogenic composition of paragraph 5, wherein the immunogenic composition comprises *S. aureus* antigens Hla209(27-319), ClfA (221-559), ClfB (203-542), SdrD (246-682), IsdA (47-324) and IsdB (48-447).
7. The immunogenic composition of any of paragraphs 1 to 6, wherein Hl antigen is a α-hemolysin (Hla), a β-hemolysin (Hlb) or a γ-hemolysin (Hl-gamma) from *S. aureus*.
8. The immunogenic composition of any of paragraphs 1 to 6, wherein Hl is wildtype Hla (WT Hla) or a Hla with a reduced hemolytic activity or is a non-hemolytic Hla protein.
9. The immunogenic composition of any of paragraphs 1 to 8, wherein the Hla antigen with a reduced hemolytic activity comprises amino acids of SEQ ID NO: 14, SEQ ID NO: 15, SEQ ID NO: 17 or SEQ ID NO: 18 or a polypeptide with at least 85% sequence identity thereto.
10. The immunogenic composition of any of paragraphs 1 to 8, wherein the Hla antigen with a reduced hemolytic activity is amino acids of SEQ ID NO: 16 or a polypeptide with at least 85% sequence identity thereto.
11. The immunogenic composition of any of paragraphs 1 to 5, wherein the ClfA antigen comprises at least SEQ ID NO: 3 or a polypeptide with at least 85% sequence identity to SEQ ID NO: 3.
12. The immunogenic composition of any of paragraphs 1 to 5, wherein the ClfA antigen comprises a fragment of at least 30 amino acids of SEQ ID NO: 2 or a polypeptide of at least 30 amino acids that has at least 85% sequence identity to a portion of SEQ ID NO: 2.
13. The immunogenic composition of any of paragraphs 1 to 5, wherein the ClfB antigen comprises at least SEQ ID NO: 5 or a polypeptide with at least 85% sequence identity to SEQ ID NO: 5.
14. The immunogenic composition of any of paragraphs 1 to 5, wherein the ClfB antigen comprises a fragment of at least 30 amino acids of SEQ ID NO: 4 or a polypeptide of at least 30 amino acids that has at least 85% sequence identity to a portion of SEQ ID NO: 4.
15. The immunogenic composition of any of paragraphs 1 to 5, wherein the SdrD antigen comprises at least SEQ ID NO: 7 or a polypeptide with at least 85% sequence identity to SEQ ID NO: 7.
16. The immunogenic composition of any of paragraphs 1 to 5, wherein the SdrD antigen comprises a fragment of at least 30 amino acids of SEQ ID NO:6 or a polypeptide of at least 30 amino acids that has at least 85% sequence identity to a portion of SEQ ID NO: 6.
17. The immunogenic composition of any of paragraphs 1 to 5, wherein the SdrE antigen comprises a fragment of at least 30 amino acids of SEQ ID NO:8 or a polypeptide of at least 30 amino acids that has at least 85% sequence identity to a portion of SEQ ID NO: 8.
18. The immunogenic composition of any of paragraphs 1 to 5, wherein the IsdA antigen comprises at least SEQ ID NO: 11 or a polypeptide with at least 85% sequence identity to SEQ ID NO: 11.
19. The immunogenic composition of any of paragraphs 1 to 5, wherein the IsdA antigen comprises a fragment of at least 30 amino acids of SEQ ID NO:10 or a polypeptide of at least 30 amino acids that has at least 85% sequence identity to a portion of SEQ ID NO: 10.
20. The immunogenic composition of any of paragraphs 1 to 5, wherein the IsdB antigen comprises at least SEQ ID NO: 13 or a polypeptide with at least 85% sequence identity to SEQ ID NO: 13.
21. The immunogenic composition of any of paragraphs 1 to 5, wherein the IsdB antigen comprises a fragment of at least 30 amino acids of SEQ ID NO:12 or a polypeptide of at least 30 amino acids that has at least 85% sequence identity to a portion of SEQ ID NO: 12.
22. The immunogenic composition of paragraph 1, wherein the first affinity molecule is biotin or a derivative or mimic molecule thereof.
23. The immunogenic composition of paragraph 1, wherein the first affinity molecule is a biotin derivative, lipoic acid, HABA (hydroxyazobenzene-benzoic acid) or/and dimethyl-HABA or an amine-PEG3-biotin ((+)-biotinylation-3-6, 9-trixaundecanediamine).

24. The immunogenic composition of paragraph 1, wherein the complementary affinity molecule is a biotin-binding protein, or an avidin-like protein.

25. The immunogenic composition of paragraph 24, wherein the avidin-like protein is selected from the group consisting of: rhizavidin, avidin, streptavidin, or a homologue or derivative thereof.

26. The immunogenic composition of paragraph 25, wherein the rhizavidin is amino acids of SEQ ID NO: 1, or 85% sequence identity to amino acids of SEQ ID NO: 1.

27. The immunogenic composition of any of paragraphs 1 to 26, wherein the S. aureus antigen is a fusion protein comprising the S. aureus antigen fused to a complementary affinity binding molecule.

28. The immunogenic composition of paragraph 1, wherein the first affinity molecule is cross-linked to the immunogenic polysaccharide.

29. The immunogenic composition of paragraph 1, wherein the first affinity molecule is cross-linked to the immunogenic polysaccharide using a cross-linking reagent selected from any in the group consisting of: CDAP (1-cyano-4-dimethylaminopyridinium tetrafluoroborate); EDC (1-Ethyl-3-[3-dimethylaminopropyl] carbodiimide hydrochloride); sodium cyanoborohydride; cyanogen bromide; and ammonium bicarbonate/iodoacetic acid.

30. The immunogenic composition of paragraph 1, wherein the first affinity molecule is cross-linked to carboxyl, hydroxyl, amino, phenoxyl, hemiacetal, and mecapto functional groups of the immunogenic polysaccharide.

31. The immunogenic composition of paragraph 1, wherein the first affinity molecule is covalently bonded to the immunogenic polysaccharide.

32. The immunogenic composition of paragraph 1, wherein the first affinity molecule and complementary affinity molecule pair can be selected from a group consisting of: biotin/biotin-binding protein, antibody/antigen, enzyme/substrate, receptor/ligand, metal/metal-binding protein, carbohydrate/carbohydrate binding protein, lipid/lipid-binding protein, His tag/His tag-binding substance.

33. The immunogenic composition of any of paragraphs 1 to 32, wherein the antigen is non-covalently attached, or covalently attached to the complementary affinity molecule.

34. The immunogenic composition of any of paragraphs 1 to 27, wherein a secretion signal peptide is located at the N terminal of the avidin-like protein.

35. The immunogenic composition of any of paragraphs 1 to 34, wherein the secretion signal sequence comprises at least MKKIWLALAGLVLAFSASA (SEQ ID NO: 23) or MKKIWLALAGLVLAFSASAAQDP (SEQ ID NO: 24) or an amino acid sequence having at least 85% identity thereof.

36. The immunogenic composition of any of paragraph 1 to 35, wherein the immunogenic polysaccharide is purified from living organisms or is a synthetic immunogenic polysaccharide.

37. The immunogenic composition of any of paragraph 1 to 36, wherein the living organism is selected from the group consisting of: bacteria, archaea, eukaryotic cells, fungi, insects, plants, animals, or chimeras thereof.

38. The immunogenic composition of any of paragraphs 1 to 37, further comprising a flexible linker peptide attached to the antigen, wherein the flexible linker peptide attaches the antigen to the complementary affinity molecule.

39. The immunogenic composition of any of paragraphs 1 to 38, comprising at least 3 S. aureus peptide or polypeptide antigens.

40. The immunogenic composition of any of paragraphs 1 to 39, comprising at least 5 S. aureus peptide or polypeptide antigens.

41. The immunogenic composition of any of paragraphs 1 to 40, comprising between 2-10 S. aureus peptide or polypeptide antigens.

42. The immunogenic composition of any of paragraphs 1 to 40, comprising between 10-15 S. aureus peptide or polypeptide antigens.

43. The immunogenic composition of any of paragraphs 1 to 41, comprising between 15-20 S. aureus peptide or polypeptide antigens.

44. The immunogenic composition of any of paragraphs 1 to 42, comprising between 20-50 S. aureus peptide or polypeptide antigens.

45. The immunogenic composition of any of paragraphs 1 to 43, comprising between 50-100 S. aureus peptide or polypeptide antigens.

46. The immunogenic composition of any of paragraphs 1 to 44, comprising more than 100 S. aureus peptide or polypeptide antigens.

47. The immunogenic composition of any of paragraphs 1 to 45, wherein the immunogenic polysaccharide is selected from a polysaccharide from the group consisting of: S. aureus, Vi polysaccharide, pneumococcal capsular polysaccharides, pneumococcal cell wall polysaccharide, Haemophilus influenzae Type b polysaccharide, Meningococcal polysaccharide, O-antigens from Gram-negative bacteria and other bacterial capsular or cell wall polysaccharides.

48. The immunogenic composition of any of paragraphs 1 to 46, wherein the immunogenic polysaccharide is selected from type 1 capsular polysaccharide of Streptococcus pneumoniae, type 5 capsular polysaccharide of S. aureus or type 8 capsular polysaccharide of S. aureus.

49. The immunogenic composition of any of paragraphs 1 to 48, further comprising at least one co-stimulation factor associated to the immunogenic polysaccharide.

50. The immunogenic composition of any of paragraphs 1 to 49, wherein the co-stimulation factor is selected from the group consisting of: Toll like receptor ligand or agonists, NOD ligand or agonists, or activator/agonists of the inflammasome.

51. The immunogenic composition of paragraph 50, wherein the co-stimulation factor is attached to immunogenic polysaccharide directly, or via a complementary affinity-molecule pair comprising: a first affinity molecule which associates with the immunogenic polysaccharide, and a complementary affinity molecule which associates with the co-stimulation factor, wherein the first affinity molecule associates with the complementary affinity molecule to link the co-stimulatory factor to the immunogenic polysaccharide.

52. The immunogenic composition of paragraph 1, wherein composition is used to elicit an immune response to S. aureus in a subject.

53. The immunogenic composition of paragraph 52, wherein the immune response is an antibody or B cell response.

54. The immunogenic composition of paragraph 52, wherein the immune response is an antibody or B cell response and T-cell response.
55. The immunogenic composition of paragraph 52, wherein the immune response is to at least one immunogenic polysaccharide and at least one peptide or polypeptide S. aureus antigen.
56. The immunogenic composition of paragraph 52, wherein the immune response is a CD4+ T cell response, including Th1, Th2, or Th17 or Th22 response, or a CD8+ T cell response, or CD4+ and CD8+ T cell response.
57. The immunogenic composition of paragraph 52, wherein the immune response is an antibody or B cell response to at least one antigenic polysaccharide and a CD4+ T cell response, including Th1, Th2, or Th17 or Th22 response, or a CD8+ T cell response, or CD4+/CD8+ T cell response to at least one peptide or polypeptide antigen.
58. The immunogenic composition of paragraph 52, wherein the immune response is an antibody or B cell response to at least one antigenic polysaccharide, and an antibody or B cell response and a CD4+ T cell response, including Th1, Th2, Th17 or Th22 responses, or a CD8+ T cell response, or CD4+/CD8+ T cell response to at least one peptide or polypeptide antigen.
59. The immunogenic composition of paragraph 52, wherein the immune response results in activation of INF-γ, IL-17A or IL-22 producing cells, or INF-γ, IL-17A and IL-22 producing cells.
60. The immunogenic composition of paragraph 48, wherein the immune response is an antibody or B cell response against the S. aureus antigen which associates with the immunogenic polysaccharide.
61. The immunogenic composition of any of paragraphs 1 to 60, further comprising at least one adjuvant.
62. The immunogenic composition of paragraphs 1 to 61 for use in a diagnostic for exposure to a pathogen or immune threat.
63. The immunogenic composition of paragraphs 1 to 61 for use in preventing infection by S. aureus.
64. The immunogenic composition of paragraphs 1 to 61 for use in preventing colonization of a subject by S. aureus.
65. A method for inducing an immune response in a subject to S. aureus, comprising administering to the subject a composition of paragraph 1 to 61.
66. A method of vaccinating a mammal against at least one antigen-bearing pathogen, the method comprising administering an immunogenic composition of paragraph 1 to 61.
67. The method of any of paragraphs 65 or 66, wherein the subject is a human.
68. The method of any of paragraphs 65 or 66, wherein the subject is an agricultural or non-domestic animal.
69. The method of any of paragraphs 65 or 66, wherein the subject is a domestic animal.
70. The method of any of paragraphs 65 or 66, wherein administration is via subcutaneous, intranasal, intradermal, or intra muscular injection, or via transdermal skin patch.
71. The method of paragraph 65, wherein the immune response is an antibody or B cell response.
72. The method of paragraph 65, wherein the immune response is an antibody or B cell response and T-cell response.
73. The method of paragraph 65, wherein the immune response is to at least one immunogenic polypeptide and at least one peptide or polypeptide S. aureus antigen.
74. The method of paragraph 65, wherein the immune response is a CD4+ T cell response, including Th1, Th2, Th17 or Th22 response, or a CD8+ T cell response, or CD4+ and CD8+ T cell response.
75. The method of paragraph 65, wherein the immune response is an antibody or B cell response to at least one antigenic polysaccharide and a CD4+ T cell response, including Th1, Th2, Th17 or Th22 response, or a CD8+ T cell response, or CD4+/CD8+ T cell response to at least one peptide or polypeptide antigen.
76. The method of paragraph 65, wherein the immune response is an antibody or B cell response to at least one antigenic polysaccharide, and an antibody or B cell response and a CD4+ T cell response, including Th1, Th2, Th17 or Th22 response, or a CD8+ T cell response, or CD4+/CD8+ T cell response to at least one peptide or polypeptide antigen.
77. The method of paragraph 65, wherein the immune response results in activation of IL-17A or IL-22, INF-γ producing cells, or IL-17A and IL-22 producing cells.
78. The method of paragraph 65, wherein the immune response is an antibody or B cell response against the S. aureus antigen which associates with the immunogenic polysaccharide.
79. A fusion protein comprising a rhizavidin protein and at least one S. aureus peptide or polypeptide antigen, wherein the rhizavidin protein comprises amino acids of SEQ ID NO: 1, or 85% sequence identity to amino acids of SEQ ID NO: 1, and the S. aureus peptide or polypeptide comprises a fragment of at least 20 amino acids of a protein selected from any of: haemolysin (Hl), Clumping factor A (ClfA), Clumping factor B (ClfB), serine-aspirate repeat protein D (SdrD), serine-aspirate repeat protein E (SdrE), Iron regulator surface protein A (IsdA), Iron regulator surface protein B (IsdB), Leukoptoxin D (LukD), or Leukoptoxin E (LukE).
80. The fusion protein of paragraph 79, wherein the S. aureus peptide is selected from any of Hla209(27-319), ClfA (221-559), ClfB (203-542), SdrD (246-682), IsdA (47-324) and IsdB (48-447).
81. A fusion protein comprising a rhizavidin protein and an S. aureus peptide or polypeptide antigen, wherein the rhizavidin protein comprises amino acids of SEQ ID NO: 1, or 85% sequence identity to amino acids of SEQ ID NO: 1, and the S. aureus peptide or polypeptide comprises a non-hemolytic variant of a Hla protein.
82. The fusion protein of paragraph 81, wherein the non-haemolytic variant of a Hla protein comprises at least SEQ ID NO: 16 or a protein of at least 20 amino acids that has at least 85% sequence identity to SEQ ID NO: 16.
83. A fusion protein comprising a rhizavidin protein and an S. aureus peptide or polypeptide antigen, wherein the rhizavidin protein comprises amino acids of SEQ ID NO: 1, or 85% sequence identity to amino acids of SEQ ID NO: 1, and the S. aureus peptide or polypeptide comprises a fragment of at least 20 amino acids of a Clumping factor A (ClfA) protein.
84. The fusion protein of paragraph 83, wherein the ClfA protein comprises at least SEQ ID NO: 3 or a protein of at least 20 amino acids that has at least 85% sequence identity to SEQ ID NO: 3.
85. A fusion protein comprising a rhizavidin protein and an *S. aureus* peptide or polypeptide antigen, wherein the rhizavidin protein comprises amino acids of SEQ ID NO: 1, or 85% sequence identity to amino acids of SEQ ID NO: 1, and the *S. aureus* peptide or polypeptide comprises a fragment of at least 20 amino acids of a Clumping factor B (ClfB) protein.
86. The fusion protein of paragraph 85, wherein the ClfB protein comprises at least SEQ ID NO: 5 or a protein of at least 20 amino acids that has at least 85% sequence identity to SEQ ID NO: 5.
87. A fusion protein comprising a rhizavidin protein and an *S. aureus* peptide or polypeptide antigen, wherein the rhizavidin protein comprises amino acids of SEQ ID NO: 1, or 85% sequence identity to amino acids of SEQ ID NO: 1, and the *S. aureus* peptide or polypeptide comprises a fragment of at least 20 amino acids of a serine-aspirate repeat protein D (SdrD) protein.
88. The fusion protein of paragraph 87, wherein the SdrD protein comprises at least SEQ ID NO: 7 or a protein of at least 20 amino acids that has at least 85% sequence identity to SEQ ID NO: 7.
89. A fusion protein comprising a rhizavidin protein and an *S. aureus* peptide or polypeptide antigen, wherein the rhizavidin protein comprises amino acids of SEQ ID NO: 1, or 85% sequence identity to amino acids of SEQ ID NO: 1, and the *S. aureus* peptide or polypeptide comprises a fragment of at least 20 amino acids of a serine-aspirate repeat protein D (SdrED) protein.
90. The fusion protein of paragraph 89, wherein the SdrE protein comprises at least SEQ ID NO: 8 or a protein of at least 20 amino acids that has at least 85% sequence identity to SEQ ID NO: 8.
91. A fusion protein comprising a rhizavidin protein and an *S. aureus* peptide or polypeptide antigen, wherein the rhizavidin protein comprises amino acids of SEQ ID NO: 1, or 85% sequence identity to amino acids of SEQ ID NO: 1, and the *S. aureus* peptide or polypeptide comprises a fragment of at least 20 amino acids of Iron regulator surface protein A (IsdA), protein.
92. The fusion protein of paragraph 91, wherein the IsdA protein comprises at least SEQ ID NO: 11 or a protein of at least 20 amino acids that has at least 85% sequence identity to SEQ ID NO: 11.
93. A fusion protein comprising a rhizavidin protein and an *S. aureus* peptide or polypeptide antigen, wherein the rhizavidin protein comprises amino acids of SEQ ID NO: 1, or 85% sequence identity to amino acids of SEQ ID NO: 1, and the *S. aureus* peptide or polypeptide comprises a fragment of at least 20 amino acids of Iron regulator surface protein B (IsdB), protein.
94. The fusion protein of paragraph 93, wherein the IsdB protein comprises at least SEQ ID NO: 13 or a protein of at least 20 amino acids that has at least 85% sequence identity to SEQ ID NO: 13.
95. A kit comprising:
(ii) a container comprising an immunogenic polysaccharide cross-linked with a plurality of first affinity molecules; and
(iii) a container comprising a complementary affinity molecule which associates with the first affinity molecule, wherein the complementary affinity molecule associates with at least one *S. aureus* antigen.
96. The kit of paragraph 95, further comprising a means to attach the complementary affinity molecule to the antigen.
97. The kit of paragraph 95, further comprising at least one co-stimulation factor.
98. The kit of paragraphs 95 to 97, further comprising a cross-linking reagent which can be selected from the group consisting of: CDAP (1-cyano-4-dimethylaminopyridinium tetrafluoroborate), EDC (1-Ethyl-3-[3-dimethylaminopropyl] carbodiimide hydrochloride), sodium cyanoborohydride, cyanogen bromide, or ammonium bicarbonate/iodoacetic acid for linking the co-factor to the polysaccharide.
99. The kit of paragraph 95, optionally comprising a container comprising an expression vector for expressing an antigen-affinity molecule fusion protein.
100. The kit of paragraph 99, wherein the expression vector can optionally comprise a sequence for a linker peptide, wherein the expression vector can express an antigen-affinity molecule fusion protein comprising a linker peptide between the antigen and the affinity molecule.
101. The kit of paragraph 95, wherein the antigen-affinity molecule fusion protein is any of those selected from paragraphs 79-94.

EXAMPLES

The examples presented herein relate to methods to generate an immunogenic complex as described herein and methods and compositions thereof. In particular, the examples relate to methods to produce a *S. aureus* multiple antigen presentation system (SA-MAPS) complex as disclosed herein, and methods of use to generate an immune response in a subject.

Materials and Methods

Bacterial strains: *S. aureus* strains USA 300/TCH959 and ATCC 29213 were originally purchased from ATCC. *S. aureus* strain USA 300 LAC was provided by BEI. Streptomycin-resistant USA 300 LAC strain (USA 300 LAC$^{strep}$) was obtained by streaking USA 300 LAC strain on blood agar plate containing 0.5 g/L streptomycin and selecting a spontaneous mutant the following morning.

Cloning and purification of *S. aureus* antigens. DNA sequences encoding ClfA (221-559), ClfB (203-542), SdrD (246-682), IsdA (47-324), IsdB (48-477) or Hla (27-319) were amplified from *S. aureus* genomic DNA (purified from USA 300 TCH959 strain) via PCR and then cloned into a pET-21b vector. A non-hemolytic toxoid of Hla was generated by substitution of residues Asp-Arg-Asp (aa209-211) (DRD) to Ala-Ala-Ala (AAA) using PCR. For rhizavidin fusion proteins, DNA sequences encoding SA antigens were inserted at the 3' end of the gene encoding rhizavidin moiety in a pET-21b vector. All constructs were transformed into *E. coli* BL21 (DE3) strain for expression. His-tagged recombinant proteins were purified using Ni-nitrilotriacetic acid (NTA) affinity chromatography (Quagen) followed by size-exclusion chromatography using a Superdex 200 column (GE lifescience). Purified proteins were stored at −80° C. until use.

Preparation of MAPS Complex. Type 1 pneumococcal capsular polysaccharide (referred to herein as CP1 or PS1 or SP PS1) was purchased from ATCC. Biotinylation of the polysaccharide was done as described previously. The SA-MAPS complex was assembled by incubation of biotinylated immunogenic polysaccharide with a mixture of rhizavidin fusions of *S. aureus* antigens at room temperature overnight. Typically, the rhizavidin fusion comprises 1:1 ratio of Rhizavidin: SA antigen. In some embodiments, the rhizavidin fusion comprises 1:2 ratio of Rhizavidin: SA antigen, in that the Rhizavidin protein can comprise 2 SA antigens, e.g., a Rhavi-A-A fusion protein, or a Rhavi-A-B fusion protein, where A is one SA antigen, and B is a different SA antigen. In some embodiments, the rhizavidin fusion comprises 1:3 ratio of Rhizavidin: SA antigen, in that the Rhizavidin protein can comprise 3 SA antigens, e.g., a Rhavi -A-A-A fusion protein, or a Rhavi-A-B-A fusion protein, or a Rhavi-A-B-C fusion protein, where A is one SA antigen, and B is a different SA antigen, and C is a different SA antigen. The order of SA antigens A, B and C attached to the rhizavidin (Rhavi) protein of SEQ ID NO: 1 can be in any order, and in some embodiments, any one of A, B or C can be a non-SA antigen as disclosed herein.

In some embodiments, the input ratio of Rhizavidin fusion proteins to polysaccharide was 3:1 (w/w). The assembled complex was isolated by size-exclusion chromatography. The fractions containing MAPS complex were pooled and concentrated by ultrafiltration. The protein concentration in a MAPS complex was measured using a bicinchoninic acid (BCA) protein assay kit (Pierce). The incorporation of target antigens was examined on a reduced SDS-PAGE gel.

Immunization and infection. Vaccines were prepared one day prior to immunization. The antigens were diluted to the appropriate concentration in saline, then mixed with aluminum hydroxide (Brenntag) and incubated at 4° C. overnight with rotation. 4-6-week-old C57BL/6 wild type or $\mu MT^{-/-}$ female mice (Jackson Laboratories) received three subcutaneous immunizations two weeks apart. Animals were bled two week after the last immunization for analysis of antibody and T-cell responses. Mice were infected with S. aureus 7-10 days later.

Rabbit antisera against S. aureus antigens were generated at Cocalico Biologicals (Reamstown, Pa.). New Zealand White rabbits were given three intramuscular immunizations, two weeks apart, with SA-MAPS vaccine. Sera were collected before the first immunization and two weeks after the last immunization. For passive immunization, 8-week-old C57BL/6 female mice received 200 μl of heat-inactivated pre- or post-vaccination rabbit sera one day prior to infection via intraperitoneal injection.

For all infections, S. aureus strains were streaked on blood agar plates and grown at 37° C. overnight. An overnight culture was then started by inoculating colonies into Tryptic soy broth (TSB, Sigma), shaking at 37° C. Cells were re-inoculated into fresh TSB medium at 1:100 dilution in the morning and incubated at 37° C. with shaking for 3 hours. Bacterial cells were collected by centrifugation, washed twice with saline and adjusted to certain concentration in saline before infection.

Sepsis infection of S. aureus was performed using the ATCC 29213 strain. Mice were anesthetized with isoflurane and infected with $2-3\times10^7$ CFU in 100 μl via retro-orbital injection. Mice were monitored for sign of illness for 14 days; any ill-appearing animal was immediately and humanely euthanized.

In the dermonecrosis infection model, mice were anesthetized and injected subcutaneously on the shaved lower back with $0.5-1\times10^7$ CFU of USA300 TCH959 strain in 100 μl volume. Mice were monitored for 14 days after infection. Pictures of infected area were taken and the sizes of dermonecrotic plaques/lesions were measured using ImageJ software.

In the skin abscess model, mice were shaved, anesthetized and infected subcutaneously with $2-5\times10^5$ of USA300 TCH959 strain in 100 μl volume. Mice were then humanely euthanized on day 4 after infection. Abscesses were dissected and homogenized by bead beater. Serial dilutions of homogenate were plated on mannitol salt plates and colonies were counted after overnight culture at 37° C. Detection limit is 22.5 CFU. In animals that were abscess-free or for culture negative samples, their CFU was set as the detection limit.

In the GI colonization model, mice were gently restrained and inoculated intranasally with $5\times10^7$ of USA300 $LAC^{strep}$ strain in 10 μl volume. Fecal pellets were collected on day 1 and day 7 after infection or as indicated. Samples were weighted, resuspended in sterile PBS at 0.1 g/ml, homogenized and then passed through CellTrics 30 μm filter. Serial dilutions of the flow-through samples were plated on mannitol salt plates containing 0.5 g/L streptomycin and colonies were counted after overnight culture at 37° C. Detection limit is 40 CFU. For culture-negative samples, CFU was set as the detection limit.

Antibody and T-cell response analysis. Antigen-specific IgG antibody was measured by ELISA using Immulon 2 HB 96-microwell plates (Thermo Scientific) coated with individual recombinant S. aureus protein (non-rhizavidin fusion). The plates were washed with PBS containing 0.05% Tween 20 (PBS-T) and then blocked with 1% BSA in PBS for 1 hour. After blocking, serial dilutions of mouse or rabbit sera were added and incubated for 2 hours, followed by 1 hour incubation with HRP-conjugated secondary antibody against mouse or rabbit IgG. The plates were then washed and developed with SureBlue TMB Microwell Peroxidase Substrate (KPL). 1 M HCl was used to terminate the reactions before the $A_{450nm}$ was analyzed using an ELISA reader. Antibody titers were expressed in arbitrary units relative to a standard serum.

For T-cell response analysis, 25 μl of heparinized blood were added to 225 μl DMEM (BioWhittaker) containing 10% low-endotoxin defined FBS (Hyclone), 50 μM 2-mercaptoethanol (Sigma) and ciprofloxacin (10 μg/ml, Cellgro). The cultures were incubated at 37° C. for 6 days in the presence of 2.5 μg/ml of the mixture of six S. aureus protein antigens (equal weight ratio, non-rhizavidin fusion). Supernatants were collected following centrifugation and analyzed by ELISA for INF-γ, IL-17A and IL-22 concentration (R&D Systems).

Hemolysis analysis. The hemolytic activity of wild type Hla, Hla209 and their rhizavidin fusions was measured as follows: 200 μl of heparinized rabbit blood was washed with cold PBS three times. Red blood cells were then resuspended in 10 ml of cold PBS (2% rabbit red blood cells) and 100 μl of 2-fold serial dilution of Hla samples in PBS with 0.1% BSA, starting from 100 μg/ml, was added into a V-bottom 96-well plate before the addition of 100 μl of red blood cells to each well. PBS containing 0.1% Triton X-100 was used as a positive control (100% hemolysis), and PBS with 0.1% BSA was used as a negative control (0% hemolysis). The plate was incubated at 37° C. for 30 min and then subjected to centrifugation at 800 g for 5 minutes. The supernatants were transferred into a flat-bottom 96-well plate and the $A_{545nm}$ was measured by an ELISA reader. One hemolytic unit (HU) was defined as the activity that causes 50% lysis of 1% rabbit red blood cells after 30 min incubation at 37° C. The activity of each Hla construct was expressed as the HU of 1 mg/ml of purified protein.

Statistical analysis. All statistical analyses were done using PRISM (version 5.01 for Windows, GraphPad Software, Inc). Antibody titer, cytokine release, size of lesions and CFU counts in abscesses or in feces were compared between groups using the Mann-Whitney U test. Differences in survival were analyzed by the Mantel-Cox test. Percentage of abscess formation was analyzed by the Fisher's exact test.

Example 1

It is well recognized that any single animal model of SA infection is unlikely to adequately represent the pathophysiology of disease in humans; therefore, evaluation of any potential candidate in several models would appear prudent. At the same time, the large number of virulence factors (including polysaccharides, surface proteins, and secreted toxins produced by SA, may provide credence to the idea that multiple, genetically conserved antigens should be included in a candidate vaccine. Finally, a closer examination of mechanisms of immunity to SA in humans may also provide clues for an effective vaccine strategy. Indeed, while humoral immunity plays a leading role in host defense against many bacterial or viral pathogens, it is unlikely that antibodies are the only or even the primary factor for resistance to SA. Patients with B-cell deficiencies do not appear to be at significantly increased risk of SA infections, and individuals with high levels of pre-existing SA-specific antibodies can still get infected by SA. On the other hand, a growing body of literature now suggests that T-cell immunity, the other arm of acquired host defense, plays a critical role in SA defense. Indeed, individuals with suppressed or impaired cellular immunity, caused by high dose prednisone therapy, HIV infection, defective interferon-γ (IFN-γ) production, defective interleukin-17 (IL-17) production, are at very high risk for SA infection and recurrence. Moreover, in murine models, IFN-γ or IL-17A/F deficiency has been shown to induce hyper-susceptibility to SA skin infections, and IL-17A deficiency in mice is also associated with prolonged nasal carriage of SA. Therefore, an approach the combines both B- and T-cell acquired immunes responses to the organism may provide optimal protection against this organism.

Based on these observations, the inventors designed and developed a SA antigen containing several conserved antigens, using a vaccine platform that can elicit a broad range of immune responses, e.g., both B- and T-cell acquired responses. The inventors have previously developed a subunit vaccine platform, referred to as the Multiple-Antigen-Presenting-System (MAPS), which is disclosed in US Application 2014/0154287, which is incorporated herein in its entirety by reference. The MAPS generates affinity-coupled complexes of antigens that can then induce broad B- and T-cell responses, and interestingly generated an immune response to both the immunogenic polypeptide as well as the antigens.

Herein, the inventors prepared a multi-component SA subunit vaccine using either a conventional approach (immunization with purified proteins alone) or proteins incorporated onto a scaffold using the MAPS technology, as disclosed in US application 2014/0154287. The inventors evaluated the immunogenicity of these two different vaccine approaches in mice, compared their protective efficacy in SA sepsis infection, dermonecrosis infection, skin abscess infection and gastrointestinal (GI) colonization models, and finally, studied the role of antigen-specific antibodies and T-cell immunity against different types of SA infection or colonization.

Preparation of vaccines. Six SA virulence factors that have been previously studied and/or proposed as vaccine candidates were selected. Among them, α-hemolysin (Hla) is one of the most studied secreted toxins of SA and has been shown to play an important role in early stages of invasive infection and skin infection. Clumping factor A (ClfA) and Clumping factor B (ClfB), and serine-aspartate repeat protein D (SdrD) are cell-wall anchored adhesins that facilitate SA binding to the extracellular matrix or epithelial cells during colonization and infection. ClfA has also been shown to be involved in accelerated cleavage of complement 3b and thus result in decreased complement-mediated phagocytosis of SA. Iron-regulated surface protein A (IsdA) and B (IsdB) function in iron-acquisition during SA infection. Antibodies against IsdA and IsdB have been shown to protect mice against lethal intravenous challenge.

Figure 1B:
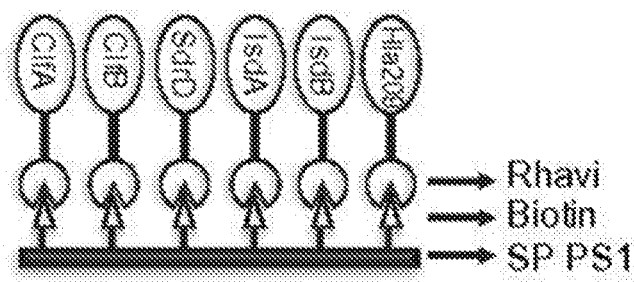
Figure 1C:
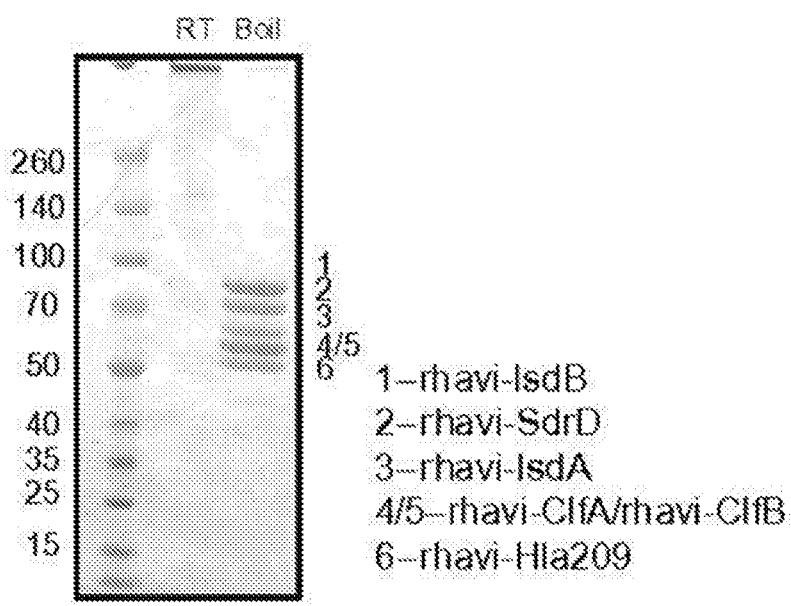

The selected antigens were cloned from the SA genome and then transformed into *E. coli* for expression and purification. A detoxified Hla mutant (Hla209) was generated by genetic substitution of residues Asp-Arg-Asp (DRD) (209-211) to Ala-Ala-Ala (AAA) which resulted in more than 700-fold reduction in hemolytic activity (FIG. 1A). A conventional subunit vaccine referred to herein as "SA-Mix") was prepared by mixing all six recombinant proteins (e.g., ClfA (221-559); ClfB (203-542); SdrD (245-682); IsdA (47-324); IsdB (48-477) and Hla209 (27-319)) at equal molar ratio (see, FIG. 1B, upper panel). For SA-MAPS preparation, the target antigens were genetically fused to rhizavidin (rhavi), a dimeric biotin-binding protein identified in Rhizobium etli, as disclosed in U.S. Pat. No. 9,499, 593 which is incorporated herein in its entirety by reference. The following Rhizavidin fusion proteins were generated, where the Rhizavidin protein of the fusion protein comprises SEQ ID NO: 1; e.g., Rhavi-ClfA (221-559); Rhavi-ClfB (203-542); Rhavi-SdrD (245-682); Rhavi-IsdA (47-324); Rhavi-IsdB (48-477) and Rhavi-Hla209(27-319). Rhavi-Hla209 fusion protein demonstrates further reduced hemolytic activity compared to Hla209 (FIG. 1A), due to the stoichiometric interference between the dimerization of rhavi and the heptameirzation of Hla which is required to initiate the hemolysis. SA-MAPS were assembled by affinity-coupling rhavi-SA antigens with biotinylated type-1 pneumococcal capsular polysaccharide (FIG. 1B, lower panel), a polysaccharide not expected to contribute to protection against SA infection. SDS-PAGE showed that all six target antigens were incorporated into SA-MAPS complexes at approximately equal molar ratio (FIG. 1C).

Example 2

Figure 2A:
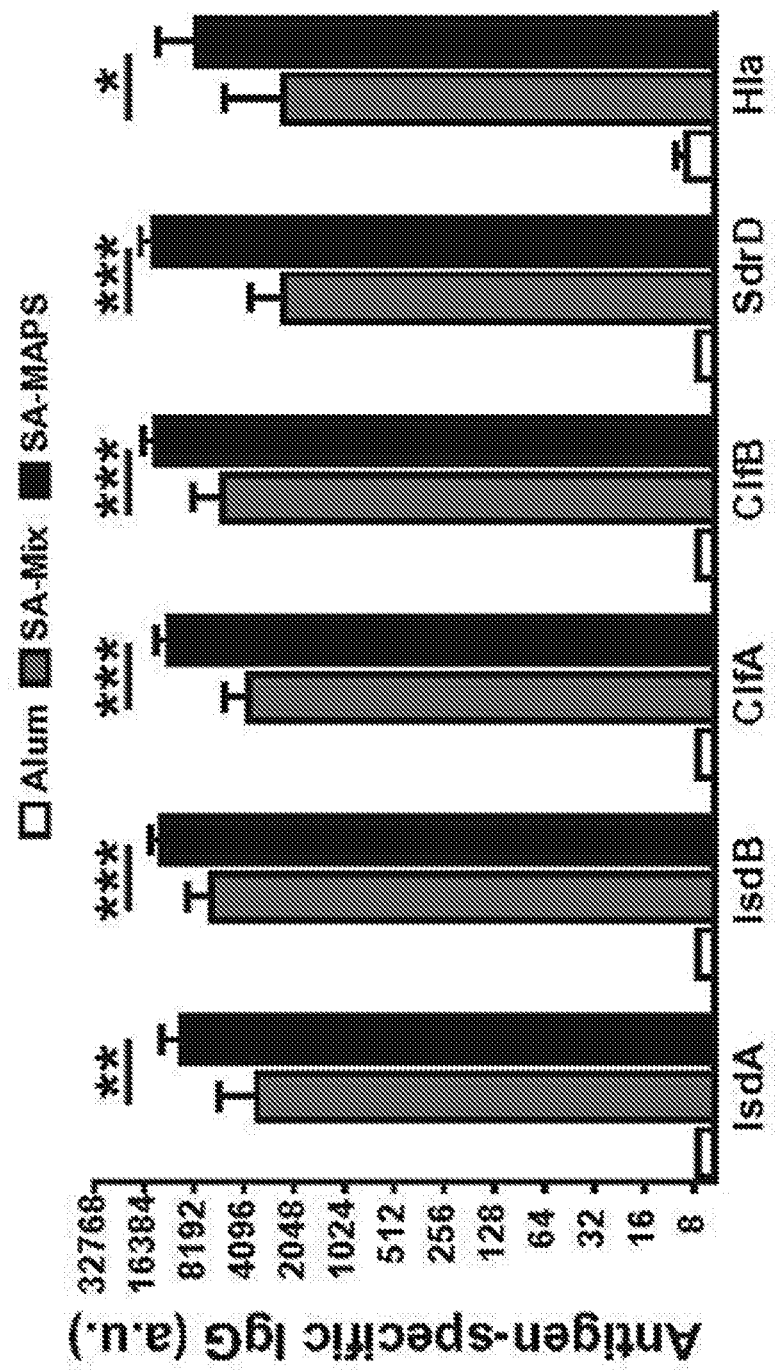
FIGS. 2A and 2B show antigen-specific immune responses induced by SA-Mix or SA-MAPS vaccine.

SA-MAPS is surprisingly significantly more immunogenic than the SA-Mix with respect to both B- and T-cell responses to the target antigens. C57BL/6 mice received three subcutaneous administrations of adjuvant alone (Alum), SA-Mix or SA-MAPS vaccine. Serum IgG antibodies against each SA protein were measured two weeks after the last immunization. While both SA-Mix and SA-MAPS vaccine induced robust antibody responses to the target antigens (FIG. 2A), the antibody titer in the SA-MAPS group was 2-6 fold higher than what was induced by SA-Mix cross all six antigens (FIG. 2A), consistent with what the inventors have previously reported with a pneumococcal MAPS vaccine.

Figure 2B:
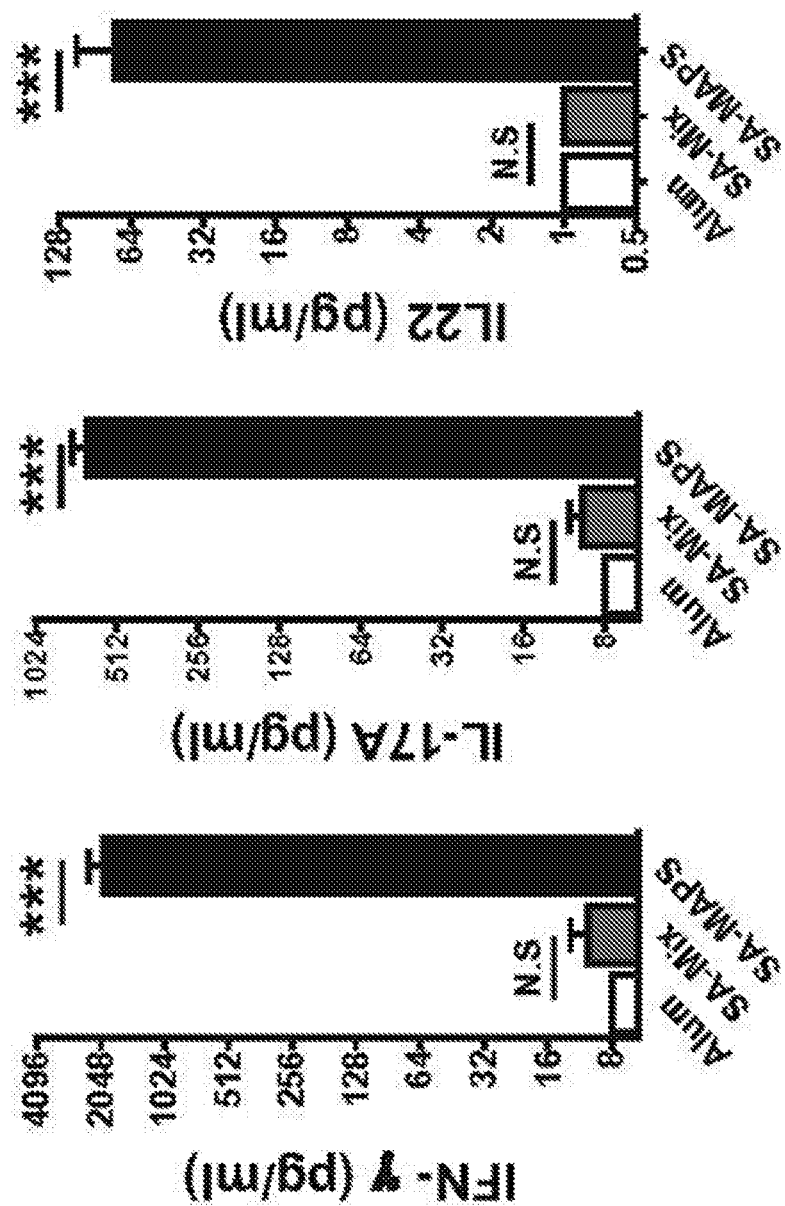

To examine antigen-specific T-cell responses, peripheral blood was collected from the immunized animals and then stimulated in vitro with a mixture of recombinant SA antigens (purified proteins without the rhavi moieity to ensure that the response is directed against the antigen rather than the affinity tag). Release of specific T-cell related cytokines in the culture supernatant was measured by ELISA after stimulation. As shown in FIG. 2B, cells obtained from mice immunized with SA-Mix, did not produce any of the evaluated cytokines. In contrast, the blood samples collected from SA-MAPS vaccinated animals responded to SA antigens and produced significant amount of IFN-γ, IL-17A and IL-22, implicating generation of Th1, Th17 and Th22 responses by the MAPS vaccine.

Example 3

Figure 3A:
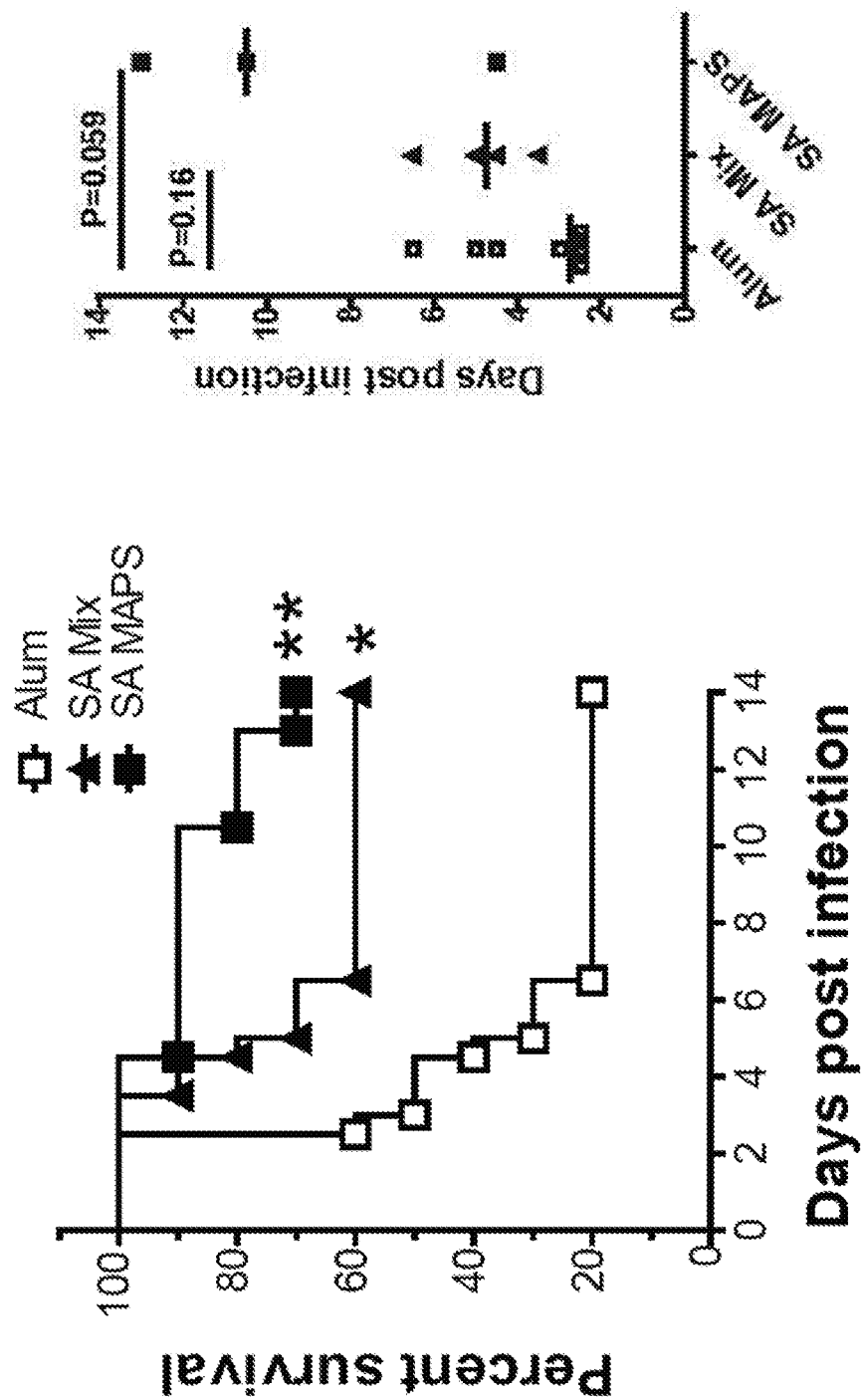
FIGS. 3A-3E show SA-MAPS confers enhanced and broad protection in models of *S. aureus* infection and colonization. Mice (n=10 per group) received three immunizations with SA-Mix or SA-MAPS vaccine. Control group received adjuvant alone (Alum). Mice were infected with *S. aureus* 3 weeks after the last immunization.

Vaccination with SA-MAPS provides broad protection against SA infection and colonization. To better assess the potency of the SA-Mix and SA-MAPS vaccines, the inventors examined them in several SA infection or colonization models. First, the inventors evaluated the performance of the SA-Mix and SA-MAPS vaccines in a mouse sepsis model: a highly invasive, systemic SA infection. Mice were injected retro-orbitally with a high dose of ATCC29213 strain which causes 60-90% death of naive animals within 7 days. In this model, vaccination with either SA-Mix or SA-MAPS significantly protected mice from SA-induced illness: when compared to the control group which had 80% mortality after infection, the mortality of the SA-Mix or SA-MAPS group was reduced to 40% or 30%, respectively (FIG. 3A). While the survival rate was comparable between the two vaccine groups, MAPS-vaccinated animals tended towards a delayed onset of illness compared to the SA-Mix group: 3 sick animals in the SA-MAPS group were found at 4.5, 10.5 days and 13 days after infection respectively, whereas all the sick animals in the control group or in the SA-Mix group were identified within 1 week (2.5 to 6.5 days) after infection.

Figure 3B:
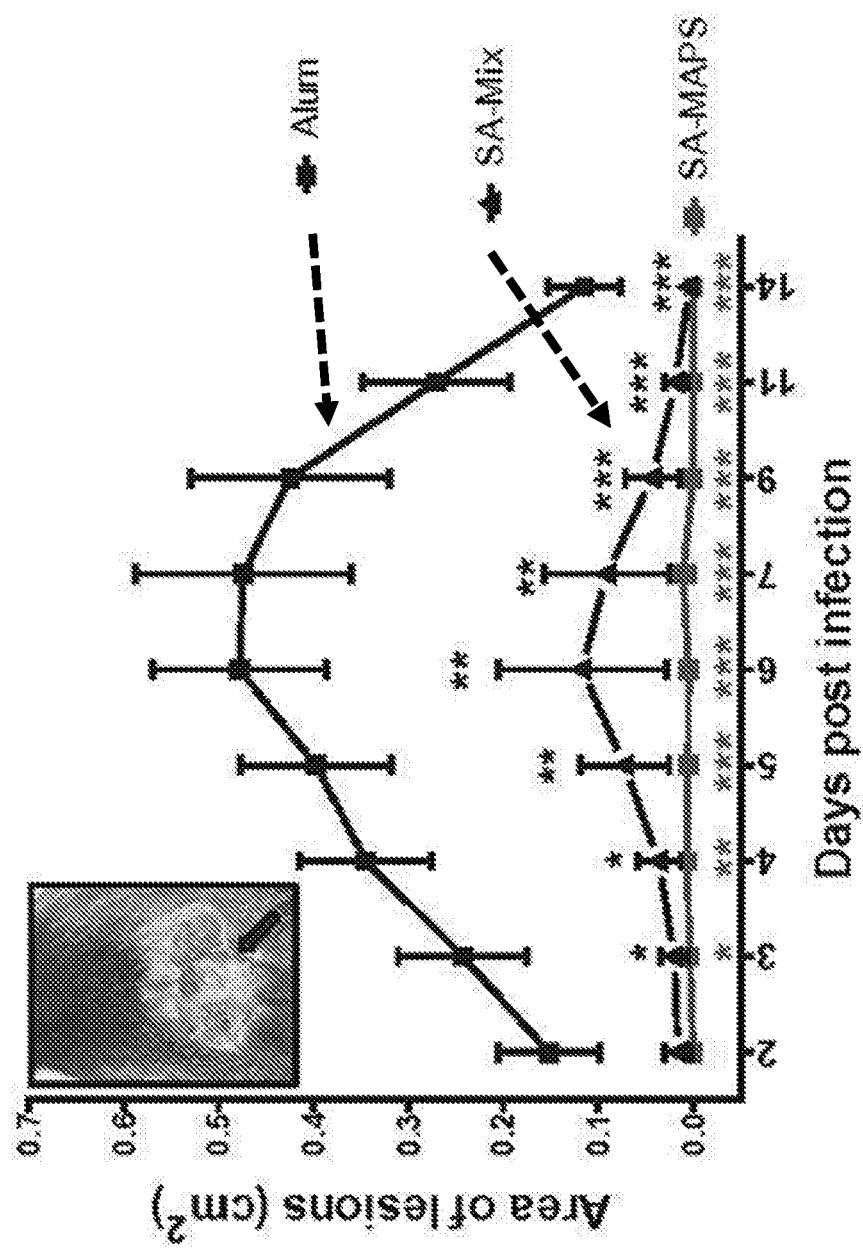
Figures 3C, 3D:
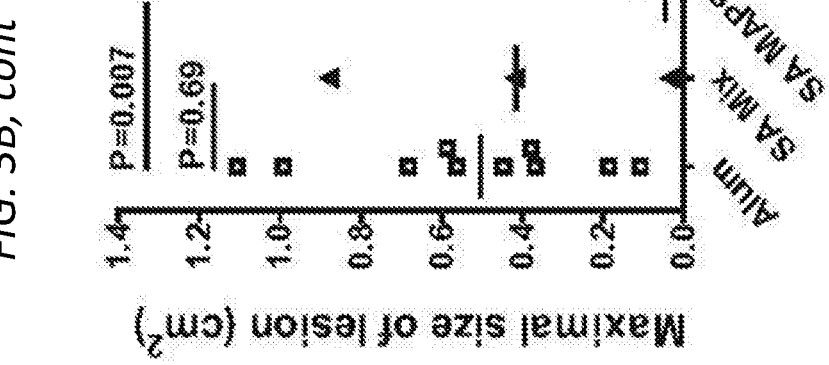

The inventors also evaluated two SSTI models: a dermonecrosis model in which the bacterial infection results in a large, measurable infected plaque and the skin abscess model in which the infection is contained within an abscess and in which the bacterial burden can be quantified by dissection and harvest of the abscess and dilutional plating. Dermonecrosis was induced by subcutaneous injection of a USA300 strain which causes dermonecrotic plaques/lesions at the injection sites as soon as 2-3 days post infection. Lesions may further progress and maximize in size in about 5-9 days post infection, often associated with peeling skins and large open wounds (FIG. 3B, inset), and then begin to heal. In this model, both SA-Mix and SA-MAPS vaccine were highly effective in mitigating the infection. Compared to the control group in which 10 out of 10 animals developed dermonecrotic lesions after infection, only 2 mice in the SA-Mix group and 1 in the SA-MAPS group had any visible dermonecrosis (FIG. 3C). Besides the significantly reduced incidence of lesions, the maximum lesion size on the MAPS-immunized mouse was also the smallest (<0.1 $cm^2$) compared to what was found on the control animals (ranging from 0.17-1.2 $cm^2$) or on the SA-Mix-vaccinated animals (0.4 and 0.89 $cm^2$) (FIG. 3B).

Figure 3E:
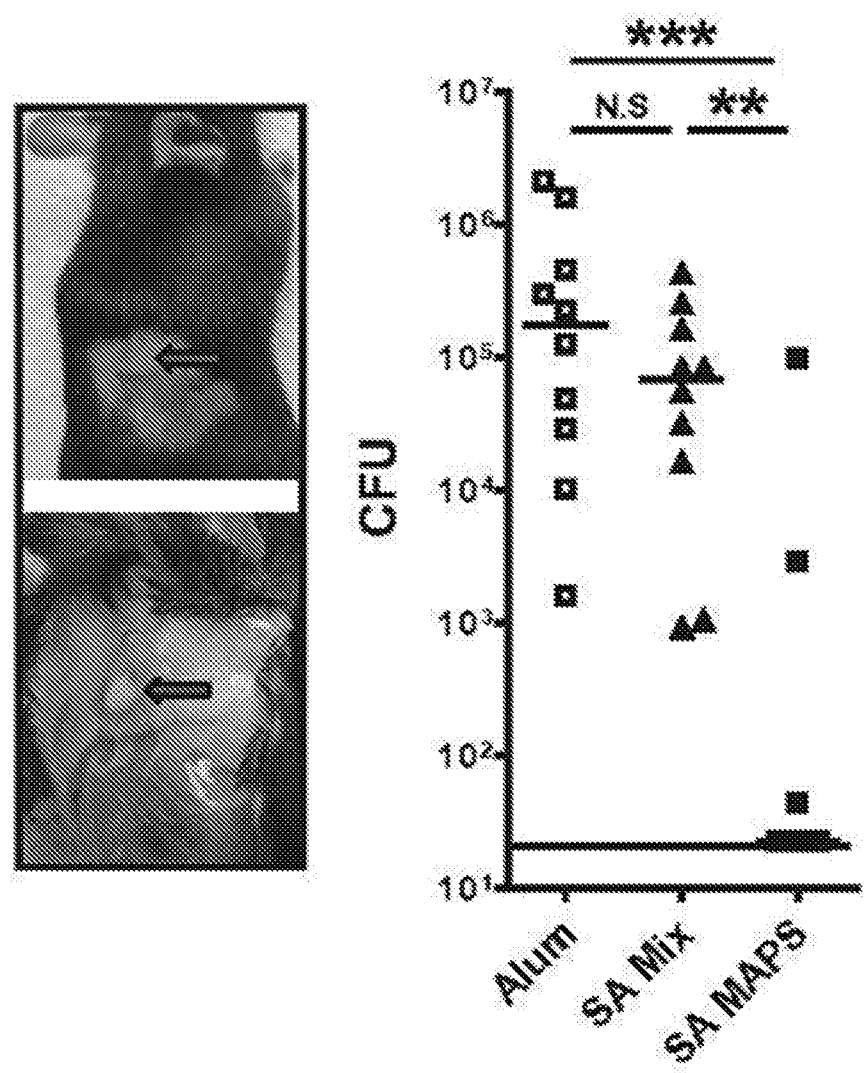

In the skin abscess model, mice were infected subcutaneously with a much lower inoculum of SA (approx. 40-50 fold lower than the dermonecrosis infection) which leads to the formation of an enclosed subdermal abscess at the injection site, with no visible skin breakdown or damage (FIG. 3D). Mice were sacrificed 4 days after infection and the abscesses were isolated for CFU enumeration. Animals that received SA-MAPS vaccine were well protected in the abscess model: 7 out of 10 mice in the SA-MAPS group were free of both abscess and bacteria on day 4 post-infection, whereas all mice in the control group developed abscesses (FIGS. 3D and 3E). Interestingly, the SA-Mix group, which was as well protected as the SA-MAPS group in the dermonecrosis model, was neither protected against abscess formation (FIG. 3D) nor did they display reduced bacterial load in the abscesses (FIG. 3E), demonstrating that the mechanism of protection against these two types of SSTI was likely distinct and, in particular, that T cell responses (which are lacking in the SA-Mix group) have a critical role in protection in the abscess model.

Figure 4A:
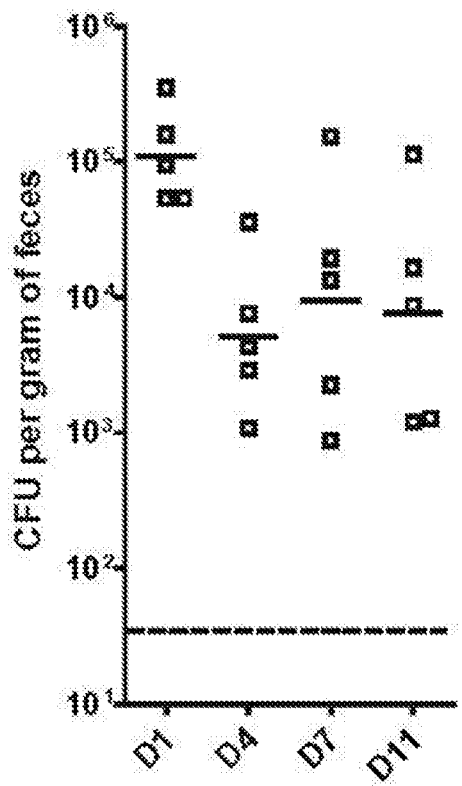
FIGS. 4A-4C show that vaccination with SA-MAPS but not with SA-Mix facilitates the clearance of GI colonization of SA.
Figure 4B:
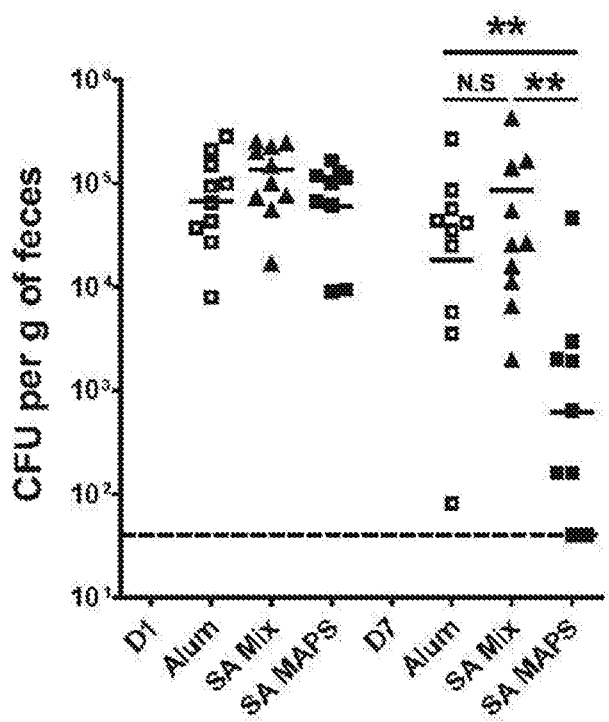
Figure 4C:
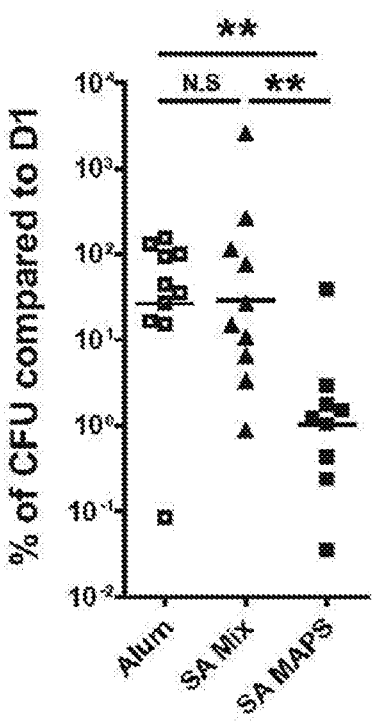

The last model the inventors examined was a GI colonization model, to mimic the non-pathogenic SA mucosal carriage condition. In this model, mice were inoculated intranasally with $5\times10^7$ CFU of the USA300 LAC strain. One day later, fecal samples were collected from each animal and CFU of bacteria were enumerated and used as the baseline density of GI carriage. For naïve animals, $0.5-3\times10^5$ CFU of SA could be recovered from 1 gram of fecal samples (FIG. 4A) on day 1. The number of bacteria in feces decreases after the initial inoculation and then reaches a relatively stable colonization density between days 4 to 11 post-inoculation, with densities ranging between $10^3$ and $10^5$ CFU per gram of feces (FIG. 4A). For vaccinated animals, fecal samples were collected on day 1 (the baseline of GI carriage) and day 7 post-inoculation for CFU analysis. Vaccination with SA-MAPS significantly reduced the density of SA GI colonization (FIG. 4B). Compared to baseline densities, fewer than 1% of bacteria (~600 CFU per gram of feces) were recovered from the SA-MAPS vaccinated animals on day 7 post-inoculation, whereas about 27% (18,000 CFU per gram of feces) of the original inoculum of SA still colonized the GI tracts of the control animals. Vaccination with SA-Mix, in contrast, did not have any protective impact on the clearance of SA carriage: about 84,000 CFU per gram of feces), or 29% of the baseline carriage, were found in the SA-Mix vaccinated animals on day 7 post-inoculation (FIGS. 4B and 4C).

Example 4

B- and T-cell immunity play different roles in protection against different types of SA infection or SA colonization. Thus, despite comprising the same SA antigenic components, it was surprising that there was such marked differences in efficiencies by the SA-Mix and SA-MAPS against SA infection or colonization. Importantly, vaccination with SA-MAPS provided broad protection in all four animal models tested, whereas SA-Mix provided protection only in the sepsis and dermonecrosis models, but not skin abscess and GI colonization. As noted above, a major and striking difference between these two vaccines is that SA-MAPS induces not only antigen-specific antibodies, but also robust, antigen-specific T-cell responses. The inventors assessed if these T cell responses explain the differences noted between the two vaccination strategies.

Figure 5A:
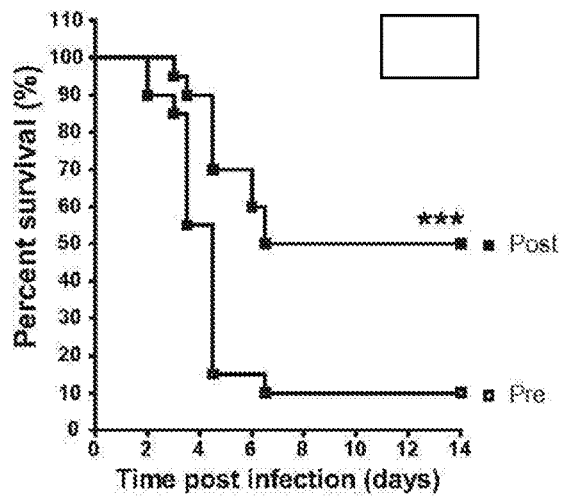
FIGS. 5A-5D show roles of antigen-specific antibodies in the protection against different types of *S. aureus* infection and colonization. Mice (n=10 per group) received intraperitoneal injection with 200 μl of heat-inactivated, pre- or post-SA-MAPS immunization rabbit sera one day prior *S. aureus* infection. Infusion with rabbit sera against *S. aureus* antigens protected mice against sepsis (FIG. 5A) and dermonecrosis infection (FIG. 5B), but had no impact on the formation of skin abscess (FIG. 5C) or the clearance of *S. aureus* from the GI tracts (FIG. 5D). Symbols in B represent Mean±SEM. Bars in C and D Geometric means. Dashed lines indicated the detection limit (22.5 CFU for abscess infection and 40 CFU for GI colonization model). N.S, not significant; *, $P<0.05$; , $P<0.01$; *, $P<0.001$.
Figure 7:
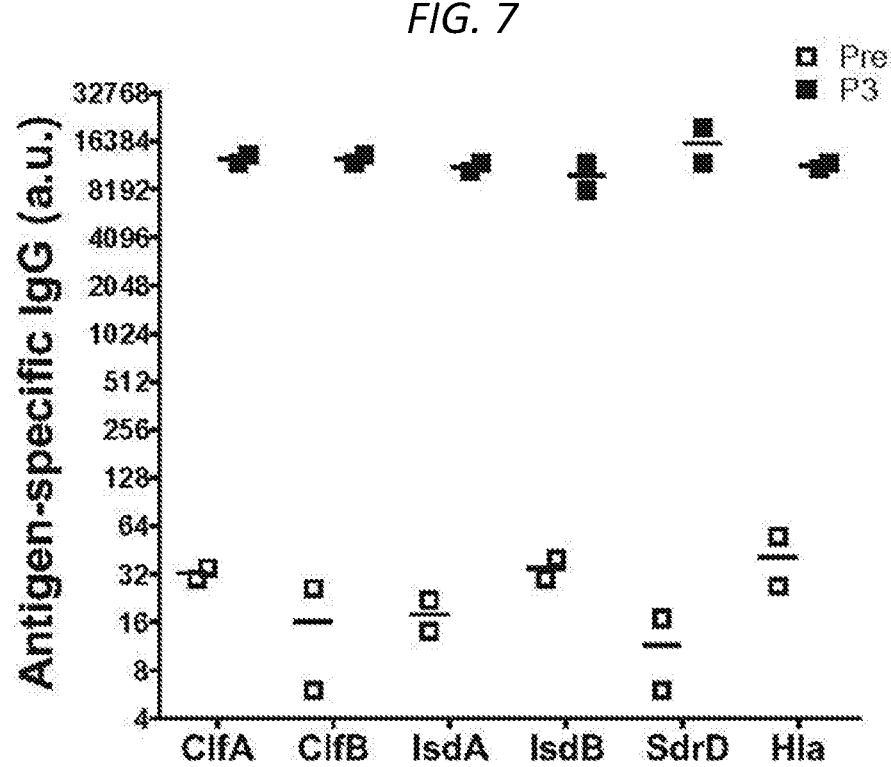
FIG. 7 shows the contribution of antibodies using passive immunization. The antigen-specific IgG for ClfA, ClfB, IsdA, IsdB, SdrD or Hla after immunizing rabbits with SA-MAPS (P3, filled squares) as compared to pre-vaccination rabbit sera (Pre, open squares) which were used as controls.

To test this hypothesis, the inventors began by evaluating the contribution of antibodies using passive immunization. Anti-SA sera were generated by immunizing rabbits with SA-MAPS (FIG. 7). Pre-vaccination rabbit sera were used as controls. Consistent with what we found with SA-Mix vaccination, which induces antibody-mediated protection exclusively, passive immunization with rabbit anti-SA sera protected mice in the sepsis and dermonecrosis infections. During sepsis infection, mice that received anti-SA sera had a significantly improved survival rate, at 50%, compared to the control group which had 10% survival (FIG. 5A).

Figure 5B:
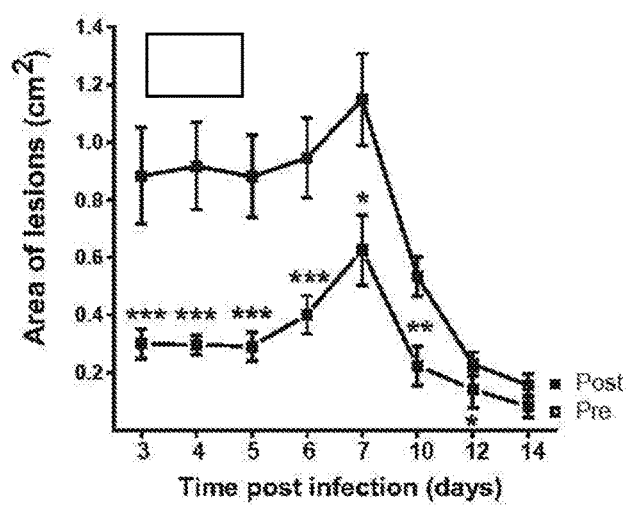
Figure 5C:
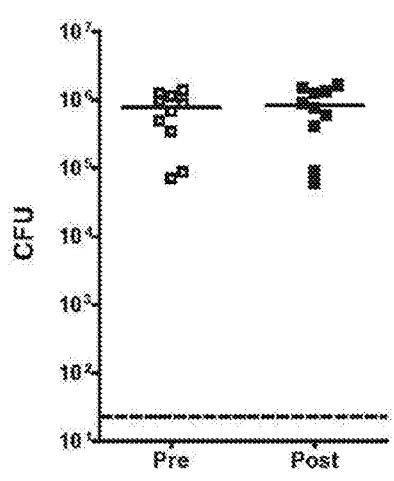
Figure 5D:
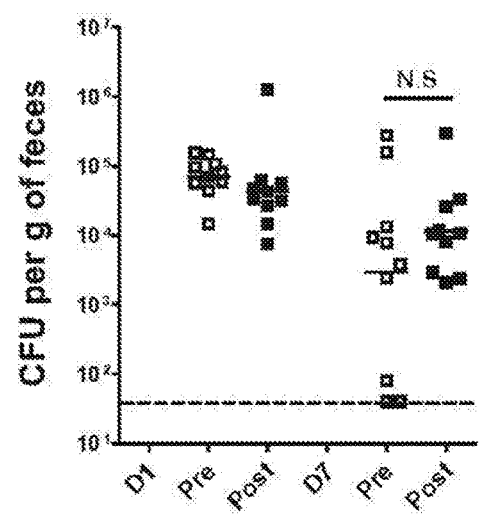

Infusion with anti-SA sera was also able to mitigate the findings in the dermonecrosis model. While most animals developed skin lesions, the size of lesions in the group that received immune anti-sera was significantly smaller than in the control group (FIG. 5B). In contrast, we could not detect any impact of passive immunization in the two other, less invasive models. In the abscess model, passive immunization with anti-SA sera showed no effect on either the formation of abscesses or the bacteria load in abscesses (FIG. 5C). Similarly, during GI colonization, with a comparable initial inoculation, the animals that received anti-SA sera did not clear bacteria sooner than controls; in fact, they appeared to have an even higher density of colonization (about 4-fold higher in geometric mean) on day-7 compared to the control group (FIG. 5D). Thus, while passive immunization provides significant protection against invasive disease and dermonecrosis, antibodies alone are ineffective in providing protection in either the skin abscess or colonization models.

Figure 6B:
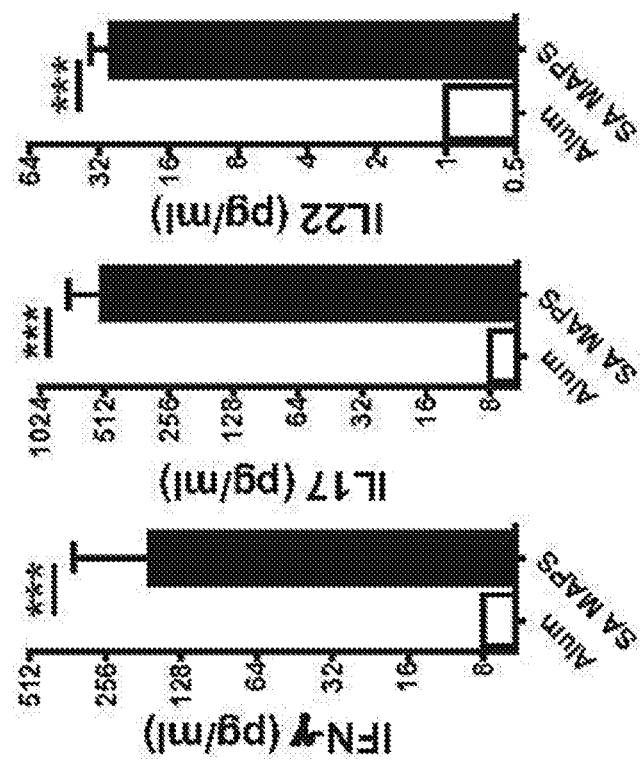
FIGS. 6A-6F show the contributions of antigen-specific T-cell responses to protection against different types of *S. aureus* infection and colonization.
Figure 6A:
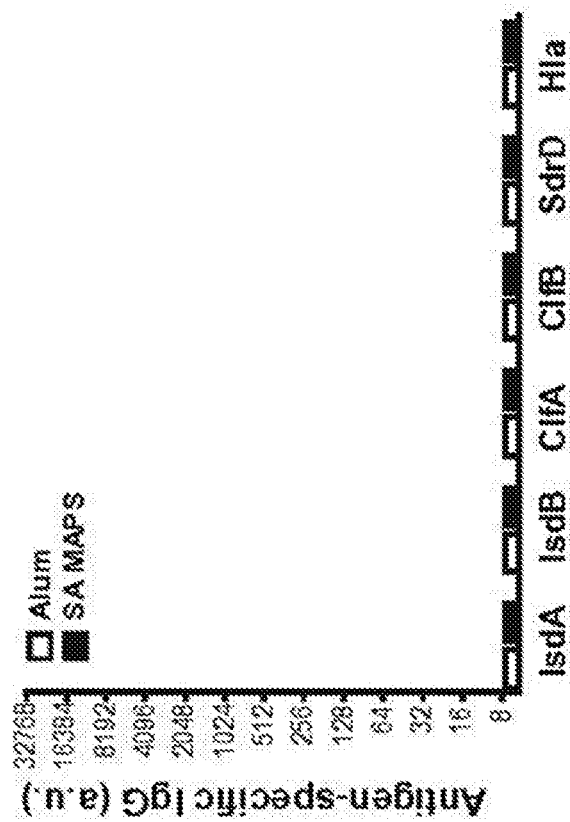
Figure 6C:
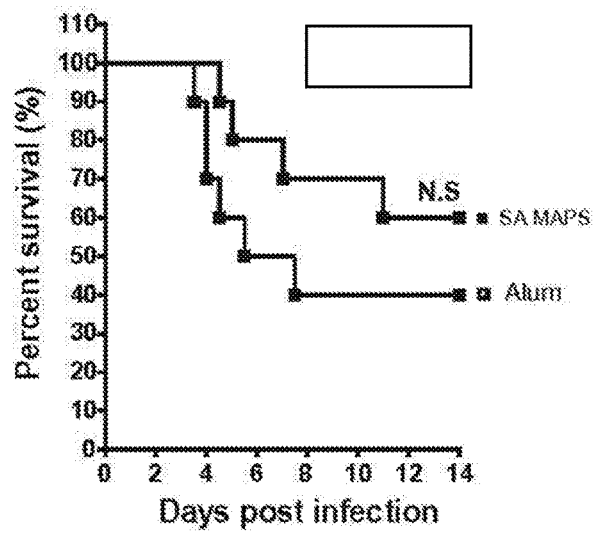
Figure 6D:
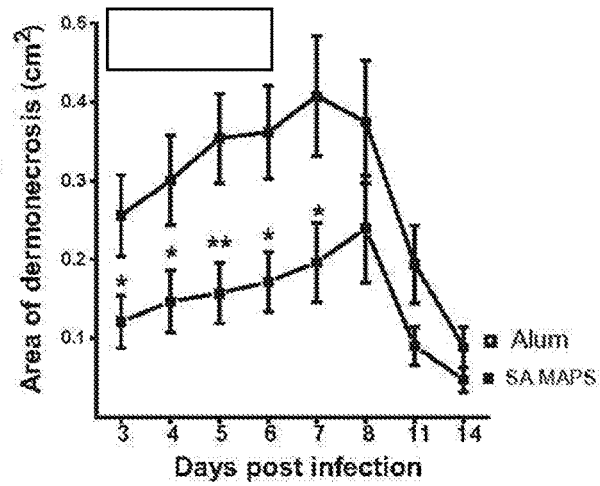
Figure 6E:
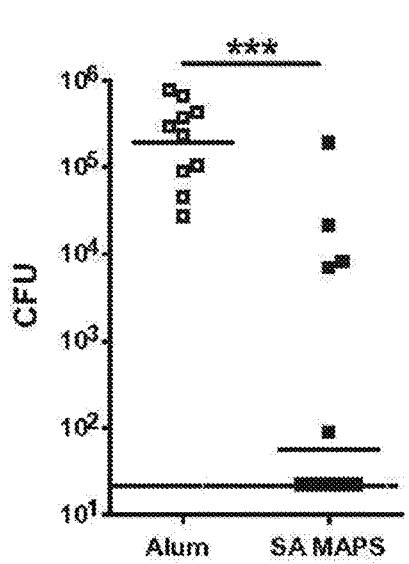
Figure 6F:
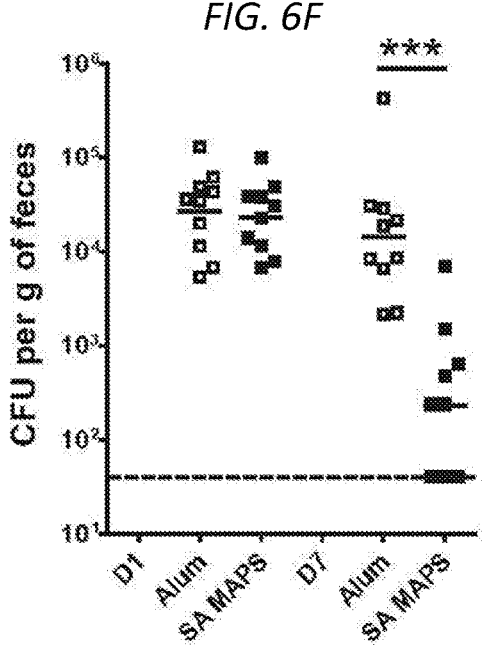

To evaluate to what degree protection in these models may be dependent on acquired T cell responses, the inventors evaluated SA-MAPS in $\mu MT^{-/-}$ mice, a mouse strain that is congenitally deficient in immunoglobulins. Vaccination of $\mu MT^{-/-}$ mice with SA-MAPS induced no antigen-specific antibodies (FIG. 6A), but normal T-cell responses, as measured by the release of IFN-γ, IL-17 and IL-22 cytokines after in vitro stimulation of the peripheral blood with SA antigens (FIG. 6B). Immunized $\mu MT^{-/-}$ mice were then challenged in our animal models. In either the sepsis or dermonecrosis infection model, against which antigen-specific antibodies provide robust protection, the impact of T-cell immunity was relatively minor. In the case sepsis infection, vaccination of $\mu MT^{-/-}$ mice with SA-MAPS only slightly improved the survival rate (from 40% to 60%), with a trend towards slower development of illness, a phenomenon we have observed earlier in MAPS-vaccinated WT mice (FIG. 3A) but not in SA-Mix vaccinated WT mice or during passive immunization when only antibody responses were induced or present (FIGS. 3A and 6C). In the case of dermonecrosis infection, antigen-specific T-cell immunity in the absence of antibodies was able to reduce the size of the lesions, especially in the first week of infection, compared to control animals (FIG. 6D). In contrast, the contribution of T-cell immunity was much more evident and in fact sufficient in either the skin abscess infection and GI colonization models, against which antibodies were ineffective. Vaccination of $\mu MT^{-/-}$ mice with SA-MAPS significantly reduced abscess formation and bacterial burden (FIG. 6E). Furthermore, MAPS-induced T-cell immunity also facilitated the clearance of SA in the GI tracts during colonization challenge. Seven days post-inoculation, mice in the MAPS-vaccinated group had greater than a 10-fold reduction of geometric mean bacterial density in fecal samples, including complete clearance of SA in 4 out of 10 mice, whereas all the animals in the control group remained colonized by SA and had only about 2-fold reduction of geometric mean bacterial density in fecal samples (FIG. 6F).

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

---

The invention claimed is:

1. An immunogenic composition comprising:
   at least one immunogenic polysaccharide,
   at least two S. aureus or polypeptide antigens, and
   at least one pair of affinity molecules,
   wherein the at least one pair of affinity molecules comprises:
   (i) a first affinity molecule comprising biotin, and
   (ii) a second affinity molecule comprising a biotin-binding protein,
   wherein in each pair of affinity molecules:
   the first affinity molecule is associated with the at least one immunogenic polysaccharide, and
   the second affinity molecule is associated with at least one of the S. aureus polypeptide antigens,
   wherein the first affinity molecule non-covalently associates with the second affinity molecule to link the S. aureus polypeptide antigens and the immunogenic polysaccharide;
   wherein the at least one immunogenic polysaccharide comprises a type 1 capsular polysaccharide of Streptococcus pneumoniae, a type 5 capsular polysaccharide of S. aureus, and/or a type 8 capsular polysaccharide of S. aureus; and
   wherein the at least two S. aureus polypeptide antigens comprise (i) a hemolysin having the amino acid sequence of SEQ ID NO: 16; and (ii) a serine-aspartate repeat protein D (SdrD) protein having the amino acid sequence of SEQ ID NO: 7.

2. The immunogenic composition of claim 1, wherein the immunogenic composition comprises two S. aureus polypeptide antigens, which are (i) a hemolysin having the amino acid sequence of SEQ ID NO: 16; and (ii) a serine-aspartate repeat protein D (SdrD) protein having the amino acid sequence of SEQ ID NO: 7.

3. The immunogenic composition of claim 1, wherein the biotin-binding protein comprises rhizavidin set forth as SEQ ID NO: 1 or an amino acid sequence that has at least 85% sequence identity to the amino acid sequence of SEQ ID NO: 1.

4. The immunogenic composition of claim 1, wherein at least one of the S. aureus polypeptide antigens is fused to the second affinity molecule.

5. The immunogenic composition of claim 1, further comprising a flexible linker peptide attached to at least one of the S. aureus polypeptide antigens, wherein the flexible linker peptide attaches the antigens to the second affinity molecule.

6. The immunogenic composition of claim 1, further comprising at least one adjuvant.

7. The immunogenic composition of claim 1 for use in any one or more of:
   a. as a diagnostic for exposure to a pathogen or immune threat,
   b. to prevent or treat an infection by S. aureus,
   c. to prevent colonization of a subject by S. aureus,
   d. to elicit an immune response to S. aureus in a subject, wherein the immune response is selected from any of:
      i. an antibody or B-cell response,
      ii. an antibody or B-cell response and T-cell response,
      iii. an immune response to at least one immunogenic polysaccharide and at least one of the S. aureus polypeptide antigens,
      iv. an immune response that is a CD4+ T cell response, including Th1, Th2, or Th17 or Th22 response, or a CD8+ T cell response, or CD4+ and CD8+ T cell response,
      v. an antibody or B cell response to at least one immunogenic polysaccharide and a CD4+ T cell response, including Th1, Th2, or Th17 or Th22 response, or a CD8+ T cell response, or CD4+/CD8+ T cell response to at least one of the S. aureus polypeptide antigens,
      vi. an antibody or B cell response to at least one immunogenic polysaccharide, and an antibody or B cell response and a CD4+ T cell response, including Th1, Th2, Th17 or Th22 responses, or a CD8+ T cell response, or CD4+/CD8+ T cell response to at least one of the S. aureus polypeptide antigens,
      vii. an immune response results in activation of INF-γ, IL-17A or IL-22 producing cells, or INF-γ, IL-17A and IL-22 producing cells, or
      viii. an antibody or B-cell response against at least one of the S. aureus polypeptide antigens which associates with the at least one immunogenic polysaccharide.

* * * * *